United States Patent
Goh et al.

[11] Patent Number: 5,262,385
[45] Date of Patent: Nov. 16, 1993

[54] HALOGEN-CONTAINING COMPOUNDS, HERBICIDAL COMPOSITION CONTAINING THE SAME AS AN ACTIVE INGREDIENT, AND INTERMEDIARY COMPOUNDS THEREFOR

[75] Inventors: Atsushi Goh, Ushiku; Sachio Kudo, Ami; Yorio Kumamoto, Abiko; Michi Watanabe, Tsuchiura; Takako Takahashi, Ami; Takako Aoki, Ami; Norishige Toshima, Ami; Keiji Endo, Ami; Hideshi Mukaida, Moriya; Shinji Kawaguchi, Ami; Rika Higurashi, Narita, all of Japan

[73] Assignee: Mitsubishi Petrochemical Co., Ltd., Tokyo, Japan

[21] Appl. No.: 734,698

[22] Filed: Jul. 23, 1991

[30] Foreign Application Priority Data

| Jul. 24, 1990 | [JP] | Japan | 2-193807 |
| Jul. 24, 1990 | [JP] | Japan | 2-193808 |
| Feb. 22, 1991 | [JP] | Japan | 3-50340 |
| Feb. 22, 1991 | [JP] | Japan | 3-50523 |
| Apr. 22, 1991 | [JP] | Japan | 3-118095 |
| May 2, 1991 | [JP] | Japan | 3-128188 |
| May 2, 1991 | [JP] | Japan | 3-128208 |

[51] Int. Cl.$^5$ .............. A01N 43/54; C07D 239/28; C07D 401/12; C07D 403/08
[52] U.S. Cl. .................. 504/239; 504/242; 504/243; 544/295; 544/296; 544/299; 544/300; 544/301; 544/302; 544/303; 544/304; 544/306; 544/309; 544/310; 544/311; 544/312; 544/313; 544/314; 544/315; 544/316; 544/317; 544/318; 544/319; 544/320; 544/321; 544/322; 544/326; 544/327; 544/328; 544/329; 544/333; 544/334; 544/335
[58] Field of Search ............... 544/299, 300, 295, 296, 544/301, 302, 303, 304, 306, 309, 310, 311, 312, 313, 314, 315, 316, 318, 319, 320, 321, 317, 322, 326, 327, 328, 329, 333, 334, 335; 71/92; 504/239, 242, 243

[56] References Cited

U.S. PATENT DOCUMENTS 4,973,354 11/1990 Hatanaka .................. 71/92

FOREIGN PATENT DOCUMENTS

| 249708 | 12/1987 | European Pat. Off. . |
| 287079 | 10/1988 | European Pat. Off. . |
| 315889 | 5/1989 | European Pat. Off. . |
| 0346789 | 12/1989 | European Pat. Off. . |
| 0431707 | 6/1991 | European Pat. Off. ............. 544/318 |
| 0439243 | 7/1991 | European Pat. Off. . |
| 31266/91 | 6/1989 | Japan . |
| 0031266 | 2/1991 | Japan ................... 544/318 |

Primary Examiner—Mukund J. Shah
Assistant Examiner—Y. N. Gupter
Attorney, Agent, or Firm—Wenderoth, Lind & Ponack

[57] ABSTRACT

A compounds represented by the formula

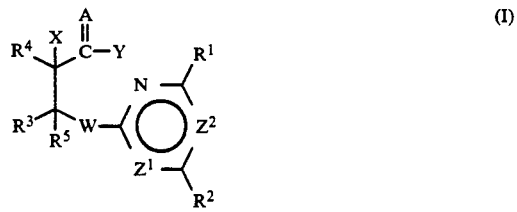

(I)

wherein
X represents a fluorine atom,
W represents an oxygen atom, sulfur atom or group —OCH$_2$—,
Z$^1$ and Z$^2$ each represent a nitrogen atom or group CH, but when Z$^1$ is a nitrogen atom, Z$^2$ represents a nitrogen atom or group CH and when Z$^1$ is a group CH, Z$^2$ represents a nitrogen atom,
R$^1$ and R$^2$ each independently represent either a hydrogen atom, halogen atom or mono- or dilower alkyl-substituted amino, or a lower alkyl, lower alkoxy or lower alkylthio each of which may be substituted with a halogen atom,
R$^3$ and R$^4$ form together with the carbon atoms to which they bind respectively a 5- to 8-membered carbon ring.

12 Claims, No Drawings

HALOGEN-CONTAINING COMPOUNDS, HERBICIDAL COMPOSITION CONTAINING THE SAME AS AN ACTIVE INGREDIENT, AND INTERMEDIARY COMPOUNDS THEREFOR

BACKGROUND OF THE INVENTION

1. Field of the Invention

This invention relates to novel halogen-containing compounds, a herbicidal composition containing the same as an active ingredient and intermediary compounds therefor. More specifically, this invention relates to pyrimidine ring or triazine ring-containing halogenated carboxylic acid derivatives, a herbicidal composition, and halogen-containing cycloalkanes useful as an intermediate therefor.

2. Description of the Prior Art

Alkanoic acids containing a pyrimidine ring or triazine ring, and herbicides containing the same as an effective ingredient are proposed, for example, in European Patent No. 346789-A and Japanese Laid-Open Patent Publication No. 85262/90.

However, compounds disclosed in the above known literatures are still not sufficiently satisfying in the points of herbicidal spectrum, the amount of such a compound to be applied, selectivity, etc.

SUMMARY OF THE INVENTION AND DETAILED DESCRIPTION OF THE PREFERRED EMBODIMENTS OF THE INVENTION

Thus, the present inventors intensely studied for developing compounds having a broader herbicidal spectrum and a higher herbicidal effect than those of the compounds disclosed in the above known literatures, and as a result it was found that halogen-containing compounds wherein the (cyclo) alkanecarboxylic acid (or its derivative) part whose specific position is halogenated and the pyrimidine ring part or triazine ring part having a substituent at the specific position bind through an oxygen atom, sulfur atom or group —OCH$_2$— are novel, and that these compounds exhibit an excellent herbicidal activity on perennial weeds as well as annual weeds and further exhibit high safety on some kinds of cultivation crops.

Thus according to this invention, are provided halogen-containing compounds represented by the following formula (I) and their salts.

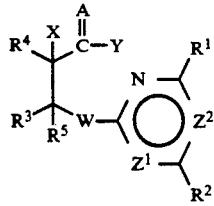
(I)

wherein

X represents a halogen atom,

W represents an oxygen atom, sulfur atom or group —OCH$_2$—, $Z^1$ and $Z^2$ each represent a nitrogen atom or group CH, but when $Z^1$ is a nitrogen atom, $Z^2$ represents a nitrogen atom or group CH and when $Z^1$ is a group CH, $Z^2$ represents a nitrogen atom, $R^1$ and $R^2$ each independently represent either a hydrogen atom, halogen atom or mono- or dilower alkyl-substituted amino, or a lower alkyl, lower alkoxy or lower alkylthio each of which may be substituted with a halogen atom, $R^3$ and $R^4$ each independently represent a hydrogen atom, halogen atom, hydroxycarbonyl, lower alkoxycarbonyl, lower alkyl, lower alkenyl, lower alkynyl, aryl or aralkyl, or $R^3$ and $R^4$ form together with the carbon atoms to which they bind respectively a 5- to 8-membered carbon ring or heterocycle and these rings may optionally be substituted with one or the same or different two of hydroxy, lower alkyl, lower alkenyl, alkenyl, lower alkynyl, lower alkoxy, lower alkoxycarbonyl, carbonyl, lower alkylcarbonyloxy and a group=O, and may have unsaturated bond(s) therein, $R^5$ represents a hydrogen atom or lower alkyl group, or may form together with part of $R^3$ a double bond, A represents an oxygen atom, sulfur atom or group=N-B wherein B represents hydroxy or lower alkylcarbonyloxy, or lower alkoxy optionally substituted with hydroxycarbonyl or lower alkoxycarbonyl, and Y either represents a hydrogen atom, a hydroxy, a mercapto, or a lower alkoxy, lower alkenoxy, lower alkynoxy, lower alkylthio, aryloxy, aralkyloxy, arylthio, aralkylthio, lower cycloalkoxy, lower cycloalkenyloxy, pyridylthio, furylmethyloxy, furylthio or thienyloxy each optionally substituted with a halogen atom, hydroxy, lower alkyl, lower alkoxy, lower alkylthio, lower alkoxycarbonyl, lower alkylcarbonyl, cyano, nitro or azido, or an azido, a trilower alkyl-substituted silyloxy or an imidooxy. represents a group

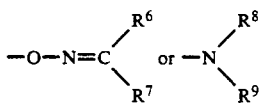

wherein $R^6$ and $R^7$ each independently represent a hydrogen atom, lower alkyl, lower alkoxy, aryl or aralkyl, or $R^6$ and $R^7$ may form together with the carbon atom to which they bind a lower cycloalkane ring, and $R^8$ and $R^9$ each independently represent a hydrogen atom, a hydroxy, a lower alkyl, a lower alkenyl, a lower alkynyl, a lower alkoxy, a lower alkylcarbonyloxy, a cyano, a lower alkylsulfonyl optionally substituted with a halogen atom, a lower alkyl substituted with lower alkoxycarbonyl, a lower alkyl substituted with hydroxycarbonyl, a lower alkoxy substituted with lower alkoxycarbonyl, a lower alkoxy substituted with hydroxycarbonyl, or an aryl, aralkyl, aryloxy, aralkyloxy, arylcarbonyloxy, pyridyl,

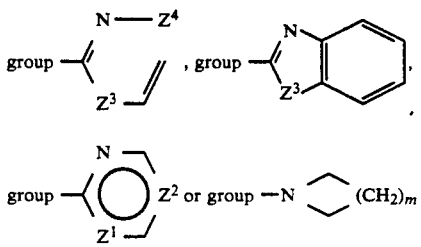

(wherein $Z^3$ represents an oxygen atom, group CH or sulfur atom, $Z^4$ represents a nitrogen atom or group CH, $Z^1$ and $Z^2$ are as defined above, and m represents an integer of 0 or 1) each optionally substituted with a halogen atom, hydroxy, lower alkyl, lower alkoxy, lower alkyl substituted with halogen atom(s), cyano, nitro, amino, mono- or diloweralkyl-substituted amino or lower alkoxycarbonyl,

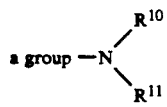

a group $-\text{N}\begin{matrix} R^{10} \\ R^{11} \end{matrix}$ (wherein $R^{10}$ and $R^{11}$ each represent a hydrogen atom, a lower alkyl, a lower alkoxycarbonyl, a lower alkyl substituted with lower alkoxycarbonyl, a lower alkyl substituted with hydroxycarbonyl, or an aryl, aralkyl, pyridyl or benzothiazolyl each optionally substituted with a halogen atom, lower alkyl, lower alkyl substituted with a halogen atom, lower alkoxy, cyano, amino or nitro)].

There are described below specific examples of the atom and groups in the definition of X, $R^1$, $R^2$, $R^3$, $R^4$, $R^5$, $R^6$, $R^7$, $R^8$, $R^9$, $R^{10}$, $R^{11}$, A and Y in the above general formula (I) of this invention.

Halogen atom

Fluorine, chlorine, bromine or iodine

Lower alkyl group

Lower alkyl group having 5 or less carbon atoms such as, for example, a methyl, ethyl, n-propyl, isopropyl, n-butyl, isobutyl sec-butyl, tert-butyl, n-pentyl, isopentyl, neopentyl or tert-pentyl group

Lower alkyl group substituted with halogen atom(s)

Lower alkyl group substituted with 1 to 3 halogen atoms such as, for example, a monochloromethyl, a trichloromethyl trifluoromethyl group

Lower alkoxy group

Lower alkoxy group having 5 or less carbon atoms such as, for example, a methoxy, ethoxy, n-propoxy, isopropoxy, n-butoxy, isobutoxy, sec-butoxy or tert-butoxy group

Lower alkoxy group substituted with halogen atom(s)

Lower alkoxy group having 5 or less carbon atoms substituted with 1 to 3 halogen atoms such as, for example, a difluoromethoxy, trifluoromethoxy, 2-chloroethoxy, 2,2-dichloroethoxy, 2,2,2-trichloroethoxy, 2-bromoethoxy, 2-fluoroethoxy, 2,2,2-trifluoroethoxy or 3-bromopropoxy group

Lower alkylthio group

Lower alkylthio group having 5 or less carbon atoms such as, for example, a methylthio, ethylthio, n-propylthio, isopropylthio, n-butylthio, sec-butylthio, isobutylthio or tert-butylthio group

Lower alkylthio group substituted with halogen atom(s)

Lower alkyl thio group having 5 or less carbon atoms substituted with 1 to 3 halogen atoms such as a difluoromethylthio, trifluoromethylthio, 2-chloroethylthio, 2,2-dichloroethylthio, 2,2,2-trichloroethylthio, 2-bromoethylthio, 2-fluoroethylthio, 2,2,2-trifluoroethylthio or 3-bromopropylthio group

Mono- or dilower alkyl-substituted amino group

Mono or dilower alkyl-substituted amino group whose alkyl part has 5 or less carbon atoms such as, for example, a methylamino, ethylamino, n-propylamino, isopropylamino, n-butylamino, sec-butylamino, isobutylamino, tert-butylamino, dimethylamino, diethylamino, di-n-propylamino, diisopropylamino, ethylmethylamino or methylpropylamino group

Lower alkylcarbonyloxy group

Carbonyloxy group to which a lower alkyl group having 5 or less carbon atoms binds such as, for example, a methylcarbonyloxy, ethylcarbonyloxy, n-propylcarbonyloxy, isopropylcarbonyloxy, n-butylcarbonyloxy, isobutylcarbonyloxy, sec-butylcarbonyloxy or tertbutylcarbonyloxy group

Lower alkoxy group substituted with a lower alkoxycarbonyl group

Lower alkoxy group having 5 or less carbon atoms substituted with a carbonyl group to which a lower alkoxy group having 5 or less carbon atoms bind such as, for example, a methoxycarbonylmethoxy, ethoxycarbonylmethoxy, n-propoxycarbonylmethoxy, isopropoxycarbonylmethoxy, n-butoxycarbonylmethoxy, isobutoxycarbonylmethoxy, sec-butoxycarbonylmethoxy, tert-butoxycarbonylmethoxy, 1-methoxycarbonyl-ethoxy, 1-ethoxycarbonylethoxy, 1-n-propoxycarbonyl-ethoxy, 1-isopropoxycarbonylethoxy, 1-n-butoxycarbonyl-ethoxy, 1-isobutoxycarbonylethoxy, 1-sec-butoxycarbonyl-ethoxy or 1-tert-butoxycarbonylethoxy group

Lower alkoxy group substituted with hydroxy

Lower alkoxy group having 5 or less carbon atoms substituted with a hydroxyl group such as, for example, a 2-hydroxyethoxy, 2-hydroxypropoxy, 3-hydroxypropoxy, 2-hydroxybutoxy, 3-hydroxybutoxy or 4-hydroxybutoxy group

Lower alkoxy group substituted with a hydroxycarbonyl group

Lower alkoxy group having 5 or less carbon atoms substituted with a hydroxycarbonyl group such as, for example, a hydroxycarbonylmethoxy or 1-hydroxycarbonyl-ethoxy group

Lower alkoxycarbonyl group

Lower alkoxycarbonyl group whose alkyl part has 5 or less carbon atoms such as, for example, a methoxycarbonyl, ethoxycarbonyl, n-propoxycarbonyl, isopropoxycarbonyl, sec-butoxycarbonyl or tert-butoxycarbonyl group

Lower alkenyl group

Lower alkenyl group having 5 or less carbon atoms such as, for example, an allyl, 2-methyl-2-propenyl, 2-butenyl, 3-butenyl or 3-methyl-2-butenyl group

Lower alkynyl group

Lower alkynyl group having 5 or less carbon atoms such as, for example, a 2-propynyl, 2-butynyl or 3-butynyl group

Lower alkylcarbonyl group

Lower alkylcarbonyl group whose alkyl part has or less carbon atoms such as, for example, a methylcarbonyl, ethylcarbonyl, n-propylcarbonyl, isopropylcarbonyl, n-butylcarbonyl, isobutylcarbonyl, secbutylcarbonyl or tert-butylcarbonyl group

Optionally substituted aryl group

Optionally substituted aryl group such as, for example, a phenyl, 2-methylphenyl, 3-methylphenyl, 4-methylphenyl, 2-chlorophenyl, 3-chlorophenyl, 4-chlorophenyl, 2-bromophenyl, 3-bromophenyl, 4-bromophenyl, 2-fluorophenyl, 3-fluorophenyl, 4-fluorophenyl, 2-nitrophenyl, 3-nitrophenyl, 4-nitrophenyl, 2-methoxyphenyl, 3-methoxyphenyl, 4-methoxyphenyl, 2-trifluoromethylphenyl, 3-trifluoromethylphenyl, 4-trifluoromethylphenyl, 2-aminophenyl, 3-aminophenyl, 4-aminophenyl, 2-hydroxyphenyl, 3-hydroxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4-dinitrophenyl, 2,6-dinitrophenyl, 3,4-dinitrophenyl, 3,5-dinitrophenyl, 2,3,5-trichlorophenyl, 2,4,6-trichlorophenyl, 1-naphthyl or 2-naphthyl group

Optionally substituted aralkyl group

Optionally substituted aralkyl group such as, for example, a benzyl, 2-bromobenzyl, 3-bromobenzyl, 4-bromobenzyl, 2-chlorobenzyl, 3-chlorobenzyl, 4-chlorobenzyl, 2-fluorobenzyl, 3-fluorobenzyl, 4-fluorobenzyl, 2-methoxybenzyl, 3-methoxybenzyl, 4-methoxybenzyl, 2-methylbenzyl, 3-methylbenzyl, 4-methylbenzyl, 2-nitrobenzyl, 3-nitrobenzyl or 4-nitrobenzyl group

Lower alkenyloxy group

Lower alkenyloxy group having 5 or less carbon atoms such as, for example, a vinyloxy, allyloxy, 3-butenyloxy, 1-methyl-2-propenoxy or 2-methyl-2-propenyloxy group

Lower alkynyloxy group

Lower alkynyloxy group having 5 or less carbon atoms such as, for example, a 2-propynyloxy, 1-methyl-2-propynyloxy, 2-butynyloxy or 3-butynyloxy group

Optionally substituted aryloxy group

Optionally substituted aryloxy group such as, for example, a phenoxy, naphthoxy, 2-bromophenoxy, 3-chlorophenoxy, 4-chlorophenoxy, 2-methylphenoxy, 3-bromophenoxy, 4-bromophenoxy, 2-chlorophenoxy, 3-methylphenoxy, 4-methylphenoxy, 2-methoxyphenoxy, 3-methoxyphenoxy, 4-methoxyphenoxy, 2-nitrophenoxy, 3-nitrophenoxy of 4-nitrophenoxy group

Optionally substituted aralkyloxy group

Optionally substituted aralkyloxy group such as, for example, a benzyloxy, 2-bromobenzyloxy, 3-bromobenzyloxy, 4-bromobenzyloxy, 2-chlorobenzyloxy, 3-chlorobenzyloxy, 4-chlorobenzyloxy, 2-fluorobenzyloxy, 3-fluorobenzyloxy, 4-fluorobenzyloxy, 2-methoxybenzyloxy, 3-methoxybenzyloxy, 4-methoxybenzyloxy, 2-methylbenzyloxy, 3-methylbenzyloxy, 4-methylbenzyloxy, 2-nitrobenzyloxy, 3-nitrobenzyloxy, 4-nitrobenzyloxy, 2,4-dinitrobenzyloxy, 3,4-dinitrobenzyloxy, 3,5-dinitrobenzyloxy or 2,4,6-trimethylbenzyloxy group

Optionally substituted arylthio group

Optionally substituted arylthio group such as, for example a phenylthio, 2-bromophenylthio, 3-bromophenylthio, 4-bromophenylthio, 2-chlorophenylthio, 3-chlorophenylthio, 4-chlorophenylthio, 4-fluorophenylthio, 2-methoxyphenylthio, 3-methoxyphenylthio, 4-methoxyphenylthio, 4-methylphenylthio or 4-nitrophenylthio group

Optionally substituted aralkylthio group

Optionally substituted aralkyl thio group such as, for example, a benzylthio, 2-, 3- or 4-bromobenzylthio, 2-,3- or 4-chlorobenzylthio, 2-, 3- or 4-fluorobenzylthio, 2-, 3- or 4-methoxybenzylthio, 2-, 3- or 4-methylbenzylthio, or 3- or 4-nitrobenzylthio group

Optionally substituted pyridylthio group

Optionally substituted pyridylthio group such as, for example, a pyridyl-2-thio or 5-nitropyridyl2-thio

Lower cycloalkoxy group

For example, a cyclopropyloxy, cyclobutoxy, cyclopentyloxy or cyclohexyloxy group

Lower cycloalkenyloxy group

For example, a 2-cyclopentenyloxy, 2-cyclohexenyloxy or 3-cyclohexenyloxy group

Furylmethyloxy group

For example, a 2-furylmethyloxy or 3-furylmethyloxy group

Furylmethylthio group

For example, a 2-furylmethylthio or 3-furylmethylthio group

Thienylmethyloxy group

For example, a 2-thienylmethyloxy or 3-thienylmethyloxy group

Lower alkylsulfonyl group optionally substituted with halogen atom(S)

Lower alkylsulfonyl group having 5 or less carbon atoms optionally substituted with 1 to 3 halogen atoms such as, for example, a methanesulfonyl, ethanesulfonyl, 1-propanesulfonyl, 2-propanesulfonyl, 1-butanesulfonyl, trichloromethanesulfonyl, trifluoromethanesulfonyl or 2,2,2-trifluoromethanesulfonyl group

5- to 8- membered carbon ring or heterocycle ring optionally containing hetero atom(s)

Carbon ring or heterocycle ring such as, for example a cyclopentane ring, cyclohexane ring, cycloheptane ring, cyclooctane ring, cyclopentene ring, cyclohexene ring, cyclooctane ring, tetrahydrofuran ring, tetrahydropyran ring, thiolane ring, thiane ring, pyrrolidine or piperidine ring

Optionally substituted arylcarbonyloxy group

Optionally substituted arylcarbonyloxy group such as, for example, a phenylcarbonyloxy, 2-chlorophenylcarbonyloxy, 3-chlorophenylcarbonyloxy, 4-chlorophenylcarbonyloxy, 2-trifluoromethylphenylcarbonyloxy, 3-trifluoromethylphenylcarbonyloxy, 4-trifluoromethylphenylcarbonyloxy, 2,4-dichlorophenylcarbonyloxy, 2,6-dichlorophenylcarbonyloxy, 3,4-dichlorophenylcarbonyloxy, 3,5-dichlorophenylcarbonyloxy or 2,4-dichloro-3-methylphenylcarbonyloxy group Optionally substituted benzothiazolyl group Optionally substituted benzothiazonyl group such as, for example, a benzothiazol-2-yl or 6-nitrobenzothiazol-2-yl group Groups not specifically mentioned as examples of the above groups can be selected by optioned combination based on the above atoms and groups or according to the common sense of this field.

When Y in the above formula (I) of the invention is a hydroxyl group, its salts are included in the compounds of the invention. Preferably, its salts are usually agriculturally acceptable salts, and examples thereof are alkali metal, ammonium and lower alkylammonium salts such as sodium, potassium, ammonium, isopropylammonium, triethylammonium salts.

One of the characteristics of the halogen-containing compounds of this invention is that X in the formula (I) is a halogen atom. Due to the fact that X is a halogen atom, the compounds of the invention have a stronger herbicidal activity than the compounds wherein X is a hydrogen atom.

Although X in the formula (I) represents a fluorine atom, chlorine atom, bromine atom or iodine atom, X is preferably a fluorine atom or chlorine atom, most preferably a fluorine atom.

Another characteristic of the compounds of the invention is that the compounds have a group

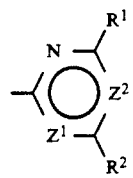

This group can specifically be classified into the following three groups:

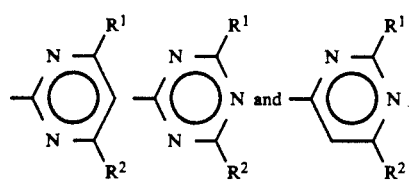

Among these three groups, preferred are

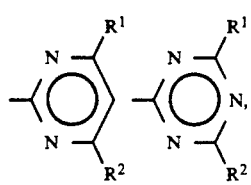

and particularly preferred is

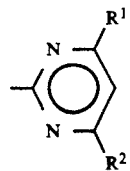

Atoms or groups preferred as $R^1$ and $R^2$ in the above three groups vary depending on whether the skeleton is pyrimidine or tryazine. Namely in case of

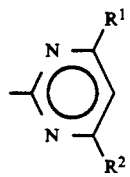

it is preferred that either both $R^1$ and $R^2$ are lower alkoxy, $R^1$ is lower alkoxy and $R^2$ is a halogen atom, or $R^1$ is a halogen atom and $R^2$ is lower alkoxy. In case of

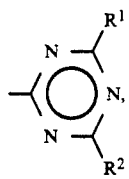

it is preferred that both $R^1$ and $R^2$ are lower alkoxy. Further, in case of

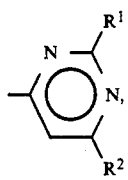

it is preferred that $R^1$ is lower alkylthio and $R^2$ is a halogen atom particularly a chlorine atom.

Preferred as the compounds of the invention are those wherein $R^3$ and $R^4$ in the formula (I) are each independently lower alkyl, lower alkenyl, lower alkynyl or aralkyl, or $R^3$ and $R^4$ combine to form a cyclopentane ring or cyclohexane ring. Further, it is preferred that A in the general formula (I) is an oxygen atom or sulfur atom rather than a group=N-B.

Further, it is preferred that W is an oxygen atom or sulfur atom among an oxygen atom, sulfur atom and group —OCH$_2$—, and an oxygen atom is particularly preferred.

It is most preferred that $R^5$ is a hydrogen atom.

Further, Y is preferably hydroxy, mercapto, lower alkoxy, lower alkenyloxy, lower alkynyloxy, a group

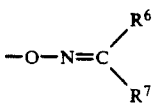

(wherein $R^6$ and $R^7$ are as defined in the formula (I)) or a group

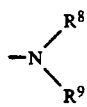

(wherein either $R^8$ and $R^9$ is a hydrogen atom), particularly preferably hydroxy, lower alkoxy, lower alkenyloxy, lower alkynyloxy or a group

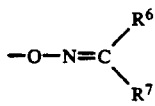

(wherein $R^6$ and $R^7$ are as defined in the formula (I)),

Preferred examples of the halogen-containing compounds of the invention represented by the formula (I) are set forth in the following (1) to (6).

(1) Halogen-containing compounds represented by the following formula (I)-i

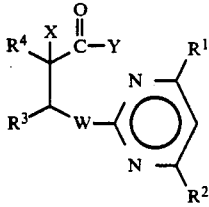

(I)-i wherein $R^1$, $R^2$, $R^3$, $R^4$, X, Y and W are as defined in the general formula (I)

(2) Halogen-containing compounds represented by the following (I)-ii

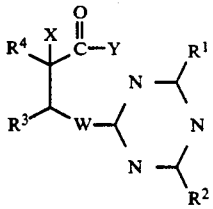

(I)-ii wherein $R^1$, $R^2$, $R^3$, $R^4$, X, Y and W are as defined in the formula (I)

(3) Halogen-containing compounds represented by the following general formula (I)-iii

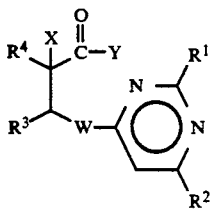

(I)-iii wherein $R^1$, $R^2$, $R^3$, $R^4$, X, Y and W are as defined in the formula (I)

(4) Halogen-containing compounds represented by the following general formula (I)-iv

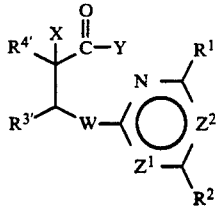

(I)-iv wherein $R^1$, $R^2$, $Z^1$, $Z^2$, X, Y and W are as defined in the general formula (I), and $R^{3'}$ and $R^{4'}$ form together with the carbon atoms to which they bind a 5- to 8-membered carbon ring or heterocycle optionally containing hetero atom(s), and these rings may optionally be substituted with one or the same or different two of hydroxy, lower alkyl, lower alkylthio, lower alkanyl, lower alkynyl, lower alkoxy, lower alkoxycarbonyl, lower alkylcarbonyloxy and a group=O (5) Halogen-containing compounds represented by the following formula (I)-v

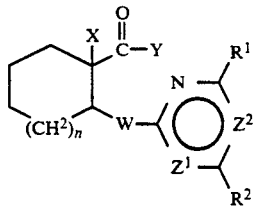

(I)-v wherein $R^1$, $R^2$, $Z^1$, $Z^2$, X, Y and W are as defined in the formula (I), and n represents 0, 1, 2 or 3

(6) Halogen-containing compounds represented by the following formula (I)-vi

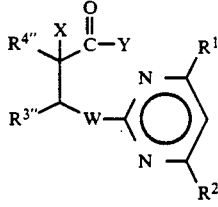

(I)-vi wherein $R^1$, $R^2$, Y and W are as defined in the formula (I), and $R^{3''}$ and $R^{4''}$ each independently represent a hydrogen atom, halogen atom, hydroxycarbonyl, lower alkoxycarbonyl, lower alkyl, lower alkenyl, lower alkynyl, aryl or aralkyl.

In the compounds of the formula (I)-vi, it is preferred that $R^{3''}$ and $R^{4''}$ are each independently a lower alkyl, lower alkenyl, lower alkynyl or aralkyl.

According to the researches by the present inventors, it was found that halogen-containing compounds represented by the above general formula (I) are novel and have a strong herbicidal activity on many kinds of weeds.

Thus according to this invention is provided a herbicidal composition which comprises a halogen-containing compound represented by the formula (I) as an active ingredient and agriculturally and horticulturally acceptable diluent(s) or carrier(s).

Further according to this invention is provided a method for exterminating weeds or preventing the generation or growth of weeds.

The herbicide composition and its application method of the invention are detailedly described later.

According to the investigation by the present inventors, it was revealed that the halogen-containing cyclic compounds of the following formula (II) are novel which can become part of the synthetic intermediates of the halogen-containing compounds of this invention having a herbicidal activity. These halogen-containing cyclic compounds (II) are encompassed in the invention, too.

Namely, according to this invention are provided halogen-containing cyclic compounds represented by the following formula (II)

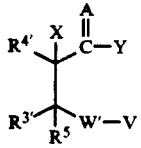
(II)

wherein
X, A and Y are as defined in the formula (I),
W' represents an oxygen atom or sulfur atom,
$R^{3'}$ and $R^{4'}$ form together with the carbon atoms to which they bind respectively a 5- to 8-membered carbon ring or heterocyclic ring optionally containing hetero atom(s), and these rings may optionally be substituted with one or the same or different two of hydroxy, lower alkyl, lower alkenyl, lower alkynyl, lower alkoxy, lower alkoxycarbonyl, lower alkylcarbonyloxy and a group=O, and may unsaturated bond(s) therein,
$R^5$ represents a hydrogen atom or lower alkyl group, or $R^5$ may form together with part of $R^3$ a double bond, and
V represents a hydrogen atom, a lower alkyl, a lower alkylcarbonyl, a lower alkylsulfonyl or an aralkyl, arylcarbonyl or arylsulfonyl each optionally substituted with a halogen atom, hydroxy, nitro, cyano, lower alkyl, lower alkoxy, halogen-substituted lower alkyl, halogen-substituted lower alkoxy, amino, or mono- or dilower alkyl-substituted amino.

The halogen-containing cyclic compounds of the invention represented by the formula (II) have their characteristics in that they have a halogen atom as X and $R^{3'}$ and $R^{4'}$ may form together with the carbon atoms to which they bind a 5- to 8-membered carbon ring or heterocycle optionally containing hetero atom(s).

In the formula (II) X is a fluorine atom, chlorine atom, bromine atom or iodine atom, preferably a fluorine atom or chlorine atom, particularly preferably a fluorine atom.

Specific examples of the 5- to 8-membered carbon ring or heterocycle which $R^{3'}$ and $R^{4'}$ combine to form ring are a cyclopentane ring, a cyclohexane ring, a cycloheptane ring, a cyclooctane ring, a cyclopentene ring, a cyclohexene ring, cycloheptene ring, a cyclooctene ring, a tetrahydrofuran ring, a tetrahydropyran ring a thiolane ring, a thiane ring, a pyrrolidine ring, a piperidine ring, etc., but the cyclopentane ring and cyclohexane ring are particularly preferred among them.

Further in the formula (II), A, Y and $R^5$ are as defined in the formula (I), and the abovementioned preferred ones in the general formula (I) are likewise preferred.

Further in the formula (II) W' is an oxygen atom or sulfur atom and an oxygen atom is preferred.

Further in the formula (II) V is a hydrogen atom, lower alkyl, lower alkylcarbonyl, lower alkyl-sulfonyl aralkyl, arylcarbonyl or arylsulfonyl. The aromatic nucleus of the aralkyl, arylcarbonyl, and arylsulfonyl among them may optionally be substituted with at least one of halogen atom(s), hydroxy, nitro, cyano, lower alkyl, lower alkoxy, halogen-substituted lower alkyl, halogen-substituted lower alkoxy, amino and mono- or dilower alkyl-substituted amino. Preferred as V are a hydrogen atom, aralkyl and arylcarbonyl.

Preferred examples of the compounds of the invention represented by the formula (II) include halogen-containing cyclic compounds represented by the following formula (II)-1

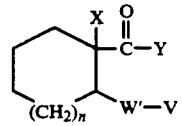
(II)-i wherein X, Y, W' and V are as defined in the formula (II), and n represents 0, 1, 2 or 3, preferably 0 or 1.

The compound of this invention may exist a number of different stereoisomeric forms according to a number of asymmetric carbon(s). For example, when two carbon atoms to which $R^3$ and $R^4$ bind respectively are both the asymmetric carbons, the compound of this invention may include four stereoisomeric forms (cis-form, trans-form erythro-form or threo-form) about its two asynmetric carbons. And, further, these isomers may include a dextrorotatory, levorotatory or racemie form.

It should be understood the compound of this invention encompasses all these stereoisomers.

Specific compounds included in the halogen-containing compounds of the invention represented by the formula (I) are examplified in Tables 1 to 7. NMR analysis values and/or physical data measured on some of the halogen-containing compounds are shown in Tables 8 to 13.

Specific compounds included in the halogen-containing cyclic compounds of the invention represented by the formula (II) are examplified in Tables 14 to 15. NMR analysis value and/or physical data measured on some of the halogen-containing cyclic compounds are shown in Table 16.

The meanings of the abbreviations in Tables 1 to 7 and Tables 14 to 15 are as follows.

Ph means a phenyl group.

Ph in Ph-2Cl, Ph-2-OCH$_3$, Ph-2NO$_2$, Ph-2-OC$_2$H$_5$ Ph-2CF$_3$, Ph-3Cl, Ph-3-OCH$_3$, Ph-3NO$_2$, Ph-3-OC$_2$H$_5$, Ph-3CF$_3$, Ph-4Cl, Ph-4-OCH , Ph-4NO$_2$, Ph-4-OC$_2$H$_5$, Ph-4CF$_3$, Ph-2Br, Ph-2CH$_3$, Ph-3Br, Ph-3CH$_3$, Ph-4Br, Ph-4CH$_3$, etc. means a phenyl group, the figure part in the "2Cl" etc. following Ph means the substitution position on the phenyl ring, and Cl, OCH$_3$, NO$_2$, OC$_2$H$_5$, CF$_3$, Br, CH$_3$, etc. mean substituents at the substition position.

Ph-2,4-DiCl means a 2,4-dichlorophenyl group, Ph-2,6-DiCl means a 2,6-dichlorophenyl group, Ph-3,4-DiCl means a 3,4-dichlorophenyl group and Ph-3,5-DiCl means a 3,5-dichlorophenyl group.

Ph-2,4 DiCl-3CH$_3$ means a 2,4-dichloro-3-methylphenyl group.

Succinimidyl means a 2,5-dioxo-1-pyrrolidinyl group.
O—N=C(—(C$_2$H$_5$)$_5$—) means a group

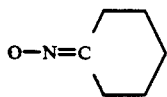

and C(—(C$_2$H$_5$—) means a cyclohexyl group.

The 2-thiadiazolyl of NH-2-thiadiazolyl means a 1,3,4-thiadiazol-2-yl group and the 2-thiadiazolvl-5-CF$_3$ in NH-2-thiadiazolyl-5-CF$_3$ means a 5-trifluoromethyl1,3,4-thiadiazol-2-yl group Cis, trans, erythro or threo means relative configuration about two substituents located at two adjacent asymmetric carbons of the corresponding compound.

Rac, + or — means racemic, dextrorotatory or levorotatory form respectively.

Mixture means mixture of racemic storeoisomers.

Further, the expressions such as axial methyl group, equatorial methyl group and equatorial t-butyl group in the compound Nos. 1276a to 1295a in Table 8 mean the orientation of each alkyl group when these alkyl groups exist on the ring of the respective compounds.

TABLE 1

[Structure: R⁴–C(R³)(X)–CH(W-Ar)–C(=O)–Y, where Ar is 4,6-dimethoxypyrimidin-2-yl (N,N ring with two OCH₃ groups)]

| Compound No. | R³ | R⁴ | X | W | Y | Remarks |
|---|---|---|---|---|---|---|
| 1001 | —(CH₂)₃— | | F | O | H | cis(rac) |
| 1002a | —(CH₂)₃— | | F | O | OH | cis(rac) |
| 1002a1 | —(CH₂)₃— | | F | O | OH | cis(+) |
| 1002a2 | —(CH₂)₃— | | F | O | OH | cis(−) |
| 1002b | —(CH₂)₃— | | F | O | OH | trans(rac) |
| 1002b1 | —(CH₂)₃— | | F | O | OH | trans(+) |
| 1002b2 | —(CH₂)₃— | | F | O | OH | trans(−) |
| 1003a | —(CH₂)₃— | | F | O | O—CH₃ | cis(rac) |
| 1003a1 | —(CH₂)₃— | | F | O | O—CH₃ | cis(+) |
| 1003a2 | —(CH₂)₃— | | F | O | O—CH₃ | cis(−) |
| 1003b | —(CH₂)₃— | | F | O | O—CH₃ | trans(rac) |
| 1003b1 | —(CH₂)₃— | | F | O | O—CH₃ | trans(+) |
| 1003b2 | —(CH₂)₃— | | F | O | O—CH₃ | trans(−) |
| 1004a | —(CH₂)₃— | | F | O | O—C₂H₅ | cis |
| 1004b | —(CH₂)₃— | | F | O | O—C₂H₅ | trans |
| 1005 | —(CH₂)₃— | | F | O | O-n-C₃H₇ | |
| 1006a | —(CH₂)₃— | | F | O | O-i-C₃H₇ | cis |
| 1006b | —(CH₂)₃— | | F | O | O-i-C₃H₇ | trans |
| 1007a | —(CH₂)₃— | | F | O | O-n-C₄H₉ | cis |
| 1007b | —(CH₂)₃— | | F | O | O-n-C₄H₉ | trans |
| 1008 | —(CH₂)₃— | | F | O | O-i-C₄H₉ | |
| 1009a | —(CH₂)₃— | | F | O | O-s-C₄H₉ | cis |
| 1009b | —(CH₂)₃— | | F | O | O-s-C₄H₉ | trans |
| 1010a | —(CH₂)₃— | | F | O | O-t-C₄H₉ | cis |
| 1010b | —(CH₂)₃— | | F | O | O-t-C₄H₉ | trans |
| 1011a | —(CH₂)₃— | | F | O | O—(CH₂)₂—Cl | cis |
| 1011b | —(CH₂)₃— | | F | O | O—(CH₂)₂—Cl | trans |
| 1012a | —(CH₂)₃— | | F | O | O—CH₂—S—CH₃ | cis |
| 1012b | —(CH₂)₃— | | F | O | O—CH₂—S—CH₃ | trans |
| 1013a | —(CH₂)₃— | | F | O | O—CH₂—Ph | cis |
| 1013b | —(CH₂)₃— | | F | O | O—CH₂—Ph | trans |
| 1014 | —(CH₂)₃— | | F | O | O—CH₂—Ph-2Cl | |
| 1015 | —(CH₂)₃— | | F | O | O—CH₂—Ph-3Cl | |
| 1016 | —(CH₂)₃— | | F | O | O—CH₂—Ph-4Cl | |
| 1017 | —(CH₂)₃— | | F | O | O—CH₂—Ph-2OCH₃ | |
| 1018 | —(CH₂)₃— | | F | O | O—CH₂—Ph-3OCH₃ | |
| 1019 | —(CH₂)₃— | | F | O | O—CH₂—Ph-4OCH₃ | |
| 1020 | —(CH₂)₃— | | F | O | O—CH₂—Ph-2NO₂ | |

-continued

| # | | | | |
|---|---|---|---|---|
| 1021 | F | —(CH₂)₃— | O—CH₂—Ph-3NO₂ | |
| 1022 | F | —(CH₂)₃— | O—CH₂—Ph-4NO₂ | |
| 1023a | F | —(CH₂)₃— | O—Ph | cis |
| 1023b | F | —(CH₂)₃— | O—Ph | trans |
| 1024a | F | —(CH₂)₃— | O—Ph-2Cl | cis |
| 1024b | F | —(CH₂)₃— | O—Ph-2Cl | trans |
| 1025 | F | —(CH₂)₃— | O—Ph-3Cl | |
| 1026 | F | —(CH₂)₃— | O—Ph-4Cl | |
| 1027 | F | —(CH₂)₃— | O—Ph-2OCH₃ | |
| 1028 | F | —(CH₂)₃— | O—Ph-3OCH₃ | |
| 1029 | F | —(CH₂)₃— | O—Ph-4OCH₃ | |
| 1030 | F | —(CH₂)₃— | O—Ph-2CH₃ | |
| 1031 | F | —(CH₂)₃— | O—Ph-3CH₃ | |
| 1032 | F | —(CH₂)₃— | O—Ph-4CH₃ | |
| 1033a | F | —(CH₂)₃— | O—CH₂—CH=CH₂ | cis |
| 1033b | F | —(CH₂)₃— | O—CH₂—CH=CH₂ | trans |
| 1034a | F | —(CH₂)₃— | O—CH₂—C≡CH | cis |
| 1034b | F | —(CH₂)₃— | O—CH₂—C≡CH | trans |
| 1035a | F | —(CH₂)₃— | O⁻ Na⁺ | cis |
| 1035b | F | —(CH₂)₃— | O⁻ Na⁺ | trans |
| 1036a | F | —(CH₂)₃— | O⁻ K⁺ | cis |
| 1036b | F | —(CH₂)₃— | O⁻ K⁺ | trans |
| 1037a | F | —(CH₂)₃— | O⁻ ½Ca⁺⁺ | cis |
| 1037b | F | —(CH₂)₃— | O⁻ ½Ca⁺⁺ | trans |
| 1038a | F | —(CH₂)₃— | O⁻ NH₄⁺ | cis |
| 1038b | F | —(CH₂)₃— | O⁻ NH₄⁺ | trans |
| 1039a | F | —(CH₂)₃— | O⁻ N⁺H₂(CH₃)₂ | cis |
| 1039b | F | —(CH₂)₃— | O⁻ N⁺H₂(CH₃)₂ | trans |
| 1040a | F | —(CH₂)₃— | O⁻ N⁺H₃-i-C₃H₇ | cis |
| 1040b | F | —(CH₂)₃— | O⁻ N⁺H₃-i-C₃H₇ | trans |
| 1041a | F | —(CH₂)₃— | O⁻ N⁺H₃-n-C₈H₁₇ | cis |
| 1041b | F | —(CH₂)₃— | O⁻ N⁺H₃-n-C₈H₁₇ | trans |
| 1042a | F | —(CH₂)₃— | O—C(CH₃)₂—CN | cis |
| 1042b | F | —(CH₂)₃— | O—C(CH₃)₂—CN | trans |
| 1043a | F | —(CH₂)₃— | O—CH(CH₃)—CH=CH₂ | cis |
| 1043b | F | —(CH₂)₃— | O—CH(CH₃)—CH=CH₂ | trans |
| 1044a | F | —(CH₂)₃— | O—CH(CH₃)—C≡CH | cis |
| 1044b | F | —(CH₂)₃— | O—CH(CH₃)—C≡CH | trans |
| 1045 | F | —(CH₂)₃— | O—CH(CH₃)—CO₂Et | |
| 1046 | F | —(CH₂)₃— | O—CH₂—CO—CH₃ | |
| 1047 | F | —(CH₂)₃— | O—CH₂—CF₃ | |
| 1048 | F | —(CH₂)₃— | O—CH₂—CN | |
| 1049 | F | —(CH₂)₃— | O—CH₂—C(Cl)=CH₂ | |
| 1050 | F | —(CH₂)₃— | O—CH₂—CH=CH—Cl | |
| 1051 | F | —(CH₂)₃— | O—CH₂—C≡C—CH₃ | |
| 1052 | F | —(CH₂)₃— | O—CH₂-2-furyl | |
| 1053 | F | —(CH₂)₃— | O—(CH₂)₂—C≡CH | |
| 1054 | F | —(CH₂)₃— | O-cyclopentyl | |
| 1055 | F | —(CH₂)₃— | O—(CH₂)₂—Br | |
| 1056 | F | —(CH₂)₃— | O—(CH₂)₂—N₃ | |
| 1057 | F | —(CH₂)₃— | O-cyclohexyl | |
| 1058 | F | —(CH₂)₃— | O—CH₂-cyclopropyl | |

-continued

| No. | | | | |
|---|---|---|---|---|
| 1060 | —(CH$_2$)$_3$— | F | O—CH$_2$—CH=CH—CH$_3$ | |
| 1061 | —(CH$_2$)$_3$— | F | O—CH$_2$—CH=C(CH$_3$)$_2$ | |
| 1062 | —(CH$_2$)$_3$— | F | O—CH$_2$—CCl$_3$ | |
| 1063 | —(CH$_2$)$_3$— | F | O—CH$_2$—CH=CHPh | |
| 1064 | —(CH$_2$)$_3$— | F | O—CH$_2$—CH(OCH$_3$)$_2$ | |
| 1065 | —(CH$_2$)$_3$— | F | O—CH$_2$—CH$_2$F | |
| 1066 | —(CH$_2$)$_3$— | F | O-2-cyclohexenyl | |
| 1067 | —(CH$_2$)$_3$— | F | O—CH$_2$-2-thienyl | |
| 1068 | —(CH$_2$)$_3$— | F | O—CH$_2$—O—C$_2$H$_5$ | |
| 1069a | —(CH$_2$)$_3$— | F | O—N=CH—Ph | cis |
| 1069b | —(CH$_2$)$_3$— | F | O—N=CH—Ph | trans |
| 1070 | —(CH$_2$)$_3$— | F | O—N=C(CH$_3$)$_2$ | |
| 1071 | —(CH$_2$)$_3$— | F | O—N=C(CH$_3$)C$_2$H$_5$ | |
| 1072 | —(CH$_2$)$_3$— | F | O—N=C(n-C$_3$H$_7$)$_2$ | |
| 1073 | —(CH$_2$)$_3$— | F | O—N=C(i-C$_3$H$_7$)$_2$ | |
| 1074 | —(CH$_2$)$_3$— | F | O—N=C(—(CH$_2$)$_5$—) | |
| 1075a | —(CH$_2$)$_3$— | F | O—N=C(CH$_3$)—O—C$_2$H$_5$ | cis |
| 1075b | —(CH$_2$)$_3$— | F | O—N=C(CH$_3$)—O—C$_2$H$_5$ | trans |
| 1076a | —(CH$_2$)$_3$— | F | O-succinimidyl | cis |
| 1076b | —(CH$_2$)$_3$— | F | O-succinimidyl | trans |
| 1077 | —(CH$_2$)$_3$— | F | O-Si(CH$_3$)$_2$-t-C$_4$H$_9$ | |
| 1078 | —(CH$_2$)$_3$— | F | O—(CH$_2$)$_2$—N(CH$_3$)$_2$ | |
| 1079 | —(CH$_2$)$_3$— | F | O—(CH$_2$)$_2$—NO$_2$ | |
| 1080 | —CH(CH$_3$)—(CH$_2$)$_2$— | F | H | mixture |
| 1081 | —CH(CH$_3$)—(CH$_2$)$_2$— | F | OH | mixture |
| 1082 | —CH(CH$_3$)—(CH$_2$)$_2$— | F | O—C$_2$H$_5$ | |
| 1083 | —CH(CH$_3$)—(CH$_2$)$_2$— | F | O-n-C$_3$H$_7$ | |
| 1084 | —CH(CH$_3$)—(CH$_2$)$_2$— | F | O-i-C$_3$H$_7$ | |
| 1085 | —CH(CH$_3$)—(CH$_2$)$_2$— | F | O-n-C$_4$H$_9$ | |
| 1086 | —CH(CH$_3$)—(CH$_2$)$_2$— | F | O-i-C$_4$H$_9$ | |
| 1087 | —CH(CH$_3$)—(CH$_2$)$_2$— | F | O-s-C$_4$H$_9$ | |
| 1088 | —CH(CH$_3$)—(CH$_2$)$_2$— | F | O-t-C$_4$H$_9$ | |
| 1089 | —CH(CH$_3$)—(CH$_2$)$_2$— | F | O—(CH$_2$)$_2$—Cl | |
| 1090 | —CH(CH$_3$)—(CH$_2$)$_2$— | F | O—CH$_2$—S—CH$_3$ | |
| 1091 | —CH(CH$_3$)—(CH$_2$)$_2$— | F | O—CH$_2$—Ph | |
| 1092 | —CH(CH$_3$)—(CH$_2$)$_2$— | F | O—Ph | |
| 1093 | —CH(CH$_3$)—(CH$_2$)$_2$— | F | O—CH$_2$—CH=CH$_2$ | |
| 1094 | —CH(CH$_3$)—(CH$_2$)$_2$— | F | O—CH$_2$—C≡CH | |
| 1095 | —CH(CH$_3$)—(CH$_2$)$_2$— | F | O—CH$_2$—O—C$_2$H$_5$ | |
| 1096 | —CH$_2$—CH(CH$_3$)—CH$_2$— | F | H | |
| 1097 | —CH$_2$—CH(CH$_3$)—CH$_2$— | F | OH | |
| 1098 | —CH$_2$—CH(CH$_3$)—CH$_2$— | F | O—C$_2$H$_5$ | |
| 1099 | —CH$_2$—CH(CH$_3$)—CH$_2$— | F | O-n-C$_3$H$_7$ | |
| 1100 | —CH$_2$—CH(CH$_3$)—CH$_2$— | F | O-i-C$_3$H$_7$ | |
| 1101 | —CH$_2$—CH(CH$_3$)—CH$_2$— | F | O-n-C$_4$H$_9$ | |
| 1102 | —CH$_2$—CH(CH$_3$)—CH$_2$— | F | O-i-C$_4$H$_9$ | |
| 1103 | —CH$_2$—CH(CH$_3$)—CH$_2$— | F | O-s-C$_4$H$_9$ | |
| 1104 | —CH$_2$—CH(CH$_3$)—CH$_2$— | F | O-t-C$_4$H$_9$ | |
| 1105 | —CH$_2$—CH(CH$_3$)—CH$_2$— | F | O—(CH$_2$)$_2$—Cl | |
| 1106 | —CH$_2$—CH(CH$_3$)—CH$_2$— | F | O—CH$_2$—S—CH$_3$ | |
| 1107 | —CH$_2$—CH(CH$_3$)—CH$_2$— | F | O—CH$_2$—Ph | |
| 1108 | —CH$_2$—CH(CH$_3$)—CH$_2$— | F | O—Ph | |
| 1109 | —CH$_2$—CH(CH$_3$)—CH$_2$— | F | O—CH$_2$—C≡CH$_2$ | |

| No. | Bridge | | F | R |
|---|---|---|---|---|
| 1110 | —CH₂—CH(CH₃)—CH₂— | O | F | O—CH₂—C≡CH |
| 1111 | —CH₂—CH(CH₃)—CH₂— | O | F | O—CH₂—O—C₂H₅ |
| 1112 | —(CH₂)₂—CH(CH₃)— | O | F | H |
| 1113 | —(CH₂)₂—CH(CH₃)— | O | F | OH |
| 1114 | —(CH₂)₂—CH(CH₃)— | O | F | O—C₂H₅ |
| 1115 | —(CH₂)₂—CH(CH₃)— | O | F | O-n-C₃H₇ |
| 1116 | —(CH₂)₂—CH(CH₃)— | O | F | O-i-C₃H₇ |
| 1117 | —(CH₂)₂—CH(CH₃)— | O | F | O-n-C₄H₉ |
| 1118 | —(CH₂)₂—CH(CH₃)— | O | F | O-i-C₄H₉ |
| 1119 | —(CH₂)₂—CH(CH₃)— | O | F | O-s-C₄H₉ |
| 1120 | —(CH₂)₂—CH(CH₃)— | O | F | O-t-C₄H₉ |
| 1121 | —(CH₂)₂—CH(CH₃)— | O | F | O—(CH₂)₂—Cl |
| 1122 | —(CH₂)₂—CH(CH₃)— | O | F | O—CH₂—S—CH₃ |
| 1123 | —(CH₂)₂—CH(CH₃)— | O | F | O—CH₂—Ph |
| 1124 | —(CH₂)₂—CH(CH₃)— | O | F | O—Ph |
| 1125 | —(CH₂)₂—CH(CH₃)— | O | F | O—CH₂—CH=CH₂ |
| 1126 | —(CH₂)₂—CH(CH₃)— | O | F | O—CH₂—C≡CH |
| 1127 | —(CH₂)₂—CH(CH₃)— | O | F | O—CH₂—O—C₂H₅ |
| 1128 | —C(CH₃)₂—(CH₂)₂— | O | F | H |
| 1129 | —C(CH₃)₂—(CH₂)₂— | O | F | OH |
| 1130 | —C(CH₃)₂—(CH₂)₂— | O | F | O—CH₃ |
| 1131 | —C(CH₃)₂—(CH₂)₂— | O | F | O—C₂H₅ |
| 1132 | —C(CH₃)₂—(CH₂)₂— | O | F | O-n-C₃H₇ |
| 1133 | —C(CH₃)₂—(CH₂)₂— | O | F | O-i-C₃H₇ |
| 1134 | —C(CH₃)₂—(CH₂)₂— | O | F | O-n-C₄H₉ |
| 1135 | —C(CH₃)₂—(CH₂)₂— | O | F | O-i-C₄H₉ |
| 1136 | —C(CH₃)₂—(CH₂)₂— | O | F | O-s-C₄H₉ |
| 1137 | —C(CH₃)₂—(CH₂)₂— | O | F | O-t-C₄H₉ |
| 1138 | —C(CH₃)₂—(CH₂)₂— | O | F | O—(CH₂)₂—Cl |
| 1139 | —C(CH₃)₂—(CH₂)₂— | O | F | O—CH₂—S—CH₃ |
| 1140 | —C(CH₃)₂—(CH₂)₂— | O | F | O—CH₂—Ph |
| 1141 | —C(CH₃)₂—(CH₂)₂— | O | F | O—Ph |
| 1142 | —C(CH₃)₂—(CH₂)₂— | O | F | O—CH₂—CH=CH₂ |
| 1143 | —C(CH₃)₂—(CH₂)₂— | O | F | O—CH₂—O—C₂H₅ |
| 1144 | —CH₂—C(CH₃)₂—CH₂— | O | F | H |
| 1145 | —CH₂—C(CH₃)₂—CH₂— | O | F | OH |
| 1146 | —CH₂—C(CH₃)₂—CH₂— | O | F | O—CH₃ |
| 1147 | —CH₂—C(CH₃)₂—CH₂— | O | F | O—C₂H₅ |
| 1148 | —CH₂—C(CH₃)₂—CH₂— | O | F | O-n-C₃H₇ |
| 1149 | —CH₂—C(CH₃)₂—CH₂— | O | F | O-i-C₃H₇ |
| 1150 | —CH₂—C(CH₃)₂—CH₂— | O | F | O-n-C₄H₉ |
| 1151 | —CH₂—C(CH₃)₂—CH₂— | O | F | O-i-C₄H₉ |
| 1152 | —CH₂—C(CH₃)₂—CH₂— | O | F | O-s-C₄H₉ |
| 1153 | —CH₂—C(CH₃)₂—CH₂— | O | F | O-t-C₄H₉ |
| 1154 | —CH₂—C(CH₃)₂—CH₂— | O | F | O—(CH₂)₂—Cl |
| 1155 | —CH₂—C(CH₃)₂—CH₂— | O | F | O—CH₂—S—CH₃ |
| 1156 | —CH₂—C(CH₃)₂—CH₂— | O | F | O—CH₂—Ph |
| 1157 | —CH₂—C(CH₃)₂—CH₂— | O | F | O—Ph |
| 1158 | —CH₂—C(CH₃)₂—CH₂— | O | F | O—CH₂—CH=CH₂ |
| 1159 | —CH₂—C(CH₃)₂—CH₂— | O | F | O—CH₂—C≡CH |
| 1160 | —CH₂—C(CH₃)₂—CH₂— | O | F | O—CH₂—O—C₂H₅ |
| 1161 | —(CH₂)₂—C(CH₃)₂— | O | F | H |

-continued

| No. | | | | | |
|---|---|---|---|---|---|
| 1163 | —(CH₂)₂—C(CH₃)₂— | F | O | OH | |
| 1164 | —(CH₂)₂—C(CH₃)₂— | F | O | O—CH₃ | |
| 1165 | —(CH₂)₂—C(CH₃)₂— | F | O | O—C₂H₅ | |
| 1166 | —(CH₂)₂—C(CH₃)₂— | F | O | O-n-C₃H₇ | |
| 1167 | —(CH₂)₂—C(CH₃)₂— | F | O | O-i-C₃H₇ | |
| 1168 | —(CH₂)₂—C(CH₃)₂— | F | O | O-n-C₄H₉ | |
| 1169 | —(CH₂)₂—C(CH₃)₂— | F | O | O-i-C₄H₉ | |
| 1170 | —(CH₂)₂—C(CH₃)₂— | F | O | O-s-C₄H₉ | |
| 1171 | —(CH₂)₂—C(CH₃)₂— | F | O | O-t-C₄H₉ | |
| 1172 | —(CH₂)₂—C(CH₃)₂— | F | O | O—(CH₂)₂—Cl | |
| 1173 | —(CH₂)₂—C(CH₃)₂— | F | O | O—CH₂—S—CH₃ | |
| 1174 | —(CH₂)₂—C(CH₃)₂— | F | O | O—CH₂—Ph | |
| 1175 | —(CH₂)₂—C(CH₃)₂— | F | O | O—Ph | |
| 1176 | —(CH₂)₂—C(CH₃)₂— | F | O | O—CH₂—CH=CH₂ | |
| 1177 | —(CH₂)₂—C(CH₃)₂— | F | O | O—CH₂—C≡CH | |
| 1178 | —(CH₂)₂—C(CH₃)₂— | F | O | O—CH₂—O—C₂H₅ | |
| 1179 | —(CH₂)₄— | F | O | H | |
| 1180a | —(CH₂)₄— | F | O | OH | cis(rac) |
| 1180a1 | —(CH₂)₄— | F | O | OH | cis(+) |
| 1180a2 | —(CH₂)₄— | F | O | OH | cis(−) |
| 1180b | —(CH₂)₄— | F | O | OH | trans(rac) |
| 1180b1 | —(CH₂)₄— | F | O | OH | trans(+) |
| 1180b2 | —(CH₂)₄— | F | O | OH | trans(−) |
| 1181a | —(CH₂)₄— | F | O | O—CH₃ | cis(rac) |
| 1181a1 | —(CH₂)₄— | F | O | O—CH₃ | cis(+) |
| 1181a2 | —(CH₂)₄— | F | O | O—CH₃ | cis(−) |
| 1181b | —(CH₂)₄— | F | O | O—CH₃ | trans(rac) |
| 1181b1 | —(CH₂)₄— | F | O | O—CH₃ | trans(+) |
| 1181b2 | —(CH₂)₄— | F | O | O—CH₃ | trans(−) |
| 1182a | —(CH₂)₄— | F | O | O—C₂H₅ | cis |
| 1182b | —(CH₂)₄— | F | O | O—C₂H₅ | trans |
| 1183a | —(CH₂)₄— | F | O | O-n-C₃H₇ | cis |
| 1183b | —(CH₂)₄— | F | O | O-n-C₃H₇ | trans |
| 1184a | —(CH₂)₄— | F | O | O-i-C₃H₇ | cis |
| 1184b | —(CH₂)₄— | F | O | O-i-C₃H₇ | trans |
| 1185a | —(CH₂)₄— | F | O | O-n-C₄H₉ | cis |
| 1185b | —(CH₂)₄— | F | O | O-n-C₄H₉ | trans |
| 1186a | —(CH₂)₄— | F | O | O-i-C₄H₉ | cis |
| 1186b | —(CH₂)₄— | F | O | O-i-C₄H₉ | trans |
| 1187a | —(CH₂)₄— | F | O | O-s-C₄H₉ | cis |
| 1187b | —(CH₂)₄— | F | O | O-s-C₄H₉ | trans |
| 1188a | —(CH₂)₄— | F | O | O-t-C₄H₉ | cis |
| 1188b | —(CH₂)₄— | F | O | O-t-C₄H₉ | trans |
| 1189a | —(CH₂)₄— | F | O | O—(CH₂)₂—Cl | cis |
| 1189b | —(CH₂)₄— | F | O | O—(CH₂)₂—Cl | trans |
| 1190a | —(CH₂)₄— | F | O | O—CH₂—S—CH₃ | cis |
| 1190b | —(CH₂)₄— | F | O | O—CH₂—S—CH₃ | trans |
| 1191a | —(CH₂)₄— | F | O | O—CH₂—Ph | cis |
| 1191b | —(CH₂)₄— | F | O | O—CH₂—Ph | trans |
| 1192 | —(CH₂)₄— | F | O | O—CH₂—Ph-2Cl | cis |
| 1193 | —(CH₂)₄— | F | O | O—CH₂—Ph-3Cl | trans |
| 1194 | —(CH₂)₄— | F | O | O—CH₂—Ph-4Cl | cis |
| 1195 | —(CH₂)₄— | F | O | O—CH₂—Ph-2OCH₃ | trans |

| | | | | |
|---|---|---|---|---|
| 1196 | —(CH₂)₄— | F | O—CH₂—Ph-3OCH₃ | |
| 1197 | —(CH₂)₄— | F | O—CH₂—Ph-4OCH₃ | |
| 1198 | —(CH₂)₄— | F | O—CH₂—Ph-2NO₂ | |
| 1199 | —(CH₂)₄— | F | O—CH₂—Ph-3NO₂ | |
| 1200 | —(CH₂)₄— | F | O—CH₂—Ph-4NO₂ | |
| 1201a | —(CH₂)₄— | F | O—Ph | cis |
| 1201b | —(CH₂)₄— | F | O—Ph | trans |
| 1202a | —(CH₂)₄— | F | O—Ph-2Cl | cis |
| 1202b | —(CH₂)₄— | F | O—Ph-2Cl | trans |
| 1203 | —(CH₂)₄— | F | O—Ph-3Cl | |
| 1204 | —(CH₂)₄— | F | O—Ph-4Cl | |
| 1205 | —(CH₂)₄— | F | O—Ph-2OCH₃ | |
| 1206 | —(CH₂)₄— | F | O—Ph-3OCH₃ | |
| 1207 | —(CH₂)₄— | F | O—Ph-4OCH₃ | |
| 1208 | —(CH₂)₄— | F | O—Ph-2CH₃ | |
| 1209 | —(CH₂)₄— | F | O—Ph-3CH₃ | |
| 1210 | —(CH₂)₄— | F | O—Ph-4CH₃ | |
| 1211a | —(CH₂)₄— | F | O—CH₂—CH=CH₂ | cis |
| 1211b | —(CH₂)₄— | F | O—CH₂—CH=CH₂ | trans |
| 1212a | —(CH₂)₄— | F | O—CH₂—C≡CH | cis |
| 1212b | —(CH₂)₄— | F | O—CH₂—C≡CH | trans |
| 1213a | —(CH₂)₄— | F | O⁻Na⁺ | cis |
| 1213b | —(CH₂)₄— | F | O⁻Na⁺ | trans |
| 1214a | —(CH₂)₄— | F | O⁻K⁺ | cis |
| 1214b | —(CH₂)₄— | F | O⁻K⁺ | trans |
| 1215a | —(CH₂)₄— | F | O⁻½Ca⁺⁺ | cis |
| 1215b | —(CH₂)₄— | F | O⁻½Ca⁺⁺ | trans |
| 1216a | —(CH₂)₄— | F | O⁻NH₄⁺ | cis |
| 1216b | —(CH₂)₄— | F | O⁻NH₄⁺ | trans |
| 1217a | —(CH₂)₄— | F | O⁻N⁺H₂(CH₃)₂ | cis |
| 1217b | —(CH₂)₄— | F | O⁻N⁺H₂(CH₃)₂ | trans |
| 1218a | —(CH₂)₄— | F | O⁻N⁺H₃-i-C₃H₇ | cis |
| 1218b | —(CH₂)₄— | F | O⁻N⁺H₃-i-C₃H₇ | trans |
| 1219a | —(CH₂)₄— | F | O⁻N⁺H₃-n-C₈H₁₇ | cis |
| 1219b | —(CH₂)₄— | F | O⁻N⁺H₃-n-C₈H₁₇ | trans |
| 1220a | —(CH₂)₄— | F | O—C(CH₃)₂—CN | cis |
| 1220b | —(CH₂)₄— | F | O—C(CH₃)₂—CN | trans |
| 1221a | —(CH₂)₄— | F | O—CH(CH₃)—CH=CH₂ | cis |
| 1221b | —(CH₂)₄— | F | O—CH(CH₃)—CH=CH₂ | trans |
| 1222a | —(CH₂)₄— | F | O—CH(CH₃)—C≡CH | cis |
| 1222b | —(CH₂)₄— | F | O—CH(CH₃)—C≡CH | trans |
| 1223a | —(CH₂)₄— | F | O—CH(CH₃)—CO₂Et | cis |
| 1223b | —(CH₂)₄— | F | O—CH(CH₃)—CO₂Et | trans |
| 1224a | —(CH₂)₄— | F | O—CH₂—CO₂Et | cis |
| 1224b | —(CH₂)₄— | F | O—CH₂—CO₂Et | trans |
| 1225a | —(CH₂)₄— | F | O—CH₂—CO—CH₃ | cis |
| 1225b | —(CH₂)₄— | F | O—CH₂—CO—CH₃ | trans |
| 1226a | —(CH₂)₄— | F | O—CH₂—CF₃ | cis |
| 1226b | —(CH₂)₄— | F | O—CH₂—CF₃ | trans |
| 1227a | —(CH₂)₄— | F | O—CH₂—CN | cis |
| 1227b | —(CH₂)₄— | F | O—CH₂—CN | trans |
| 1228a | —(CH₂)₄— | F | O—CH₂—C(Cl)=CH₂ | cis |
| 1228b | —(CH₂)₄— | F | O—CH₂—C(Cl)=CH₂ | trans |

-continued

| | | | | |
|---|---|---|---|---|
| 1229a | —(CH₂)₄— | F | O—CH₂—CH=CH—Cl | cis |
| 1229b | —(CH₂)₄— | F | O—CH₂—CH=CH—Cl | trans |
| 1230a | —(CH₂)₄— | F | O—CH₂—C≡C—CH₃ | cis |
| 1230b | —(CH₂)₄— | F | O—CH₂—C≡C—CH₃ | trans |
| 1231a | —(CH₂)₄— | F | O—CH₂-2-furyl | cis |
| 1231b | —(CH₂)₄— | F | O—CH₂-2-furyl | trans |
| 1232a | —(CH₂)₄— | F | O—(CH₂)₂—C≡CH | cis |
| 1232b | —(CH₂)₄— | F | O—(CH₂)₂—C≡CH | trans |
| 1233a | —(CH₂)₄— | F | O-cyclopentyl | cis |
| 1233b | —(CH₂)₄— | F | O-cyclopentyl | trans |
| 1234a | —(CH₂)₄— | F | O—(CH₂)₂—Br | cis |
| 1234b | —(CH₂)₄— | F | O—(CH₂)₂—Br | trans |
| 1235a | —(CH₂)₄— | F | O—(CH₂)₂—N₃ | cis |
| 1235b | —(CH₂)₄— | F | O—(CH₂)₂—N₃ | trans |
| 1236a | —(CH₂)₄— | F | O-cyclohexyl | cis |
| 1236b | —(CH₂)₄— | F | O-cyclohexyl | trans |
| 1237a | —(CH₂)₄— | F | O—CH₂-cyclopropyl | cis |
| 1237b | —(CH₂)₄— | F | O—CH₂-cyclopropyl | trans |
| 1238a | —(CH₂)₄— | F | O—CH₂—CH=CH—CH₃ | cis |
| 1238b | —(CH₂)₄— | F | O—CH₂—CH=CH—CH₃ | trans |
| 1239a | —(CH₂)₄— | F | O—CH₂—CH=C(CH₃)₂ | cis |
| 1239b | —(CH₂)₄— | F | O—CH₂—CH=C(CH₃)₂ | trans |
| 1240a | —(CH₂)₄— | F | O—CH₂—CCl₃ | cis |
| 1240b | —(CH₂)₄— | F | O—CH₂—CCl₃ | trans |
| 1241a | —(CH₂)₄— | F | O—CH₂—CH=CHPh | cis |
| 1241b | —(CH₂)₄— | F | O—CH₂—CH=CHPh | trans |
| 1242a | —(CH₂)₄— | F | O—CH₂—CH(OCH₃)₂ | cis |
| 1242b | —(CH₂)₄— | F | O—CH₂—CH(OCH₃)₂ | trans |
| 1243a | —(CH₂)₄— | F | O—CH₂—CH₂F | cis |
| 1243b | —(CH₂)₄— | F | O—CH₂—CH₂F | trans |
| 1244a | —(CH₂)₄— | F | O-2-cyclohexenyl | cis |
| 1244b | —(CH₂)₄— | F | O-2-cyclohexenyl | trans |
| 1245a | —(CH₂)₄— | F | O—CH₂-2-thienyl | cis |
| 1245b | —(CH₂)₄— | F | O—CH₂-2-thienyl | trans |
| 1246a | —(CH₂)₄— | F | O—CH₂—O—C₂H₅ | cis |
| 1246b | —(CH₂)₄— | F | O—CH₂—O—C₂H₅ | trans |
| 1247a | —(CH₂)₄— | F | O—N=CH—Ph | cis |
| 1247b | —(CH₂)₄— | F | O—N=CH—Ph | trans |
| 1248a | —(CH₂)₄— | F | O—N=C(CH₃)₂ | cis |
| 1248b | —(CH₂)₄— | F | O—N=C(CH₃)₂ | trans |
| 1249a | —(CH₂)₄— | F | O—N=C(CH₃)C₂H₅ | cis |
| 1249b | —(CH₂)₄— | F | O—N=C(CH₃)C₂H₅ | trans |
| 1250a | —(CH₂)₄— | F | O—N=C(n-C₃H₇)₂ | cis |
| 1250b | —(CH₂)₄— | F | O—N=C(n-C₃H₇)₂ | trans |
| 1251a | —(CH₂)₄— | F | O—N=C(i-C₃H₇)₂ | cis |
| 1251b | —(CH₂)₄— | F | O—N=C(i-C₃H₇)₂ | trans |
| 1252a | —(CH₂)₄— | F | O—N=C(—(CH₂)₅—) | cis |
| 1252b | —(CH₂)₄— | F | O—N=C(—(CH₂)₅—) | trans |
| 1253a | —(CH₂)₄— | F | O—N=C(CH₃)—O—C₂H₅ | cis |
| 1253b | —(CH₂)₄— | F | O—N=C(CH₃)—O—C₂H₅ | trans |
| 1254 | —(CH₂)₄— | F | O-succinimidyl | |
| 1255a | —(CH₂)₄— | F | O—Si(CH₃)₂-t-C₄H₉ | cis |
| 1255b | —(CH₂)₄— | F | O—Si(CH₃)₂-t-C₄H₉ | trans |

-continued

| No. | | | | | |
|---|---|---|---|---|---|
| 1256 | —(CH₂)₄— | F | O | O—(CH₂)₂—N(CH₃)₂ | |
| 1257 | —(CH₂)₄— | F | O | O—(CH₂)₂—NO₂ | |
| 1258 | —(CH₂)₃—CH(CH₃)— | F | O | H | |
| 1259 | —(CH₂)₃—CH(CH₃)— | F | O | OH | |
| 1260 | —(CH₂)₃—CH(CH₃)— | F | O | O—CH₃ | |
| 1261 | —(CH₂)₃—CH(CH₃)— | F | O | O—C₂H₅ | |
| 1262 | —(CH₂)₃—CH(CH₃)— | F | O | O-n-C₃H₇ | |
| 1263 | —(CH₂)₃—CH(CH₃)— | F | O | O-i-C₃H₇ | |
| 1264 | —(CH₂)₃—CH(CH₃)— | F | O | O-n-C₄H₉ | |
| 1265 | —(CH₂)₃—CH(CH₃)— | F | O | O-i-C₄H₉ | |
| 1266 | —(CH₂)₃—CH(CH₃)— | F | O | O-s-C₄H₉ | |
| 1267 | —(CH₂)₃—CH(CH₃)— | F | O | O-t-C₄H₉ | |
| 1268 | —(CH₂)₃—CH(CH₃)— | F | O | O—(CH₂)₂—Cl | |
| 1269 | —(CH₂)₃—CH(CH₃)— | F | O | O—CH₂—S—CH₃ | |
| 1270 | —(CH₂)₃—CH(CH₃)— | F | O | O—CH₂—Ph | |
| 1271 | —(CH₂)₃—CH(CH₃)— | F | O | O—Ph | |
| 1272 | —(CH₂)₃—CH(CH₃)— | F | O | O—CH₂—CH=CH₂ | |
| 1273 | —(CH₂)₃—CH(CH₃)— | F | O | O—CH₂—C≡CH | |
| 1274 | —(CH₂)₃—CH(CH₃)— | F | O | O—CH₂—O—C₂H₅ | |
| 1275 | —(CH₂)₂—CH(CH₃)—CH₂— | F | O | H | |
| 1276a | —(CH₂)₂—CH(CH₃)—CH₂— | F | O | OH | cis |
| 1276b | —(CH₂)₂—CH(CH₃)—CH₂— | F | O | OH | trans |
| 1277 | —(CH₂)₂—CH(CH₃)—CH₂— | F | O | O—CH₃ | |
| 1278a | —(CH₂)₂—CH(CH₃)—CH₂— | F | O | O—C₂H₅ | cis |
| 1278b | —(CH₂)₂—CH(CH₃)—CH₂— | F | O | O—C₂H₅ | trans |
| 1279 | —(CH₂)₂—CH(CH₃)—CH₂— | F | O | O-n-C₃H₇ | |
| 1280 | —(CH₂)₂—CH(CH₃)—CH₂— | F | O | O-i-C₃H₇ | |
| 1281 | —(CH₂)₂—CH(CH₃)—CH₂— | F | O | O-n-C₄H₉ | |
| 1282 | —(CH₂)₂—CH(CH₃)—CH₂— | F | O | O-i-C₄H₉ | |
| 1283 | —(CH₂)₂—CH(CH₃)—CH₂— | F | O | O-s-C₄H₉ | |
| 1284 | —(CH₂)₂—CH(CH₃)—CH₂— | F | O | O-t-C₄H₉ | |
| 1285 | —(CH₂)₂—CH(CH₃)—CH₂— | F | O | O—(CH₂)₂—Cl | |
| 1286 | —(CH₂)₂—CH(CH₃)—CH₂— | F | O | O—CH₂—S—CH₃ | |
| 1287 | —(CH₂)₂—CH(CH₃)—CH₂— | F | O | O—CH₂—Ph | |
| 1288 | —(CH₂)₂—CH(CH₃)—CH₂— | F | O | O—Ph | |
| 1289 | —(CH₂)₂—CH(CH₃)—CH₂— | F | O | O—CH₂—CH=CH₂ | |
| 1290 | —(CH₂)₂—CH(CH₃)—CH₂— | F | O | O—CH₂—C≡CH | |
| 1291 | —(CH₂)₂—CH(CH₃)—CH₂— | F | O | O—CH₂—O—C₂H₅ | |
| 1292 | —(CH₂)₂—CH((C₄H₉)—CH₂— | F | O | H | |
| 1293a | —(CH₂)₂—CH((C₄H₉)—CH₂— | F | O | OH | cis |
| 1293b | —(CH₂)₂—CH((C₄H₉)—CH₂— | F | O | OH | trans |
| 1294 | —(CH₂)₂—CH((C₄H₉)—CH₂— | F | O | O—CH₃ | |
| 1295a | —(CH₂)₂—CH((C₄H₉)—CH₂— | F | O | O—C₂H₅ | cis |
| 1295b | —(CH₂)₂—CH((C₄H₉)—CH₂— | F | O | O—C₂H₅ | trans |
| 1296 | —(CH₂)₂—CH((C₄H₉)—CH₂— | F | O | O-n-C₃H₇ | |
| 1297 | —(CH₂)₂—CH((C₄H₉)—CH₂— | F | O | O-n-C₄H₉ | |
| 1298 | —(CH₂)₂—CH((C₄H₉)—CH₂— | F | O | O-i-C₄H₉ | |
| 1299 | —(CH₂)₂—CH((C₄H₉)—CH₂— | F | O | O-s-C₄H₉ | |
| 1300 | —(CH₂)₂—CH((C₄H₉)—CH₂— | F | O | O-t-C₄H₉ | |
| 1301 | —(CH₂)₂—CH((C₄H₉)—CH₂— | F | O | O—(CH₂)₂—Cl | |
| 1302 | —(CH₂)₂—CH((C₄H₉)—CH₂— | F | O | O—CH₂—S—CH₃ | |
| 1303 | —(CH₂)₂—CH((C₄H₉)—CH₂— | F | O | O—CH₂—Ph | |
| 1304 | —(CH₂)₂—CH((C₄H₉)—CH₂— | F | O | | |

-continued

| | | | |
|---|---|---|---|
| 1305 | —(CH$_2$)$_2$—CH((C$_4$H$_9$)—CH$_2$— | F | O—Ph |
| 1306 | —(CH$_2$)$_2$—CH((C$_4$H$_9$)—CH$_2$— | F | O—CH$_2$CH=CH$_2$ |
| 1307 | —(CH$_2$)$_2$—CH((C$_4$H$_9$)—CH$_2$— | F | O—CH$_2$—C≡CH |
| 1308 | —(CH$_2$)$_2$—CH((C$_4$H$_9$)—CH$_2$— | F | O—CH$_2$—O—C$_2$H$_5$ |
| 1309 | —CH$_2$—CH(CH$_3$)—(CH$_2$)$_2$— | F | H |

| No. | Linker | X | | R | Stereo |
|---|---|---|---|---|---|
| 1310 | —CH₂—CH(CH₃)—(CH₂)₂— | F | O | OH | |
| 1311 | —CH₂—CH(CH₃)—(CH₂)₂— | F | O | O—CH₃ | |
| 1312 | —CH₂—CH(CH₃)—(CH₂)₂— | F | O | O—C₂H₅ | |
| 1313 | —CH₂—CH(CH₃)—(CH₂)₂— | F | O | O-n-C₃H₇ | |
| 1314 | —CH₂—CH(CH₃)—(CH₂)₂— | F | O | O-i-C₃H₇ | |
| 1315 | —CH₂—CH(CH₃)—(CH₂)₂— | F | O | O-n-C₄H₉ | |
| 1316 | —CH₂—CH(CH₃)—(CH₂)₂— | F | O | O-i-C₄H₉ | |
| 1317 | —CH₂—CH(CH₃)—(CH₂)₂— | F | O | O-s-C₄H₉ | |
| 1318 | —CH₂—CH(CH₃)—(CH₂)₂— | F | O | O-t-C₄H₉ | |
| 1319 | —CH₂—CH(CH₃)—(CH₂)₂— | F | O | O—(CH₂)₂—Cl | |
| 1320 | —CH₂—CH(CH₃)—(CH₂)₂— | F | O | O—CH₂—S—CH₃ | |
| 1321 | —CH₂—CH(CH₃)—(CH₂)₂— | F | O | O—CH₂—Ph | |
| 1322 | —CH₂—CH(CH₃)—(CH₂)₂— | F | O | O—Ph | |
| 1323 | —CH₂—CH(CH₃)—(CH₂)₂— | F | O | O—CH₂—CH=CH₂ | |
| 1324 | —CH₂—CH(CH₃)—(CH₂)₂— | F | O | O—CH₂—C≡CH | |
| 1325 | —CH₂—CH(CH₃)—(CH₂)₂— | F | O | O—CH₂—O—C₂H₅ | |
| 1326 | —CH₂—CH(CH₃)—(CH₂)₂— | F | O | H | |
| 1327 | —CH(CH₃)—(CH₂)₃— | F | O | OH | |
| 1328 | —CH(CH₃)—(CH₂)₃— | F | O | O—CH₃ | |
| 1329 | —CH(CH₃)—(CH₂)₃— | F | O | O—C₂H₅ | |
| 1330 | —CH(CH₃)—(CH₂)₃— | F | O | O-n-C₃H₇ | |
| 1331 | —CH(CH₃)—(CH₂)₃— | F | O | O-i-C₃H₇ | |
| 1332 | —CH(CH₃)—(CH₂)₃— | F | O | O-n-C₄H₉ | |
| 1333 | —CH(CH₃)—(CH₂)₃— | F | O | O-i-C₄H₉ | |
| 1334 | —CH(CH₃)—(CH₂)₃— | F | O | O-s-C₄H₉ | |
| 1335 | —CH(CH₃)—(CH₂)₃— | F | O | O-t-C₄H₉ | |
| 1336 | —CH(CH₃)—(CH₂)₃— | F | O | O—(CH₂)₂—Cl | |
| 1337 | —CH(CH₃)—(CH₂)₃— | F | O | O—CH₂—S—CH₃ | |
| 1338 | —CH(CH₃)—(CH₂)₃— | F | O | O—CH₂—Ph | |
| 1339 | —CH(CH₃)—(CH₂)₃— | F | O | O—Ph | |
| 1340 | —CH(CH₃)—(CH₂)₃— | F | O | O—CH₂—CH=CH₂ | |
| 1341 | —CH(CH₃)—(CH₂)₃— | F | O | O—CH₂—C≡CH | |
| 1342 | —CH(CH₃)—(CH₂)₃— | F | O | O—CH₂—O—C₂H₅ | |
| 1343 | —CH(CH₃)—(CH₂)₃— | F | O | H | |
| 1344a | —C(CH₃)₂—(CH₂)₃— | F | O | OH | cis |
| 1344b | —C(CH₃)₂—(CH₂)₃— | F | O | OH | trans |
| 1345a | —C(CH₃)₂—(CH₂)₃— | F | O | O—CH₃ | cis |
| 1345b | —C(CH₃)₂—(CH₂)₃— | F | O | O—CH₃ | trans |
| 1346a | —C(CH₃)₂—(CH₂)₃— | F | O | O—CH₃ | cis |
| 1346b | —C(CH₃)₂—(CH₂)₃— | F | O | O—CH₃ | trans |
| 1347 | —C(CH₃)₂—(CH₂)₃— | F | O | O—C₂H₅ | |
| 1348 | —C(CH₃)₂—(CH₂)₃— | F | O | O-n-C₃H₇ | |
| 1349 | —C(CH₃)₂—(CH₂)₃— | F | O | O-i-C₃H₇ | |
| 1350 | —C(CH₃)₂—(CH₂)₃— | F | O | O-n-C₄H₉ | |
| 1351 | —C(CH₃)₂—(CH₂)₃— | F | O | O-i-C₄H₉ | |
| 1352 | —C(CH₃)₂—(CH₂)₃— | F | O | O-s-C₄H₉ | |
| 1353 | —C(CH₃)₂—(CH₂)₃— | F | O | O-t-C₄H₉ | |
| 1354 | —C(CH₃)₂—(CH₂)₃— | F | O | O—(CH₂)₂—Cl | |
| 1355 | —C(CH₃)₂—(CH₂)₃— | F | O | O—CH₂—S—CH₃ | |
| 1356 | —C(CH₃)₂—(CH₂)₃— | F | O | O—CH₂—Ph | |
| 1357 | —C(CH₃)₂—(CH₂)₃— | F | O | O—Ph | |
| 1358 | —C(CH₃)₂—(CH₂)₃— | F | O | O—CH₂—CH=CH₂ | |
| 1359 | —C(CH₃)₂—(CH₂)₃— | F | O | O—CH₂—C≡CH | |
| 1360 | —CH₂—C(CH₃)₂—(CH₂)₂— | F | O | O—CH₂—O—C₂H₅ | |
| | | | | H | |

| No. | | | |
|---|---|---|---|
| 1361 | —CH₂—C(CH₃)₂—(CH₂)₂— | F | OH |
| 1362 | —CH₂—C(CH₃)₂—(CH₂)₂— | F | O—CH₃ |
| 1363 | —CH₂—C(CH₃)₂—(CH₂)₂— | F | O—C₂H₅ |
| 1364 | —CH₂—C(CH₃)₂—(CH₂)₂— | F | O-n-C₃H₇ |
| 1365 | —CH₂—C(CH₃)₂—(CH₂)₂— | F | O-i-C₃H₇ |
| 1366 | —CH₂—C(CH₃)₂—(CH₂)₂— | F | O-n-C₄H₉ |
| 1367 | —CH₂—C(CH₃)₂—(CH₂)₂— | F | O-i-C₄H₉ |
| 1368 | —CH₂—C(CH₃)₂—(CH₂)₂— | F | O-s-C₄H₉ |
| 1369 | —CH₂—C(CH₃)₂—(CH₂)₂— | F | O-t-C₄H₉ |
| 1370 | —CH₂—C(CH₃)₂—(CH₂)₂— | F | O—(CH₂)₂—Cl |
| 1371 | —CH₂—C(CH₃)₂—(CH₂)₂— | F | O—CH₂—S—CH₃ |
| 1372 | —CH₂—C(CH₃)₂—(CH₂)₂— | F | O—CH₂—Ph |
| 1373 | —CH₂—C(CH₃)₂—(CH₂)₂— | F | O—Ph |
| 1374 | —CH₂—C(CH₃)₂—(CH₂)₂— | F | O—CH₂—CH=CH₂ |
| 1375 | —CH₂—C(CH₃)₂—(CH₂)₂— | F | O—CH₂—C≡CH |
| 1376 | —CH₂—C(CH₃)₂—(CH₂)₂— | F | O—CH₂—O—C₂H₅ |
| 1377 | —(CH₂)₂—C(CH₃)₂—CH₂— | F | H |
| 1378 | —(CH₂)₂—C(CH₃)₂—CH₂— | F | OH |
| 1379 | —(CH₂)₂—C(CH₃)₂—CH₂— | F | O—CH₃ |
| 1380 | —(CH₂)₂—C(CH₃)₂—CH₂— | F | O—C₂H₅ |
| 1381 | —(CH₂)₂—C(CH₃)₂—CH₂— | F | O-n-C₃H₇ |
| 1382 | —(CH₂)₂—C(CH₃)₂—CH₂— | F | O-i-C₃H₇ |
| 1383 | —(CH₂)₂—C(CH₃)₂—CH₂— | F | O-n-C₄H₉ |
| 1384 | —(CH₂)₂—C(CH₃)₂—CH₂— | F | O-i-C₄H₉ |
| 1385 | —(CH₂)₂—C(CH₃)₂—CH₂— | F | O-s-C₄H₉ |
| 1386 | —(CH₂)₂—C(CH₃)₂—CH₂— | F | O-t-C₄H₉ |
| 1387 | —(CH₂)₂—C(CH₃)₂—CH₂— | F | O—(CH₂)₂—Cl |
| 1388 | —(CH₂)₂—C(CH₃)₂—CH₂— | F | O—CH₂—S—CH₃ |
| 1389 | —(CH₂)₂—C(CH₃)₂—CH₂— | F | O—CH₂—Ph |
| 1390 | —(CH₂)₂—C(CH₃)₂—CH₂— | F | O—Ph |
| 1391 | —(CH₂)₂—C(CH₃)₂—CH₂— | F | O—CH₂—CH=CH₂ |
| 1392 | —(CH₂)₂—C(CH₃)₂—CH₂— | F | O—CH₂—C≡CH |
| 1393 | —(CH₂)₂—C(CH₃)₂—CH₂— | F | O—CH₂—O—C₂H₅ |
| 1394 | —(CH₂)₃—C(CH₃)₂— | F | H |
| 1395 | —(CH₂)₃—C(CH₃)₂— | F | OH |
| 1396 | —(CH₂)₃—C(CH₃)₂— | F | O—CH₃ |
| 1397 | —(CH₂)₃—C(CH₃)₂— | F | O—C₂H₅ |
| 1398 | —(CH₂)₃—C(CH₃)₂— | F | O-n-C₃H₇ |
| 1399 | —(CH₂)₃—C(CH₃)₂— | F | O-i-C₃H₇ |
| 1400 | —(CH₂)₃—C(CH₃)₂— | F | O-n-C₄H₉ |
| 1401 | —(CH₂)₃—C(CH₃)₂— | F | O-i-C₄H₉ |
| 1402 | —(CH₂)₃—C(CH₃)₂— | F | O-s-C₄H₉ |
| 1403 | —(CH₂)₃—C(CH₃)₂— | F | O-t-C₄H₉ |
| 1404 | —(CH₂)₃—C(CH₃)₂— | F | O—(CH₂)₂—Cl |
| 1405 | —(CH₂)₃—C(CH₃)₂— | F | O—CH₂—S—CH₃ |
| 1406 | —(CH₂)₃—C(CH₃)₂— | F | O—CH₂—Ph |
| 1407 | —(CH₂)₃—C(CH₃)₂— | F | O—Ph |
| 1408 | —(CH₂)₃—C(CH₃)₂— | F | O—CH₂—CH=CH₂ |
| 1409 | —(CH₂)₃—C(CH₃)₂— | F | O—CH₂—C≡CH |
| 1410 | —(CH₂)₃—C(CH₃)₂— | F | O—CH₂—O—C₂H₅ |

| No. | Linker | X | | R | cis/trans |
|---|---|---|---|---|---|
| 1411a | —(CH₂)₅— | F | O | OH | cis |
| 1411b | —(CH₂)₅— | F | O | OH | trans |
| 1412a | —(CH₂)₅— | F | O | O—CH₃ | cis |
| 1412b | —(CH₂)₅— | F | O | O—CH₃ | trans |
| 1413a | —(CH₂)₅— | F | O | O—C₂H₅ | cis |
| 1413b | —(CH₂)₅— | F | O | O—C₂H₅ | trans |
| 1414 | —(CH₂)₅— | F | O | O-n-C₃H₇ | |
| 1415 | —(CH₂)₅— | F | O | O-i-C₃H₇ | |
| 1416 | —(CH₂)₅— | F | O | O-n-C₄H₉ | |
| 1417 | —(CH₂)₅— | F | O | O-i-C₄H₉ | |
| 1418 | —(CH₂)₅— | F | O | O-s-C₄H₉ | |
| 1419 | —(CH₂)₅— | F | O | O-t-C₄H₉ | |
| 1420 | —(CH₂)₅— | F | O | O—(CH₂)₂—Cl | |
| 1421 | —(CH₂)₅— | F | O | O—CH₂—S—CH₃ | |
| 1422 | —(CH₂)₅— | F | O | O—CH₂-Ph | |
| 1423 | —(CH₂)₅— | F | O | O—Ph | |
| 1424 | —(CH₂)₅— | F | O | O—CH₂—CH=CH₂ | |
| 1425 | —(CH₂)₅— | F | O | O—CH₂—C≡CH | |
| 1426 | —(CH₂)₅— | F | O | O—CH₂O—C₂H₅ | |
| 1427a | —(CH₂)₆— | F | O | OH | cis |
| 1427b | —(CH₂)₆— | F | O | OH | trans |
| 1428a | —(CH₂)₆— | F | O | O—CH₃ | cis |
| 1428b | —(CH₂)₆— | F | O | O—CH₃ | trans |
| 1429 | —(CH₂)₆— | F | O | O—C₂H₅ | |
| 1430 | —(CH₂)₆— | F | O | O-n-C₃H₇ | |
| 1431 | —(CH₂)₆— | F | O | O-i-C₃H₇ | |
| 1432 | —(CH₂)₆— | F | O | O-n-C₄H₉ | |
| 1433 | —(CH₂)₆— | F | O | O-i-C₄H₉ | |
| 1434 | —(CH₂)₆— | F | O | O-s-C₄H₉ | |
| 1435 | —(CH₂)₆— | F | O | O-t-C₄H₉ | |
| 1436 | —(CH₂)₃— | F | O | H | |
| 1437 | —(CH₂)₃— | Cl | O | OH | |
| 1438 | —(CH₂)₃— | Cl | O | O—CH₃ | |
| 1439 | —(CH₂)₃— | Cl | O | O—C₂H₅ | |
| 1440 | —(CH₂)₃— | Cl | O | O-n-C₃H₇ | |
| 1441 | —(CH₂)₃— | Cl | O | O-i-C₃H₇ | |
| 1442 | —(CH₂)₃— | Cl | O | O-n-C₄H₉ | |
| 1443 | —(CH₂)₃— | Cl | O | O-i-C₄H₉ | |
| 1444 | —(CH₂)₃— | Cl | O | O-s-C₄H₉ | |
| 1445 | —(CH₂)₃— | Cl | O | O-t-C₄H₉ | |
| 1446 | —(CH₂)₃— | Cl | O | O—(CH₂)₂—Cl | |
| 1447 | —(CH₂)₃— | Cl | O | O—CH₂—S—CH₃ | |
| 1448 | —(CH₂)₃— | Cl | O | O—CH₂-Ph | |
| 1449 | —(CH₂)₃— | Cl | O | O—Ph | |
| 1450 | —(CH₂)₃— | Cl | O | O—CH₂CH=CH₂ | |
| 1451 | —(CH₂)₃— | Cl | O | O—CH₂—C≡CH | |
| 1452 | —(CH₂)₃— | Cl | O | O—CH₂—O—C₂H₅ | |
| 1453 | —(CH₂)₃— | Cl | O | H | |
| 1454a | —(CH₂)₄— | Cl | O | OH | cis |
| 1454b | —(CH₂)₄— | Cl | O | OH | trans |
| 1455a | —(CH₂)₄— | Cl | O | O—C₂H₅ | cis |
| 1455b | —(CH₂)₄— | Cl | O | O—C₂H₅ | trans |
| 1456 | —(CH₂)₄— | Cl | O | O-n-C₃H₇ | |
| 1457 | —(CH₂)₄— | Cl | O | O-i-C₃H₇ | |

-continued

| No. | Linker | X | Y | R | Notes |
|---|---|---|---|---|---|
| 1458 | —(CH₂)₄— | Cl | O | O-n-C₄H₉ | |
| 1459 | —(CH₂)₄— | Cl | O | O-i-C₄H₉ | |
| 1460 | —(CH₂)₄— | Cl | O | O-s-C₄H₉ | |
| 1461 | —(CH₂)₄— | Cl | O | O-t-C₄H₉ | |
| 1462 | —(CH₂)₄— | Cl | O | O—(CH₂)₂—Cl | |
| 1463 | —(CH₂)₄— | Cl | O | O—CH₂—S—CH₃ | |
| 1464 | —(CH₂)₄— | Cl | O | O—CH₂—Ph | |
| 1465 | —(CH₂)₄— | Co | O | O—Ph | |
| 1466 | —(CH₂)₄— | Cl | O | O—CH₂—CH=CH₂ | |
| 1467a | —(CH₂)₄— | Cl | O | O—CH₂—C≡CH | cis |
| 1467b | —(CH₂)₄— | Cl | O | O—CH₂—C≡CH | trans |
| 1468b | —(CH₂)₄— | Cl | O | O—CH₂—O—C₂H₅ | |
| 1469 | —(CH₂)₄— | Br | O | O—CH₃ | |
| 1470 | —(CH₂)₄— | Br | O | O—C₂H₅ | |
| 1471 | —(CH₂)₃— | Br | O | O-n-C₃H₇ | |
| 1472 | —(CH₂)₃— | Br | O | O-i-C₃H₇ | |
| 1473 | —(CH₂)₄— | Br | O | O-n-C₄H₉ | |
| 1474 | —(CH₂)₄— | Br | O | O-i-C₄H₉ | |
| 1475 | —(CH₂)₄— | Br | O | O-s-C₄H₉ | |
| 1476 | —(CH₂)₄— | Br | O | O-t-C₄H₉ | |
| 1477 | —(CH₂)₃— | F | S | H | |
| 1478 | —(CH₂)₃— | F | S | SH | |
| 1479 | —(CH₂)₃— | F | S | O—CH₃ | |
| 1480 | —(CH₂)₃— | F | S | O—C₂H₅ | |
| 1481 | —(CH₂)₃— | F | S | O-n-C₃H₇ | |
| 1482 | —(CH₂)₃— | F | S | O-i-C₃H₇ | |
| 1483 | —(CH₂)₃— | F | S | O-n-C₄H₉ | |
| 1484 | —(CH₂)₃— | F | S | O-i-C₄H₉ | |
| 1485 | —(CH₂)₃— | F | S | O-s-C₄H₉ | |
| 1486 | —(CH₂)₃— | F | S | O-t-C₄H₉ | |
| 1487 | —(CH₂)₃— | F | S | O—(CH₂)₂—Cl | |
| 1488 | —(CH₂)₃— | F | S | O—CH₂—S—CH₃ | |
| 1489 | —(CH₂)₃— | F | S | O—CH—Ph | |
| 1490 | —(CH₂)₃— | F | S | O—Ph | |
| 1491 | —(CH₂)₃— | F | S | O—CH₂—CH=CH₂ | |
| 1492 | —(CH₂)₃— | F | S | O—CH₂—C≡CH | |
| 1493 | —(CH₂)₃— | F | S | O—CH₂—O—C₂H₅ | |
| 1494 | —(CH₂)₄— | F | S | H | |
| 1495 | —(CH₂)₄— | F | S | OH | |
| 1496 | —(CH₂)₄— | F | S | O—CH₃ | |
| 1497 | —(CH₂)₄— | F | S | O—C₂H₅ | |
| 1498 | —(CH₂)₄— | F | S | O-n-C₃H₇ | |
| 1499 | —(CH₂)₄— | F | S | O-i-C₃H₇ | |
| 1500 | —(CH₂)₄— | F | S | O-n-C₄H₉ | |
| 1501 | —(CH₂)₄— | F | S | O-i-C₄H₉ | |
| 1502 | —(CH₂)₄— | F | S | O-s-C₄H₉ | |
| 1503 | —(CH₂)₄— | F | S | O-t-C₄H₉ | |
| 1504 | —(CH₂)₄— | F | S | O—(CH₂)₂—Cl | |
| 1505 | —(CH₂)₄— | F | S | O—CH₂—S—CH₃ | |
| 1506 | —(CH₂)₄— | F | S | O—CH₂—Ph | |
| 1507 | —(CH₂)₄— | F | S | O—Ph | |
| 1508 | —(CH₂)₄— | F | S | O—CH₂—CH=CH₂ | |
| 1509 | —(CH₂)₄— | F | S | O—CH₂—C≡CH | |
| 1510 | —(CH₂)₄— | F | S | O—CH₂—O—C₂H₅ | |

| No. | A | X | Y | R | Note |
|---|---|---|---|---|---|
| 1511 | —CH=CH—(CH2)2— | O | F | H | |
| 1512 | —CH=CH—(CH2)2— | O | F | OH | |
| 1513 | —CH=CH—(CH2)2— | O | F | O—CH3 | |
| 1514 | —CH=CH—(CH2)2— | O | F | O—C2H5 | |
| 1515 | —CH=CH—(CH2)2— | O | F | O-n-C3H7 | |
| 1516 | —CH=CH—(CH2)2— | O | F | O-i-C3H7 | |
| 1517 | —CH=CH—(CH2)2— | O | F | O-n-C4H9 | |
| 1518 | —CH=CH—(CH2)2— | O | F | O-i-C4H9 | |
| 1519 | —CH=CH—(CH2)2— | O | F | O-s-C4H9 | |
| 1520 | —CH=CH—(CH2)2— | O | F | O-t-C4H9 | |
| 1521 | —CH=CH—(CH2)2— | O | F | O—(CH2)2—Cl | |
| 1522 | —CH=CH—(CH2)2— | O | F | O—CH2—S—CH3 | |
| 1523 | —CH=CH—(CH2)2— | O | F | O—CH2—Ph | |
| 1524 | —CH=CH—(CH2)2— | O | F | O—Ph | |
| 1525 | —CH=CH—(CH2)2— | O | F | O—CH2—CH=CH2 | |
| 1526 | —CH=CH—(CH2)2— | O | F | O—CH2—C≡CH | |
| 1527 | —CH=CH—(CH2)2— | O | F | O—CH2—O—C2H5 | |
| 1528 | —CH2—CH=CH—CH2— | O | F | H | |
| 1529 | —CH2—CH=CH—CH2— | O | F | OH | |
| 1530 | —CH2—CH=CH—CH2— | O | F | O—CH3 | |
| 1531 | —CH2—CH=CH—CH2— | O | F | O—C2H5 | |
| 1532 | —CH2—CH=CH—CH2— | O | F | O-n-C3H7 | |
| 1533 | —CH2—CH=CH—CH2— | O | F | O-i-C3H7 | |
| 1534 | —CH2—CH=CH—CH2— | O | F | O-n-C4H9 | |
| 1535 | —CH2—CH=CH—CH2— | O | F | O-i-C4H9 | |
| 1536 | —CH2—CH=CH—CH2— | O | F | O-s-C4H9 | |
| 1537 | —CH2—CH=CH—CH2— | O | F | O-t-C4H9 | |
| 1538 | —CH2—CH=CH—CH2— | O | F | O—(CH2)2—Cl | |
| 1539 | —CH2—CH=CH—CH2— | O | F | O—CH2—S—CH3 | |
| 1540 | —CH2—CH=CH—CH2— | O | F | O—CH2—Ph | |
| 1541 | —CH2—CH=CH—CH2— | O | F | O—Ph | |
| 1542 | —CH2—CH=CH—CH2— | O | F | O—CH2—CH=CH2 | |
| 1543 | —CH2—CH=CH—CH2— | O | F | O—CH2—C≡CH | |
| 1544 | —CH2—CH=CH—CH2— | O | F | O—CH2—O—C2H5 | |
| 1545 | —(CH2)2—CH=CH— | O | F | H | |
| 1546 | —(CH2)2—CH=CH— | O | F | OH | |
| 1547 | —(CH2)2—CH=CH— | O | F | O—CH3 | |
| 1548 | —(CH2)2—CH=CH— | O | F | O—C2H5 | |
| 1549 | —(CH2)2—CH=CH— | O | F | O-n-C3H7 | |
| 1550 | —(CH2)2—CH=CH— | O | F | O-i-C3H7 | |
| 1551 | —(CH2)2—CH=CH— | O | F | O-n-C4H9 | |
| 1552 | —(CH2)2—CH=CH— | O | F | O-i-C4H9 | |
| 1553 | —(CH2)2—CH=CH— | O | F | O-s-C4H9 | |
| 1554 | —(CH2)2—CH=CH— | O | F | O-t-C4H9 | |
| 1555 | —(CH2)2—CH=CH— | O | F | O—(CH2)2—Cl | |
| 1556 | —(CH2)2—CH=CH— | O | F | —CH2—S—CH3 | |
| 1557 | —(CH2)2—CH=CH— | O | F | O—CH2—Ph | |
| 1558 | —(CH2)2—CH=CH— | O | F | O—Ph | |
| 1559 | —(CH2)2—CH=CH— | O | F | O—CH2—CH=CH2 | |
| 1560 | —(CH2)2—CH=CH— | O | F | O—CH2—C≡CH | |
| 1561 | —(CH2)2—CH=CH— | O | F | O—CH2—O—C2H5 | |
| 1562 | —(CH2)3— | —OCH2— | F | H | |
| 1563a | —(CH2)3— | —OCH2— | F | OH | cis |

| | | | | |
|---|---|---|---|---|
| 1563b | —(CH₂)₃— | —OCH₂— | OH | trans |
| 1564a | —(CH₂)₃— | —OCH₂— | O—CH₃ | cis |
| 1564b | —(CH₂)₃— | —OCH₂— | O—CH₃ | trans |
| 1565 | —(CH₂)₃— | —OCH₂— | O—C₂H₅ | |
| 1566 | —(CH₂)₃— | —OCH₂— | O—n-C₃H₇ | |
| 1567 | —(CH₂)₃— | —OCH₂— | O—i-C₃H₇ | |
| 1568 | —(CH₂)₃— | —OCH₂— | O—n-C₄H₉ | |
| 1569 | —(CH₂)₃— | —OCH₂— | O—i-C₄H₉ | |
| 1570 | —(CH₂)₃— | —OCH₂— | O—s-C₄H₉ | |
| 1571 | —(CH₂)₃— | —OCH₂— | O—t-C₄H₉ | |
| 1572 | —(CH₂)₃— | —OCH₂— | O—(CH₂)₂—Cl | |
| 1573 | —(CH₂)₃— | —OCH₂— | O—CH₂—S—CH₃ | |
| 1574 | —(CH₂)₃— | —OCH₂— | O—CH₂—Ph | |
| 1575 | —(CH₂)₃— | —OCH₂— | O—Ph | |
| 1576 | —(CH₂)₃— | —OCH₂— | O—CH₂—CH=CH₂ | |
| 1577 | —(CH₂)₃— | —OCH₂— | O—CH₂—C≡CH | |
| 1578 | —(CH₂)₃— | —OCH₂— | O—CH₂—O—C₂H₅ | |
| 1579 | —(CH₂)₄— | —OCH₂— | H | |
| 1580a | —(CH₂)₄— | —OCH₂— | OH | cis |
| 1580b | —(CH₂)₄— | —OCH₂— | OH | trans |
| 1581 | —(CH₂)₄— | —OCH₂— | O-CH₃ | |
| 1582a | —(CH₂)₄— | —OCH₂— | O—C₂H₅ | cis |
| 1582b | —(CH₂)₄— | —OCH₂— | O—C₂H₅ | trans |
| 1583 | —(CH₂)₄— | —OCH₂— | O—n-C₃H₇ | |
| 1584 | —(CH₂)₄— | —OCH₂— | O—i-C₃H₇ | |
| 1585 | —(CH₂)₄— | —OCH₂— | O—n-C₄₉ | |
| 1586 | —(CH₂)₄— | —OCH₂— | O—i-C₄H₉ | |
| 1587 | —(CH₂)₄— | —OCH₂— | O—s-C₄H₉ | |
| 1588 | —(CH₂)₄— | —OCH₂— | O—t-C₄H₉ | |
| 1589 | —(CH₂)₄— | —OCH₂— | O—(CH₂)₂—Cl | |
| 1590 | —(CH₂)₄— | —OCH₂— | O—CH₂—S—CH₃ | |
| 1591 | —(CH₂)₄— | —OCH₂— | O—CH₂—Ph | |
| 1592 | —(CH₂)₄— | —OCH₂— | O—Ph | |
| 1593 | —(CH₂)₄— | —OCH₂— | O—CH₂—CH=CH₂ | |
| 1594 | —(CH₂)₄— | —OCH₂— | O—CH₂—C≡CH | |
| 1595 | —(CH₂)₄— | —OCH₂— | O—CH₂—O—C₂H₅ | |
| 1596 | —CH₂—CH(OH)—CH₂— | O | OH | |
| 1597 | —CH₂—CH(OH)—CH₂— | O | O—CH₃ | |
| 1598 | —CH₂—CH(OH)—CH₂— | O | O—C₂H₅ | |
| 1599 | —(CH₂)₂—CH(OH)—CH₂— | O | OH | |
| 1600 | —(CH₂)₂—CH(OH)—CH₂— | O | O—CH₃ | |
| 1601 | —(CH₂)₂—CH(OH)—CH₂— | O | O—C₂H₅ | |
| 1602 | —(CH₂)₂—CH(OCH₃)—CH₂— | O | OH | |
| 1603 | —(CH₂)₂—CH(OCH₃)—CH₂— | O | O—CH₃ | |
| 1604 | —(CH₂)₂—CH(OCH₃)—CH₂— | O | O—C₂H₅ | |
| 1605 | —CH₂—C(=O)—CH₂— | O | OH | |
| 1606 | —CH₂—C(=O)—CH₂— | O | O—CH₃ | |
| 1607 | —CH₂—C(=O)—CH₂— | O | O—C₂H₅ | |
| 1608 | —CH₂—CH(OH)—CH₂—CH₂— | O | OH | |
| 1609 | —CH₂—CH(OH)—CH₂—CH₂— | O | O—CH₃ | |
| 1610 | —CH₂—CH(OH)—CH₂—CH₂— | O | O—C₂H₅ | |
| 1611 | —CH₂—CH(OCH₃)—CH₂—CH₂— | O | OH | |
| 1612 | —CH₂—C(=O)—CH₂—CH₂— | O | O—CH₃ | |
| 1613 | —CH₂—C(=O)—CH₂—CH₂— | O | O—C₂H₅ | |

(All rows have F in the unlabeled column)

-continued

| # | Chain | | | |
|---|---|---|---|---|
| 1614 | —CH(OH)—(CH₂)₂— | F | O | OH |
| 1615 | —CH(OH)—(CH₂)₂— | F | O | O—CH₃ |
| 1616 | —CH(OH)—(CH₂)₂— | F | O | O—C₂H₅ |
| 1617 | —CH(OCH₃)—(CH₂)₂— | F | O | OH |
| 1618 | —CH(OCH₃)—(CH₂)₂— | F | O | O—CH₃ |
| 1619 | —CH(OCH₃)—(CH₂)₂— | F | O | O—C₂H₅ |
| 1620 | —C(=O)—(CH₂)₂— | F | O | OH |
| 1621 | —C(=O)—(CH₂)₂— | F | O | O—CH₃ |
| 1622 | —C(=O)—(CH₂)₂— | F | O | O—C₂H₅ |
| 1623 | —(CH₂)₃—CH(OH)— | F | O | OH |
| 1624 | —(CH₂)₃—CH(OH)— | F | O | O—CH₃ |
| 1625 | —(CH₂)₃—CH(OH)— | F | O | O—C₂H₅ |
| 1626 | —(CH₂)₃—CH(OCH₃)—CH₂— | F | O | OH |
| 1627 | —(CH₂)₃—CH(OCH₃)—CH₂— | F | O | O—CH₃ |
| 1628 | —(CH₂)₃—CH(OCH₃)—CH₂— | F | O | O—C₂H₅ |
| 1629 | —(CH₂)₃—C(=O)— | F | O | OH |
| 1630 | —(CH₂)₃—C(=O)— | F | O | O—CH₃ |
| 1631 | —(CH₂)₃—C(=O)— | F | O | O—C₂H₅ |
| 1632 | —(CH₂)₂—CH(OH)—(CH₂)— | F | O | OH |
| 1633 | —(CH₂)₂—CH(OH)—(CH₂)— | F | O | O—CH₃ |
| 1634 | —(CH₂)₂—CH(OH)—(CH₂)— | F | O | O—C₂H₅ |
| 1635 | —(CH₂)₂—CH(OCH₃)—CH₂— | F | O | OH |
| 1636 | —(CH₂)₂—CH(OCH₃)—CH₂— | F | O | O—CH₃ |
| 1637 | —(CH₂)₂—CH(OCH₃)—CH₂— | F | O | O—C₂H₅ |
| 1638 | —(CH₂)₂—C(=O)—(CH₂)— | F | O | OH |
| 1639 | —(CH₂)₂—C(=O)—(CH₂)— | F | O | O—CH₃ |
| 1640 | —(CH₂)₂—C(=O)—(CH₂)— | F | O | O—C₂H₅ |
| 1641 | —CH₂—CH(OH)—(CH₂)₂— | F | O | OH |
| 1642 | —CH₂—CH(OH)—(CH₂)₂— | F | O | O—CH₃ |
| 1643 | —CH₂—CH(OH)—(CH₂)₂— | F | O | O—C₂H₅ |
| 1644 | —CH₂—CH(OCH₃)—(CH₂)₂— | F | O | OH |
| 1645 | —CH₂—CH(OCH₃)—(CH₂)₂— | F | O | O—CH₃ |
| 1646 | —CH₂—CH(OCH₃)—(CH₂)₂— | F | O | O—C₂H₅ |
| 1647 | —CH₂—C(=O)—(CH₂)₂— | F | O | OH |
| 1648 | —CH₂—C(=O)—(CH₂)₂— | F | O | O—CH₃ |
| 1649 | —CH₂—C(=O)—(CH₂)₂— | F | O | O—C₂H₅ |
| 1650 | —CH(OH)—(CH₂)₂— | F | O | OH |
| 1651 | —CH(OH)—(CH₂)₂— | F | O | O—CH₃ |
| 1652 | —CH(OH)—(CH₂)₂— | F | O | O—C₂H₅ |
| 1653 | —CH(OCH₃)—(CH₂)₃— | F | O | OH |
| 1654 | —CH(OCH₃)—(CH₂)₃— | F | O | O—CH₃ |
| 1655 | —CH(OCH₃)—(CH₂)₃— | F | O | O—C₂H₅ |
| 1656 | —C(=O)—(CH₂)₂— | F | O | OH |
| 1657 | —C(=O)—(CH₂)₂— | F | O | O—CH₃ |
| 1658 | —C(=O)—(CH₂)₂— | F | O | O—C₂H₅ |

TABLE 2

$$R^4-\underset{R^3}{\underset{|}{C}}(F)-\underset{}{\overset{O}{\overset{\|}{C}}}-Y \quad W-Q$$

$$Q = Q_1 = \text{pyridine with } R^1, R^2$$

| Compound No. | R³ | R⁴ | W | Y | Q | R¹ | R² | Remarks |
|---|---|---|---|---|---|---|---|---|
| 2001 | —(CH₂)₃— | | O | H | Q₁ | CH₃ | CH₃ | |
| 2002 | —(CH₂)₃— | | O | OH | Q₁ | CH₃ | CH₃ | |
| 2003 | —(CH₂)₃— | | O | O—CH₃ | Q₁ | CH₃ | CH₃ | |
| 2004 | —(CH₂)₃— | | O | O—C₂H₅ | Q₁ | CH₃ | CH₃ | |
| 2005 | —(CH₂)₃— | | O | O—n-C₃H₇ | Q₁ | CH₃ | CH₃ | |
| 2006 | —(CH₂)₃— | | O | O—i-C₃H₇ | Q₁ | CH₃ | CH₃ | |
| 2007 | —(CH₂)₃— | | O | O—n-C₄H₉ | Q₁ | CH₃ | CH₃ | |
| 2008 | —(CH₂)₃— | | O | O—i-C₄H₉ | Q₁ | CH₃ | CH₃ | |
| 2009 | —(CH₂)₃— | | O | O—s-C₄H₉ | Q₁ | CH₃ | CH₃ | |
| 2010 | —(CH₂)₃— | | O | O—t-C₄H₉ | Q₁ | CH₃ | CH₃ | |
| 2011 | —(CH₂)₃— | | O | O—(CH₂)₂—Cl | Q₁ | CH₃ | CH₃ | |
| 2012 | —(CH₂)₃— | | O | O—CH₂—S—CH₃ | Q₁ | CH₃ | CH₃ | |
| 2013 | —(CH₂)₃— | | O | O—CH₂—Ph | Q₁ | CH₃ | CH₃ | |
| 2014 | —(CH₂)₃— | | O | O—Ph | Q₁ | CH₃ | CH₃ | |
| 2015 | —(CH₂)₃— | | O | O—Ph—2Cl | Q₁ | CH₃ | CH₃ | |
| 2016 | —(CH₂)₃— | | O | O—CH₂—CH=CH₂ | Q₁ | CH₃ | CH₃ | |
| 2017 | —(CH₂)₃— | | O | O—CH₂—C≡CH | Q₁ | CH₃ | CH₃ | |
| 2018 | —(CH₂)₃— | | O | O—CH₂—O—C₂H₅ | Q₁ | CH₃ | CH₃ | |
| 2019 | —(CH₂)₃— | | O | H | Q₁ | CH₃ | OCH₃ | |
| 2020 | —(CH₂)₃— | | O | OH | Q₁ | CH₃ | OCH₃ | |
| 2021a | —(CH₂)₃— | | O | O—CH₃ | Q₁ | CH₃ | OCH₃ | cis |
| 2021b | —(CH₂)₃— | | O | O—CH₃ | Q₁ | CH₃ | OCH₃ | trans |
| 2022 | —(CH₂)₃— | | O | O—C₂H₅ | Q₁ | CH₃ | OCH₃ | |
| 2023 | —(CH₂)₃— | | O | O—n-C₃H₇ | Q₁ | CH₃ | OCH₃ | |
| 2024 | —(CH₂)₃— | | O | O—i-C₃H₇ | Q₁ | CH₃ | OCH₃ | |
| 2025 | —(CH₂)₃— | | O | O—n-C₄H₉ | Q₁ | CH₃ | OCH₃ | |
| 2026 | —(CH₂)₃— | | O | O—i-C₄H₉ | Q₁ | CH₃ | OCH₃ | |
| 2027 | —(CH₂)₃— | | O | O—s-C₄H₉ | Q₁ | CH₃ | OCH₃ | |
| 2028 | —(CH₂)₃— | | O | O—t-C₄H₉ | Q₁ | CH₃ | OCH₃ | |
| 2029 | —(CH₂)₃— | | O | O—(CH₂)₂—Cl | Q₁ | CH₃ | OCH₃ | |
| 2030 | —(CH₂)₃— | | O | O—CH₂—S—CH₃ | Q₁ | CH₃ | OCH₃ | |
| 2031 | —(CH₂)₃— | | O | O—CH₂—Ph | Q₁ | CH₃ | OCH₃ | |
| 2032 | —(CH₂)₃— | | O | O—Ph | Q₁ | CH₃ | OCH₃ | |
| 2033 | —(CH₂)₃— | | O | O—Ph—2Cl | Q₁ | CH₃ | OCH₃ | |
| 2034 | —(CH₂)₃— | | O | O—CH₂—CH=CH₂ | Q₁ | CH₃ | OCH₃ | |
| 2035 | —(CH₂)₃— | | O | O—CH₂—C≡CH | Q₁ | CH₃ | OCH₃ | |
| 2036 | —(CH₂)₃— | | O | O—CH₂—O—C₂H₅ | Q₁ | CH₃ | OCH₃ | |
| 2037 | —(CH₂)₃— | | O | H | Q₁ | CH₃ | OCH₃ | |
| 2038 | —(CH₂)₃— | | O | OH | Q₁ | F | OCH₃ | |
| 2039 | —(CH₂)₃— | | O | O—CH₃ | Q₁ | F | OCH₃ | |
| 2040 | —(CH₂)₃— | | O | O—C₂H₅ | Q₁ | F | OCH₃ | |
| 2041 | —(CH₂)₃— | | O | O—n-C₃H₇ | Q₁ | F | OCH₃ | mixture |

| No. | | | | | | |
|---|---|---|---|---|---|---|
| 2042 | —(CH$_2$)$_3$— | O | O-i-C$_3$H$_7$ | F | OCH$_3$ | |
| 2043 | —(CH$_2$)$_3$— | O | O-n-C$_4$H$_9$ | F | OCH$_3$ | |
| 2044 | —(CH$_2$)$_3$— | O | O-i-C$_4$H$_9$ | F | OCH$_3$ | |
| 2045 | —(CH$_2$)$_3$— | O | O-s-C$_4$H$_9$ | F | OCH$_3$ | |
| 2046 | —(CH$_2$)$_3$— | O | O-t-C$_4$H$_9$ | F | OCH$_3$ | |
| 2047 | —(CH$_2$)$_3$— | O | O—(CH$_2$)$_2$—Cl | F | OCH$_3$ | |
| 2048 | —(CH$_2$)$_3$— | O | O—CH$_2$—S—CH$_3$ | F | OCH$_3$ | |
| 2049 | —(CH$_2$)$_3$— | O | O—CH$_2$—Ph | F | OCH$_3$ | |
| 2050 | —(CH$_2$)$_3$— | O | O—Ph | F | OCH$_3$ | |
| 2051 | —(CH$_2$)$_3$— | O | O—Ph—2Cl | F | OCH$_3$ | |
| 2052 | —(CH$_2$)$_3$— | O | O—CH$_2$—CH=CH$_2$ | F | OCH$_3$ | |
| 2053 | —(CH$_2$)$_3$— | O | O—CH$_2$—C≡CH | F | OCH$_3$ | |
| 2054 | —(CH$_2$)$_3$— | O | O—CH$_2$—O—C$_2$H$_5$ | F | OCH$_3$ | |
| 2055 | —(CH$_2$)$_3$— | O | H | F | OCH$_3$ | |
| 2056 | —(CH$_2$)$_3$— | O | OH | F | OCH$_3$ | |
| 2057a | —(CH$_2$)$_3$— | O | O—CH$_3$ | F | OCH$_3$ | cis |
| 2057b | —(CH$_2$)$_3$— | O | O—CH$_3$ | F | OCH$_3$ | trans |
| 2058a | —(CH$_2$)$_3$— | O | O—C$_2$H$_5$ | F | OCH$_3$ | cis |
| 2058b | —(CH$_2$)$_3$— | O | O—C$_2$H$_5$ | F | OCH$_3$ | trans |
| 2059 | —(CH$_2$)$_3$— | O | O-n-C$_3$H$_7$ | Cl | OCH$_3$ | |
| 2060 | —(CH$_2$)$_3$— | O | O-i-C$_3$H$_7$ | Cl | OCH$_3$ | |
| 2061 | —(CH$_2$)$_3$— | O | O-n-C$_4$H$_9$ | Cl | OCH$_3$ | |
| 2062 | —(CH$_2$)$_3$— | O | O-i-C$_4$H$_9$ | Cl | OCH$_3$ | |
| 2063 | —(CH$_2$)$_3$— | O | O-s-C$_4$H$_9$ | Cl | OCH$_3$ | |
| 2064 | —(CH$_2$)$_3$— | O | O-t-C$_4$H$_9$ | Cl | OCH$_3$ | |
| 2065 | —(CH$_2$)$_3$— | O | O—(CH$_2$)$_2$—Cl | Cl | OCH$_3$ | |
| 2066 | —(CH$_2$)$_3$— | O | O—CH$_2$—S—CH$_3$ | Cl | OCH$_3$ | |
| 2067 | —(CH$_2$)$_3$— | O | O—CH$_2$—Ph | Cl | OCH$_3$ | |
| 2068 | —(CH$_2$)$_3$— | O | O—Ph | Cl | OCH$_3$ | |
| 2069 | —(CH$_2$)$_3$— | O | O—Ph—2Cl | Cl | OCH$_3$ | |
| 2070 | —(CH$_2$)$_3$— | O | O—CH$_2$—CH=CH$_2$ | Cl | OCH$_3$ | |
| 2071 | —(CH$_2$)$_3$— | O | O—CH$_2$—C≡CH | Cl | OCH$_3$ | |
| 2072 | —(CH$_2$)$_3$— | O | O—CH$_2$—O—C$_2$H$_5$ | Cl | OCH$_3$ | |
| 2073 | —(CH$_2$)$_3$— | O | H | Cl | OCH$_3$ | |
| 2074 | —(CH$_2$)$_3$— | O | OH | Cl | OCH$_3$ | |
| 2075 | —(CH$_2$)$_3$— | O | O—CH$_3$ | Cl | Cl | |
| 2076 | —(CH$_2$)$_3$— | O | O—C$_2$H$_5$ | Cl | Cl | |
| 2077 | —(CH$_2$)$_3$— | O | O-n-C$_3$H$_7$ | Cl | Cl | |
| 2078 | —(CH$_2$)$_3$— | O | O-i-C$_3$H$_7$ | Cl | Cl | |
| 2079 | —(CH$_2$)$_3$— | O | O-n-C$_4$H$_9$ | Cl | Cl | |
| 2080 | —(CH$_2$)$_3$— | O | O-i-C$_4$H$_9$ | Cl | Cl | |
| 2081 | —(CH$_2$)$_3$— | O | O-s-C$_4$H$_9$ | Cl | Cl | |
| 2082 | —(CH$_2$)$_3$— | O | O-t-C$_4$H$_9$ | Cl | Cl | |
| 2083 | —(CH$_2$)$_3$— | O | O—(CH$_2$)$_2$—Cl | Cl | Cl | |
| 2084 | —(CH$_2$)$_3$— | O | O—CH$_2$—S—CH$_3$ | Cl | Cl | |
| 2085 | —(CH$_2$)$_3$— | O | O—CH$_2$—Ph | Cl | Cl | |
| 2086 | —(CH$_2$)$_3$— | O | O—Ph | Cl | Cl | |
| 2087 | —(CH$_2$)$_3$— | O | O—Ph—2Cl | Cl | Cl | |
| 2088 | —(CH$_2$)$_3$— | O | O—CH$_2$—CH=CH$_2$ | Cl | Cl | |
| 2089 | —(CH$_2$)$_3$— | O | O—CH$_2$—C≡CH | Cl | Cl | |
| 2090 | —(CH$_2$)$_3$— | O | O—CH$_2$—O—C$_2$H$_5$ | Cl | Cl | |
| 2091 | —(CH$_2$)$_3$— | O | H | Cl | Cl | |
| 2092 | —(CH$_2$)$_3$— | O | OH | Cl | Cl | |
| 2093a | —(CH$_2$)$_3$— | O | O—CH$_3$ | Cl | O—C$_2$H$_5$ | cis |

-continued

| No. | | | | | | | | |
|---|---|---|---|---|---|---|---|---|
| 2093b | —(CH$_2$)$_3$— | O | O—CH$_3$ | Q1 | Cl | | O—C$_2$H$_5$ | trans |
| 2094 | —(CH$_2$)$_3$— | O | O—C$_2$H$_5$ | Q1 | Cl | | O—C$_2$H$_5$ | |
| 2095 | —(CH$_2$)$_3$— | O | O—n-C$_3$H$_7$ | Q1 | Cl | | O—C$_2$H$_5$ | |
| 2096 | —(CH$_2$)$_3$— | O | O—i-C$_3$H$_7$ | Q1 | Cl | | O—C$_2$H$_5$ | |
| 2097 | —(CH$_2$)$_3$— | O | O—n-C$_4$H$_9$ | Q1 | Cl | | O—C$_2$H$_5$ | |
| 2098 | —(CH$_2$)$_3$— | O | O—i-C$_4$H$_9$ | Q1 | Cl | | O—C$_2$H$_5$ | |
| 2099 | —(CH$_2$)$_3$— | O | O—s-C$_4$H$_9$ | Q1 | Cl | | O—C$_2$H$_5$ | |
| 2100 | —(CH$_2$)$_3$— | O | O—t-C$_4$H$_9$ | Q1 | Cl | | O—C$_2$H$_5$ | |
| 2101 | —(CH$_2$)$_3$— | O | O—(CH$_2$)$_2$—Cl | Q1 | Cl | | O—C$_2$H$_5$ | |
| 2102 | —(CH$_2$)$_3$— | O | O—CH$_2$—S—CH$_3$ | Q1 | Cl | | O—C$_2$H$_5$ | |
| 2103 | —(CH$_2$)$_3$— | O | O—CH$_2$—Ph | Q1 | Cl | | O—C$_2$H$_5$ | |
| 2104 | —(CH$_2$)$_3$— | O | O—Ph | Q1 | Cl | | O—C$_2$H$_5$ | |
| 2105 | —(CH$_2$)$_3$— | O | O—Ph—2Cl | Q1 | Cl | | O—C$_2$H$_5$ | |
| 2106 | —(CH$_2$)$_3$— | O | O—CH$_2$—CH=CH$_2$ | Q1 | Cl | | O—C$_2$H$_5$ | |
| 2107 | —(CH$_2$)$_3$— | O | O—CH$_2$—C≡CH | Q1 | Cl | | O—C$_2$H$_5$ | |
| 2108 | —(CH$_2$)$_3$— | O | O—CH$_2$—O—C$_2$H$_5$ | Q1 | Cl | | O—C$_2$H$_5$ | |
| 2109 | —(CH$_2$)$_3$— | O | H | Q1 | O—CH$_3$ | CH$_3$ | O—C$_2$H$_5$ | |
| 2110 | —(CH$_2$)$_3$— | O | OH | Q1 | O—CH$_3$ | CH$_3$ | O—C$_2$H$_5$ | |
| 2111a | —(CH$_2$)$_3$— | O | O—CH$_3$ | Q1 | O—CH$_3$ | CH$_3$ | O—C$_2$H$_5$ | cis |
| 2111b | —(CH$_2$)$_3$— | O | O—CH$_3$ | Q1 | O—CH$_3$ | CH$_3$ | O—C$_2$H$_5$ | trans |
| 2112 | —(CH$_2$)$_3$— | O | O—C$_2$H$_5$ | Q1 | O—CH$_3$ | CH$_3$ | O—C$_2$H$_5$ | |
| 2113 | —(CH$_2$)$_3$— | O | O—n-C$_3$H$_7$ | Q1 | O—CH$_3$ | CH$_3$ | O—C$_2$H$_5$ | |
| 2114 | —(CH$_2$)$_3$— | O | O—i-C$_3$H$_7$ | Q1 | O—CH$_3$ | CH$_3$ | O—C$_2$H$_5$ | |
| 2115 | —(CH$_2$)$_3$— | O | O—n-C$_4$H$_9$ | Q1 | O—CH$_3$ | CH$_3$ | O—C$_2$H$_5$ | |
| 2116 | —(CH$_2$)$_3$— | O | O—i-C$_4$H$_9$ | Q1 | O—CH$_3$ | CH$_3$ | O—C$_2$H$_5$ | |
| 2117 | —(CH$_2$)$_3$— | O | O—s-C$_4$H$_9$ | Q1 | O—CH$_3$ | CH$_3$ | O—C$_2$H$_5$ | |
| 2118 | —(CH$_2$)$_3$— | O | O—t-C$_4$H$_9$ | Q1 | O—CH$_3$ | CH$_3$ | O—C$_2$H$_5$ | |
| 2119 | —(CH$_2$)$_3$— | O | O—(CH$_2$)$_2$—Cl | Q1 | O—CH$_3$ | CH$_3$ | O—C$_2$H$_5$ | |
| 2120 | —(CH$_2$)$_3$— | O | O—CH$_2$—S—CH$_3$ | Q1 | O—CH$_3$ | CH$_3$ | O—C$_2$H$_5$ | |
| 2121 | —(CH$_2$)$_3$— | O | O—CH$_2$—Ph | Q1 | O—CH$_3$ | CH$_3$ | O—C$_2$H$_5$ | |
| 2122 | —(CH$_2$)$_3$— | O | O—Ph | Q1 | O—CH$_3$ | CH$_3$ | O—C$_2$H$_5$ | |
| 2123 | —(CH$_2$)$_3$— | O | O—Ph—2Cl | Q1 | O—CH$_3$ | CH$_3$ | O—C$_2$H$_5$ | |
| 2124 | —(CH$_2$)$_3$— | O | O—CH$_2$—CH=CH$_2$ | Q1 | O—CH$_3$ | CH$_3$ | O—C$_2$H$_5$ | |
| 2125 | —(CH$_2$)$_3$— | O | O—CH$_2$—C≡CH | Q1 | O—CH$_3$ | CH$_3$ | O—C$_2$H$_5$ | |
| 2126 | —(CH$_2$)$_3$— | O | O—CH$_2$—O—C$_2$H$_5$ | Q1 | O—CH$_3$ | CH$_3$ | O—C$_2$H$_5$ | |
| 2127 | —(CH$_2$)$_3$— | O | H | Q1 | O—C$_2$H$_5$ | C$_2$H$_5$ | O—C$_2$H$_5$ | |
| 2128a | —(CH$_2$)$_3$— | O | OH | Q1 | O—C$_2$H$_5$ | C$_2$H$_5$ | O—C$_2$H$_5$ | cis |
| 2128b | —(CH$_2$)$_3$— | O | OH | Q1 | O—C$_2$H$_5$ | C$_2$H$_5$ | O—C$_2$H$_5$ | trans |
| 2129a | —(CH$_2$)$_3$— | O | O—CH$_3$ | Q1 | O—C$_2$H$_5$ | C$_2$H$_5$ | O—C$_2$H$_5$ | cis |
| 2129b | —(CH$_2$)$_3$— | O | O—CH$_3$ | Q1 | O—C$_2$H$_5$ | C$_2$H$_5$ | O—C$_2$H$_5$ | trans |
| 2130 | —(CH$_2$)$_3$— | O | O—C$_2$H$_5$ | Q1 | O—C$_2$H$_5$ | C$_2$H$_5$ | O—C$_2$H$_5$ | |
| 2131 | —(CH$_2$)$_3$— | O | O—n-C$_3$H$_7$ | Q1 | O—C$_2$H$_5$ | C$_2$H$_5$ | O—C$_2$H$_5$ | |
| 2132 | —(CH$_2$)$_3$— | O | O—i-C$_3$H$_7$ | Q1 | O—C$_2$H$_5$ | C$_2$H$_5$ | O—C$_2$H$_5$ | |
| 2133 | —(CH$_2$)$_3$— | O | O—n-C$_4$H$_9$ | Q1 | O—C$_2$H$_5$ | C$_2$H$_5$ | O—C$_2$H$_5$ | |
| 2134 | —(CH$_2$)$_3$— | O | O—i-C$_4$H$_9$ | Q1 | O—C$_2$H$_5$ | C$_2$H$_5$ | O—C$_2$H$_5$ | |
| 2135 | —(CH$_2$)$_3$— | O | O—s-C$_4$H$_9$ | Q1 | O—C$_2$H$_5$ | C$_2$H$_5$ | O—C$_2$H$_5$ | |
| 2136 | —(CH$_2$)$_3$— | O | O—t-C$_4$H$_9$ | Q1 | O—C$_2$H$_5$ | C$_2$H$_5$ | O—C$_2$H$_5$ | |
| 2137 | —(CH$_2$)$_3$— | O | O—(CH$_2$)$_2$—Cl | Q1 | O—C$_2$H$_5$ | C$_2$H$_5$ | O—C$_2$H$_5$ | |
| 2138 | —(CH$_2$)$_3$— | O | O—CH$_2$—S—CH$_3$ | Q1 | O—C$_2$H$_5$ | C$_2$H$_5$ | O—C$_2$H$_5$ | |
| 2139 | —(CH$_2$)$_3$— | O | O—CH$_2$—Ph | Q1 | O—C$_2$H$_5$ | C$_2$H$_5$ | O—C$_2$H$_5$ | |
| 2140 | —(CH$_2$)$_3$— | O | O—Ph | Q1 | O—C$_2$H$_5$ | C$_2$H$_5$ | O—C$_2$H$_5$ | |
| 2141 | —(CH$_2$)$_3$— | O | O—Ph—2Cl | Q1 | O—C$_2$H$_5$ | C$_2$H$_5$ | O—C$_2$H$_5$ | |
| 2142a | —(CH$_2$)$_3$— | O | O—CH$_2$—CH=CH$_2$ | Q1 | O—C$_2$H$_5$ | C$_2$H$_5$ | O—C$_2$H$_5$ | cis |
| 2142b | —(CH$_2$)$_3$— | O | O—CH$_2$—CH=CH$_2$ | Q1 | O—C$_2$H$_5$ | C$_2$H$_5$ | O—C$_2$H$_5$ | trans |

-continued

| No. | | | | | | | |
|---|---|---|---|---|---|---|---|
| 2143a | —(CH₂)₃— | O | O—CH₂—C≡CH | O | O—C₂H₅ | O—C₂H₅ | cis |
| 2143b | —(CH₂)₃— | O | O—CH₂—C≡CH | O | O—C₂H₅ | O—C₂H₅ | trans |
| 2144 | —(CH₂)₃— | O | O—CH₂—O—C₂H₅ | O | O—C₂H₅ | O—C₂H₅ | |
| 2145 | —(CH₂)₃— | O | H | O | O—n-C₃H₇ | O—n-C₃H₇ | |
| 2146 | —(CH₂)₃— | O | OH | O | O—n-C₃H₇ | O—n-C₃H₇ | |
| 2147a | —(CH₂)₃— | O | O—CH₃ | O | O—n-C₃H₇ | O—n-C₃H₇ | cis |
| 2147b | —(CH₂)₃— | O | O—CH₃ | O | O—n-C₃H₇ | O—n-C₃H₇ | trans |
| 2148 | —(CH₂)₃— | O | O—C₂H₅ | O | O—n-C₃H₇ | O—n-C₃H₇ | |
| 2149 | —(CH₂)₃— | O | O—n-C₃H₇ | O | O—n-C₃H₇ | O—n-C₃H₇ | |
| 2150 | —(CH₂)₃— | O | O—i-C₃H₇ | O | O—n-C₃H₇ | O—n-C₃H₇ | |
| 2151 | —(CH₂)₃— | O | O—n-C₄H₉ | O | O—n-C₃H₇ | O—n-C₃H₇ | |
| 2152 | —(CH₂)₃— | O | O—i-C₄H₉ | O | O—n-C₃H₇ | O—n-C₃H₇ | |
| 2153 | —(CH₂)₃— | O | O—s-C₄H₉ | O | O—n-C₃H₇ | O—n-C₃H₇ | |
| 2154 | —(CH₂)₃— | O | O—t-C₄H₉ | O | O—n-C₃H₇ | O—n-C₃H₇ | |
| 2155 | —(CH₂)₃— | O | O—(CH₂)₂—Cl | O | O—n-C₃H₇ | O—n-C₃H₇ | |
| 2156 | —(CH₂)₃— | O | O—CH₂—S—CH₃ | O | O—n-C₃H₇ | O—n-C₃H₇ | |
| 2157 | —(CH₂)₃— | O | O—CH₂—Ph | O | O—n-C₃H₇ | O—n-C₃H₇ | |
| 2158 | —(CH₂)₃— | O | O—Ph | O | O—n-C₃H₇ | O—n-C₃H₇ | |
| 2159 | —(CH₂)₃— | O | O—Ph—2Cl | O | O—n-C₃H₇ | O—n-C₃H₇ | |
| 2160 | —(CH₂)₃— | O | O—CH₂—CH=CH₂ | O | O—n-C₃H₇ | O—n-C₃H₇ | |
| 2161 | —(CH₂)₃— | O | O—CH₂—C≡CH | O | O—n-C₃H₇ | O—n-C₃H₇ | |
| 2162 | —(CH₂)₃— | O | O—CH₂—O—C₂H₅ | O | O—n-C₃H₇ | O—n-C₃H₇ | |
| 2163 | —(CH₂)₃— | O | H | O | O—i-C₃H₇ | O—i-C₃H₇ | |
| 2164a | —(CH₂)₃— | O | OH | O | O—i-C₃H₇ | O—i-C₃H₇ | cis |
| 2164b | —(CH₂)₃— | O | OH | O | O—i-C₃H₇ | O—i-C₃H₇ | trans |
| 2165a | —(CH₂)₃— | O | O—CH₃ | O | O—i-C₃H₇ | O—i-C₃H₇ | cis |
| 2165b | —(CH₂)₃— | O | O—CH₃ | O | O—i-C₃H₇ | O—i-C₃H₇ | trans |
| 2166 | —(CH₂)₃— | O | O—C₂H₅ | O | O—i-C₃H₇ | O—i-C₃H₇ | |
| 2167 | —(CH₂)₃— | O | O—n-C₃H₇ | O | O—i-C₃H₇ | O—i-C₃H₇ | |
| 2168 | —(CH₂)₃— | O | O—i-C₃H₇ | O | O—i-C₃H₇ | O—i-C₃H₇ | |
| 2169 | —(CH₂)₃— | O | O—n-C₄H₉ | O | O—i-C₃H₇ | O—i-C₃H₇ | |
| 2170 | —(CH₂)₃— | O | O—i-C₄H₉ | O | O—i-C₃H₇ | O—i-C₃H₇ | |
| 2171 | —(CH₂)₃— | O | O—s-C₄H₉ | O | O—i-C₃H₇ | O—i-C₃H₇ | |
| 2172 | —(CH₂)₃— | O | O—t-C₄H₉ | O | O—i-C₃H₇ | O—i-C₃H₇ | |
| 2173 | —(CH₂)₃— | O | O—(CH₂)₂—Cl | O | O—i-C₃H₇ | O—i-C₃H₇ | |
| 2174 | —(CH₂)₃— | O | O—CH₂—S—CH₃ | O | O—i-C₃H₇ | O—i-C₃H₇ | |
| 2175 | —(CH₂)₃— | O | O—CH₂—Ph | O | O—i-C₃H₇ | O—i-C₃H₇ | |
| 2176 | —(CH₂)₃— | O | O—Ph | O | O—i-C₃H₇ | O—i-C₃H₇ | |
| 2177 | —(CH₂)₃— | O | O—Ph—2Cl | O | O—i-C₃H₇ | O—i-C₃H₇ | |
| 2178 | —(CH₂)₃— | O | O—CH₂—CH=CH₂ | O | O—i-C₃H₇ | O—i-C₃H₇ | cis |
| 2179 | —(CH₂)₃— | O | O—CH₂—C≡CH | O | O—i-C₃H₇ | O—i-C₃H₇ | trans |
| 2180 | —(CH₂)₃— | O | O—CH₂—O—C₂H₅ | O | O—i-C₃H₇ | O—i-C₃H₇ | |
| 2181 | —(CH₂)₃— | O | H | O | O—CHF₂ | O—CHF₂ | |
| 2182 | —(CH₂)₃— | O | OH | O | O—CHF₂ | O—CHF₂ | |
| 2183a | —(CH₂)₃— | O | O—CH₃ | O | O—CHF₂ | O—CHF₂ | cis |
| 2183b | —(CH₂)₃— | O | O—CH₃ | O | O—CHF₂ | O—CHF₂ | trans |
| 2184 | —(CH₂)₃— | O | O—C₂H₅ | O | O—CHF₂ | O—CHF₂ | |
| 2185 | —(CH₂)₃— | O | O—n-C₃H₇ | O | O—CHF₂ | O—CHF₂ | |
| 2186 | —(CH₂)₃— | O | O—i-C₃H₇ | O | O—CHF₂ | O—CHF₂ | |
| 2187 | —(CH₂)₃— | O | O—n-C₄H₉ | O | O—CHF₂ | O—CHF₂ | |
| 2188 | —(CH₂)₃— | O | O—i-C₄H₉ | O | O—CHF₂ | O—CHF₂ | |
| 2189 | —(CH₂)₃— | O | O—s-C₄H₉ | O | O—CHF₂ | O—CHF₂ | |
| 2190 | —(CH₂)₃— | O | O—t-C₄H₉ | O | O—CHF₂ | O—CHF₂ | |
| 2191 | —(CH₂)₃— | O | O—(CH₂)₂—Cl | O | O—CHF₂ | O—CHF₂ | |

-continued

| No. | | | | | | |
|---|---|---|---|---|---|---|
| 2192 | —(CH₂)₃— | O | O—CH₂—S—CH₃ | Cl | O—CHF₂ | O—CHF₂ |
| 2193 | —(CH₂)₃— | O | O—CH₂—Ph | Cl | O—CHF₂ | O—CHF₂ |
| 2194 | —(CH₂)₃— | O | O—Ph | Cl | O—CHF₂ | O—CHF₂ |
| 2195 | —(CH₂)₃— | O | O—Ph—2Cl | Cl | O—CHF₂ | O—CHF₂ |
| 2196 | —(CH₂)₃— | O | O—CH₂—CH=CH₂ | Cl | O—CHF₂ | O—CHF₂ |
| 2197 | —(CH₂)₃— | O | O—CH₂—C≡CH | Cl | O—CHF₂ | O—CHF₂ |
| 2198 | —(CH₂)₃— | O | O—CH₂—O—C₂H₅ | Cl | O—CHF₂ | O—CHF₂ |
| 2199 | —(CH₂)₃— | O | H | Cl | S—CH₃ | O—CH₃ |
| 2200 | —(CH₂)₃— | O | OH | Cl | S—CH₃ | O—CH₃ |
| 2201 | —(CH₂)₃— | O | O—CH₃ | Cl | S—CH₃ | O—CH₃ |
| 2202 | —(CH₂)₃— | O | O—C₂H₅ | Cl | S—CH₃ | O—CH₃ |
| 2203 | —(CH₂)₃— | O | O-n-C₃H₇ | Cl | S—CH₃ | O—CH₃ |
| 2204 | —(CH₂)₃— | O | O-i-C₃H₇ | Cl | S—CH₃ | O—CH₃ |
| 2205 | —(CH₂)₃— | O | O-n-C₄H₉ | Cl | S—CH₃ | O—CH₃ |
| 2206 | —(CH₂)₃— | O | O-i-C₄H₉ | Cl | S—CH₃ | O—CH₃ |
| 2207 | —(CH₂)₃— | O | O-s-C₄H₉ | Cl | S—CH₃ | O—CH₃ |
| 2208 | —(CH₂)₃— | O | O-t-C₄H₉ | Cl | S—CH₃ | O—CH₃ |
| 2209 | —(CH₂)₃— | O | O—(CH₂)₂—Cl | Cl | S—CH₃ | O—CH₃ |
| 2210 | —(CH₂)₃— | O | O—CH₂—S—CH₃ | Cl | S—CH₃ | O—CH₃ |
| 2211 | —(CH₂)₃— | O | O—CH₂—Ph | Cl | S—CH₃ | O—CH₃ |
| 2212 | —(CH₂)₃— | O | O—Ph | Cl | S—CH₃ | O—CH₃ |
| 2213 | —(CH₂)₃— | O | O—Ph—2Cl | Cl | S—CH₃ | O—CH₃ |
| 2214 | —(CH₂)₃— | O | O—CH₂—CH=CH₂ | Cl | S—CH₃ | O—CH₃ |
| 2215 | —(CH₂)₃— | O | O—CH₂—C≡CH | Cl | S—CH₃ | O—CH₃ |
| 2216 | —(CH₂)₃— | O | O—CH₂—O—C₂H₅ | Cl | S—CH₃ | O—CH₃ |
| 2217 | —(CH₂)₃— | O | H | Cl | S—CH₃ | Cl |
| 2218 | —(CH₂)₃— | O | OH | Cl | S—CH₃ | Cl |
| 2219 | —(CH₂)₃— | O | O—CH₃ | Cl | S—CH₃ | Cl |
| 2220 | —(CH₂)₃— | O | O—C₂H₅ | Cl | S—CH₃ | Cl |
| 2221 | —(CH₂)₃— | O | O-n-C₃H₇ | Cl | S—CH₃ | Cl |
| 2222 | —(CH₂)₃— | O | O-i-C₃H₇ | Cl | S—CH₃ | Cl |
| 2223 | —(CH₂)₃— | O | O-n-C₄H₉ | Cl | S—CH₃ | Cl |
| 2224 | —(CH₂)₃— | O | O-i-C₄H₉ | Cl | S—CH₃ | Cl |
| 2225 | —(CH₂)₃— | O | O-s-C₄H₉ | Cl | S—CH₃ | Cl |
| 2226 | —(CH₂)₃— | O | O-t-C₄H₉ | Cl | S—CH₃ | Cl |
| 2227 | —(CH₂)₃— | O | O—(CH₂)₂—Cl | Cl | S—CH₃ | Cl |
| 2228 | —(CH₂)₃— | O | O—CH₂—S—CH₃ | Cl | S—CH₃ | Cl |
| 2229 | —(CH₂)₃— | O | O—CH₂—Ph | Cl | S—CH₃ | Cl |
| 2230 | —(CH₂)₃— | O | O—Ph | Cl | S—CH₃ | Cl |
| 2231 | —(CH₂)₃— | O | O—Ph—2Cl | Cl | S—CH₃ | Cl |
| 2232 | —(CH₂)₃— | O | O—CH₂—CH=CH₂ | Cl | S—CH₃ | Cl |
| 2233 | —(CH₂)₃— | O | O—CH₂—C≡CH | Cl | S—CH₃ | Cl |
| 2234 | —(CH₂)₃— | O | O—CH₂—O—C₂H₅ | Cl | S—CH₃ | Cl |
| 2235 | —(CH₂)₃— | O | H | Cl | S—CH₃ | CH₃ |
| 2236 | —(CH₂)₃— | O | OH | Cl | S—CH₃ | CH₃ |
| 2237 | —(CH₂)₃— | O | O—CH₃ | Cl | S—CH₃ | CH₃ |
| 2238 | —(CH₂)₃— | O | O—C₂H₅ | Cl | S—CH₃ | CH₃ |
| 2239 | —(CH₂)₃— | O | O-n-C₃H₇ | Cl | S—CH₃ | CH₃ |
| 2240 | —(CH₂)₃— | O | O-i-C₃H₇ | Cl | S—CH₃ | CH₃ |
| 2241 | —(CH₂)₃— | O | O-n-C₄H₉ | Cl | S—CH₃ | CH₃ |
| 2242 | —(CH₂)₃— | O | O-i-C₄H₉ | Cl | S—CH₃ | CH₃ |
| 2243 | —(CH₂)₃— | O | O-s-C₄H₉ | Cl | S—CH₃ | CH₃ |
| 2244 | —(CH₂)₃— | O | O-t-C₄H₉ | Cl | S—CH₃ | CH₃ |
| 2245 | —(CH₂)₃— | O | O—(CH₂)₂—Cl | Cl | S—CH₃ | CH₃ |

-continued

| No. | | | | | |
|---|---|---|---|---|---|
| 2246 | —(CH₂)₃— | O | O—CH₂—S—CH₃ | S—CH₃ | CH₃ |
| 2247 | —(CH₂)₃— | O | O—CH₂—Ph | S—CH₃ | CH₃ |
| 2248 | —(CH₂)₃— | O | O—Ph—2Cl | S—CH₃ | CH₃ |
| 2249 | —(CH₂)₃— | O | O—CH₂—CH=CH₂ | C—CH₃ | CH₃ |
| 2250 | —(CH₂)₃— | O | O—CH₂—C≡CH | S—CH₃ | CH₃ |
| 2251 | —(CH₂)₃— | O | O—CH₂—O—C₂H₅ | S—CH₃ | CH₃ |
| 2252 | —(CH₂)₃— | O | H | Cl | N(CH₃)₂ |
| 2253 | —(CH₂)₃— | O | OH | Cl | N(CH₃)₂ |
| 2254 | —(CH₂)₃— | O | O—CH₃ | Cl | N(CH₃)₂ |
| 2255 | —(CH₂)₃— | O | O—C₂H₅ | Cl | N(CH₃)₂ |
| 2256 | —(CH₂)₃— | O | O-n-C₃H₇ | Cl | N(CH₃)₂ |
| 2257 | —(CH₂)₃— | O | O-i-C₃H₇ | Cl | N(CH₃)₂ |
| 2258 | —(CH₂)₃— | O | O-n-C₄H₉ | Cl | N(CH₃)₂ |
| 2259 | —(CH₂)₃— | O | O-i-C₄H₉ | Cl | N(CH₃)₂ |
| 2260 | —(CH₂)₃— | O | O-s-C₄H₉ | Cl | N(CH₃)₂ |
| 2261 | —(CH₂)₃— | O | O-t-C₄H₉ | Cl | N(CH₃)₂ |
| 2262 | —(CH₂)₃— | O | O—(CH₂)₂—Cl | Cl | N(CH₃)₂ |
| 2263 | —(CH₂)₃— | O | O—CH₂—S—CH₃ | Cl | N(CH₃)₂ |
| 2264 | —(CH₂)₃— | O | O—CH₂—Ph | Cl | N(CH₃)₂ |
| 2265 | —(CH₂)₃— | O | O—Ph | Cl | N(CH₃)₂ |
| 2266 | —(CH₂)₃— | O | O—Ph—2Cl | Cl | N(CH₃)₂ |
| 2267 | —(CH₂)₃— | O | O—CH₂—CH=CH₂ | Cl | N(CH₃)₂ |
| 2268 | —(CH₂)₃— | O | O—CH₂—C≡CH | Cl | N(CH₃)₂ |
| 2269 | —(CH₂)₃— | O | O—CH₂—O—C₂H₅ | Cl | N(CH₃)₂ |
| 2270 | —(CH₂)₃— | O | H | O—CH₃ | N(CH₃)₂ |
| 2271 | —(CH₂)₃— | O | OH | O—CH₃ | N(CH₃)₂ |
| 2272 | —(CH₂)₃— | O | O—CH₃ | O—CH₃ | N(CH₃)₂ |
| 2273 | —(CH₂)₃— | O | O—C₂H₅ | O—CH₃ | N(CH₃)₂ |
| 2274 | —(CH₂)₃— | O | O-n-C₃H₇ | O—CH₃ | N(CH₃)₂ |
| 2275 | —(CH₂)₃— | O | O-i-C₃H₇ | O—CH₃ | N(CH₃)₂ |
| 2276 | —(CH₂)₃— | O | O-n-C₄H₉ | O—CH₃ | N(CH₃)₂ |
| 2277 | —(CH₂)₃— | O | O-i-C₄H₉ | O—CH₃ | N(CH₃)₂ |
| 2278 | —(CH₂)₃— | O | O-s-C₄H₉ | O—CH₃ | N(CH₃)₂ |
| 2279 | —(CH₂)₃— | O | O-t-C₄H₉ | O—CH₃ | N(CH₃)₂ |
| 2280 | —(CH₂)₃— | O | O—(CH₂)₂—Cl | O—CH₃ | N(CH₃)₂ |
| 2281 | —(CH₂)₃— | O | O—CH₂—S—CH₃ | O—CH₃ | N(CH₃)₂ |
| 2282 | —(CH₂)₃— | O | O—CH₂—Ph | O—CH₃ | N(CH₃)₂ |
| 2283 | —(CH₂)₃— | O | O—Ph | O—CH₃ | N(CH₃)₂ |
| 2284 | —(CH₂)₃— | O | O—Ph—2Cl | O—CH₃ | N(CH₃)₂ |
| 2285 | —(CH₂)₃— | O | O—CH₂—CH=CH₂ | O—CH₃ | N(CH₃)₂ |
| 2286 | —(CH₂)₃— | O | O—CH₂—C≡CH | O—CH₃ | N(CH₃)₂ |
| 2287 | —(CH₂)₃— | O | O—CH₂—O—C₂H₅ | O—CH₃ | N(CH₃)₂ |
| 2288 | —(CH₂)₃— | O | H | CH₃ | CH₃ |
| 2289 | —(CH₂)₃— | O | OH | CH₃ | CH₃ |
| 2290 | —(CH₂)₃— | O | O—CH₃ | CH₃ | CH₃ |
| 2291 | —(CH₂)₃— | O | | | |

| No. | | | R | | X | Y | |
|---|---|---|---|---|---|---|---|
| 2292 | —(CH₂)₄— | O | O—C₂H₅ | Cl | CH₃ | CH₃ | |
| 2293 | —(CH₂)₄— | O | O-n-C₃H₇ | Cl | CH₃ | CH₃ | |
| 2294 | —(CH₂)₄— | O | O-i-C₃H₇ | Cl | CH₃ | CH₃ | |
| 2295 | —(CH₂)₄— | O | O-n-C₄H₉ | Cl | CH₃ | CH₃ | |
| 2296 | —(CH₂)₄— | O | O-i-C₄H₉ | Cl | CH₃ | CH₃ | |
| 2297 | —(CH₂)₄— | O | O-s-C₄H₉ | Cl | CH₃ | CH₃ | |
| 2298 | —(CH₂)₄— | O | O-t-C₄H₉ | Cl | CH₃ | CH₃ | |
| 2299 | —(CH₂)₄— | O | O—(CH₂)₂—Cl | Cl | CH₃ | CH₃ | |
| 2300 | —(CH₂)₄— | O | O—CH₂—S—CH₃ | Cl | CH₃ | CH₃ | |
| 2301 | —(CH₂)₄— | O | O—CH₂—Ph | Cl | CH₃ | CH₃ | |
| 2302 | —(CH₂)₄— | O | O—Ph | Cl | CH₃ | CH₃ | |
| 2303 | —(CH₂)₄— | O | O—Ph—2Cl | Cl | CH₃ | CH₃ | |
| 2304 | —(CH₂)₄— | O | O—CH₂—CH=CH₂ | Cl | CH₃ | CH₃ | |
| 2305 | —(CH₂)₄— | O | O—CH₂—C≡CH | Cl | CH₃ | CH₃ | |
| 2306 | —(CH₂)₄— | O | O—CH₂—O—C₂H₅ | Cl | CH₃ | CH₃ | |
| 2307 | —(CH₂)₄— | O | H | Cl | CH₃ | CH₃ | |
| 2308 | —(CH₂)₄— | O | OH | Cl | CH₃ | CH₃ | |
| 2309 | —(CH₂)₄— | O | O—CH₃ | Cl | CH₃ | OCH₃ | |
| 2310 | —(CH₂)₄— | O | O—C₂H₅ | Cl | CH₃ | OCH₃ | |
| 2311 | —(CH₂)₄— | O | O-n-C₃H₇ | Cl | CH₃ | OCH₃ | |
| 2312 | —(CH₂)₄— | O | O-i-C₃H₇ | Cl | CH₃ | OCH₃ | |
| 2313 | —(CH₂)₄— | O | O-n-C₄H₉ | Cl | CH₃ | OCH₃ | |
| 2314 | —(CH₂)₄— | O | O-i-C₄H₉ | Cl | CH₃ | OCH₃ | |
| 2315 | —(CH₂)₄— | O | O-s-C₄H₉ | Cl | CH₃ | OCH₃ | |
| 2316 | —(CH₂)₄— | O | O-t-C₄H₉ | Cl | CH₃ | OCH₃ | |
| 2317 | —(CH₂)₄— | O | O—(CH₂)₂—Cl | Cl | CH₃ | OCH₃ | |
| 2318 | —(CH₂)₄— | O | O—CH₂—S—CH₃ | Cl | CH₃ | OCH₃ | |
| 2319 | —(CH₂)₄— | O | O—CH₂—Ph | Cl | CH₃ | OCH₃ | |
| 2320 | —(CH₂)₄— | O | O—Ph | Cl | CH₃ | OCH₃ | |
| 2321 | —(CH₂)₄— | O | O—Ph—2Cl | Cl | CH₃ | OCH₃ | |
| 2322 | —(CH₂)₄— | O | O—CH₂—CH=CH₂ | Cl | CH₃ | OCH₃ | |
| 2323 | —(CH₂)₄— | O | O—CH₂—C≡CH | Cl | CH₃ | OCH₃ | |
| 2324 | —(CH₂)₄— | O | O—CH₂—O—C₂H₅ | Cl | CH₃ | OCH₃ | |
| 2325 | —(CH₂)₄— | O | H | Cl | CH₃ | OCH₃ | |
| 2326 | —(CH₂)₄— | O | OH | Cl | F | OCH₃ | |
| 2327 | —(CH₂)₄— | O | O—CH₃ | Cl | F | OCH₃ | |
| 2328 | —(CH₂)₄— | O | O—C₂H₅ | Cl | F | OCH₃ | |
| 2329 | —(CH₂)₄— | O | O-n-C₃H₇ | Cl | F | OCH₃ | |
| 2330 | —(CH₂)₄— | O | O-i-C₃H₇ | Cl | F | OCH₃ | |
| 2331 | —(CH₂)₄— | O | O-n-C₄H₉ | Cl | F | OCH₃ | |
| 2332 | —(CH₂)₄— | O | O-i-C₄H₉ | Cl | F | OCH₃ | |
| 2333 | —(CH₂)₄— | O | O-s-C₄H₉ | Cl | F | OCH₃ | |
| 2334 | —(CH₂)₄— | O | o-t-C₄H₉ | Cl | F | OCH₃ | |
| 2335 | —(CH₂)₄— | O | O—(CH₂)₂—Cl | Cl | F | OCH₃ | |
| 2336 | —(CH₂)₄— | O | O—CH₂—S—CH₃ | Cl | F | OCH₃ | |
| 2337 | —(CH₂)₄— | O | O—CH₂—Ph | Cl | F | OCH₃ | |
| 2338 | —(CH₂)₄— | O | O—Ph | Cl | F | OCH₃ | |
| 2339 | —(CH₂)₄— | O | O—Ph—2Cl | Cl | F | OCH₃ | |
| 2340 | —(CH₂)₄— | O | O—CH₂—CH=CH₂ | Cl | F | OCH₃ | |
| 2341 | —(CH₂)₄— | O | O—CH₂—C≡CH | Cl | F | OCH₃ | |
| 2342 | —(CH₂)₄— | O | O—CH₂—O—C₂H₅ | Cl | F | OCH₃ | |
| 2343 | —(CH₂)₄— | O | H | Cl | F | OCH₃ | |
| 2344a | —(CH₂)₄— | O | OH | Cl | Cl | OCH₃ | cis |
| 2344b | —(CH₂)₄— | O | OH | Cl | Cl | OCH₃ | trans |

-continued

| No. | | | | | | | |
|---|---|---|---|---|---|---|---|
| 2345a | —(CH₂)₄— | O | O—CH₃ | Cl | Cl | OCH₃ | cis |
| 2345b | —(CH₂)₄— | O | O—CH₃ | Cl | Cl | OCH₃ | trans |
| 2346a | —(CH₂)₄— | O | O—C₂H₅ | Cl | Cl | OCH₃ | cis |
| 2346b | —(CH₂)₄— | O | O—C₂H₅ | Cl | Cl | OCH₃ | trans |
| 2347 | —(CH₂)₄— | O | O-n-C₃H₇ | Cl | Cl | OCH₃ | |
| 2348a | —(CH₂)₄— | O | O-i-C₃H₇ | Cl | Cl | OCH₃ | cis |
| 2348b | —(CH₂)₄— | O | O-i-C₃H₇ | Cl | Cl | OCH₃ | trans |
| 2349 | —(CH₂)₄— | O | O-n-C₄H₉ | Cl | Cl | OCH₃ | |
| 2350 | —(CH₂)₄— | O | O-i-C₄H₉ | Cl | Cl | OCH₃ | |
| 2351a | —(CH₂)₄— | O | O-s-C₄H₉ | Cl | Cl | OCH₃ | cis |
| 2351b | —(CH₂)₄— | O | O-s-C₄H₉ | Cl | Cl | OCH₃ | trans |
| 2352 | —(CH₂)₄— | O | O-t-C₄H₉ | Cl | Cl | OCH₃ | |
| 2353a | —(CH₂)₄— | O | O—(CH₂)₂—Cl | Cl | Cl | OCH₃ | cis |
| 2353b | —(CH₂)₄— | O | O—(CH₂)₂—Cl | Cl | Cl | OCH₃ | trans |
| 2354 | —(CH₂)₄— | O | O—CH₂—S—CH₃ | Cl | Cl | OCH₃ | |
| 2355 | —(CH₂)₄— | O | O—CH₂—Ph | Cl | Cl | OCH₃ | |
| 2356 | —(CH₂)₄— | O | O—Ph | Cl | Cl | OCH₃ | |
| 2357 | —(CH₂)₄— | O | O—Ph—2Cl | Cl | Cl | OCH₃ | |
| 2358 | —(CH₂)₄— | O | O—CH₂—CH=CH₂ | Cl | Cl | OCH₃ | |
| 2359 | —(CH₂)₄— | O | O—CH₂—C≡CH | Cl | Cl | OCH₃ | |
| 2360 | —(CH₂)₄— | O | O—CH₂—O—C₂H₅ | Cl | Cl | OCH₃ | |
| 2361 | —(CH₂)₄— | O | H | Cl | Cl | Cl | |
| 2362 | —(CH₂)₄— | O | OH | Cl | Cl | Cl | |
| 2363 | —(CH₂)₄— | O | O—CH₃ | Cl | Cl | Cl | |
| 2364 | —(CH₂)₄— | O | O—C₂H₅ | Cl | Cl | Cl | |
| 2365 | —(CH₂)₄— | O | O-n-C₃H₇ | Cl | Cl | Cl | |
| 2366 | —(CH₂)₄— | O | O-i-C₃H₇ | Cl | Cl | Cl | |
| 2367 | —(CH₂)₄— | O | O-n-C₄H₉ | Cl | Cl | Cl | |
| 2368 | —(CH₂)₄— | O | O-i-C₄H₉ | Cl | Cl | Cl | |
| 2369 | —(CH₂)₄— | O | O-s-C₄H₉ | Cl | Cl | Cl | |
| 2370 | —(CH₂)₄— | O | O-t-C₄H₉ | Cl | Cl | Cl | |
| 2371 | —(CH₂)₄— | O | O—(CH₂)₂—Cl | Cl | Cl | Cl | |
| 2372 | —(CH₂)₄— | O | O—CH₂—S—CH₃ | Cl | Cl | Cl | |
| 2373 | —(CH₂)₄— | O | O—CH₂—Ph | Cl | Cl | Cl | |
| 2374 | —(CH₂)₄— | O | O—Ph | Cl | Cl | Cl | |
| 2375 | —(CH₂)₄— | O | O—Ph—2Cl | Cl | Cl | Cl | |
| 2376 | —(CH₂)₄— | O | O—CH₂—CH=CH₂ | Cl | Cl | Cl | |
| 2377 | —(CH₂)₄— | O | O—CH₂—C≡CH | Cl | Cl | Cl | |
| 2378 | —(CH₂)₄— | O | O—CH₂—O—C₂H₅ | Cl | Cl | Cl | |
| 2379 | —(CH₂)₄— | O | H | Cl | Cl | Cl | |
| 2380a | —(CH₂)₄— | O | OH | Cl | Cl | O—C₂H₅ | cis |
| 2380b | —(CH₂)₄— | O | OH | Cl | Cl | O—C₂H₅ | trans |
| 2381 | —(CH₂)₄— | O | O—CH₃ | Cl | Cl | O—C₂H₅ | |
| 2382a | —(CH₂)₄— | O | O—C₂H₅ | Cl | Cl | O—C₂H₅ | cis |
| 2382b | —(CH₂)₄— | O | O—C₂H₅ | Cl | Cl | O—C₂H₅ | trans |
| 2383 | —(CH₂)₄— | O | O-n-C₃H₇ | Cl | Cl | O—C₂H₅ | |
| 2384 | —(CH₂)₄— | O | O-i-C₃H₇ | Cl | Cl | O—C₂H₅ | |
| 2385 | —(CH₂)₄— | O | O-n-C₄H₉ | Cl | Cl | O—C₂H₅ | |
| 2386 | —(CH₂)₄— | O | O-i-C₄H₉ | Cl | Cl | O—C₂H₅ | |
| 2387 | —(CH₂)₄— | O | O-s-C₄H₉ | Cl | Cl | O—C₂H₅ | |
| 2388 | —(CH₂)₄— | O | O-t-C₄H₉ | Cl | Cl | O—C₂H₅ | |
| 2389 | —(CH₂)₄— | O | O—(CH₂)₂—Cl | Cl | Cl | O—C₂H₅ | |
| 2390 | —(CH₂)₄— | O | O—CH₂—S—CH₃ | Cl | Cl | O—C₂H₅ | |
| 2391 | —(CH₂)₄— | O | O—CH₂—Ph | Cl | Cl | O—C₂H₅ | |

-continued

| No. | | | | | | | |
|---|---|---|---|---|---|---|---|
| 2392 | —(CH₂)₄— | O | O—Ph | Q1 | Cl | O—C₂H₅ | |
| 2393 | —(CH₂)₄— | O | O—Ph—2Cl | Q1 | Cl | O—C₂H₅ | |
| 2394 | —(CH₂)₄— | O | O—CH₂—CH=CH₂ | Q1 | Cl | O—C₂H₅ | |
| 2395 | —(CH₂)₄— | O | O—CH₂—C≡CH | Q1 | Cl | O—C₂H₅ | |
| 2396 | —(CH₂)₄— | O | O—CH₂—O—C₂H₅ | Q1 | Cl | O—C₂H₅ | |
| 2397 | —(CH₂)₄— | O | H | Q1 | O—CH₃ | O—C₂H₅ | |
| 2398 | —(CH₂)₄— | O | OH | Q1 | O—CH₃ | O—C₂H₅ | |
| 2399 | —(CH₂)₄— | O | O—CH₃ | Q1 | O—CH₃ | O—C₂H₅ | |
| 2400 | —(CH₂)₄— | O | O—C₂H₅ | Q1 | O—CH₃ | O—C₂H₅ | |
| 2401 | —(CH₂)₄— | O | O-n-C₃H₇ | Q1 | O—CH₃ | O—C₂H₅ | |
| 2402 | —(CH₂)₄— | O | O-i-C₃H₇ | Q1 | O—CH₃ | O—C₂H₅ | |
| 2403 | —(CH₂)₄— | O | O-n-C₄H₉ | Q1 | O—CH₃ | O—C₂H₅ | |
| 2404 | —(CH₂)₄— | O | O-i-C₄H₉ | Q1 | O—CH₃ | O—C₂H₅ | |
| 2405 | —(CH₂)₄— | O | O-s-C₄H₉ | Q1 | O—CH₃ | O—C₂H₅ | |
| 2406 | —(CH₂)₄— | O | O-t-C₄H₉ | Q1 | O—CH₃ | O—C₂H₅ | |
| 2407 | —(CH₂)₄— | O | O—(CH₂)₂—Cl | Q1 | O—CH₃ | O—C₂H₅ | |
| 2408 | —(CH₂)₄— | O | O—CH₂—S—CH₃ | Q1 | O—CH₃ | O—C₂H₅ | |
| 2409 | —(CH₂)₄— | O | O—CH₂—Ph | Q1 | O—CH₃ | O—C₂H₅ | |
| 2410 | —(CH₂)₄— | O | O—Ph | Q1 | O—CH₃ | O—C₂H₅ | |
| 2411 | —(CH₂)₄— | O | O—Ph—2Cl | Q1 | O—CH₃ | O—C₂H₅ | |
| 2412 | —(CH₂)₄— | O | O—CH₂—CH=CH₂ | Q1 | O—CH₃ | O—C₂H₅ | |
| 2413 | —(CH₂)₄— | O | O—CH₂—C≡CH | Q1 | O—CH₃ | O—C₂H₅ | |
| 2414 | —(CH₂)₄— | O | O—CH₂—O—C₂H₅ | Q1 | O—CH₃ | O—C₂H₅ | |
| 2415 | —(CH₂)₄— | O | H | Q1 | O—C₂H₅ | O—C₂H₅ | |
| 2416a | —(CH₂)₄— | O | OH | Q1 | O—C₂H₅ | O—C₂H₅ | cis |
| 2416b | —(CH₂)₄— | O | OH | Q1 | O—C₂H₅ | O—C₂H₅ | trans |
| 2417 | —(CH₂)₄— | O | O—CH₃ | Q1 | O—C₂H₅ | O—C₂H₅ | |
| 2418a | —(CH₂)₄— | O | O—C₂H₅ | Q1 | O—C₂H₅ | O—C₂H₅ | cis |
| 2418b | —(CH₂)₄— | O | O—C₂H₅ | Q1 | O—C₂H₅ | O—C₂H₅ | trans |
| 2419 | —(CH₂)₄— | O | O-n-C₃H₇ | Q1 | O—C₂H₅ | O—C₂H₅ | |
| 2420 | —(CH₂)₄— | O | O-i-C₃H₇ | Q1 | O—C₂H₅ | O—C₂H₅ | |
| 2421 | —(CH₂)₄— | O | O-n-C₄H₉ | Q1 | O—C₂H₅ | O—C₂H₅ | |
| 2422 | —(CH₂)₄— | O | O-i-C₄H₉ | Q1 | O—C₂H₅ | O—C₂H₅ | |
| 2423 | —(CH₂)₄— | O | O-s-C₄H₉ | Q1 | O—C₂H₅ | O—C₂H₅ | |
| 2424 | —(CH₂)₄— | O | O-t-C₄H₉ | Q1 | O—C₂H₅ | O—C₂H₅ | |
| 2425 | —(CH₂)₄— | O | O—(CH₂)₂—Cl | Q1 | O—C₂H₅ | O—C₂H₅ | |
| 2426 | —(CH₂)₄— | O | O—CH₂—S—CH₃ | Q1 | O—C₂H₅ | O—C₂H₅ | |
| 2427 | —(CH₂)₄— | O | O—CH₂—Ph | Q1 | O—C₂H₅ | O—C₂H₅ | |
| 2428 | —(CH₂)₄— | O | O—Ph | Q1 | O—C₂H₅ | O—C₂H₅ | |
| 2429 | —(CH₂)₄— | O | O—Ph—2Cl | Q1 | O—C₂H₅ | O—C₂H₅ | |
| 2430 | —(CH₂)₄— | O | O—CH₂—CH=CH₂ | Q1 | O—C₂H₅ | O—C₂H₅ | |
| 2431 | —(CH₂)₄— | O | O—CH₂—C≡CH | Q1 | O—C₂H₅ | O—C₂H₅ | |
| 2432 | —(CH₂)₄— | O | O—CH₂—O—C₂H₅ | Q1 | O—C₂H₅ | O—C₂H₅ | |
| 2433 | —(CH₂)₄— | O | H | Q1 | O-n-C₃H₇ | O-n-C₃H₇ | |
| 2434a | —(CH₂)₄— | O | OH | Q1 | O-n-C₃H₇ | O-n-C₃H₇ | cis |
| 2434b | —(CH₂)₄— | O | OH | Q1 | O-n-C₃H₇ | O-n-C₃H₇ | trans |
| 2435 | —(CH₂)₄— | O | O—CH₃ | Q1 | O-n-C₃H₇ | O-n-C₃H₇ | |
| 2436a | —(CH₂)₄— | O | O—C₂H₅ | Q1 | O-n-C₃H₇ | O-n-C₃H₇ | cis |
| 2436b | —(CH₂)₄— | O | O—C₂H₅ | Q1 | O-n-C₃H₇ | O-n-C₃H₇ | trans |
| 2437 | —(CH₂)₄— | O | O-n-C₃H₇ | Q1 | O-n-C₃H₇ | O-n-C₃H₇ | |
| 2438 | —(CH₂)₄— | O | O-i-C₃H₇ | Q1 | O-n-C₃H₇ | O-n-C₃H₇ | |
| 2439 | —(CH₂)₄— | O | O-n-C₄H₉ | Q1 | O-n-C₃H₇ | O-n-C₃H₇ | |
| 2440 | —(CH₂)₄— | O | O-i-C₄H₉ | Q1 | O-n-C₃H₇ | O-n-C₃H₇ | |
| 2441 | —(CH₂)₄— | O | O-s-C₄H₉ | Q1 | O-n-C₃H₇ | O-n-C₃H₇ | |

| No. | | | | | | | |
|---|---|---|---|---|---|---|---|
| 2442 | —(CH₂)₄— | O | O—t-C₄H₉ | Cl | O-n-C₃H₇ | O-n-C₃H₇ | |
| 2443 | —(CH₂)₄— | O | O—(CH₂)₂—Cl | Cl | O-n-C₃H₇ | O-n-C₃H₇ | |
| 2444 | —(CH₂)₄— | O | O—CH₂—S—CH₃ | Cl | O-n-C₃H₇ | O-n-C₃H₇ | |
| 2445 | —(CH₂)₄— | O | O—CH₂—Ph | Cl | O-n-C₃H₇ | O-n-C₃H₇ | |
| 2446 | —(CH₂)₄— | O | O—Ph | Cl | O-n-C₃H₇ | O-n-C₃H₇ | |
| 2447 | —(CH₂)₄— | O | O—Ph—2Cl | Cl | O-n-C₃H₇ | O-n-C₃H₇ | |
| 2448 | —(CH₂)₄— | O | O—CH₂—CH=CH₂ | Cl | O-n-C₃H₇ | O-n-C₃H₇ | |
| 2449 | —(CH₂)₄— | O | O—CH₂—C≡CH | Cl | O-n-C₃H₇ | O-n-C₃H₇ | |
| 2450 | —(CH₂)₄— | O | O—CH₂—O—C₂H₅ | Cl | O-n-C₃H₇ | O-n-C₃H₇ | |
| 2451 | —(CH₂)₄— | O | H | Cl | O-n-C₃H₇ | O-n-C₃H₇ | |
| 2452 | —(CH₂)₄— | O | OH | Cl | O-i-C₃H₇ | O-i-C₃H₇ | |
| 2453 | —(CH₂)₄— | O | O—CH₃ | Cl | O-i-C₃H₇ | O-i-C₃H₇ | |
| 2454 | —(CH₂)₄— | O | O—C₂H₅ | Cl | O-i-C₃H₇ | O-i-C₃H₇ | |
| 2455 | —(CH₂)₄— | O | O-n-C₃H₇ | Cl | O-i-C₃H₇ | O-i-C₃H₇ | |
| 2456 | —(CH₂)₄— | O | O-i-C₃H₇ | Cl | O-i-C₃H₇ | O-i-C₃H₇ | |
| 2457 | —(CH₂)₄— | O | O-n-C₄H₉ | Cl | O-i-C₃H₇ | O-i-C₃H₇ | |
| 2458 | —(CH₂)₄— | O | O-i-C₄H₉ | Cl | O-i-C₃H₇ | O-i-C₃H₇ | |
| 2459 | —(CH₂)₄— | O | O-s-C₄H₉ | Cl | O-i-C₃H₇ | O-i-C₃H₇ | |
| 2460 | —(CH₂)₄— | O | O-t-C₄H₉ | Cl | O-i-C₃H₇ | O-i-C₃H₇ | |
| 2461 | —(CH₂)₄— | O | O—(CH₂)₂—Cl | Cl | O-i-C₃H₇ | O-i-C₃H₇ | |
| 2462 | —(CH₂)₄— | O | O—CH₂—S—CH₃ | Cl | O-i-C₃H₇ | O-i-C₃H₇ | |
| 2463 | —(CH₂)₄— | O | O—CH₂—Ph | Cl | O-i-C₃H₇ | O-i-C₃H₇ | |
| 2464 | —(CH₂)₄— | O | O—Ph | Cl | O-i-C₃H₇ | O-i-C₃H₇ | |
| 2465 | —(CH₂)₄— | O | O—Ph—2Cl | Cl | O-i-C₃H₇ | O-i-C₃H₇ | |
| 2466 | —(CH₂)₄— | O | O—CH₂—CH=CH₂ | Cl | O-i-C₃H₇ | O-i-C₃H₇ | |
| 2467 | —(CH₂)₄— | O | O—CH₂—C≡CH | Cl | O-i-C₃H₇ | O-i-C₃H₇ | |
| 2468 | —(CH₂)₄— | O | O—CH₂—O—C₂H₅ | Cl | O-i-C₃H₇ | O-i-C₃H₇ | |
| 2469 | —(CH₂)₄— | O | H | Cl | O-i-C₃H₇ | O-i-C₃H₇ | |
| 2470 | —(CH₂)₄— | O | OH | Cl | O—CHF₂ | O—CHF₂ | |
| 2471 | —(CH₂)₄— | O | O—CH₃ | Cl | O—CHF₂ | O—CHF₂ | |
| 2472 | —(CH₂)₄— | O | O—C₂H₅ | Cl | O—CHF₂ | O—CHF₂ | |
| 2473 | —(CH₂)₄— | O | O-n-C₃H₇ | Cl | O—CHF₂ | O—CHF₂ | |
| 2474 | —(CH₂)₄— | O | O-i-C₃H₇ | Cl | O—CHF₂ | O—CHF₂ | |
| 2475 | —(CH₂)₄— | O | O-n-C₄H₉ | Cl | O—CHF₂ | O—CHF₂ | |
| 2476 | —(CH₂)₄— | O | O-i-C₄H₉ | Cl | O—CHF₂ | O—CHF₂ | |
| 2477 | —(CH₂)₄— | O | O-s-C₄H₉ | Cl | O—CHF₂ | O—CHF₂ | |
| 2478 | —(CH₂)₄— | O | O-t-C₄H₉ | Cl | O—CHF₂ | O—CHF₂ | |
| 2479 | —(CH₂)₄— | O | O—(CH₂)₂—Cl | Cl | O—CHF₂ | O—CHF₂ | |
| 2480 | —(CH₂)₄— | O | O—CH₂—S—CH₃ | Cl | O—CHF₂ | O—CHF₂ | |
| 2481 | —(CH₂)₄— | O | O—CH₂—Ph | Cl | O—CHF₂ | O—CHF₂ | |
| 2482 | —(CH₂)₄— | O | O—Ph | Cl | O—CHF₂ | O—CHF₂ | |
| 2483 | —(CH₂)₄— | O | O—Ph—2Cl | Cl | O—CHF₂ | O—CHF₂ | |
| 2484 | —(CH₂)₄— | O | O—CH₂—CH=CH₂ | Cl | O—CHF₂ | O—CHF₂ | |
| 2485 | —(CH₂)₄— | O | O—CH₂—C≡CH | Cl | O—CHF₂ | O—CHF₂ | |
| 2486 | —(CH₂)₄— | O | O—CH₂—O—C₂H₅ | Cl | O—CHF₂ | O—CHF₂ | |
| 2487 | —(CH₂)₄— | O | H | Cl | O—CHF₂ | O—CHF₂ | |
| 2488 | —(CH₂)₄— | O | OH | Cl | S—CH₃ | O—CH₃ | |
| 2489a | —(CH₂)₄— | O | O—CH₃ | Cl | S—CH₃ | O—CH₃ | cis |
| 2489b | —(CH₂)₄— | O | O—CH₃ | Cl | S—CH₃ | O—CH₃ | trans |
| 2490 | —(CH₂)₄— | O | O—C₂H₅ | Cl | S—CH₃ | O—CH₃ | |
| 2491 | —(CH₂)₄— | O | O-n-C₃H₇ | Cl | S—CH₃ | O—CH₃ | |
| 2492 | —(CH₂)₄— | O | O-i-C₃H₇ | Cl | S—CH₃ | O—CH₃ | |
| 2493 | —(CH₂)₄— | O | O-n-C₄H₉ | Cl | S—CH₃ | O—CH₃ | |
| 2494 | —(CH₂)₄— | O | O-i-C₄H₉ | Cl | S—CH₃ | O—CH₃ | |

-continued

| | | | | | | |
|---|---|---|---|---|---|---|
| 2495 | —(CH₂)₄— | O | O-s-C₄H₉ | O | S—CH₃ | O—CH₃ |
| 2496 | —(CH₂)₄— | O | O-t-C₄H₉ | O | S—CH₃ | O—CH₃ |
| 2497 | —(CH₂)₄— | O | O—(CH₂)₂—Cl | O | S—CH₃ | O—CH₃ |
| 2498 | —(CH₂)₄— | O | O—CH₂—S—CH₃ | O | S—CH₃ | O—CH₃ |
| 2499 | —(CH₂)₄— | O | O—CH₂—Ph | O | S—CH₃ | O—CH₃ |
| 2500 | —(CH₂)₄— | O | O—Ph | O | S—CH₃ | O—CH₃ |
| 2501 | —(CH₂)₄— | O | O—Ph—2Cl | O | S—CH₃ | O—CH₃ |
| 2502 | —(CH₂)₄— | O | O—CH₂—CH=CH₂ | O | S—CH₃ | O—CH₃ |
| 2503 | —(CH₂)₄— | O | O—CH₂—C≡CH | O | S—CH₃ | |
| 2504 | —(CH₂)₄— | O | O—CH₂—O—C₂H₅ | O | S—CH₃ | |
| 2505 | —(CH₂)₄— | O | H | O | S—CH₃ | Cl |
| 2506 | —(CH₂)₄— | O | OH | O | S—CH₃ | Cl |
| 2507 | —(CH₂)₄— | O | O—CH₃ | O | S—CH₃ | Cl |
| 2508a | —(CH₂)₄— | O | O—C₂H₅ | O | S—CH₃ | Cl cis |
| 2508b | —(CH₂)₄— | O | O—C₂H₅ | O | S—CH₃ | Cl trans |
| 2509 | —(CH₂)₄— | O | O-n-C₃H₇ | O | S—CH₃ | Cl |
| 2510 | —(CH₂)₄— | O | O-i-C₃H₇ | O | S—CH₃ | Cl |
| 2511 | —(CH₂)₄— | O | O-n-C₄H₉ | O | S—CH₃ | Cl |
| 2512 | —(CH₂)₄— | O | O-i-C₄H₉ | O | S—CH₃ | Cl |
| 2513 | —(CH₂)₄— | O | O-s-C₄H₉ | O | S—CH₃ | Cl |
| 2514 | —(CH₂)₄— | O | O-t-C₄H₉ | O | S—CH₃ | Cl |
| 2515 | —(CH₂)₄— | O | O—(CH₂)₂—Cl | O | S—CH₃ | Cl |
| 2516 | —(CH₂)₄— | O | O—CH₂—S—CH₃ | O | S—CH₃ | Cl |
| 2517 | —(CH₂)₄— | O | O—CH₂—Ph | O | S—CH₃ | Cl |
| 2518 | —(CH₂)₄— | O | O—Ph | O | S—CH₃ | Cl |
| 2519 | —(CH₂)₄— | O | O—Ph—2Cl | O | S—CH₃ | Cl |
| 2520 | —(CH₂)₄— | O | O—CH₂—CH=CH₂ | O | S—CH₃ | Cl |
| 2521 | —(CH₂)₄— | O | O—CH₂—C≡CH | O | S—CH₃ | Cl |
| 2522 | —(CH₂)₄— | O | O—CH₂—O—C₂H₅ | O | S—CH₃ | Cl |
| 2523 | —(CH₂)₄— | O | H | O | S—CH₃ | CH₃ |
| 2524 | —(CH₂)₄— | O | OH | O | S—CH₃ | CH₃ |
| 2525 | —(CH₂)₄— | O | O—CH₃ | O | S—CH₃ | CH₃ |
| 2526 | —(CH₂)₄— | O | O—C₂H₅ | O | S—CH₃ | CH₃ |
| 2527 | —(CH₂)₄— | O | O-n-C₃H₇ | O | S—CH₃ | CH₃ |
| 2528 | —(CH₂)₄— | O | O-i-C₃H₇ | O | S—CH₃ | CH₃ |
| 2529 | —(CH₂)₄— | O | O-n-C₄H₉ | O | S—CH₃ | CH₃ |
| 2530 | —(CH₂)₄— | O | O-i-C₄H₉ | O | S—CH₃ | CH₃ |
| 2531 | —(CH₂)₄— | O | O-s-C₄H₉ | O | S—CH₃ | CH₃ |
| 2532 | —(CH₂)₄— | O | O-t-C₄H₉ | O | S—CH₃ | CH₃ |
| 2533 | —(CH₂)₄— | O | O—(CH₂)₂—Cl | O | S—CH₃ | CH₃ |
| 2534 | —(CH₂)₄— | O | O—CH₂—S—CH₃ | O | S—CH₃ | CH₃ |
| 2535 | —(CH₂)₄— | O | O—CH₂—Ph | O | S—CH₃ | CH₃ |
| 2536 | —(CH₂)₄— | O | O—Ph | O | S—CH₃ | CH₃ |
| 2537 | —(CH₂)₄— | O | O—Ph—2Cl | O | S—CH₃ | CH₃ |
| 2538 | —(CH₂)₄— | O | O—CH₂—CH=CH₂ | O | S—CH₃ | CH₃ |
| 2539 | —(CH₂)₄— | O | O—CH₂—C≡CH | O | S—CH₃ | CH₃ |
| 2540 | —(CH₂)₄— | O | O—CH₂—O—C₂H₅ | O | S—CH₃ | CH₃ |
| 2541 | —(CH₂)₄— | O | H | O | Cl | N(CH₃)₂ |
| 2542a | —(CH₂)₄— | O | OH | O | Cl | N(CH₃)₂ cis |
| 2542b | —(CH₂)₄— | O | OH | O | Cl | N(CH₃)₂ trans |
| 2543a | —(CH₂)₄— | O | O—C₂H₅ | O | Cl | N(CH₃)₂ cis |
| 2543b | —(CH₂)₄— | O | O—C₂H₅ | O | Cl | N(CH₃)₂ trans |
| 2544 | —(CH₂)₄— | O | O-n-C₃H₇ | O | Cl | N(CH₃)₂ |
| 2545 | —(CH₂)₄— | O | O-i-C₃H₇ | O | Cl | N(CH₃)₂ |

-continued

| | | | | |
|---|---|---|---|---|
| 2546 | —(CH₂)₄— | O | O-n-C₄H₉ | Cl | N(CH₃)₂ |
| 2547 | —(CH₂)₄— | O | O-i-C₄H₉ | Cl | N(CH₃)₂ |
| 2548 | —(CH₂)₄— | O | O-s-C₄H₉ | Cl | N(CH₃)₂ |
| 2549 | —(CH₂)₄— | O | O-t-C₄H₉ | Cl | N(CH₃)₂ |
| 2550 | —(CH₂)₄— | O | O—(CH₂)₂—Cl | Cl | N(CH₃)₂ |
| 2551 | —(CH₂)₄— | O | O—CH₂—S—CH₃ | Cl | N(CH₃)₂ |
| 2552 | —(CH₂)₄— | O | O—CH₂—Ph | Cl | N(CH₃)₂ |
| 2553 | —(CH₂)₄— | O | O—Ph | Cl | N(CH₃)₂ |
| 2554 | —(CH₂)₄— | O | O—Ph—2Cl | Cl | N(CH₃)₂ |
| 2555 | —(CH₂)₄— | O | O—CH₂—CH=CH₂ | Cl | N(CH₃)₂ |
| 2556 | —(CH₂)₄— | O | O—CH₂—C≡CH | Cl | N(CH₃)₂ |
| 2557 | —(CH₂)₄— | O | O—CH₂—O—C₂H₅ | Cl | N(CH₃)₂ |
| 2558 | —(CH₂)₄— | O | H | O—CH₃ | N(CH₃)₂ |
| 2559a | —(CH₂)₄— | O | OH | O—CH₃ | N(CH₃)₂ | cis |
| 2559b | —(CH₂)₄— | O | OH | O—CH₃ | N(CH₃)₂ | trans |
| 2560a | —(CH₂)₄— | O | O—C₂H₅ | O—CH₃ | N(CH₃)₂ | cis |
| 2560b | —(CH₂)₄— | O | O—C₂H₅ | O—CH₃ | N(CH₃)₂ | trans |
| 2561 | —(CH₂)₄— | O | O-n-C₃H₇ | O—CH₃ | N(CH₃)₂ |
| 2562 | —(CH₂)₄— | O | O-i-C₃H₇ | O—CH₃ | N(CH₃)₂ |
| 2563 | —(CH₂)₄— | O | O-n-C₄H₉ | O—CH₃ | N(CH₃)₂ |
| 2564 | —(CH₂)₄— | O | O-i-C₄H₉ | O—CH₃ | N(CH₃)₂ |
| 2565 | —(CH₂)₄— | O | O-s-C₄H₉ | O—CH₃ | N(CH₃)₂ |
| 2566 | —(CH₂)₄— | O | O-t-C₄H₉ | O—CH₃ | N(CH₃)₂ |
| 2567 | —(CH₂)₄— | O | O—(CH₂)₂—Cl | O—CH₃ | N(CH₃)₂ |
| 2568 | —(CH₂)₄— | O | O—CH₂—S—CH₃ | O—CH₃ | N(CH₃)₂ |
| 2569 | —(CH₂)₄— | O | O—CH₂—Ph | O—CH₃ | N(CH₃)₂ |
| 2570 | —(CH₂)₄— | O | O—Ph | O—CH₃ | N(CH₃)₂ |
| 2571 | —(CH₂)₄— | O | O—Ph—2Cl | O—CH₃ | N(CH₃)₂ |
| 2572 | —(CH₂)₄— | O | O—CH₂—CH=CH₂ | O—CH₃ | N(CH₃)₂ |
| 2573 | —(CH₂)₄— | O | O—CH₂—C≡CH | O—CH₃ | N(CH₃)₂ |
| 2574 | —(CH₂)₄— | O | O—CH₂—O—C₂H₅ | O—CH₃ | N(CH₃)₂ |

TABLE 3

$$R^4\underset{R^3}{\overset{F}{\underset{|}{C}}}\overset{O}{\overset{\|}{C}}-Y \quad Q=Q_2= \underset{\underset{R^2}{N}}{\overset{\overset{R^1}{N}}{\bigcirc}} \text{ or } Q=Q_1= \underset{\underset{R^2}{N}}{\overset{\overset{R^1}{N}}{\bigcirc}}$$

| Compound No. | R³ | R⁴ | W | Y | Q | R¹ | R² | Remarks |
|---|---|---|---|---|---|---|---|---|
| 3001 | —(CH₂)₃— | | O | H | Q₂ | O—CH₃ | O—CH₃ | |
| 3002 | —(CH₂)₃— | | O | OH | Q₂ | O—CH₃ | O—CH₃ | |
| 3003a | —(CH₂)₃— | | O | O—CH₃ | Q₂ | O—CH₃ | O—CH₃ | cis |
| 3003b | —(CH₂)₃— | | O | O—CH₃ | Q₂ | O—CH₃ | O—CH₃ | trans |
| 3004 | —(CH₂)₃— | | O | O—C₂H₅ | Q₂ | O—CH₃ | O—CH₃ | |
| 3005 | —(CH₂)₃— | | O | O-n-C₃H₇ | Q₂ | O—CH₃ | O—CH₃ | |
| 3006 | —(CH₂)₃— | | O | O-i-C₃H₇ | Q₂ | O—CH₃ | O—CH₃ | |
| 3007 | —(CH₂)₃— | | O | O-n-C₄H₉ | Q₂ | O—CH₃ | O—CH₃ | |
| 3008 | —(CH₂)₃— | | O | O-i-C₄H₉ | Q₂ | O—CH₃ | O—CH₃ | |
| 3009 | —(CH₂)₃— | | O | O-s-C₄H₉ | Q₂ | O—CH₃ | O—CH₃ | |
| 3010 | —(CH₂)₃— | | O | O-t-C₄H₉ | Q₂ | O—CH₃ | O—CH₃ | |
| 3011 | —(CH₂)₃— | | O | O—(CH₂)₂—Cl | Q₂ | O—CH₃ | O—CH₃ | |
| 3012 | —(CH₂)₃— | | O | O—CH₂S—CH₃ | Q₂ | O—CH₃ | O—CH₃ | |
| 3013 | —(CH₂)₃— | | O | O—CH₂—Ph | Q₂ | O—CH₃ | O—CH₃ | |
| 3014 | —(CH₂)₃— | | O | O—Ph | Q₂ | O—CH₃ | O—CH₃ | |
| 3015 | —(CH₂)₃— | | O | O—Ph-2Cl | Q₂ | O—CH₃ | O—CH₃ | |
| 3016 | —(CH₂)₃— | | O | O—CH₂—CH=CH₂ | Q₂ | O—CH₃ | O—CH₃ | |
| 3017 | —(CH₂)₃— | | O | O—CH₂—C≡CH | Q₂ | O—CH₃ | O—CH₃ | |
| 3018 | —(CH₂)₃— | | O | O—CH₂—O—C₂H₅ | Q₂ | O—CH₃ | O—CH₃ | |
| 3019 | —(CH₂)₃— | | O | H | Q₂ | Cl | O—CH₃ | |
| 3020 | —(CH₂)₃— | | O | OH | Q₂ | Cl | O—CH₃ | |
| 3021 | —(CH₂)₃— | | O | O—CH₃ | Q₂ | Cl | O—CH₃ | |
| 3022 | —(CH₂)₃— | | O | O—C₂H₅ | Q₂ | Cl | O—CH₃ | |
| 3023 | —(CH₂)₃— | | O | O-n-C₃H₇ | Q₂ | Cl | O—CH₃ | |
| 3024 | —(CH₂)₃— | | O | O-i-C₃H₇ | Q₂ | Cl | O—CH₃ | |
| 3025 | —(CH₂)₃— | | O | O-n-C₄H₉ | Q₂ | Cl | O—CH₃ | |
| 3026 | —(CH₂)₃— | | O | O-i-C₄H₉ | Q₂ | Cl | O—CH₃ | |
| 3027 | —(CH₂)₃— | | O | O-s-C₄H₉ | Q₂ | Cl | O—CH₃ | |
| 3028 | —(CH₂)₃— | | O | O-t-C₄H₉ | Q₂ | Cl | O—CH₃ | |
| 3029 | —(CH₂)₃— | | O | O—(CH₂)₂—Cl | Q₂ | Cl | O—CH₃ | |
| 3030 | —(CH₂)₃— | | O | O—CH₂—S—CH₃ | Q₂ | Cl | O—CH₃ | |
| 3031 | —(CH₂)₃— | | O | O—CH₂—Ph | Q₂ | Cl | O—CH₃ | |
| 3032 | —(CH₂)₃— | | O | O—Ph | Q₂ | Cl | O—CH₃ | |
| 3033 | —(CH₂)₃— | | O | O—Ph-2Cl | Q₂ | Cl | O—CH₃ | |
| 3034 | —(CH₂)₃— | | O | O—CH₂—CH=CH₂ | Q₂ | Cl | O—CH₃ | |
| 3035 | —(CH₂)₃— | | O | O—CH₂—C≡CH | Q₂ | Cl | O—CH₃ | |
| 3036 | —(CH₂)₃— | | O | O—CH₂—O—C₂H₅ | Q₂ | Cl | O—CH₃ | |
| 3037 | —(CH₂)₃— | | O | H | Q₂ | O—CH₃ | O—C₂H₅ | |
| 3038 | —(CH₂)₃— | | O | OH | Q₂ | O—CH₃ | O—C₂H₅ | |
| 3039 | —(CH₂)₃— | | O | O—CH₃ | Q₂ | O—CH₃ | O—C₂H₅ | |
| 3040 | —(CH₂)₃— | | O | O—C₂H₅ | Q₂ | O—CH₃ | O—C₂H₅ | |
| 3041 | —(CH₂)₃— | | O | O-n-C₃H₇ | Q₂ | O—CH₃ | O—C₂H₅ | |

TABLE 3-continued

| Compound No. | R³ | R⁴ | W | Y | Q | R¹ | R² | Remarks |
|---|---|---|---|---|---|---|---|---|
| 3042 | —(CH₂)₃— | | O | O-i-C₃H₇ | Q₂ | O—CH₃ | O—C₂H₅ | |
| 3043 | —(CH₂)₃— | | O | O-n-C₄H₉ | Q₂ | O—CH₃ | O—C₂H₅ | |
| 3044 | —(CH₂)₃— | | O | O-i-C₄H₉ | Q₂ | O—CH₃ | O—C₂H₅ | |
| 3045 | —(CH₂)₃— | | O | O-s-C₄H₉ | Q₂ | O—CH₃ | O—C₂H₅ | |
| 3046 | —(CH₂)₃— | | O | O-t-C₄H₉ | Q₂ | O—CH₃ | O—C₂H₅ | |
| 3047 | —(CH₂)₃— | | O | O—(CH₂)₂—Cl | Q₂ | O—CH₃ | O—C₂H₅ | |
| 3048 | —(CH₂)₃— | | O | O—CH₂—S—CH₃ | Q₂ | O—CH₃ | O—C₂H₅ | |
| 3049 | —(CH₂)₃— | | O | O—CH₂—Ph | Q₂ | O—CH₃ | O—C₂H₅ | |
| 3050 | —(CH₂)₃— | | O | O—Ph | Q₂ | O—CH₃ | O—C₂H₅ | |
| 3051 | —(CH₂)₃— | | O | O—Ph-2Cl | Q₂ | O—CH₃ | O—C₂H₅ | |
| 3052 | —(CH₂)₃— | | O | O—CH₂—CH=CH₂ | Q₂ | O—CH₃ | O—C₂H₅ | |
| 3053 | —(CH₂)₃— | | O | O—CH₂—C≡CH | Q₂ | O—CH₃ | O—C₂H₅ | |
| 3054 | —(CH₂)₃— | | O | O—CH₂—O—C₂H₅ | Q₂ | O—CH₃ | O—C₂H₅ | |
| 3055 | —(CH₂)₃— | | O | H | Q₂ | O—C₂H₅ | O—C₂H₅ | |
| 3056 | —(CH₂)₃— | | O | OH | Q₂ | O—C₂H₅ | O—C₂H₅ | |
| 3057 | —(CH₂)₃— | | O | O—CH₃ | Q₂ | O—C₂H₅ | O—C₂H₅ | |
| 3058 | —(CH₂)₃— | | O | O—C₂H₅ | Q₂ | O—C₂H₅ | O—C₂H₅ | |
| 3059 | —(CH₂)₃— | | O | O-n-C₃H₇ | Q₂ | O—C₂H₅ | O—C₂H₅ | |
| 3060 | —(CH₂)₃— | | O | O-i-C₃H₇ | Q₂ | O—C₂H₅ | O—C₂H₅ | |
| 3061 | —(CH₂)₃— | | O | O-n-C₄H₉ | Q₂ | O—C₂H₅ | O—C₂H₅ | |
| 3062 | —(CH₂)₃— | | O | O-s-C₄H₉ | Q₂ | O—C₂H₅ | O—C₂H₅ | |
| 3063 | —(CH₂)₃— | | O | O-i-C₄H₉ | Q₂ | O—C₂H₅ | O—C₂H₅ | |
| 3064 | —(CH₂)₃— | | O | O-t-C₄H₉ | Q₂ | O—C₂H₅ | O—C₂H₅ | |
| 3065 | —(CH₂)₃— | | O | O—(CH₂)₂—Cl | Q₂ | O—C₂H₅ | O—C₂H₅ | |
| 3066 | —(CH₂)₃— | | O | O—CH₂—S—CH₃ | Q₂ | O—C₂H₅ | O—C₂H₅ | |
| 3067 | —(CH₂)₃— | | O | O—CH₂—Ph | Q₂ | O—C₂H₅ | O—C₂H₅ | |
| 3068 | —(CH₂)₃— | | O | O—Ph | Q₂ | O—C₂H₅ | O—C₂H₅ | |
| 3069 | —(CH₂)₃— | | O | O—Ph-2Cl | Q₂ | O—C₂H₅ | O—C₂H₅ | |
| 3070 | —(CH₂)₃— | | O | O—CH₂—CH=CH₂ | Q₂ | O—C₂H₅ | O—C₂H₅ | |
| 3071 | —(CH₂)₃— | | O | O—CH₂—C≡CH | Q₂ | O—C₂H₅ | O—C₂H₅ | |
| 3072 | —(CH₂)₃— | | O | O—CH₂—O—C₂H₅ | Q₂ | O—C₂H₅ | O—C₂H₅ | |
| 3073 | —(CH₂)₃— | | O | O—CH₂—C≡CH | Q₂ | O—CH₃ | O—C₂H₅ | |
| 3074 | —(CH₂)₃— | | O | O—CH₂—O—C₂H₅ | Q₂ | O—CH₃ | O—C₂H₅ | |
| 3075 | —(CH₂)₃— | | O | H | Q₃ | O—CH₃ | Cl | |
| 3076 | —(CH₂)₃— | | O | OH | Q₃ | S—CH₃ | Cl | |
| 3077a | —(CH₂)₃— | | O | O—CH₃ | Q₃ | S—CH₃ | Cl | cis |
| 3077b | —(CH₂)₃— | | O | O—CH₃ | Q₃ | S—CH₃ | Cl | trans |
| 3078 | —(CH₂)₃— | | O | O—C₂H₅ | Q₃ | S—CH₃ | Cl | |
| 3079 | —(CH₂)₃— | | O | O-n-C₃H₇ | Q₃ | S—CH₃ | Cl | |
| 3080 | —(CH₂)₃— | | O | O-i-C₃H₇ | Q₃ | S—CH₃ | Cl | |
| 3081 | —(CH₂)₃— | | O | O-n-C₄H₉ | Q₃ | S—CH₃ | Cl | |
| 3082 | —(CH₂)₃— | | O | O-i-C₄H₉ | Q₃ | S—CH₃ | Cl | |

TABLE 3-continued $$R^4 \overset{F}{\underset{R^3}{C}} \overset{O}{\underset{}{C}} - Y \quad Q=Q_2= \begin{array}{c} R^1 \\ N \\ N \end{array} R^2 \quad or \quad Q=Q_3= \begin{array}{c} R^1 \\ N \\ \end{array} R^2$$

W—Q

| Compound No. | R³ | R⁴ | W | Y | Q | R¹ | R² | Remarks |
|---|---|---|---|---|---|---|---|---|
| 3083 | —(CH₂)₃— | | O | O-s-C₄H₉ | Q₂ | S—CH₃ | Cl | |
| 3084 | —(CH₂)₃— | | O | O-t-C₄H₉ | Q₂ | S—CH₃ | Cl | |
| 3085 | —(CH₂)₃— | | O | O—(CH₂)₂—Cl | Q₂ | S—CH₃ | Cl | |
| 3086 | —(CH₂)₃— | | O | O—CH₂—S—CH₃ | Q₂ | S—CH₃ | Cl | |
| 3087 | —(CH₂)₃— | | O | O—CH₂—Ph | Q₂ | S—CH₃ | Cl | |
| 3088 | —(CH₂)₃— | | O | O—Ph | Q₂ | S—CH₃ | Cl | |
| 3089 | —(CH₂)₃— | | O | O—Ph-2Cl | Q₂ | S—CH₃ | Cl | |
| 3090 | —(CH₂)₃— | | O | O—CH₂—CH=CH₂ | Q₂ | S—CH₃ | Cl | |
| 3091 | —(CH₂)₃— | | O | O—CH₂—C≡CH | Q₂ | S—CH₃ | Cl | |
| 3092 | —(CH₂)₃— | | O | O—CH₂—O—C₂H₅ | Q₂ | S—CH₃ | Cl | |
| 3093 | —(CH₂)₃— | | O | H | Q₂ | S—CH₃ | Cl | |
| 3094a | —(CH₂)₃— | | O | OH | Q₂ | S—CH₃ | Cl | cis |
| 3094b | —(CH₂)₃— | | O | OH | Q₂ | S—CH₃ | Cl | trans |
| 3095a | —(CH₂)₃— | | O | O—C₂H₅ | Q₂ | S—CH₃ | Cl | cis |
| 3095b | —(CH₂)₃— | | O | O—C₂H₅ | Q₂ | S—CH₃ | Cl | trans |
| 3096 | —(CH₂)₃— | | O | O-n-C₃H₇ | Q₂ | S—CH₃ | O—CH₃ | |
| 3097 | —(CH₂)₃— | | O | O-i-C₃H₇ | Q₂ | S—CH₃ | O—CH₃ | |
| 3098 | —(CH₂)₃— | | O | O-n-C₄H₉ | Q₂ | S—CH₃ | O—CH₃ | |
| 3099 | —(CH₂)₃— | | O | O-i-C₄H₉ | Q₂ | S—CH₃ | O—CH₃ | |
| 3100 | —(CH₂)₃— | | O | O-s-C₄H₉ | Q₂ | S—CH₃ | O—CH₃ | |
| 3101 | —(CH₂)₃— | | O | O-t-C₄H₉ | Q₂ | S—CH₃ | O—CH₃ | |
| 3102 | —(CH₂)₃— | | O | O—(CH₂)₂—Cl | Q₂ | S—CH₃ | O—CH₃ | |
| 3103 | —(CH₂)₃— | | O | O—CH₂—S—CH₃ | Q₂ | S—CH₃ | O—CH₃ | |
| 3104 | —(CH₂)₃— | | O | O—CH₂—Ph | Q₂ | S—CH₃ | O—CH₃ | |
| 3105 | —(CH₂)₃— | | O | O—Ph | Q₂ | S—CH₃ | O—CH₃ | |
| 3106 | —(CH₂)₃— | | O | O—Ph-2Cl | Q₂ | S—CH₃ | O—CH₃ | |
| 3107 | —(CH₂)₃— | | O | O—CH₂—CH=CH₂ | Q₂ | S—CH₃ | O—CH₃ | |
| 3108 | —(CH₂)₃— | | O | O—CH₂—C≡CH | Q₂ | S—CH₃ | O—CH₃ | |
| 3109 | —(CH₂)₃— | | O | O—CH₂—O—C₂H₅ | Q₂ | S—CH₃ | O—CH₃ | |
| 3110 | —(CH₂)₃— | | O | H | Q₂ | S—CH₃ | O—CH₃ | |
| 3111 | —(CH₂)₃— | | O | OH | Q₂ | SO₂CH₃ | Cl | |
| 3112 | —(CH₂)₃— | | O | O—CH₃ | Q₂ | SO₂CH₃ | Cl | |
| 3113 | —(CH₂)₃— | | O | O—C₂H₅ | Q₂ | SO₂CH₃ | Cl | |
| 3114 | —(CH₂)₃— | | O | O-n-C₃H₇ | Q₂ | SO₂CH₃ | Cl | |
| 3115 | —(CH₂)₃— | | O | O-i-C₃H₇ | Q₂ | SO₂CH₃ | Cl | |
| 3116 | —(CH₂)₃— | | O | O-n-C₄H₉ | Q₂ | SO₂CH₃ | Cl | |
| 3117 | —(CH₂)₃— | | O | O-i-C₄H₉ | Q₂ | SO₂CH₃ | Cl | |
| 3118 | —(CH₂)₃— | | O | O-s-C₄H₉ | Q₂ | SO₂CH₃ | Cl | |
| 3119 | —(CH₂)₃— | | O | O-t-C₄H₉ | Q₂ | SO₂CH₃ | Cl | |
| 3120 | —(CH₂)₃— | | O | O—(CH₂)₂—Cl | Q₂ | SO₂CH₃ | Cl | |
| 3121 | —(CH₂)₃— | | O | O—CH₂—S—CH₃ | Q₂ | SO₂CH₃ | Cl | |
| 3122 | —(CH₂)₃— | | O | O—CH₂—Ph | Q₂ | SO₂CH₃ | Cl | |

TABLE 3-continued

| Compound No. | R³ | R⁴ | W | Y | Q | R¹ | R² | Remarks |
|---|---|---|---|---|---|---|---|---|
| 3123 | —(CH₂)₃— | | O | O—Ph | Q₃ | SO₂CH₃ | Cl | |
| 3124 | —(CH₂)₃— | | O | O—Ph-2Cl | Q₃ | SO₂CH₃ | Cl | |
| 3125 | —(CH₂)₃— | | O | O—CH₂—CH=CH₂ | Q₃ | SO₂CH₃ | Cl | |
| 3126 | —(CH₂)₃— | | O | O—CH₂—C≡CH | Q₃ | SO₂CH₃ | Cl | |
| 3127 | —(CH₂)₃— | | O | O—CH₂—O—C₂H₅ | Q₃ | SO₂CH₃ | Cl | |
| 3128 | —(CH₂)₃— | | O | H | Q₃ | SO₂CH₃ | O—CH₃ | |
| 3129 | —(CH₂)₃— | | O | OH | Q₃ | SO₂CH₃ | O—CH₃ | |
| 3130 | —(CH₂)₃— | | O | O—CH₃ | Q₃ | SO₂CH₃ | O—CH₃ | |
| 3131 | —(CH₂)₃— | | O | O—C₂H₅ | Q₃ | SO₂CH₃ | O—CH₃ | |
| 3133 | —(CH₂)₃— | | O | O-n-C₃H₇ | Q₃ | SO₂CH₃ | O—CH₃ | |
| 3134 | —(CH₂)₃— | | O | O-i-C₃H₇ | Q₃ | SO₂CH₃ | O—CH₃ | |
| 3135 | —(CH₂)₃— | | O | O-n-C₄H₉ | Q₃ | SO₂CH₃ | O—CH₃ | |
| 3136 | —(CH₂)₃— | | O | O-i-C₄H₉ | Q₃ | SO₂CH₃ | O—CH₃ | |
| 3137 | —(CH₂)₃— | | O | O-s-C₄H₉ | Q₃ | SO₂CH₃ | O—CH₃ | |
| 3138 | —(CH₂)₃— | | O | O-t-C₄H₉ | Q₃ | SO₂CH₃ | O—CH₃ | |
| 3139 | —(CH₂)₃— | | O | O—(CH₂)₂—Cl | Q₃ | SO₂CH₃ | O—CH₃ | |
| 3140 | —(CH₂)₃— | | O | O—CH₂—S—CH₃ | Q₃ | SO₂CH₃ | O—CH₃ | |
| 3141 | —(CH₂)₃— | | O | O—CH₂—Ph | Q₃ | SO₂CH₃ | O—CH₃ | |
| 3142 | —(CH₂)₃— | | O | O—Ph | Q₃ | SO₂CH₃ | O—CH₃ | |
| 3143 | —(CH₂)₃— | | O | O—Ph-2Cl | Q₃ | SO₂CH₃ | O—CH₃ | |
| 3144 | —(CH₂)₃— | | O | O—CH₂—CH=CH₂ | Q₃ | SO₂CH₃ | O—CH₃ | |
| 3145 | —(CH₂)₃— | | O | O—CH₂—C≡CH | Q₃ | SO₂CH₃ | O—CH₃ | |
| 3146 | —(CH₂)₃— | | O | O—CH₂—O—C₂H₅ | Q₃ | SO₂CH₃ | O—CH₃ | |
| 3147 | —(CH₂)₃— | | O | H | Q₃ | O—CH₃ | Cl | |
| 3148 | —(CH₂)₃— | | O | OH | Q₃ | O—CH₃ | Cl | |
| 3149 | —(CH₂)₃— | | O | O—CH₃ | Q₃ | O—CH₃ | Cl | |
| 3150 | —(CH₂)₃— | | O | O—C₂H₅ | Q₃ | O—CH₃ | Cl | |
| 3151 | —(CH₂)₃— | | O | O-n-C₃H₇ | Q₃ | O—CH₃ | Cl | |
| 3152 | —(CH₂)₃— | | O | O-i-C₃H₇ | Q₃ | O—CH₃ | Cl | |
| 3153 | —(CH₂)₃— | | O | O-n-C₄H₉ | Q₃ | O—CH₃ | Cl | |
| 3154 | —(CH₂)₃— | | O | O-i-C₄H₉ | Q₃ | O—CH₃ | Cl | |
| 3155 | —(CH₂)₃— | | O | O-s-C₄H₉ | Q₃ | O—CH₃ | Cl | |
| 3156 | —(CH₂)₃— | | O | O-t-C₄H₉ | Q₃ | O—CH₃ | Cl | |
| 3157 | —(CH₂)₃— | | O | O—(CH₂)₂—Cl | Q₃ | O—CH₃ | Cl | |
| 3158 | —(CH₂)₃— | | O | O—CH₂—S—CH₃ | Q₃ | O—CH₃ | Cl | |
| 3159 | —(CH₂)₃— | | O | O—CH₂—Ph | Q₃ | O—CH₃ | Cl | |
| 3160 | —(CH₂)₃— | | O | O—Ph | Q₃ | O—CH₃ | Cl | |
| 3161 | —(CH₂)₃— | | O | O—Ph-2Cl | Q₃ | O—CH₃ | Cl | |
| 3162 | —(CH₂)₃— | | O | O—CH₂—CH=CH₂ | Q₃ | O—CH₃ | Cl | |
| 3163 | —(CH₂)₃— | | O | O—CH₂—C≡CH | Q₃ | O—CH₃ | Cl | |
| 3164 | —(CH₂)₃— | | O | O—CH₂—O—C₂H₅ | Q₃ | O—CH₃ | Cl | |
| 3165 | —(CH₂)₃— | | O | H | Q₃ | O—CH₃ | O—CH₃ | |

TABLE 3-continued

| Compound No. | R³ | R⁴ | W | Y | Q | R¹ | R² | Remarks |
|---|---|---|---|---|---|---|---|---|
| 3166 | — | $-(CH_2)_3-$ | O | OH | $Q_3$ | $O-CH_3$ | $O-CH_3$ | |
| 3167 | — | $-(CH_2)_3-$ | O | $O-CH_3$ | $Q_3$ | $O-CH_3$ | $O-CH_3$ | |
| 3168 | — | $-(CH_2)_3-$ | O | $O-C_2H_5$ | $Q_3$ | $O-CH_3$ | $O-CH_3$ | |
| 3169 | — | $-(CH_2)_3-$ | O | $O-n-C_3H_7$ | $Q_3$ | $O-CH_3$ | $O-CH_3$ | |
| 3170 | — | $-(CH_2)_3-$ | O | $O-i-C_3H_7$ | $Q_3$ | $O-CH_3$ | $O-CH_3$ | |
| 3171 | — | $-(CH_2)_3-$ | O | $O-n-C_4H_9$ | $Q_3$ | $O-CH_3$ | $O-CH_3$ | |
| 3172 | — | $-(CH_2)_3-$ | O | $O-i-C_4H_9$ | $Q_3$ | $O-CH_3$ | $O-CH_3$ | |
| 3173 | — | $-(CH_2)_3-$ | O | $O-s-C_4H_9$ | $Q_3$ | $O-CH_3$ | $O-CH_3$ | |
| 3174 | — | $-(CH_2)_3-$ | O | $O-t-C_4H_9$ | $Q_3$ | $O-CH_3$ | $O-CH_3$ | |
| 3175 | — | $-(CH_2)_3-$ | O | $O-(CH_2)_2-Cl$ | $Q_3$ | $O-CH_3$ | $O-CH_3$ | |
| 3176 | — | $-(CH_2)_3-$ | O | $O-CH_2-S-CH_3$ | $Q_3$ | $O-CH_3$ | $O-CH_3$ | |
| 3177 | — | $-(CH_2)_3-$ | O | $O-CH_2-Ph$ | $Q_3$ | $O-CH_3$ | $O-CH_3$ | |
| 3178 | — | $-(CH_2)_3-$ | O | $O-Ph$ | $Q_3$ | $O-CH_3$ | $O-CH_3$ | |
| 3179 | — | $-(CH_2)_3-$ | O | $O-Ph-2Cl$ | $Q_3$ | $O-CH_3$ | $O-CH_3$ | |
| 3180 | — | $-(CH_2)_3-$ | O | $O-CH_2-CH=CH_2$ | $Q_3$ | $O-CH_3$ | $O-CH_3$ | |
| 3181 | — | $-(CH_2)_3-$ | O | $O-CH_2-C\equiv CH$ | $Q_3$ | $O-CH_3$ | $O-CH_3$ | |
| 3182 | — | $-(CH_2)_3-$ | O | $O-CH_2-O-C_2H_5$ | $Q_3$ | $O-CH_3$ | $O-CH_3$ | |
| 3183 | — | $-(CH_2)_3-$ | O | H | $Q_3$ | $N(CH_3)_2$ | Cl | |
| 3184 | — | $-(CH_2)_3-$ | O | OH | $Q_3$ | $N(CH_3)_2$ | Cl | |
| 3185 | — | $-(CH_2)_3-$ | O | $O-CH_3$ | $Q_3$ | $N(CH_3)_2$ | Cl | |
| 3186 | — | $-(CH_2)_3-$ | O | $O-C_2H_5$ | $Q_3$ | $N(CH_3)_2$ | Cl | |
| 3187 | — | $-(CH_2)_3-$ | O | $O-n-C_3H_7$ | $Q_3$ | $N(CH_3)_2$ | Cl | |
| 3188 | — | $-(CH_2)_3-$ | O | $O-i-C_3H_7$ | $Q_3$ | $N(CH_3)_2$ | Cl | |
| 3189 | — | $-(CH_2)_3-$ | O | $O-n-C_4H_9$ | $Q_3$ | $N(CH_3)_2$ | Cl | |
| 3190 | — | $-(CH_2)_3-$ | O | $O-i-C_4H_9$ | $Q_3$ | $N(CH_3)_2$ | Cl | |
| 3191 | — | $-(CH_2)_3-$ | O | $O-s-C_4H_9$ | $Q_3$ | $N(CH_3)_2$ | Cl | |
| 3192 | — | $-(CH_2)_3-$ | O | $O-t-C_4H_9$ | $Q_3$ | $N(CH_3)_2$ | Cl | |
| 3193 | — | $-(CH_2)_3-$ | O | $O-(CH_2)_2-Cl$ | $Q_3$ | $N(CH_3)_2$ | Cl | |
| 3194 | — | $-(CH_2)_3-$ | O | $O-CH_2-S-CH_3$ | $Q_3$ | $N(CH_3)_2$ | Cl | |
| 3195 | — | $-(CH_2)_3-$ | O | $O-CH_2-Ph$ | $Q_3$ | $N(CH_3)_2$ | Cl | |
| 3196 | — | $-(CH_2)_3-$ | O | $O-Ph$ | $Q_3$ | $N(CH_3)_2$ | Cl | |
| 3197 | — | $-(CH_2)_3-$ | O | $O-Ph-2Cl$ | $Q_3$ | $N(CH_3)_2$ | Cl | |
| 3198 | — | $-(CH_2)_3-$ | O | $O-CH_2-CH=CH_2$ | $Q_3$ | $N(CH_3)_2$ | Cl | |
| 3199 | — | $-(CH_2)_3-$ | O | $O-CH_2-C\equiv CH$ | $Q_3$ | $N(CH_3)_2$ | Cl | |
| 3200 | — | $-(CH_2)_3-$ | O | $O-CH_2-O-C_2H_5$ | $Q_3$ | $N(CH_3)_2$ | Cl | |
| 3201 | — | $-(CH_2)_3-$ | O | H | $Q_3$ | $N(CH_3)_2$ | $O-CH_3$ | |
| 3202 | — | $-(CH_2)_3-$ | O | OH | $Q_3$ | $N(CH_3)_2$ | $O-CH_3$ | |
| 3203 | — | $-(CH_2)_3-$ | O | $O-CH_3$ | $Q_3$ | $N(CH_3)_2$ | $O-CH_3$ | |
| 3204 | — | $-(CH_2)_3-$ | O | $O-C_2H_5$ | $Q_3$ | $N(CH_3)_2$ | $O-CH_3$ | |
| 3205 | — | $-(CH_2)_3-$ | O | $O-n-C_3H_7$ | $Q_3$ | $N(CH_3)_2$ | $O-CH_3$ | |
| 3206 | — | $-(CH_2)_3-$ | O | $O-i-C_3H_7$ | $Q_3$ | $N(CH_3)_2$ | $O-CH_3$ | |
| 3207 | — | $-(CH_2)_3-$ | O | $O-n-C_4H_9$ | $Q_3$ | $N(CH_3)_2$ | $O-CH_3$ | |

TABLE 3-continued $$R^4 \underset{F}{\overset{O}{\underset{|}{C}}} - Y \quad Q = Q_2 = \underset{R^1}{\overset{N}{\underset{N}{\bigcirc}}} \underset{R^2}{\overset{N}{\bigcirc}} \quad \text{or} \quad Q = Q_3 = \underset{R^1}{\overset{N}{\underset{N}{\bigcirc}}} \underset{R^2}{\overset{N}{\bigcirc}}$$

$$R^3 \overset{|}{\underset{}{}} W - Q$$

| Compound No. | $R^3$ | $R^4$ | W | Y | Q | $R^1$ | $R^2$ | Remarks |
|---|---|---|---|---|---|---|---|---|
| 3208 | —(CH$_2$)$_3$— | | O | O-i-C$_4$H$_9$ | Q$_3$ | N(CH$_3$)$_2$ | O—CH$_3$ | |
| 3209 | —(CH$_2$)$_3$— | | O | O-s-C$_4$H$_9$ | Q$_3$ | N(CH$_3$)$_2$ | O—CH$_3$ | |
| 3210 | —(CH$_2$)$_3$— | | O | O-t-C$_4$H$_9$ | Q$_3$ | N(CH$_3$)$_2$ | O—CH$_3$ | |
| 3211 | —(CH$_2$)$_3$— | | O | O—(CH$_2$)$_2$—Cl | Q$_3$ | N(CH$_3$)$_2$ | O—CH$_3$ | |
| 3212 | —(CH$_2$)$_3$— | | O | O—CH$_2$—S—CH$_3$ | Q$_3$ | N(CH$_3$)$_2$ | O—CH$_3$ | |
| 3213 | —(CH$_2$)$_3$— | | O | O—CH$_2$—Ph | Q$_3$ | N(CH$_3$)$_2$ | O—CH$_3$ | |
| 3214 | —(CH$_2$)$_3$— | | O | O—Ph | Q$_3$ | N(CH$_3$)$_2$ | O—CH$_3$ | |
| 3215 | —(CH$_2$)$_3$— | | O | O—Ph-2Cl | Q$_3$ | N(CH$_3$)$_2$ | O—CH$_3$ | |
| 3216 | —(CH$_2$)$_3$— | | O | O—CH$_2$—CH=CH$_2$ | Q$_3$ | N(CH$_3$)$_2$ | O—CH$_3$ | |
| 3217 | —(CH$_2$)$_3$— | | O | O—CH$_2$—C≡CH | Q$_3$ | N(CH$_3$)$_2$ | O—CH$_3$ | |
| 3218 | —(CH$_2$)$_3$— | | O | O—CH$_2$—O—C$_2$H$_5$ | Q$_3$ | N(CH$_3$)$_2$ | O—CH$_3$ | |
| 3219 | —(CH$_2$)$_3$— | | O | H | Q$_3$ | N(CH$_3$)$_2$ | O—CH$_3$ | |
| 3220 | —(CH$_2$)$_4$— | | O | OH | Q$_3$ | N(CH$_3$)$_2$ | O—CH$_3$ | |
| 3221 | —(CH$_2$)$_4$— | | O | O—CH$_3$ | Q$_3$ | N(CH$_3$)$_2$ | O—CH$_3$ | |
| 3222 | —(CH$_2$)$_4$— | | O | O—C$_2$H$_5$ | Q$_3$ | N(CH$_3$)$_2$ | O—CH$_3$ | |
| 3223 | —(CH$_2$)$_4$— | | O | O-n-C$_3$H$_7$ | Q$_3$ | N(CH$_3$)$_2$ | O—CH$_3$ | |
| 3224 | —(CH$_2$)$_4$— | | O | O-i-C$_3$H$_7$ | Q$_3$ | N(CH$_3$)$_2$ | O—CH$_3$ | |
| 3225 | —(CH$_2$)$_4$— | | O | O-n-C$_4$H$_9$ | Q$_3$ | N(CH$_3$)$_2$ | O—CH$_3$ | |
| 3226 | —(CH$_2$)$_4$— | | O | O-i-C$_4$H$_9$ | Q$_3$ | N(CH$_3$)$_2$ | O—CH$_3$ | |
| 3227 | —(CH$_2$)$_4$— | | O | O-s-C$_4$H$_9$ | Q$_3$ | N(CH$_3$)$_2$ | O—CH$_3$ | |
| 3228 | —(CH$_2$)$_4$— | | O | O-t-C$_4$H$_9$ | Q$_3$ | N(CH$_3$)$_2$ | O—CH$_3$ | |
| 3229 | —(CH$_2$)$_4$— | | O | O—(CH$_2$)$_2$—Cl | Q$_3$ | N(CH$_3$)$_2$ | O—CH$_3$ | |
| 3230 | —(CH$_2$)$_4$— | | O | O—CH$_2$—S—CH$_3$ | Q$_3$ | N(CH$_3$)$_2$ | O—CH$_3$ | |
| 3231 | —(CH$_2$)$_4$— | | O | O—CH$_2$—Ph | Q$_3$ | N(CH$_3$)$_2$ | O—CH$_3$ | |
| 3232 | —(CH$_2$)$_4$— | | O | O—Ph | Q$_3$ | N(CH$_3$)$_2$ | O—CH$_3$ | |
| 3233 | —(CH$_2$)$_4$— | | O | O—Ph-2Cl | Q$_3$ | N(CH$_3$)$_2$ | O—CH$_3$ | |
| 3234 | —(CH$_2$)$_4$— | | O | O—CH$_2$—CH=CH$_2$ | Q$_3$ | N(CH$_3$)$_2$ | O—CH$_3$ | |
| 3235 | —(CH$_2$)$_4$— | | O | O—CH$_2$—C≡CH | Q$_3$ | N(CH$_3$)$_2$ | O—CH$_3$ | |
| 3236 | —(CH$_2$)$_4$— | | O | O—CH$_2$—O—C$_2$H$_5$ | Q$_3$ | N(CH$_3$)$_2$ | O—CH$_3$ | |
| 3237 | —(CH$_2$)$_4$— | | O | H | Q$_3$ | N(CH$_3$)$_2$ | O—CH$_3$ | |
| 3238 | —(CH$_2$)$_4$— | | O | OH | Q$_3$ | Cl | O—CH$_3$ | |
| 3239 | —(CH$_2$)$_4$— | | O | O—CH$_3$ | Q$_3$ | Cl | O—CH$_3$ | |
| 3240 | —(CH$_2$)$_4$— | | O | O—C$_2$H$_5$ | Q$_3$ | Cl | O—CH$_3$ | |
| 3241 | —(CH$_2$)$_4$— | | O | O-n-C$_3$H$_7$ | Q$_3$ | Cl | O—CH$_3$ | |
| 3242 | —(CH$_2$)$_4$— | | O | O-i-C$_3$H$_7$ | Q$_3$ | Cl | O—CH$_3$ | |
| 3243 | —(CH$_2$)$_4$— | | O | O-n-C$_4$H$_9$ | Q$_3$ | Cl | O—CH$_3$ | |
| 3244 | —(CH$_2$)$_4$— | | O | O-i-C$_4$H$_9$ | Q$_3$ | Cl | O—CH$_3$ | |
| 3245 | —(CH$_2$)$_4$— | | O | O-s-C$_4$H$_9$ | Q$_3$ | Cl | O—CH$_3$ | |
| 3246 | —(CH$_2$)$_4$— | | O | O-t-C$_4$H$_9$ | Q$_3$ | Cl | O—CH$_3$ | |
| 3247 | —(CH$_2$)$_4$— | | O | O—(CH$_2$)$_2$—Cl | Q$_3$ | Cl | O—CH$_3$ | |
| 3248 | —(CH$_2$)$_4$— | | O | O—CH$_2$—S—CH$_3$ | Q$_3$ | Cl | O—CH$_3$ | |
| 3249 | —(CH$_2$)$_4$— | | O | O—CH$_2$—Ph | Q$_3$ | Cl | O—CH$_3$ | |

TABLE 3-continued

Structure:
$$R^4 \underset{R^3}{\overset{F}{\underset{|}{C}}} \overset{O}{\underset{\|}{C}} - Y \quad Q = Q_2 = \underset{N}{\overset{R^1}{\bigcirc}} \overset{N}{\underset{R^2}{\bigcirc}} \quad \text{or} \quad Q = Q_3 = \underset{N}{\overset{R^1}{\bigcirc}} \overset{N}{\underset{R^2}{\bigcirc}}$$

W—Q

| Compound No. | R³ | R⁴ | W | Y | Q | R¹ | R² | Remarks |
|---|---|---|---|---|---|---|---|---|
| 3250 | —(CH₂)₄— | | O | O—Ph | Q₃ | Cl | O—CH₃ | |
| 3251 | —(CH₂)₄— | | O | O—Ph-2Cl | Q₃ | Cl | O—CH₃ | |
| 3252 | —(CH₂)₄— | | O | O—CH₂—CH=CH₂ | Q₃ | Cl | O—CH₃ | |
| 3253 | —(CH₂)₄— | | O | O—CH₂—C≡CH | Q₃ | Cl | O—CH₃ | |
| 3254 | —(CH₂)₄— | | O | O—CH₂—O—C₂H₅ | Q₃ | Cl | O—CH₃ | |
| 3255 | —(CH₂)₄— | | O | H | Q₂ | O—CH₃ | O—CH₃ | |
| 3256 | —(CH₂)₄— | | O | OH | Q₂ | O—CH₃ | O—CH₃ | |
| 3257 | —(CH₂)₄— | | O | O—CH₃ | Q₂ | O—CH₃ | O—C₂H₅ | |
| 3258 | —(CH₂)₄— | | O | O—C₂H₅ | Q₂ | O—CH₃ | O—C₂H₅ | |
| 3259 | —(CH₂)₄— | | O | O-n-C₃H₇ | Q₂ | O—CH₃ | O—C₂H₅ | |
| 3260 | —(CH₂)₄— | | O | O-i-C₃H₇ | Q₂ | O—CH₃ | O—C₂H₅ | |
| 3261 | —(CH₂)₄— | | O | O-n-C₄H₉ | Q₂ | O—CH₃ | O—C₂H₅ | |
| 3262 | —(CH₂)₄— | | O | O-i-C₄H₉ | Q₂ | O—CH₃ | O—C₂H₅ | |
| 3263 | —(CH₂)₄— | | O | O-s-C₄H₉ | Q₂ | O—CH₃ | O—C₂H₅ | |
| 3264 | —(CH₂)₄— | | O | O-t-C₄H₉ | Q₂ | O—CH₃ | O—C₂H₅ | |
| 3265 | —(CH₂)₄— | | O | O—(CH₂)₂—Cl | Q₂ | O—CH₃ | O—C₂H₅ | |
| 3266 | —(CH₂)₄— | | O | O—CH₂—S—CH₃ | Q₂ | O—CH₃ | O—C₂H₅ | |
| 3267 | —(CH₂)₄— | | O | O—CH₂—Ph | Q₂ | O—CH₃ | O—C₂H₅ | |
| 3268 | —(CH₂)₄— | | O | O—Ph | Q₂ | O—CH₃ | O—C₂H₅ | |
| 3269 | —(CH₂)₄— | | O | O—Ph-2Cl | Q₂ | O—CH₃ | O—C₂H₅ | |
| 3270 | —(CH₂)₄— | | O | O—CH₂—CH=CH₂ | Q₂ | O—CH₃ | O—C₂H₅ | |
| 3271 | —(CH₂)₄— | | O | O—CH₂—C≡CH | Q₂ | O—CH₃ | O—C₂H₅ | |
| 3272 | —(CH₂)₄— | | O | O—CH₂—O—C₂H₅ | Q₂ | O—CH₃ | O—C₂H₅ | |
| 3273 | —(CH₂)₄— | | O | H | Q₂ | O—C₂H₅ | O—C₂H₅ | |
| 3274 | —(CH₂)₄— | | O | OH | Q₂ | O—C₂H₅ | O—C₂H₅ | |
| 3275 | —(CH₂)₄— | | O | O—CH₃ | Q₂ | O—C₂H₅ | O—C₂H₅ | |
| 3276 | —(CH₂)₄— | | O | O—C₂H₅ | Q₂ | O—C₂H₅ | O—C₂H₅ | |
| 3277 | —(CH₂)₄— | | O | O-n-C₃H₇ | Q₂ | O—C₂H₅ | O—C₂H₅ | |
| 3278 | —(CH₂)₄— | | O | O-i-C₃H₇ | Q₂ | O—C₂H₅ | O—C₂H₅ | |
| 3279 | —(CH₂)₄— | | O | O-n-C₄H₉ | Q₂ | O—C₂H₅ | O—C₂H₅ | |
| 3280 | —(CH₂)₄— | | O | O-i-C₄H₉ | Q₂ | O—C₂H₅ | O—C₂H₅ | |
| 3281 | —(CH₂)₄— | | O | O-s-C₄H₉ | Q₂ | O—C₂H₅ | O—C₂H₅ | |
| 3282 | —(CH₂)₄— | | O | O-t-C₄H₉ | Q₂ | O—C₂H₅ | O—C₂H₅ | |
| 3283 | —(CH₂)₄— | | O | O—(CH₂)₂—Cl | Q₂ | O—C₂H₅ | O—C₂H₅ | |
| 3284 | —(CH₂)₄— | | O | O—CH₂—S—CH₃ | Q₂ | O—C₂H₅ | O—C₂H₅ | |
| 3285 | —(CH₂)₄— | | O | O—CH₂—Ph | Q₂ | O—C₂H₅ | O—C₂H₅ | |
| 3286 | —(CH₂)₄— | | O | O—Ph | Q₂ | O—C₂H₅ | O—C₂H₅ | |
| 3287 | —(CH₂)₄— | | O | O—Ph-2Cl | Q₂ | O—C₂H₅ | O—C₂H₅ | |
| 3288 | —(CH₂)₄— | | O | O—CH₂—CH=CH₂ | Q₂ | O—C₂H₅ | O—C₂H₅ | |
| 3289 | —(CH₂)₄— | | O | O—CH₂—C≡CH | Q₂ | O—C₂H₅ | O—C₂H₅ | |
| 3290 | —(CH₂)₄— | | O | O—CH₂—O—C₂H₅ | Q₂ | O—C₂H₅ | O—C₂H₅ | |
| 3291 | —(CH₂)₄— | | O | H | Q₃ | S—CH₃ | Cl | |

TABLE 3-continued $$R^4\underset{\underset{R^3}{|}}{\overset{\overset{F}{|}}{C}}-\underset{\underset{W-Q}{|}}{\overset{\overset{O}{\|}}{C}}-Y \quad Q=Q_2=\text{[pyrimidine with }R^1, R^2\text{]} \quad \text{or} \quad Q=Q_3=\text{[pyrimidine with }R^1, R^2\text{]}$$

| Compound No. | R³ | R⁴ | W | Y | Q | R¹ | R² | Remarks |
|---|---|---|---|---|---|---|---|---|
| 3292a | —(CH₂)₄— | | O | OH | Q₃ | S—CH₃ | Cl | cis |
| 3292b | —(CH₂)₄— | | O | OH | Q₃ | S—CH₃ | Cl | trans |
| 3293a | —(CH₂)₄— | | O | O—CH₃ | Q₃ | S—CH₃ | Cl | cis |
| 3293b | —(CH₂)₄— | | O | O—CH₃ | Q₃ | S—CH₃ | Cl | trans |
| 3294a | —(CH₂)₄— | | O | O—C₂H₅ | Q₃ | S—CH₃ | Cl | cis |
| 3294b | —(CH₂)₄— | | O | O—C₂H₅ | Q₃ | S—CH₃ | Cl | trans |
| 3295 | —(CH₂)₄— | | O | O-n-C₃H₇ | Q₃ | S—CH₃ | Cl | |
| 3296 | —(CH₂)₄— | | O | O-i-C₃H₇ | Q₃ | S—CH₃ | Cl | |
| 3297 | —(CH₂)₄— | | O | O-n-C₄H₉ | Q₃ | S—CH₃ | Cl | |
| 3298 | —(CH₂)₄— | | O | O-i-C₄H₉ | Q₃ | S—CH₃ | Cl | |
| 3299 | —(CH₂)₄— | | O | O-s-C₄H₉ | Q₃ | S—CH₃ | Cl | |
| 3300 | —(CH₂)₄— | | O | O-t-C₄H₉ | Q₃ | S—CH₃ | Cl | |
| 3301 | —(CH₂)₄— | | O | O—(CH₂)₂—Cl | Q₃ | S—CH₃ | Cl | |
| 3302 | —(CH₂)₄— | | O | O—CH₂—S—CH₃ | Q₃ | S—CH₃ | Cl | |
| 3303 | —(CH₂)₄— | | O | O—CH₂—Ph | Q₃ | S—CH₃ | Cl | |
| 3304 | —(CH₂)₄— | | O | O—Ph | Q₃ | S—CH₃ | Cl | |
| 3305 | —(CH₂)₄— | | O | O—Ph-2Cl | Q₃ | S—CH₃ | Cl | |
| 3306 | —(CH₂)₄— | | O | O—CH₂—CH=CH₂ | Q₃ | S—CH₃ | Cl | |
| 3307 | —(CH₂)₄— | | O | O—CH₂—C≡CH | Q₃ | S—CH₃ | Cl | |
| 3308 | —(CH₂)₄— | | O | O—CH₂—O—C₂H₅ | Q₃ | S—CH₃ | Cl | |
| 3309 | —(CH₂)₄— | | O | H | Q₃ | S—CH₃ | Cl | |
| 3310a | —(CH₂)₄— | | O | OH | Q₃ | S—CH₃ | O—CH₃ | cis |
| 3310b | —(CH₂)₄— | | O | OH | Q₃ | S—CH₃ | O—CH₃ | trans |
| 3311 | —(CH₂)₄— | | O | O—CH₃ | Q₃ | S—CH₃ | O—CH₃ | |
| 3312a | —(CH₂)₄— | | O | O—C₂H₅ | Q₃ | S—CH₃ | O—CH₃ | cis |
| 3312b | —(CH₂)₄— | | O | O—C₂H₅ | Q₃ | S—CH₃ | O—CH₃ | trans |
| 3313 | —(CH₂)₄— | | O | O-n-C₃H₇ | Q₃ | S—CH₃ | O—CH₃ | |
| 3314 | —(CH₂)₄— | | O | O-i-C₃H₇ | Q₃ | S—CH₃ | O—CH₃ | |
| 3315 | —(CH₂)₄— | | O | O-n-C₄H₉ | Q₃ | S—CH₃ | O—CH₃ | |
| 3316 | —(CH₂)₄— | | O | O-i-C₄H₉ | Q₃ | S—CH₃ | O—CH₃ | |
| 3317 | —(CH₂)₄— | | O | O-s-C₄H₉ | Q₃ | S—CH₃ | O—CH₃ | |
| 3318 | —(CH₂)₄— | | O | O-t-C₄H₉ | Q₃ | S—CH₃ | O—CH₃ | |
| 3319 | —(CH₂)₄— | | O | O—(CH₂)₂—Cl | Q₃ | S—CH₃ | O—CH₃ | |
| 3320 | —(CH₂)₄— | | O | O—CH₂—S—CH₃ | Q₃ | S—CH₃ | O—CH₃ | |
| 3321 | —(CH₂)₄— | | O | O—CH₂—Ph | Q₃ | S—CH₃ | O—CH₃ | |
| 3322 | —(CH₂)₄— | | O | O—Ph | Q₃ | S—CH₃ | O—CH₃ | |
| 3323 | —(CH₂)₄— | | O | O—Ph-2Cl | Q₃ | S—CH₃ | O—CH₃ | |
| 3324 | —(CH₂)₄— | | O | O—CH₂—CH=CH₂ | Q₃ | S—CH₃ | O—CH₃ | |
| 3325 | —(CH₂)₄— | | O | O—CH₂—C≡CH | Q₃ | S—CH₃ | O—CH₃ | |
| 3326 | —(CH₂)₄— | | O | O—CH₂—O—C₂H₅ | Q₃ | S—CH₃ | O—CH₃ | |
| 3327 | —(CH₂)₄— | | O | H | Q₃ | S—CH₃ | O—CH₃ | |
| 3328 | —(CH₂)₄— | | O | OH | Q₃ | SO₂CH₃ | Cl | |

TABLE 3-continued $$R^4\underset{R^3}{\overset{F}{\underset{|}{C}}}\overset{O}{\underset{||}{C}}-Y \quad Q=Q_2=\begin{array}{c}R^1\\\diagup\\N\\\diagdown\\\diagdown\\R^2\end{array} \text{ or } Q=Q_3=\begin{array}{c}R^1\\\diagup\\N\\\diagdown\\R^2\end{array}$$

$$W-Q$$

| Compound No. | R³ | R⁴ | W | Y | Q | R¹ | R² | Remarks |
|---|---|---|---|---|---|---|---|---|
| 3329 | —(CH₂)₄— | | O | O—CH₃ | Q₃ | SO₂CH₃ | Cl | |
| 3330a | —(CH₂)₄— | | O | O—C₂H₅ | Q₃ | SO₂CH₃ | Cl | cis |
| 3330b | —(CH₂)₄— | | O | O—C₂H₅ | Q₃ | SO₂CH₃ | Cl | trans |
| 3331 | —(CH₂)₄— | | O | O—n-C₃H₇ | Q₃ | SO₂CH₃ | Cl | |
| 3332 | —(CH₂)₄— | | O | O-i-C₃H₇ | Q₃ | SO₂CH₃ | Cl | |
| 3333 | —(CH₂)₄— | | O | O—n-C₄H₉ | Q₃ | SO₂CH₃ | Cl | |
| 3334 | —(CH₂)₄— | | O | O-i-C₄H₉ | Q₃ | SO₂CH₃ | Cl | |
| 3335 | —(CH₂)₄— | | O | O-s-C₄H₉ | Q₃ | SO₂CH₃ | Cl | |
| 3336 | —(CH₂)₄— | | O | O-t-C₄H₉ | Q₃ | SO₂CH₃ | Cl | |
| 3337 | —(CH₂)₄— | | O | O—(CH₂)₂—Cl | Q₃ | SO₂CH₃ | Cl | |
| 3338 | —(CH₂)₄— | | O | O—CH₂—S—CH₃ | Q₃ | SO₂CH₃ | Cl | |
| 3339 | —(CH₂)₄— | | O | O—CH₂—Ph | Q₃ | SO₂CH₃ | Cl | |
| 3340 | —(CH₂)₄— | | O | O—Ph | Q₃ | SO₂CH₃ | Cl | |
| 3341 | —(CH₂)₄— | | O | O—Ph-2Cl | Q₃ | SO₂CH₃ | Cl | |
| 3342 | —(CH₂)₄— | | O | O—CH₂—CH=CH₂ | Q₃ | SO₂CH₃ | Cl | |
| 3343 | —(CH₂)₄— | | O | O—CH₂—C≡CH | Q₃ | SO₂CH₃ | Cl | |
| 3344 | —(CH₂)₄— | | O | O—CH₂—O—C₂H₅ | Q₃ | SO₂CH₃ | Cl | |
| 3345 | —(CH₂)₄— | | O | H | Q₃ | SO₂CH₃ | Cl | |
| 3346 | —(CH₂)₄— | | O | OH | Q₃ | SO₂CH₃ | Cl | |
| 3347 | —(CH₂)₄— | | O | O—CH₃ | Q₃ | SO₂CH₃ | O—CH₃ | |
| 3348 | —(CH₂)₄— | | O | O—C₂H₅ | Q₃ | SO₂CH₃ | O—CH₃ | |
| 3349 | —(CH₂)₄— | | O | O—n-C₃H₇ | Q₃ | SO₂CH₃ | O—CH₃ | |
| 3350 | —(CH₂)₄— | | O | O-i-C₃H₇ | Q₃ | SO₂CH₃ | O—CH₃ | |
| 3351 | —(CH₂)₄— | | O | O—n-C₄H₉ | Q₃ | SO₂CH₃ | O—CH₃ | |
| 3352 | —(CH₂)₄— | | O | O-i-C₄H₉ | Q₃ | SO₂CH₃ | O—CH₃ | |
| 3353 | —(CH₂)₄— | | O | O-s-C₄H₉ | Q₃ | SO₂CH₃ | O—CH₃ | |
| 3354 | —(CH₂)₄— | | O | O-t-C₄H₉ | Q₃ | SO₂CH₃ | O—CH₃ | |
| 3355 | —(CH₂)₄— | | O | O—(CH₂)₂—Cl | Q₃ | SO₂CH₃ | O—CH₃ | |
| 3356 | —(CH₂)₄— | | O | O—CH₂—S—CH₃ | Q₃ | SO₂CH₃ | O—CH₃ | |
| 3357 | —(CH₂)₄— | | O | O—CH₂—Ph | Q₃ | SO₂CH₃ | O—CH₃ | |
| 3358 | —(CH₂)₄— | | O | O—Ph | Q₃ | SO₂CH₃ | O—CH₃ | |
| 3359 | —(CH₂)₄— | | O | O—Ph-2Cl | Q₃ | SO₂CH₃ | O—CH₃ | |
| 3360 | —(CH₂)₄— | | O | O—CH₂—CH=CH₂ | Q₃ | SO₂CH₃ | O—CH₃ | |
| 3361 | —(CH₂)₄— | | O | O—CH₂—C≡CH | Q₃ | SO₂CH₃ | O—CH₃ | |
| 3362 | —(CH₂)₄— | | O | O—CH₂—O—C₂H₅ | Q₃ | SO₂CH₃ | O—CH₃ | |
| 3363 | —(CH₂)₄— | | O | H | Q₃ | SO₂CH₃ | O—CH₃ | |
| 3364 | —(CH₂)₄— | | O | OH | Q₃ | SO₂CH₃ | O—CH₃ | |
| 3365 | —(CH₂)₄— | | O | O—CH₃ | Q₃ | O—CH₃ | O—CH₃ | |
| 3366a | —(CH₂)₄— | | O | O—C₂H₅ | Q₃ | O—CH₃ | Cl | cis |
| 3366b | —(CH₂)₄— | | O | O—C₂H₅ | Q₃ | O—CH₃ | Cl | trans |
| 3367 | —(CH₂)₄— | | O | O—n-C₃H₇ | Q₃ | O—CH₃ | Cl | |
| 3368 | —(CH₂)₄— | | O | O-i-C₃H₇ | Q₃ | O—CH₃ | Cl | |

TABLE 3-continued

Structure: R⁴-CF(C(=O)-Y)-CR³(W-Q) where Q = Q₂ = pyrimidine with R¹, R² or Q = Q₃ = triazine with R¹, R²

| Compound No. | R³ | R⁴ | W | Y | Q | R¹ | R² | Remarks |
|---|---|---|---|---|---|---|---|---|
| 3369 | —(CH₂)₄— | | O | O-n-C₄H₉ | Q₃ | O—CH₃ | Cl | |
| 3370 | —(CH₂)₄— | | O | O-i-C₄H₉ | Q₃ | O—CH₃ | Cl | |
| 3371 | —(CH₂)₄— | | O | O-s-C₄H₉ | Q₃ | O—CH₃ | Cl | |
| 3372 | —(CH₂)₄— | | O | O-t-C₄H₉ | Q₃ | O—CH₃ | Cl | |
| 3373 | —(CH₂)₄— | | O | O—(CH₂)₂—Cl | Q₃ | O—CH₃ | Cl | |
| 3374 | —(CH₂)₄— | | O | O—CH₂—S—CH₃ | Q₃ | O—CH₃ | Cl | |
| 3375 | —(CH₂)₄— | | O | O—CH₂—Ph | Q₃ | O—CH₃ | Cl | |
| 3376 | —(CH₂)₄— | | O | O—Ph | Q₃ | O—CH₃ | Cl | |
| 3377 | —(CH₂)₄— | | O | O—Ph-2Cl | Q₃ | O—CH₃ | Cl | |
| 3378 | —(CH₂)₄— | | O | O—CH₂—CH=CH₂ | Q₃ | O—CH₃ | Cl | |
| 3379a | —(CH₂)₄— | | O | O—CH₂—C≡CH | Q₃ | O—CH₃ | Cl | cis |
| 3379b | —(CH₂)₄— | | O | O—CH₂—C≡CH | Q₃ | O—CH₃ | Cl | trans |
| 3380 | —(CH₂)₄— | | O | O—CH₂—O—C₂H₅ | Q₃ | O—CH₃ | Cl | |
| 3381 | —(CH₂)₄— | | O | H | Q₃ | O—CH₃ | O—CH₃ | |
| 3382 | —(CH₂)₄— | | O | OH | Q₃ | O—CH₃ | O—CH₃ | |
| 3383 | —(CH₂)₄— | | O | O—CH₃ | Q₃ | O—CH₃ | O—CH₃ | |
| 3384 | —(CH₂)₄— | | O | O—C₂H₅ | Q₃ | O—CH₃ | O—CH₃ | |
| 3385 | —(CH₂)₄— | | O | O-n-C₃H₇ | Q₃ | O—CH₃ | O—CH₃ | |
| 3386 | —(CH₂)₄— | | O | O-i-C₃H₇ | Q₃ | O—CH₃ | O—CH₃ | |
| 3387 | —(CH₂)₄— | | O | O-n-C₄H₉ | Q₃ | O—CH₃ | O—CH₃ | |
| 3388 | —(CH₂)₄— | | O | O-i-C₄H₉ | Q₃ | O—CH₃ | O—CH₃ | |
| 3389 | —(CH₂)₄— | | O | O-s-C₄H₉ | Q₃ | O—CH₃ | O—CH₃ | |
| 3390 | —(CH₂)₄— | | O | O-t-C₄H₉ | Q₃ | O—CH₃ | O—CH₃ | |
| 3391 | —(CH₂)₄— | | O | O—(CH₂)₂—Cl | Q₃ | O—CH₃ | O—CH₃ | |
| 3392 | —(CH₂)₄— | | O | O—CH₂—S—CH₃ | Q₃ | O—CH₃ | O—CH₃ | |
| 3393 | —(CH₂)₄— | | O | O—CH₂—Ph | Q₃ | O—CH₃ | O—CH₃ | |
| 3394 | —(CH₂)₄— | | O | O—Ph | Q₃ | O—CH₃ | O—CH₃ | |
| 3395 | —(CH₂)₄— | | O | O—Ph-2Cl | Q₃ | O—CH₃ | O—CH₃ | |
| 3396 | —(CH₂)₄— | | O | O—CH₂—CH=CH₂ | Q₃ | O—CH₃ | O—CH₃ | |
| 3397 | —(CH₂)₄— | | O | O—CH₂—C≡CH | Q₃ | O—CH₃ | O—CH₃ | |
| 3398 | —(CH₂)₄— | | O | O—CH₂—O—C₂H₅ | Q₃ | O—CH₃ | O—CH₃ | |
| 3399 | —(CH₂)₄— | | O | H | Q₃ | N(CH₃)₂ | Cl | |
| 3400 | —(CH₂)₄— | | O | OH | Q₃ | N(CH₃)₂ | Cl | |
| 3401 | —(CH₂)₄— | | O | O—CH₃ | Q₃ | N(CH₃)₂ | Cl | |
| 3402 | —(CH₂)₄— | | O | O—C₂H₅ | Q₃ | N(CH₃)₂ | Cl | |
| 3403 | —(CH₂)₄— | | O | O-n-C₃H₇ | Q₃ | N(CH₃)₂ | Cl | |
| 3404 | —(CH₂)₄— | | O | O-i-C₃H₇ | Q₃ | N(CH₃)₂ | Cl | |
| 3405 | —(CH₂)₄— | | O | O-n-C₄H₉ | Q₃ | N(CH₃)₂ | Cl | |
| 3406 | —(CH₂)₄— | | O | O-i-C₄H₉ | Q₃ | N(CH₃)₂ | Cl | |
| 3407 | —(CH₂)₄— | | O | O-s-C₄H₉ | Q₃ | N(CH₃)₂ | Cl | |
| 3408 | —(CH₂)₄— | | O | O-t-C₄H₉ | Q₃ | N(CH₃)₂ | Cl | |
| 3409 | —(CH₂)₄— | | O | O—(CH₂)₂—Cl | Q₃ | N(CH₃)₂ | Cl | |

TABLE 3-continued $$R^4 \underset{R^3}{\overset{F}{\underset{|}{C}}} \underset{W-Q}{\overset{O}{\underset{||}{C}-Y}} \quad Q = Q_2 = \underset{N}{\underset{\parallel}{\bigcirc}}\overset{R^1}{\underset{N}{\bigcirc}}\overset{}{R^2} \text{ or } Q = Q_3 = \underset{N}{\underset{\parallel}{\bigcirc}}\overset{R^1}{\underset{}{\bigcirc}}R^2$$

| Compound No. | $R^3$ | $R^4$ | W | Y | Q | $R^1$ | $R^2$ | Remarks |
|---|---|---|---|---|---|---|---|---|
| 3410 | —(CH$_2$)$_4$— | | O | O—CH$_2$—S—CH$_3$ | Q$_3$ | O—CH$_3$ | O—CH$_3$ | |
| 3411 | —(CH$_2$)$_4$— | | O | O—CH$_2$—Ph | Q$_3$ | N(CH$_3$)$_2$ | Cl | |
| 3412 | —(CH$_2$)$_4$— | | O | O—Ph | Q$_3$ | N(CH$_3$)$_2$ | Cl | |
| 3413 | —(CH$_2$)$_4$— | | O | O—Ph-2Cl | Q$_3$ | N(CH$_3$)$_2$ | Cl | |
| 3414 | —(CH$_2$)$_4$— | | O | O—CH$_2$—CH=CH$_2$ | Q$_3$ | N(CH$_3$)$_2$ | Cl | |
| 3415 | —(CH$_2$)$_4$— | | O | O—CH$_2$—C≡CH | Q$_3$ | N(CH$_3$)$_2$ | Cl | |
| 3416 | —(CH$_2$)$_4$— | | O | O—CH$_2$—O—C$_2$H$_5$ | Q$_3$ | N(CH$_3$)$_2$ | Cl | |
| 3417 | —(CH$_2$)$_4$— | | O | H | Q$_3$ | N(CH$_3$)$_2$ | O—CH$_3$ | |
| 3418 | —(CH$_2$)$_4$— | | O | OH | Q$_3$ | N(CH$_3$)$_2$ | O—CH$_3$ | |
| 3419 | —(CH$_2$)$_4$— | | O | O—CH$_3$ | Q$_3$ | N(CH$_3$)$_2$ | O—CH$_3$ | |
| 3420 | —(CH$_2$)$_4$— | | O | O—C$_2$H$_5$ | Q$_3$ | N(CH$_3$)$_2$ | O—CH$_3$ | |
| 3421 | —(CH$_2$)$_4$— | | O | O-n-C$_3$H$_7$ | Q$_3$ | N(CH$_3$)$_2$ | O—CH$_3$ | |
| 3422 | —(CH$_2$)$_4$— | | O | O-i-C$_3$H$_7$ | Q$_3$ | N(CH$_3$)$_2$ | O—CH$_3$ | |
| 3423 | —(CH$_2$)$_4$— | | O | O-n-C$_4$H$_9$ | Q$_3$ | N(CH$_3$)$_2$ | O—CH$_3$ | |
| 3424 | —(CH$_2$)$_4$— | | O | O-i-C$_4$H$_9$ | Q$_3$ | N(CH$_3$)$_2$ | O—CH$_3$ | |
| 3425 | —(CH$_2$)$_4$— | | O | O-s-C$_4$H$_9$ | Q$_3$ | N(CH$_3$)$_2$ | O—CH$_3$ | |
| 3426 | —(CH$_2$)$_4$— | | O | O-t-C$_4$H$_9$ | Q$_3$ | N(CH$_3$)$_2$ | O—CH$_3$ | |
| 3427 | —(CH$_2$)$_4$— | | O | O—(CH$_2$)$_2$—Cl | Q$_3$ | N(CH$_3$)$_2$ | O—CH$_3$ | |
| 3428 | —(CH$_2$)$_4$— | | O | O—CH$_2$—S—CH$_3$ | Q$_3$ | N(CH$_3$)$_2$ | O—CH$_3$ | |
| 3429 | —(CH$_2$)$_4$— | | O | O—CH$_2$—Ph | Q$_3$ | N(CH$_3$)$_2$ | O—CH$_3$ | |
| 3430 | —(CH$_2$)$_4$— | | O | O—Ph | Q$_3$ | N(CH$_3$)$_2$ | O—CH$_3$ | |
| 3431 | —(CH$_2$)$_4$— | | O | O—Ph-2Cl | Q$_3$ | N(CH$_3$)$_2$ | O—CH$_3$ | |
| 3432 | —(CH$_2$)$_4$— | | O | O—CH$_2$—CH=CH$_2$ | Q$_3$ | N(CH$_3$)$_2$ | O—CH$_3$ | |
| 3433 | —(CH$_2$)$_4$— | | O | O—CH$_2$—C≡CH | Q$_3$ | N(CH$_3$)$_2$ | O—CH$_3$ | |
| 3434 | —(CH$_2$)$_4$— | | O | O—CH$_2$—O—C$_2$H$_5$ | Q$_3$ | N(CH$_3$)$_2$ | O—CH$_3$ | |

TABLE 4

Structure: R⁴-C(X)(R³)-C(=A)-Y attached via O to a pyrimidine ring with R¹ and R² substituents.

| Compound No. | R³ R⁴ | X | A | Y | R¹ | R² | Remarks |
|---|---|---|---|---|---|---|---|
| 4001a | —(CH₂)₃— | F | O | NH₂ | O—CH₃ | O—CH₃ | cis |
| 4001b | —(CH₂)₃— | F | O | NH₂ | O—CH₃ | O—CH₃ | trans |
| 4002a | —(CH₂)₃— | F | O | NH—CH₃ | O—CH₃ | O—CH₃ | cis |
| 4002b | —(CH₂)₃— | F | O | NH—CH₃ | O—CH₃ | O—CH₃ | trans |
| 4003a | —(CH₂)₃— | F | O | NH—C₂H₅ | O—CH₃ | O—CH₃ | cis |
| 4003b | —(CH₂)₃— | F | O | NH—C₂H₅ | O—CH₃ | O—CH₃ | trans |
| 4004 | —(CH₂)₃— | F | O | NH-n-C₃H₅ | O—CH₃ | O—CH₃ | |
| 4005 | —(CH₂)₃— | F | O | NH-i-C₃H₅ | O—CH₃ | O—CH₃ | |
| 4006 | —(CH₂)₃— | F | O | NH-n-C₄H₉ | O—CH₃ | O—CH₃ | |
| 4007 | —(CH₃)₃— | F | O | NH-i-C₄H₉ | O—CH₃ | O—CH₃ | |
| 4008 | —(CH₂)₃— | F | O | NH-s-C₄H₉ | O—CH₃ | O—CH₃ | |
| 4009a | —(CH₂)₃— | F | O | NH-t-C₄H₉ | O—CH₃ | O—CH₃ | cis |
| 4009b | —(CH₂)₃— | F | O | NH-t-C₄H₉ | O—CH₃ | O—CH₃ | trans |
| 4010a | —(CH₂)₃— | F | O | N(CH₃)₂ | O—CH₃ | O—CH₃ | cis |
| 4010b | —(CH₂)₃— | F | O | N(CH₃)₂ | O—CH₃ | O—CH₃ | trans |
| 4011 | —(CH₃)₃— | F | O | N—CH₂—CH=CH₂ | O—CH₃ | O—CH₃ | |
| 4012 | —(CH₂)₃— | F | O | N—CH₂C≡CH | O—CH₃ | O—CH₃ | |
| 4013a | —(CH₂)₃— | F | O | NH-Ph | O—CH₃ | O—CH₃ | cis |
| 4013b | —(CH₂)₃— | F | O | NH-Ph | O—CH₃ | O—CH₃ | trans |
| 4014 | —(CH₂)₃— | F | O | NH-Ph-2Cl | O—CH₃ | O—CH₃ | |
| 4015 | —(CH₂)₃— | F | O | NH-Ph-3Cl | O—CH₃ | O—CH₃ | |
| 4016 | —(CH₂)₃— | F | O | NH-Ph-4Cl | O—CH₃ | O—CH₃ | |
| 4017 | —(CH₂)₃— | F | O | NH-Ph-2-OC₂H₅ | O—CH₃ | O—CH₃ | |
| 4018 | —(CH₂)₃— | F | O | NH-Ph-3-OC₂H₅ | O—CH₃ | O—CH₃ | |
| 4019 | —(CH₂)₃— | F | O | NH-Ph-4-OC₂H₅ | O—CH₃ | O—CH₃ | |
| 4020 | —(CH₂)₃— | F | O | NH-Ph-2CF₃ | O—CH₃ | O—CH₃ | |
| 4021 | —(CH₂)₃— | F | O | NH-Ph-3CF₃ | O—CH₃ | O—CH₃ | |
| 4022 | —(CH₂)₃— | F | O | NH-Ph-4CF₃ | O—CH₃ | O—CH₃ | |
| 4023 | —(CH₂)₃— | F | O | N(CH₃)-Ph | O—CH₃ | O—CH₃ | |
| 4024 | —(CH₃)₃— | F | O | NH—CH₂Ph | O—CH₃ | O—CH₃ | |
| 4025 | —(CH₂)₃— | F | O | NH—CH₂Ph-2Cl | O—CH₃ | O—CH₃ | |
| 4026 | —(CH₂)₃— | F | O | NH—CH₂Ph-3Cl | O—CH₃ | O—CH₃ | |
| 4027 | —(CH₃)₃— | F | O | NH—CH₂Ph-4Cl | O—CH₃ | O—CH₃ | |
| 4028 | —(CH₂)₃— | F | O | NH—CH₂Ph-2-OCH₃ | O—CH₃ | O—CH₃ | |
| 4029 | —(CH₂)₃— | F | O | NH—CH₂Ph-3-OCH₃ | O—CH₃ | O—CH₃ | |
| 4030 | —(CH₂)₃— | F | O | NH—CH₂Ph-4-OCH₃ | O—CH₃ | O—CH₃ | |
| 4031 | —(CH₂)₃— | F | O | NH—CH₂-2-furyl | O—CH₃ | O—CH₃ | |
| 4032 | —(CH₂)₃— | F | O | NH—CN | O—CH₃ | O—CH₃ | |
| 4033 | —(CH₂)₃— | F | O | NH—SO₂CH₃ | O—CH₃ | O—CH₃ | |

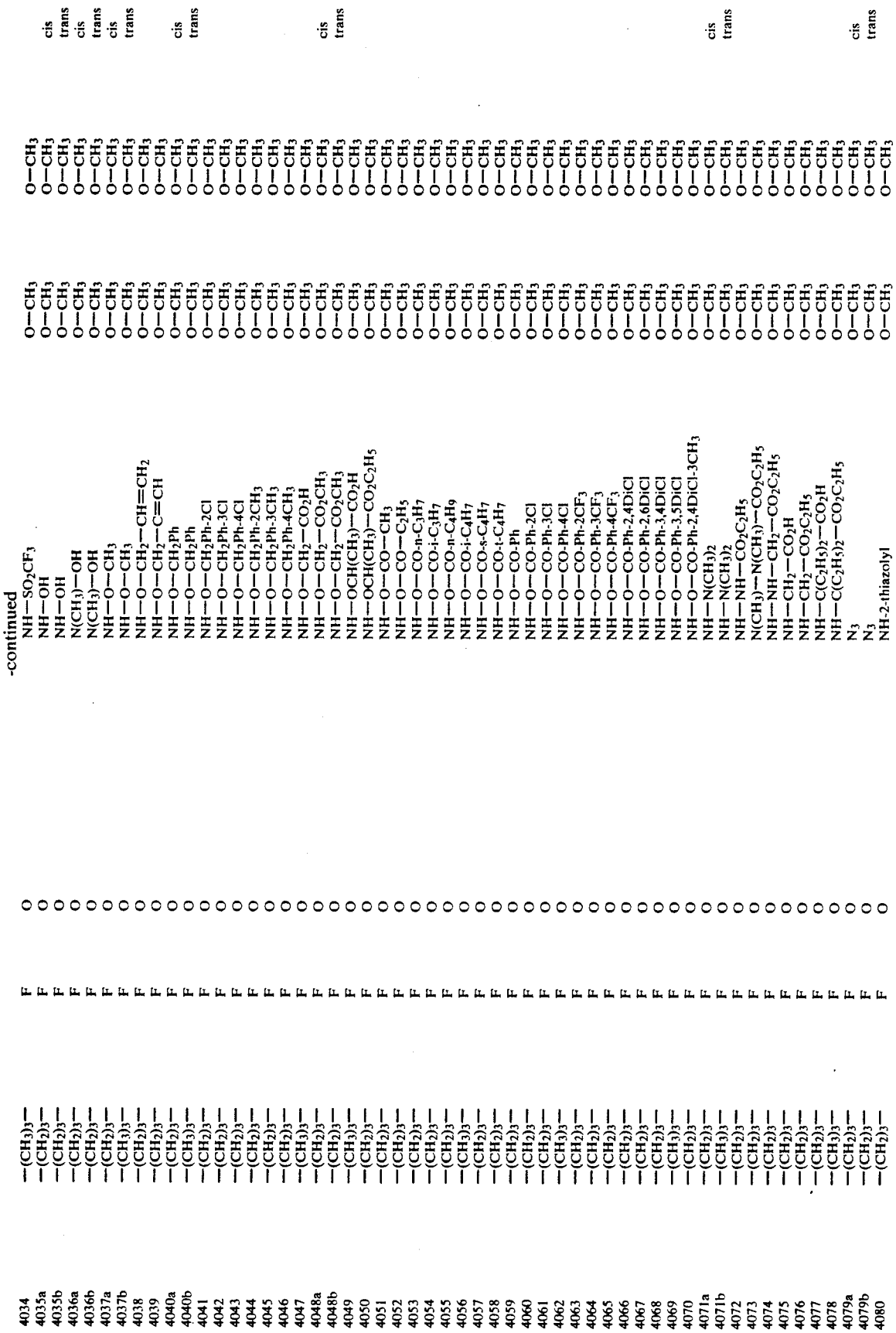

-continued

| | | | | | | |
|---|---|---|---|---|---|---|
| 4081 | —(CH₂)₃— | F | O | | NH-2-thiadiazolyl | O—CH₃ | O—CH₃ |
| 4082 | —(CH₂)₃— | F | O | | NH-2-thiadiazolyl-5CF₃ | O—CH₃ | O—CH₃ |
| 4083 | —(CH₂)₃— | F | O | | NH-2-pyridyl | O—CH₃ | O—CH₃ |
| 4084 | —(CH₂)₃— | F | O | | NH-3-pyridyl | O—CH₃ | O—CH₃ |
| 4085 | —(CH₂)₃— | F | O | | NH-4-pyridyl | O—CH₃ | O—CH₃ |
| 4086 | —(CH₂)₃— | F | O | | NH-2-benzothiazolyl | O—CH₃ | O—CH₃ |
| 4087 | —(CH₂)₃— | F | O | | NH—NH-2-pyridyl | O—CH₃ | O—CH₃ |
| 4088 | —(CH₂)₃— | F | O | | NH—NH-2-benzothiazolyl | O—CH₃ | O—CH₃ |
| 4089 | —(CH₂)₃— | F | O | N—OH | O—CH₃ | O—CH₃ | O—CH₃ |
| 4090 | —(CH₂)₃— | F | O | N—O—CH₃ | O—CH₃ | O—CH₃ | O—CH₃ |
| 4091 | —(CH₂)₃— | F | O | N—O—CH₂—CH=CH₂ | O—CH₃ | O—CH₃ | O—CH₃ |
| 4092 | —(CH₂)₃— | F | O | N—O—CH₂—C≡CH | O—CH₃ | O—CH₃ | O—CH₃ |
| 4093 | —(CH₂)₃— | F | O | N—O—CH₂-Ph | O—CH₃ | O—CH₃ | O—CH₃ |
| 4094 | —(CH₂)₃— | F | O | N—O—CH₂—CO₂H | O—CH₃ | O—CH₃ | O—CH₃ |
| 4095a | —(CH₂)₃— | F | O | N—O—CH₂—CO₂H | O—CH₃ | O—CH₃ cis |
| 4095b | —(CH₂)₃— | F | O | N—O—CH₂—CO₂CH₃ | O—CH₃ | O—CH₃ trans |
| 4096a | —(CH₂)₃— | F | O | N—O—CH₂—CO₂CH₃ | O—CH₃ | O—CH₃ cis |
| 4096b | —(CH₂)₃— | F | O | N—O—CH₂—CO₂CH₃ | O—CH₃ | O—CH₃ trans |
| 4097 | —(CH₂)₃— | F | O | N—O—CH₂—CO—CH₃ | O—CH₃ | O—CH₃ |
| 4098 | —(CH₂)₃— | F | O | N—O—CH₂—CO—C₂H₅ | O—CH₃ | O—CH₃ |
| 4099 | —(CH₂)₃— | F | O | N—O—CH₂—CO-n-C₃H₇ | O—CH₃ | O—CH₃ |
| 4100 | —(CH₂)₃— | F | O | N—O—CH₂—CO-i-C₃H₇ | O—CH₃ | O—CH₃ |
| 4101 | —(CH₂)₃— | F | O | N—O—CH₂—CO-n-C₄H₉ | O—CH₃ | O—CH₃ |
| 4102 | —(CH₂)₃— | F | O | N—O—CH₂—CO-i-C₄H₇ | O—CH₃ | O—CH₃ |
| 4103 | —(CH₂)₃— | F | O | N—O—CH₂—CO-s-C₄H₇ | O—CH₃ | O—CH₃ |
| 4104 | —(CH₂)₃— | F | O | N—O—CH₂—CO-t-C₄H₇ | O—CH₃ | O—CH₃ |
| 4105 | —(CH₂)₃— | F | O | N—O—CH₂—CO-Ph | O—CH₃ | O—CH₃ |
| 4106 | —(CH₂)₃— | F | S | | NH₂ | O—CH₃ | O—CH₃ |
| 4107 | —(CH₂)₃— | F | S | | NH—CH₃ | O—CH₃ | O—CH₃ |
| 4108 | —(CH₂)₃— | F | S | | NH—C₂H₅ | O—CH₃ | O—CH₃ |
| 4109 | —(CH₂)₃— | F | S | | NH-n-C₃H₇ | O—CH₃ | O—CH₃ |
| 4110 | —(CH₂)₃— | F | S | | NH—OH | O—CH₃ | O—CH₃ |
| 4111 | —(CH₂)₃— | F | O | | NH—O—CH₃ | O—CH₃ | O—CH₃ |
| 4112 | —(CH₂)₃— | F | O | | NH—O—CH₂-Ph | O—CH₃ | O—CH₃ |
| 4113 | —(CH₂)₃— | F | O | | NH—O—CH₂—CO₂CH₃ | O—CH₃ | O—CH₃ |
| 4114 | —(CH₂)₃— | Cl | O | | NH₂ | O—CH₃ | O—CH₃ |
| 4115 | —(CH₂)₃— | Cl | O | | NH—CH₃ | O—CH₃ | O—CH₃ |
| 4116 | —(CH₂)₃— | Cl | O | | NHC₂H₅ | O—CH₃ | O—CH₃ |
| 4117 | —(CH₂)₃— | Cl | O | | NH-n-C₃H₇ | O—CH₃ | O—CH₃ |
| 4118 | —(CH₂)₃— | Cl | O | | NH-i-C₃H₇ | O—CH₃ | O—CH₃ |
| 4119 | —(CH₂)₃— | Cl | O | | NH-n-C₄H₉ | O—CH₃ | O—CH₃ |
| 4120 | —(CH₂)₃— | Cl | O | | NH-i-C₄H₉ | O—CH₃ | O—CH₃ |
| 4121 | —(CH₂)₃— | Cl | O | | NH-s-C₄H₉ | O—CH₃ | O—CH₃ |
| 4122 | —(CH₂)₃— | Cl | O | | NH-t-C₄H₉ | O—CH₃ | O—CH₃ |
| 4123 | —(CH₂)₃— | Cl | O | | N(CH₃)₂ | O—CH₃ | O—CH₃ |
| 4124 | —(CH₂)₃— | Cl | O | | N—CH₂—CH=CH₂ | O—CH₃ | O—CH₃ |
| 4125 | —(CH₂)₃— | Cl | O | | N—CH₂—C≡CH | O—CH₃ | O—CH₃ |
| 4126 | —(CH₂)₃— | Cl | O | | NH-Ph | O—CH₃ | O—CH₃ |
| 4127 | —(CH₂)₃— | Cl | O | | NH-Ph-2Cl | O—CH₃ | O—CH₃ |
| 4128 | —(CH₂)₃— | Cl | O | | NH-Ph-3Cl | O—CH₃ | O—CH₃ |
| 4129 | —(CH₂)₃— | Cl | O | | NH-Ph-4Cl | O—CH₃ | O—CH₃ |
| 4130 | —(CH₂)₃— | Cl | O | | NH-Ph-2-OC₂H₅ | O—CH₃ | O—CH₃ |
| 4131 | —(CH₂)₃— | Cl | O | | NH-Ph-3-OC₂H₅ | O—CH₃ | O—CH₃ |
| 4132 | —(CH₂)₃— | Cl | O | | NH-Ph-4-OC₂H₅ | O—CH₃ | O—CH₃ |

| No. | | | | | | |
|---|---|---|---|---|---|---|
| 4133 | —(CH₂)₃— | Cl | O | NH-Ph-2CF₃ | O—CH₃ | O—CH₃ |
| 4134 | —(CH₂)₃— | Cl | O | NH-Ph-3CF₃ | O—CH₃ | O—CH₃ |
| 4135 | —(CH₂)₃— | Cl | O | NH-Ph₄-CF₃ | O—CH₃ | O—CH₃ |
| 4136 | —(CH₂)₃— | Cl | O | N(CH₃)-Ph | O—CH₃ | O—CH₃ |
| 4137 | —(CH₂)₃— | Cl | O | NH—CH₂Ph | O—CH₃ | O—CH₃ |
| 4138 | —(CH₂)₃— | Cl | O | NH—CH₂Ph-2Cl | O—CH₃ | O—CH₃ |
| 4139 | —(CH₂)₃— | Cl | O | NH—CH₂Ph-3Cl | O—CH₃ | O—CH₃ |
| 4140 | —(CH₂)₃— | Cl | O | NH—CH₂Ph-4Cl | O—CH₃ | O—CH₃ |
| 4141 | —(CH₂)₃— | Cl | O | NH—CH₂Ph-2-OCH₃ | O—CH₃ | O—CH₃ |
| 4142 | —(CH₂)₃— | Cl | O | NH—CH₂Ph-3-OCH₃ | O—CH₃ | O—CH₃ |
| 4143 | —(CH₂)₃— | Cl | O | NH—CH₂Ph-4-OCH₃ | O—CH₃ | O—CH₃ |
| 4144 | —(CH₂)₃— | Cl | O | NH—CH₂-2-furyl | O—CH₃ | O—CH₃ |
| 4145 | —(CH₂)₃— | Cl | O | NH—CN | O—CH₃ | O—CH₃ |
| 4146 | —(CH₂)₃— | Cl | O | NH—SO₂CH₃ | O—CH₃ | O—CH₃ |
| 4147 | —(CH₂)₃— | Cl | O | NH—SO₂CF₃ | O—CH₃ | O—CH₃ |
| 4148 | —(CH₂)₃— | Cl | O | NH—OH | O—CH₃ | O—CH₃ |
| 4149 | —(CH₂)₃— | Cl | O | N(CH₃)—OH | O—CH₃ | O—CH₃ |
| 4150 | —(CH₂)₃— | Cl | O | NH—O—CH₃ | O—CH₃ | O—CH₃ |
| 4151 | —(CH₂)₃— | Cl | O | NH—O—CH₂—CH=CH₂ | O—CH₃ | O—CH₃ |
| 4152 | —(CH₂)₃— | Cl | O | NH—O—CH₂—C≡CH | O—CH₃ | O—CH₃ |
| 4153 | —(CH₂)₃— | Cl | O | NH—O—CH₂Ph | O—CH₃ | O—CH₃ |
| 4154 | —(CH₂)₃— | Cl | O | NH—O—CH₂Ph-2Cl | O—CH₃ | O—CH₃ |
| 4155 | —(CH₂)₃— | Cl | O | NH—O—CH₂Ph-3Cl | O—CH₃ | O—CH₃ |
| 4156 | —(CH₂)₃— | Cl | O | NH—O—CH2Ph-4Cl | O—CH₃ | O—CH₃ |
| 4157 | —(CH₂)₃— | Cl | O | NH—O—CH₂Ph-2CH₃ | O—CH₃ | O—CH₃ |
| 4158 | —(CH₂)₃— | Cl | O | NH—O—CH₂Ph-3CH₃ | O—CH₃ | O—CH₃ |
| 4159 | —(CH₂)₃— | Cl | O | NH—O—CH₂Ph-4CH₃ | O—CH₃ | O—CH₃ |
| 4160 | —(CH₂)₃— | Cl | O | NH—O—CH₂—CO₂H | O—CH₃ | O—CH₃ |
| 4161 | —(CH₂)₃— | Cl | O | NH—O—CH₂—CO₂CH₃ | O—CH₃ | O—CH₃ |
| 4162 | —(CH₂)₃— | Cl | O | NH—OCH(CH₃)—CO₂H | O—CH₃ | O—CH₃ |
| 4163 | —(CH₂)₃— | Cl | O | NH—OCH(CH₃)—CO₂C₂H₅ | O—CH₃ | O—CH₃ |
| 4164 | —(CH₂)₃— | Cl | O | NH—O—CO—CH₃ | O—CH₃ | O—CH₃ |
| 4165 | —(CH₂)₃— | Cl | O | NH—O—CO—C₂H₅ | O—CH₃ | O—CH₃ |
| 4166 | —(CH₂)₃— | Cl | O | NH—O—CO-n-C₃H₇ | O—CH₃ | O—CH₃ |
| 4167 | —(CH₂)₃— | Cl | O | NH—O—CO-i-C₃H₇ | O—CH₃ | O—CH₃ |
| 4168 | —(CH₂)₃— | Cl | O | NH—O—CO-n-C₄H₉ | O—CH₃ | O—CH₃ |
| 4169 | —(CH₂)₃— | Cl | O | NH—O—CO-i-C₄H₇ | O—CH₃ | O—CH₃ |
| 4170 | —(CH₂)₃— | Cl | O | NH—O—CO-s-C₄H₇ | O—CH₃ | O—CH₃ |
| 4171 | —(CH₂)₃— | Cl | O | NH—O—CO-t-C₄H₇ | O—CH₃ | O—CH₃ |
| 4172 | —(CH₂)₃— | Cl | O | NH—O—CO-Ph | O—CH₃ | O—CH₃ |
| 4173 | —(CH₂)₃— | Cl | O | NH—O—CO-Ph-2Cl | O—CH₃ | O—CH₃ |
| 4174 | —(CH₂)₃— | Cl | O | NH—O—CO-Ph-3Cl | O—CH₃ | O—CH₃ |
| 4175 | —(CH₂)₃— | Cl | O | NH—O—CO-Ph-4Cl | O—CH₃ | O—CH₃ |
| 4176 | —(CH₂)₃— | Cl | O | NH—O—CO-Ph-2CF₃ | O—CH₃ | O—CH₃ |
| 4177 | —(CH₂)₃— | Cl | O | NH—O—CO-Ph-3CF₃ | O—CH₃ | O—CH₃ |
| 4178 | —(CH₂)₃— | Cl | O | NH—O—CO-Ph-4CF₃ | O—CH₃ | O—CH₃ |
| 4179 | —(CH₂)₃— | Cl | O | NH—O—CO-Ph-2,4DiCl | O—CH₃ | O—CH₃ |
| 4180 | —(CH₂)₃— | Cl | O | NH—O—CO-Ph-2,6DiCl | O—CH₃ | O—CH₃ |
| 4181 | —(CH₂)₃— | Cl | O | NH—O—CO-Ph-3,4DiCl | O—CH₃ | O—CH₃ |
| 4182 | —(CH₂)₃— | Cl | O | NH—O—CO-Ph-3,5DiCl | O—CH₃ | O—CH₃ |
| 4183 | —(CH₂)₃— | Cl | O | NH—O—CO-Ph-2,4DiCl-3CH₃ | O—CH₃ | O—CH₃ |
| 4184 | —(CH₂)₃— | Cl | O | NH—N(CH₃)₂ | O—CH₃ | O—CH₃ |
| 4185 | —(CH₂)₃— | Cl | O | NHNH—CO₂C₂H₅ | O—CH₃ | O—CH₃ |
| 4186 | —(CH₂)₃— | Cl | O | N(CH₃)—N(CH₃)—CO₂C₂H₅ | O—CH₃ | O—CH₃ |

| No. | | | | | | | |
|---|---|---|---|---|---|---|---|
| | | | | | | | |

-continued

| No. | L | X | Y | R | R' | R'' | isomer |
|---|---|---|---|---|---|---|---|
| 4187 | —(CH₂)₃— | Cl | O | NH—NH—CH₂—CO₂H | O—CH₃ | O—CH₃ | |
| 4188 | —(CH₂)₃— | Cl | O | NH—CH₂—CO₂H | O—CH₃ | O—CH₃ | |
| 4189 | —(CH₂)₃— | Cl | O | NH—CH₂—CO₂C₂H₅ | O—CH₃ | O—CH₃ | |
| 4190 | —(CH₂)₃— | Cl | O | NH—C(C₂H₅)₂—CO₂H | O—CH₃ | O—CH₃ | |
| 4191 | —(CH₃)₃— | Cl | O | NH—C(C₂H₅)₂—CO₂C₂H₅ | O—CH₃ | O—CH₃ | |
| 4192 | —(CH₂)₃— | Cl | O | N₃ | O—CH₃ | O—CH₃ | |
| 4193 | —(CH₂)₃— | Cl | O | NH-2-thiazolyl | O—CH₃ | O—CH₃ | |
| 4194 | —(CH₂)₃— | Cl | O | NH-2-thiadiazolyl | O—CH₃ | O—CH₃ | |
| 4195 | —(CH₂)₃— | Cl | O | NH-2-thiadiazolyl-5CF₃ | O—CH₃ | O—CH₃ | |
| 4196 | —(CH₂)₃— | Cl | O | NH-2-pyridyl | O—CH₃ | O—CH₃ | |
| 4197 | —(CH₂)₃— | Cl | O | NH-3-pyridyl | O—CH₃ | O—CH₃ | |
| 4198 | —(CH₂)₃— | Cl | O | NH-4-pyridyl | O—CH₃ | O—CH₃ | |
| 4199 | —(CH₂)₃— | Cl | O | NH-1-pyrrolidinyl | O—CH₃ | O—CH₃ | |
| 4200 | —(CH₂)₃— | Cl | O | NH-2-benzothiazolyl | O—CH₃ | O—CH₃ | |
| 4201 | —(CH₃)₃— | Cl | O | NH—NH-2-pyridyl | O—CH₃ | O—CH₃ | |
| 4202 | —(CH₂)₃— | Cl | O | NH—NH-2-benzothiazolyl | O—CH₃ | O—CH₃ | |
| 4203 | —(CH₂)₃— | Cl | NH—OH | O—CH₃ | O—CH₃ | O—CH₃ | |
| 4204 | —(CH₂)₃— | Cl | N—O—CH₃ | O—CH₃ | O—CH₃ | O—CH₃ | |
| 4205 | —(CH₂)₃— | Cl | N—O—CH₂—CH=CH₂ | O—CH₃ | O—CH₃ | O—CH₃ | |
| 4206 | —(CH₂)₃— | Cl | N—O—CH₂—C≡CH | O—CH₃ | O—CH₃ | O—CH₃ | |
| 4207 | —(CH₂)₃— | Cl | N—O—CH₂-Ph | O—CH₃ | O—CH₃ | O—CH₃ | |
| 4208 | —(CH₂)₃— | Cl | N—O—CH₂—CO₂H | O—CH₃ | O—CH₃ | O—CH₃ | |
| 4209 | —(CH₂)₃— | Cl | N—O—CH₂—CO₂CH₃ | O—CH₃ | O—CH₃ | O—CH₃ | |
| 4210 | —(CH₂)₃— | Cl | N—O—CH₂—CO—C₂H₅ | O—CH₃ | O—CH₃ | O—CH₃ | |
| 4211 | —(CH₂)₃— | Cl | N—O—CH₂—CO—CH₃ | O—CH₃ | O—CH₃ | O—CH₃ | |
| 4212 | —(CH₂)₃— | Cl | N—O—CH₂—CO-n-C₃H₇ | O—CH₃ | O—CH₃ | O—CH₃ | |
| 4213 | —(CH₂)₃— | Cl | N—O—CH₂—CO-i-C₃H₇ | O—CH₃ | O—CH₃ | O—CH₃ | |
| 4214 | —(CH₂)₃— | Cl | N—O—CH₂—CO-n-C₄H₉ | O—CH₃ | O—CH₃ | O—CH₃ | |
| 4215 | —(CH₃)₃— | Cl | N—O—CH₂—CO-i-C₄H₇ | O—CH₃ | O—CH₃ | O—CH₃ | |
| 4216 | —(CH₂)₃— | Cl | N—O—CH₂—CO-s-C₄H₇ | O—CH₃ | O—CH₃ | O—CH₃ | |
| 4217 | —(CH₂)₃— | Cl | N—O—CH₂—CO-t-C₄H₇ | O—CH₃ | O—CH₃ | O—CH₃ | |
| 4218 | —(CH₂)₃— | Cl | N—O—CH₂—CO-Ph | O—CH₃ | O—CH₃ | O—CH₃ | |
| 4219 | —(CH₂)₃— | Cl | S | NH₂ | O—CH₃ | O—CH₃ | |
| 4220 | —(CH₂)₃— | Cl | S | NH—CH₃ | O—CH₃ | O—CH₃ | |
| 4221 | —(CH₂)₃— | Cl | S | NH—C₂H₅ | O—CH₃ | O—CH₃ | |
| 4222 | —(CH₂)₃— | Cl | S | NH-n-C₃H₇ | O—CH₃ | O—CH₃ | |
| 4223 | —(CH₂)₃— | Cl | S | NH—OH | O—CH₃ | O—CH₃ | |
| 4224 | —(CH₂)₃— | Cl | S | NH—O—CH₃ | O—CH₃ | O—CH₃ | |
| 4225 | —(CH₂)₃— | Cl | S | NH—O—CH₂-Ph | O—CH₃ | O—CH₃ | |
| 4226 | —(CH₂)₃— | Cl | S | NH—O—CH₂—CO₂CH₃ | O—CH₃ | O—CH₃ | |
| 4227 | —(CH₂)₃— | F | O | S—CH₃ | O—CH₃ | O—CH₃ | |
| 4228a | —(CH₂)₃— | F | O | S—C₂H₅ | O—CH₃ | O—CH₃ | cis |
| 4228b | —(CH₂)₃— | F | O | S—C₂H₅ | O—CH₃ | O—CH₃ | trans |
| 4229 | —(CH₂)₃— | F | O | S-n-C₃H₇ | O—CH₃ | O—CH₃ | |
| 4230a | —(CH₂)₃— | F | O | S-i-C₃H₇ | O—CH₃ | O—CH₃ | cis |
| 4230b | —(CH₂)₃— | F | O | S-i-C₃H₇ | O—CH₃ | O—CH₃ | trans |
| 4231 | —(CH₂)₃— | F | O | S-n-C₄H₉ | O—CH₃ | O—CH₃ | |
| 4232 | —(CH₂)₃— | F | O | S-i-C₄H₉ | O—CH₃ | O—CH₃ | |
| 4233 | —(CH₂)₃— | F | O | S-s-C₄H₉ | O—CH₃ | O—CH₃ | |
| 4234a | —(CH₂)₃— | F | O | S-t-C₄H₉ | O—CH₃ | O—CH₃ | cis |
| 4234b | —(CH₂)₃— | F | O | S-t-C₄H₉ | O—CH₃ | O—CH₃ | trans |
| 4235 | —(CH₂)₃— | F | O | S—CH₂—CH=CH₂ | O—CH₃ | O—CH₃ | |
| 4236a | —(CH₂)₃— | F | O | S—CH₂-Ph | O—CH₃ | O—CH₃ | cis |
| 4236b | —(CH₂)₃— | F | O | S—CH₂-Ph | O—CH₃ | O—CH₃ | trans |

| No. | | X | | | | | |
|---|---|---|---|---|---|---|---|
| | | | | -continued | | | |
| 4237 | —(CH₂)₃— | F | O | S—CH₂-Ph-2Cl | O—CH₃ | O—CH₃ | |
| 4238 | —(CH₂)₃— | F | O | S—CH₂-Ph-3Cl | O—CH₃ | O—CH₃ | |
| 4239a | —(CH₂)₃— | F | O | S-2-pyridyl | O—CH₃ | O—CH₃ | cis |
| 4239b | —(CH₂)₃— | F | O | S-2-pyridyl | O—CH₃ | O—CH₃ | trans |
| 4240a | —(CH₂)₃— | F | O | S—CH₂-furyl | O—CH₃ | O—CH₃ | cis |
| 4240b | —(CH₂)₃— | F | O | S—CH₂-furyl | O—CH₃ | O—CH₃ | trans |
| 4241 | —(CH₂)₃— | F | O | S-Ph | O—CH₃ | O—CH₃ | |
| 4242 | —(CH₂)₃— | F | O | S-Ph-2Cl | O—CH₃ | O—CH₃ | |
| 4243 | —(CH₂)₃— | F | O | S-Ph-3Cl | O—CH₃ | O—CH₃ | |
| 4244 | —(CH₂)₃— | F | O | S-Ph-4Cl | O—CH₃ | O—CH₃ | |
| 4245 | —(CH₂)₃— | F | O | S-Ph-2-OCH₃ | O—CH₃ | O—CH₃ | |
| 4246 | —(CH₂)₃— | F | O | S-Ph-3-OCH₃ | O—CH₃ | O—CH₃ | |
| 4247 | —(CH₂)₃— | F | O | S-Ph-4-OCH₃ | O—CH₃ | O—CH₃ | |
| 4248 | —(CH₂)₃— | F | O | S-Ph-2-Br | O—CH₃ | O—CH₃ | |
| 4249 | —(CH₂)₃— | F | O | S-Ph-3-Br | O—CH₃ | O—CH₃ | |
| 4250 | —(CH₂)₃— | F | O | S-Ph-4-Br | O—CH₃ | O—CH₃ | |
| 4251 | —(CH₂)₃— | F | O | S—CH₃ | O—CH₃ | O—CH₃ | |
| 4252 | —(CH₂)₃— | F | O | S—C₂H₅ | O—CH₃ | O—CH₃ | |
| 4253 | —(CH₂)₃— | F | O | S-n-C₃H₇ | O—CH₃ | O—CH₃ | |
| 4254 | —(CH₂)₃— | F | O | S-i-C₃H₇ | O—CH₃ | O—CH₃ | |
| 4255 | —(CH₂)₃— | F | O | S-n-C₄H₉ | O—CH₃ | O—CH₃ | |
| 4256 | —(CH₂)₃— | F | O | S-i-C₄H₉ | O—CH₃ | O—CH₃ | |
| 4257 | —(CH₂)₃— | F | O | S-s-C₄H₉ | O—CH₃ | O—CH₃ | |
| 4258 | —(CH₂)₃— | F | O | S-t-C₄H₉ | O—CH₃ | O—CH₃ | |
| 4259 | —(CH₂)₃— | F | O | S—CH₂—CH=CH₂ | O—CH₃ | O—CH₃ | |
| 4260 | —(CH₂)₃— | Cl | O | S—CH₂-Ph | O—CH₃ | O—CH₃ | |
| 4261 | —(CH₂)₃— | Cl | O | S—CH₂-Ph-2Cl | O—CH₃ | O—CH₃ | |
| 4262 | —(CH₂)₃— | Cl | O | S—CH₂-Ph-3Cl | O—CH₃ | O—CH₃ | |
| 4263 | —(CH₂)₃— | Cl | O | S-2-pyridyl | O—CH₃ | O—CH₃ | |
| 4264 | —(CH₂)₃— | Cl | O | S—CH₂-furyl | O—CH₃ | O—CH₃ | |
| 4265 | —(CH₂)₃— | Cl | O | S-Ph | O—CH₃ | O—CH₃ | |
| 4266 | —(CH₂)₃— | Cl | O | S-Ph-2Cl | O—CH₃ | O—CH₃ | |
| 4267 | —(CH₂)₃— | Cl | O | S-Ph-3Cl | O—CH₃ | O—CH₃ | |
| 4268 | —(CH₂)₃— | Cl | O | S-Ph-4Cl | O—CH₃ | O—CH₃ | |
| 4269 | —(CH₂)₃— | Cl | O | S-Ph-2-OCH₃ | O—CH₃ | O—CH₃ | |
| 4270 | —(CH₂)₃— | Cl | O | S-Ph-3-OCH₃ | O—CH₃ | O—CH₃ | |
| 4271 | —(CH₂)₃— | Cl | O | S-Ph-4-OCH₃ | O—CH₃ | O—CH₃ | |
| 4272 | —(CH₂)₃— | Cl | O | S-Ph-2-Br | O—CH₃ | O—CH₃ | |
| 4273 | —(CH₂)₃— | Cl | O | S-Ph-3-Br | O—CH₃ | O—CH₃ | |
| 4274 | —(CH₂)₃— | Cl | O | S-Ph-4-Br | O—CH₃ | O—CH₃ | |

| No. | R1 | R2 | R3 | R4 | R5 | R6 | isomer |
|---|---|---|---|---|---|---|---|
| 4275a | —(CH$_2$)$_4$— | F | O | NH$_2$ | O—CH$_3$ | O—CH$_3$ | cis |
| 4275b | —(CH$_2$)$_4$— | F | O | NH$_2$ | O—CH$_3$ | O—CH$_3$ | trans |
| 4276a | —(CH$_3$)$_4$— | F | O | NH—CH$_3$ | O—CH$_3$ | O—CH$_3$ | cis |
| 4276b | —(CH$_2$)$_4$— | F | O | NH—CH$_3$ | O—CH$_3$ | O—CH$_3$ | trans |
| 4277a | —(CH$_2$)$_4$— | F | O | NH—C$_2$H$_5$ | O—CH$_3$ | O—CH$_3$ | cis |
| 4277b | —(CH$_2$)$_4$— | F | O | NH—C$_2$H$_5$ | O—CH$_3$ | O—CH$_3$ | trans |
| 4278 | —(CH$_2$)$_4$— | F | O | NH—n-C$_3$H$_7$ | O—CH$_3$ | O—CH$_3$ | |
| 4279 | —(CH$_2$)$_4$— | F | O | NH-i-C$_3$H$_7$ | O—CH$_3$ | O—CH$_3$ | |
| 4280 | —(CH$_2$)$_4$— | F | O | NH-n-C$_4$H$_9$ | O—CH$_3$ | O—CH$_3$ | |
| 4281 | —(CH$_2$)$_4$— | F | O | NH-i-C$_4$H$_9$ | O—CH$_3$ | O—CH$_3$ | |
| 4282 | —(CH$_2$)$_4$— | F | O | NH-s-C$_4$H$_9$ | O—CH$_3$ | O—CH$_3$ | |
| 4283a | —(CH$_3$)$_4$— | F | O | NH-t-C$_4$H$_9$ | O—CH$_3$ | O—CH$_3$ | cis |
| 4283b | —(CH$_2$)$_4$— | F | O | NH-t-C$_4$H$_9$ | O—CH$_3$ | O—CH$_3$ | trans |
| 4284 | —(CH$_2$)$_4$— | F | O | N(CH$_3$)$_2$ | O—CH$_3$ | O—CH$_3$ | |
| 4285 | —(CH$_2$)$_4$— | F | O | N—CH$_2$—CH=CH$_2$ | O—CH$_3$ | O—CH$_3$ | |
| 4286 | —(CH$_2$)$_4$— | F | O | N—CH$_2$—C≡CH | O—CH$_3$ | O—CH$_3$ | |
| 4287a | —(CH$_2$)$_4$— | F | O | NH-Ph | O—CH$_3$ | O—CH$_3$ | cis |
| 4287b | —(CH$_2$)$_4$— | F | O | NH-Ph | O—CH$_3$ | O—CH$_3$ | trans |
| 4288 | —(CH$_2$)$_4$— | F | O | NH-Ph-2Cl | O—CH$_3$ | O—CH$_3$ | |
| 4289 | —(CH$_2$)$_4$— | F | O | NH-Ph-3Cl | O—CH$_3$ | O—CH$_3$ | |
| 4290 | —(CH$_2$)$_4$— | F | O | NH-Ph-4Cl | O—CH$_3$ | O—CH$_3$ | |
| 4291 | —(CH$_2$)$_4$— | F | O | NH-Ph-2-OC$_2$H$_5$ | O—CH$_3$ | O—CH$_3$ | |
| 4292 | —(CH$_2$)$_4$— | F | O | NH-Ph-3-OC$_2$H$_5$ | O—CH$_3$ | O—CH$_3$ | |
| 4293a | —(CH$_2$)$_4$— | F | O | NH-Ph-4-OC$_2$H$_5$ | O—CH$_3$ | O—CH$_3$ | cis |
| 4293b | —(CH$_2$)$_4$— | F | O | NH-Ph-4-OC$_2$H$_5$ | O—CH$_3$ | O—CH$_3$ | trans |
| 4294 | —(CH$_2$)$_4$— | F | O | NH-Ph-2CF$_3$ | O—CH$_3$ | O—CH$_3$ | |
| 4295a | —(CH$_2$)$_4$— | F | O | NH-Ph-3CF$_3$ | O—CH$_3$ | O—CH$_3$ | cis |
| 4295b | —(CH$_2$)$_4$— | F | O | NH-Ph-3CF$_3$ | O—CH$_3$ | O—CH$_3$ | trans |
| 4296 | —(CH$_2$)$_4$— | F | O | NH-Ph-4CF$_3$ | O—CH$_3$ | O—CH$_3$ | |
| 4297a | —(CH$_2$)$_4$— | F | O | N(CH$_3$)-Ph | O—CH$_3$ | O—CH$_3$ | cis |
| 4297b | —(CH$_2$)$_4$— | F | O | N(CH$_3$)-Ph | O—CH$_3$ | O—CH$_3$ | trans |
| 4298 | —(CH$_2$)$_4$— | F | O | NH—CH$_2$Ph | O—CH$_3$ | O—CH$_3$ | |
| 4299 | —(CH$_2$)$_4$— | F | O | NH—CH$_2$Ph-2Cl | O—CH$_3$ | O—CH$_3$ | |
| 4300 | —(CH$_2$)$_4$— | F | O | NH—CH$_2$Ph-3Cl | O—CH$_3$ | O—CH$_3$ | |
| 4301 | —(CH$_2$)$_4$— | F | O | NH—CH$_2$Ph-4Cl | O—CH$_3$ | O—CH$_3$ | |
| 4302 | —(CH$_2$)$_4$— | F | O | NH—CH$_2$Ph-2-OCH$_3$ | O—CH$_3$ | O—CH$_3$ | |
| 4303 | —(CH$_2$)$_4$— | F | O | NH—CH$_2$Ph-3-OCH$_3$ | O—CH$_3$ | O—CH$_3$ | |
| 4304 | —(CH$_2$)$_4$— | F | O | NH—CH$_2$Ph-4-OCH$_3$ | O—CH$_3$ | O—CH$_3$ | |
| 4305a | —(CH$_2$)$_4$— | F | O | NH—CH$_2$-2-furyl | O—CH$_3$ | O—CH$_3$ | cis |
| 4305b | —(CH$_2$)$_4$— | F | O | NH—CH$_2$-2-furyl | O—CH$_3$ | O—CH$_3$ | trans |
| 4306 | —(CH$_2$)$_4$— | F | O | NH—CN | O—CH$_3$ | O—CH$_3$ | |
| 4307 | —(CH$_2$)$_4$— | F | O | NH—SO$_2$CH$_3$ | O—CH$_3$ | O—CH$_3$ | |
| 4308 | —(CH$_2$)$_4$— | F | O | NH—SO$_2$CF$_3$ | O—CH$_3$ | O—CH$_3$ | |
| 4309a | —(CH$_2$)$_4$— | F | O | NH—OH | O—CH$_3$ | O—CH$_3$ | cis |
| 4309b | —(CH$_2$)$_4$— | F | O | NH—OH | O—CH$_3$ | O—CH$_3$ | trans |
| 4310 | —(CH$_2$)$_4$— | F | O | N(CH$_3$)—OH | O—CH$_3$ | O—CH$_3$ | |
| 4311a | —(CH$_2$)$_4$— | F | O | NH—O—CH$_3$ | O—CH$_3$ | O—CH$_3$ | cis |
| 4311b | —(CH$_2$)$_4$— | F | O | NH—O—CH$_3$ | O—CH$_3$ | O—CH$_3$ | trans |
| 4312 | —(CH$_2$)$_4$— | F | O | NH—O—CH$_2$—CH=CH$_2$ | O—CH$_3$ | O—CH$_3$ | |
| 4313 | —(CH$_2$)$_4$— | F | O | NH—O—CH$_2$—C≡CH | O—CH$_3$ | O—CH$_3$ | |
| 4314a | —(CH$_2$)$_4$— | F | O | NH—O—CH$_2$-Ph | O—CH$_3$ | O—CH$_3$ | cis |
| 4314b | —(CH$_2$)$_4$— | F | O | NH—O—CH$_2$-Ph | O—CH$_3$ | O—CH$_3$ | trans |
| 4315 | —(CH$_2$)$_4$— | F | O | NH—O—CH$_2$Ph-2Cl | O—CH$_3$ | O—CH$_3$ | |
| 4316 | —(CH$_2$)$_4$— | F | O | NH—O—CH$_2$Ph-3Cl | O—CH$_3$ | O—CH$_3$ | |

-continued

| No. | | | | | | | |
|---|---|---|---|---|---|---|---|
| 4317 | —(CH$_2$)$_4$— | F | o | NH—O—CH$_2$Ph-4Cl | O—CH$_3$ | O—CH$_3$ | |
| 4318 | —(CH$_2$)$_4$— | F | o | NH—O—CH$_2$Ph-2CH$_3$ | O—CH$_3$ | O—CH$_3$ | |
| 4319 | —(CH$_2$)$_4$— | F | o | NH—O—CH$_2$Ph-3CH$_3$ | O—CH$_3$ | O—CH$_3$ | |
| 4320 | —(CH$_2$)$_4$— | F | o | NH—O—CH$_2$Ph-4CH$_3$ | O—CH$_3$ | O—CH$_3$ | |
| 4321 | —(CH$_2$)$_4$— | F | o | NH—O—CH$_2$—CO$_2$H | O—CH$_3$ | O—CH$_3$ | |
| 4322a | —(CH$_2$)$_4$— | F | o | NH—O—CH$_2$—CO$_2$CH$_3$ | O—CH$_3$ | O—CH$_3$ | cis |
| 4322b | —(CH$_2$)$_4$— | F | o | NH—O—CH$_2$—CO$_2$CH$_3$ | O—CH$_3$ | O—CH$_3$ | trans |
| 4323 | —(CH$_2$)$_4$— | F | o | NH—O—CH(CH$_3$)—CO$_2$H | O—CH$_3$ | O—CH$_3$ | |
| 4324 | —(CH$_2$)$_4$— | F | o | NH—O—CH(CH$_3$)—CO$_2$C$_2$H$_5$ | O—CH$_3$ | O—CH$_3$ | |
| 4325a | —(CH$_2$)$_4$— | F | o | NH—O—CO—CH$_3$ | O—CH$_3$ | O—CH$_3$ | cis |
| 4325b | —(CH$_2$)$_4$— | F | o | NH—O—CO—CH$_3$ | O—CH$_3$ | O—CH$_3$ | trans |
| 4326 | —(CH$_2$)$_4$— | F | o | NH—O—CO—C$_2$H$_5$ | O—CH$_3$ | O—CH$_3$ | |
| 4327 | —(CH$_2$)$_4$— | F | o | NH—O—CO-n-C$_3$H$_7$ | O—CH$_3$ | O—CH$_3$ | |
| 4328 | —(CH$_2$)$_4$— | F | o | NH—O—CO-i-C$_3$H$_7$ | O—CH$_3$ | O—CH$_3$ | |
| 4329 | —(CH$_2$)$_4$— | F | o | NH—O—CO-n-C$_4$H$_9$ | O—CH$_3$ | O—CH$_3$ | |
| 4330 | —(CH$_2$)$_4$— | F | o | NH—O—CO-i-C$_4$H$_7$ | O—CH$_3$ | O—CH$_3$ | |
| 4331 | —(CH$_2$)$_4$— | F | o | NH—O—CO-s-C$_4$H$_7$ | O—CH$_3$ | O—CH$_3$ | |
| 4332a | —(CH$_2$)$_4$— | F | o | NH—O—CO-t-C$_4$H$_7$ | O—CH$_3$ | O—CH$_3$ | cis |
| 4332b | —(CH$_2$)$_4$— | F | o | NH—O—CO-t-C$_4$H$_7$ | O—CH$_3$ | O—CH$_3$ | trans |
| 4333 | —(CH$_2$)$_4$— | F | o | NH—O—CO-Ph | O—CH$_3$ | O—CH$_3$ | |
| 4334 | —(CH$_2$)$_4$— | F | o | NH—O—CO-Ph-2Cl | O—CH$_3$ | O—CH$_3$ | |
| 4335 | —(CH$_2$)$_4$— | F | o | NH—O—CO-Ph-3Cl | O—CH$_3$ | O—CH$_3$ | |
| 4336 | —(CH$_2$)$_4$— | F | o | NH—O—CO-Ph-4Cl | O—CH$_3$ | O—CH$_3$ | |
| 4337 | —(CH$_2$)$_4$— | F | o | NH—O—CO-Ph-2CF$_3$ | O—CH$_3$ | O—CH$_3$ | |
| 4338 | —(CH$_2$)$_4$— | F | o | NH—O—CO-Ph-3CF$_3$ | O—CH$_3$ | O—CH$_3$ | |
| 4339 | —(CH$_2$)$_4$— | F | o | NH—O—CO-Ph-4CF$_3$ | O—CH$_3$ | O—CH$_3$ | |
| 4340 | —(CH$_2$)$_4$— | F | o | NH—O—CO-Ph-2,4DiCl | O—CH$_3$ | O—CH$_3$ | |
| 4341 | —(CH$_2$)$_4$— | F | o | NH—O—CO-Ph-2,6DiCl | O—CH$_3$ | O—CH$_3$ | |
| 4342 | —(CH$_2$)$_4$— | F | o | NH—O—CO-Ph-3,4DiCl | O—CH$_3$ | O—CH$_3$ | |
| 4343 | —(CH$_2$)$_4$— | F | o | NH—O—CO-Ph-3,5DiCl | O—CH$_3$ | O—CH$_3$ | |
| 4344a | —(CH$_2$)$_4$— | F | o | NH—O—CO-Ph-2,4DiCl-3CH$_3$ | O—CH$_3$ | O—CH$_3$ | cis |
| 4344b | —(CH$_2$)$_4$— | F | o | NH—O—CO-Ph-2,4DiCl-3CH$_3$ | O—CH$_3$ | O—CH$_3$ | trans |
| 4345 | —(CH$_2$)$_4$— | F | o | NH—N(CH$_3$)$_2$ | O—CH$_3$ | O—CH$_3$ | |
| 4346a | —(CH$_2$)$_4$— | F | o | NH—NH—CO$_2$C$_2$H$_5$ | O—CH$_3$ | O—CH$_3$ | cis |
| 4346b | —(CH$_2$)$_4$— | F | o | NH—NH—CO$_2$C$_2$H$_5$ | O—CH$_3$ | O—CH$_3$ | trans |
| 4347a | —(CH$_2$)$_4$— | F | o | N(CH$_3$)—N(CH$_3$)—CO$_2$C$_2$H$_5$ | O—CH$_3$ | O—CH$_3$ | cis |
| 4347b | —(CH$_2$)$_4$— | F | o | N(CH$_3$)—N(CH$_3$)—CO$_2$C$_2$H$_5$ | O—CH$_3$ | O—CH$_3$ | trans |
| 4348a | —(CH$_2$)$_4$— | F | o | NH—NH—CH$_2$—CO$_2$C$_2$H$_5$ | O—CH$_3$ | O—CH$_3$ | cis |
| 4348b | —(CH$_2$)$_4$— | F | o | NH—NH—CH$_2$—CO$_2$C$_2$H$_5$ | O—CH$_3$ | O—CH$_3$ | trans |
| 4349 | —(CH$_2$)$_4$— | F | o | NH—CH$_2$—CO$_2$H | O—CH$_3$ | O—CH$_3$ | |
| 4350a | —(CH$_2$)$_4$— | F | o | NH—CH$_2$—CO$_2$C$_2$H$_5$ | O—CH$_3$ | O—CH$_3$ | cis |
| 4350b | —(CH$_2$)$_4$— | F | o | NH—CH$_2$—CO$_2$C$_2$H$_5$ | O—CH$_3$ | O—CH$_3$ | trans |
| 4351a | —(CH$_2$)$_4$— | F | o | NH—C(C$_2$H$_5$)$_2$—CO$_2$C$_2$H$_5$ | O—CH$_3$ | O—CH$_3$ | cis |
| 4351b | —(CH$_2$)$_4$— | F | o | NH—C(C$_2$H$_5$)$_2$—CO$_2$C$_2$H$_5$ | O—CH$_3$ | O—CH$_3$ | trans |
| 4352a | —(CH$_2$)$_4$— | F | o | N$_3$ | O—CH$_3$ | O—CH$_3$ | cis |
| 4352b | —(CH$_2$)$_4$— | F | o | N$_3$ | O—CH$_3$ | O—CH$_3$ | trans |
| 4353a | —(CH$_2$)$_4$— | F | o | NH-2-thiazolyl | O—CH$_3$ | O—CH$_3$ | cis |
| 4353b | —(CH$_2$)$_4$— | F | o | NH-2-thiazolyl | O—CH$_3$ | O—CH$_3$ | trans |
| 4354a | —(CH$_2$)$_4$— | F | o | NH-2-thiadiazolyl | O—CH$_3$ | O—CH$_3$ | cis |
| 4354b | —(CH$_2$)$_4$— | F | o | NH-2-thiadiazolyl | O—CH$_3$ | O—CH$_3$ | trans |
| 4355a | —(CH$_2$)$_4$— | F | o | NH-2-thiadiazolyl-5CF$_3$ | O—CH$_3$ | O—CH$_3$ | cis |
| 4355b | —(CH$_2$)$_4$— | F | o | NH-2-thiadiazolyl-5CF$_3$ | O—CH$_3$ | O—CH$_3$ | trans |
| 4356a | —(CH$_2$)$_4$— | F | o | NH-2-pyridyl | O—CH$_3$ | O—CH$_3$ | cis |
| 4356b | —(CH$_2$)$_4$— | F | o | NH-2-pyridyl | O—CH$_3$ | O—CH$_3$ | trans |

-continued

| | | | | | | |
|---|---|---|---|---|---|---|
| 4357a | —(CH₂)₄— | F | O | N—OH | O—CH₃ | O—CH₃ | cis |
| 4357b | —(CH₂)₄— | F | O | N—OH | O—CH₃ | O—CH₃ | trans |
| 4358a | —(CH₂)₄— | F | O | N—O—CH₃ | O—CH₃ | O—CH₃ | cis |
| 4358b | —(CH₂)₄— | F | O | N—O—CH₃ | O—CH₃ | O—CH₃ | trans |
| 4359a | —(CH₂)₄— | F | O | N—O—CH₂—CH=CH₂ | O—CH₃ | O—CH₃ | cis |
| 4359b | —(CH₂)₄— | F | O | N—O—CH₂—CH=CH₂ | O—CH₃ | O—CH₃ | trans |
| 4360a | —(CH₂)₄— | F | O | N—O—CH₂C≡CH | O—CH₃ | O—CH₃ | cis |
| 4360b | —(CH₂)₄— | F | O | N—O—CH₂C≡CH | O—CH₃ | O—CH₃ | trans |
| 4361a | —(CH₂)₄— | F | O | N—O—CH₂-Ph | O—CH₃ | O—CH₃ | cis |
| 4361b | —(CH₂)₄— | F | O | N—O—CH₂-Ph | O—CH₃ | O—CH₃ | trans |
| 4362 | —(CH₂)₄— | F | O | N—O—CH₂—CO₂H | O—CH₃ | O—CH₃ | |
| 4363 | —(CH₂)₄— | F | O | N—O—CH₂—CO₂CH₃ | O—CH₃ | O—CH₃ | |
| 4364 | —(CH₂)₄— | F | O | N—O—CH₂—CO₂C₂H₅ | O—CH₃ | O—CH₃ | |
| 4365 | —(CH₂)₄— | F | O | N—O—CH₂—CO—CH₃ | O—CH₃ | O—CH₃ | |
| 4366 | —(CH₂)₄— | F | O | N—O—CH₂—CO—C₂H₅ | O—CH₃ | O—CH₃ | |
| 4367 | —(CH₂)₄— | F | O | N—O—CH₂—CO-n-C₃H₇ | O—CH₃ | O—CH₃ | |
| 4368 | —(CH₂)₄— | F | O | N—O—CH₂—CO-i-C₃H₇ | O—CH₃ | O—CH₃ | |
| 4369a | —(CH₂)₄— | F | O | N—O—CH₂—CO-n-C₄H₉ | O—CH₃ | O—CH₃ | cis |
| 4369b | —(CH₂)₄— | F | O | N—O—CH₂—CO-n-C₄H₉ | O—CH₃ | O—CH₃ | trans |
| 4370 | —(CH₂)₄— | F | O | N—O—CH₂—CO-i-C₄H₇ | O—CH₃ | O—CH₃ | |
| 4371 | —(CH₂)₄— | F | O | N—O—CH₂—CO-s-C₄H₇ | O—CH₃ | O—CH₃ | |
| 4372 | —(CH₂)₄— | F | O | N—O—CH₂—CO-t-C₄H₇ | O—CH₃ | O—CH₃ | |
| 4373 | —(CH₂)₄— | F | O | N—O—CH₂—CO-Ph | O—CH₃ | O—CH₃ | |
| 4374 | —(CH₂)₄— | F | O | O—CH₃ | O—CH₃ | O—CH₃ | |
| 4375 | —(CH₂)₄— | F | O | O—CH₃ | O—CH₃ | O—CH₃ | |
| 4376 | —(CH₂)₄— | F | O | O—CH₃ | O—CH₃ | O—CH₃ | |
| 4377 | —(CH₂)₄— | F | O | O—CH₃ | O—CH₃ | O—CH₃ | |
| 4378 | —(CH₂)₄— | F | S | O—CH₃ | O—CH₃ | O—CH₃ | |
| 4379a | —(CH₂)₄— | F | S | NH₂ | O—CH₃ | O—CH₃ | cis |
| 4379b | —(CH₂)₄— | F | S | NH₂ | O—CH₃ | O—CH₃ | trans |
| 4380 | —(CH₂)₄— | F | S | NH—CH₃ | O—CH₃ | O—CH₃ | |
| 4381 | —(CH₂)₄— | F | S | NH—C₂H₅ | O—CH₃ | O—CH₃ | |
| 4382 | —(CH₂)₄— | F | S | NH-n-C₃H₇ | O—CH₃ | O—CH₃ | |
| 4383 | —(CH₂)₄— | F | S | NH—OH | O—CH₃ | O—CH₃ | |
| 4384 | —(CH₂)₄— | F | S | NH—O—CH₃ | O—CH₃ | O—CH₃ | |
| 4385 | —(CH₂)₄— | F | O | NH—O—CH₂-Ph | O—CH₃ | O—CH₃ | |
| 4386 | —(CH₂)₄— | F | O | NH—O—CH₂—CO₂CH₃ | O—CH₃ | O—CH₃ | |
| 4387 | —(CH₂)₄— | Cl | O | NH₂ | O—CH₃ | O—CH₃ | |
| 4388 | —(CH₂)₄— | Cl | O | NH—CH₃ | O—CH₃ | O—CH₃ | |
| 4389 | —(CH₂)₄— | Cl | O | NH—C₂H₅ | O—CH₃ | O—CH₃ | |
| 4390 | —(CH₂)₄— | Cl | O | NH-n-C₃H₅ | O—CH₃ | O—CH₃ | |
| 4391 | —(CH₂)₄— | Cl | O | NH-i-C₃H₅ | O—CH₃ | O—CH₃ | |
| 4392 | —(CH₂)₄— | Cl | O | NH-n-C₄H₉ | O—CH₃ | O—CH₃ | |
| 4393 | —(CH₂)₄— | Cl | O | NH-i-C₄H₉ | O—CH₃ | O—CH₃ | |
| 4394 | —(CH₂)₄— | Cl | O | NH-s-C₄H₉ | O—CH₃ | O—CH₃ | |
| 4395 | —(CH₂)₄— | Cl | O | NH-t-C₄H₉ | O—CH₃ | O—CH₃ | |
| 4396a | —(CH₂)₄— | Cl | O | N(CH₃)₂ | O—CH₃ | O—CH₃ | cis |
| 4396b | —(CH₂)₄— | Cl | O | N(CH₃)₂ | O—CH₃ | O—CH₃ | trans |
| 4397 | —(CH₂)₄— | Cl | O | N—CH₂—C≡CH | O—CH₃ | O—CH₃ | |
| 4398 | —(CH₂)₄— | Cl | O | NH-Ph | O—CH₃ | O—CH₃ | |
| 4399 | —(CH₂)₄— | Cl | O | NH-Ph-2Cl | O—CH₃ | O—CH₃ | |
| 4400 | —(CH₂)₄— | Cl | O | NH-Ph-3Cl | O—CH₃ | O—CH₃ | |
| 4401 | —(CH₂)₄— | Cl | O | NH-Ph-4Cl | O—CH₃ | O—CH₃ | |
| 4402 | —(CH₂)₄— | Cl | O | NH-Ph-2-OC₂H₅ | O—CH₃ | O—CH₃ | |

-continued

| No. | | | | | | |
|---|---|---|---|---|---|---|
| 4403 | —(CH₂)₄— | NH-Ph-3-OC₂H₅ | Cl | O | O—CH₃ | O—CH₃ |
| 4404 | —(CH₂)₄— | NH-Ph-4-OC₂H₅ | Cl | O | O—CH₃ | O—CH₃ |
| 4405 | —(CH₂)₄— | NH-Ph-2CF₃ | Cl | O | O—CH₃ | O—CH₃ |
| 4406 | —(CH₂)₄— | NH-Ph-3CF₃ | Cl | O | O—CH₃ | O—CH₃ |
| 4407 | —(CH₂)₄— | NH-Ph-4CF₃ | Cl | O | O—CH₃ | O—CH₃ |
| 4408 | —(CH₃)₄— | N(CH₃)-Ph | Cl | O | O—CH₃ | O—CH₃ |
| 4409 | —(CH₂)₄— | NH—CH₂Ph | Cl | O | O—CH₃ | O—CH₃ |
| 4410 | —(CH₂)₄— | NH—CH₂Ph-2Cl | Cl | O | O—CH₃ | O—CH₃ |
| 4411 | —(CH₂)₄— | NH—CH₂Ph-3Cl | Cl | O | O—CH₃ | O—CH₃ |
| 4412 | —(CH₂)₄— | NH—CH₂Ph-4Cl | Cl | O | O—CH₃ | O—CH₃ |
| 4413 | —(CH₂)₄— | NH—CH₂Ph-2-OCH₃ | Cl | O | O—CH₃ | O—CH₃ |
| 4414 | —(CH₂)₄— | NH—CH₂Ph-3-OCH₃ | Cl | O | O—CH₃ | O—CH₃ |
| 4415 | —(CH₂)₄— | NH—CH₂Ph-4-OCH₃ | Cl | O | O—CH₃ | O—CH₃ |
| 4416 | —(CH₂)₄— | NH—CH₂-2-furyl | Cl | O | O—CH₃ | O—CH₃ |
| 4417 | —(CH₂)₄— | NH—CN | Cl | O | O—CH₃ | O—CH₃ |
| 4418 | —(CH₃)₄— | NH—SO₂CH₃ | Cl | O | O—CH₃ | O—CH₃ |
| 4419 | —(CH₂)₄— | NH—SO₂CF₃ | Cl | O | O—CH₃ | O—CH₃ |
| 4420 | —(CH₂)₄— | NH—OH | Cl | O | O—CH₃ | O—CH₃ |
| 4421 | —(CH₂)₄— | N(CH₃)—OH | Cl | O | O—CH₃ | O—CH₃ |
| 4422 | —(CH₃)₄— | NH—O—CH₃ | Cl | O | O—CH₃ | O—CH₃ |
| 4423 | —(CH₂)₄— | NH—O—CH₂—CH=CH₂ | Cl | O | O—CH₃ | O—CH₃ |
| 4424 | —(CH₂)₄— | NH—O—CH₂—C≡CH | Cl | O | O—CH₃ | O—CH₃ |
| 4425 | —(CH₃)₄— | NH—O—CH₂Ph | Cl | O | O—CH₃ | O—CH₃ |
| 4426 | —(CH₂)₄— | NH—O—CH₂Ph-2Cl | Cl | O | O—CH₃ | O—CH₃ |
| 4427 | —(CH₂)₄— | NH—O—CH₂Ph-3Cl | Cl | O | O—CH₃ | O—CH₃ |
| 4428 | —(CH₂)₄— | NH—O—CH₂Ph-4Cl | Cl | O | O—CH₃ | O—CH₃ |
| 4429 | —(CH₂)₄— | NH—O—CH₂Ph-2CH₃ | Cl | O | O—CH₃ | O—CH₃ |
| 4430 | —(CH₂)₄— | NH—O—CH₂Ph-3CH₃ | Cl | O | O—CH₃ | O—CH₃ |
| 4431 | —(CH₂)₄— | NH—O—CH₂Ph-4CH₃ | Cl | O | O—CH₃ | O—CH₃ |
| 4432 | —(CH₂)₄— | NH—O—CH₂—CO₂H | Cl | O | O—CH₃ | O—CH₃ |
| 4433 | —(CH₂)₄— | NH—O—CH₂—CO₂CH₃ | Cl | O | O—CH₃ | O—CH₃ |
| 4434 | —(CH₂)₄— | NH—OCH(CH₃)—CO₂H | Cl | O | O—CH₃ | O—CH₃ |
| 4435 | —(CH₂)₄— | NH—OCH(CH₃)—CO₂CH₃ | Cl | O | O—CH₃ | O—CH₃ |
| 4436 | —(CH₂)₄— | NH—OCH(CH₃)—CO₂C₂H₅ | Cl | O | O—CH₃ | O—CH₃ |
| 4437 | —(CH₂)₄— | NH—O—CO—CH₃ | Cl | O | O—CH₃ | O—CH₃ |
| 4438 | —(CH₂)₄— | NH—O—CO—C₂H₅ | Cl | O | O—CH₃ | O—CH₃ |
| 4439 | —(CH₂)₄— | NH—O—CO-n-C₃H₇ | Cl | O | O—CH₃ | O—CH₃ |
| 4440 | —(CH₃)₄— | NH—O—CO-i-C₃H₇ | Cl | O | O—CH₃ | O—CH₃ |
| 4441 | —(CH₂)₄— | NH—O—CO-n-C₄H₉ | Cl | O | O—CH₃ | O—CH₃ |
| 4442 | —(CH₂)₄— | NH—CH₂-2-furyl | Cl | O | O—CH₃ | O—CH₃ |
| 4443 | —(CH₂)₄— | NH—CN | Cl | O | O—CH₃ | O—CH₃ |
| 4444 | —(CH₃)₄— | NH—SO₂CH₃ | Cl | O | O—CH₃ | O—CH₃ |
| 4445 | —(CH₂)₄— | NH—SO₂CF₃ | Cl | O | O—CH₃ | O—CH₃ |
| 4446 | —(CH₂)₄— | NH—OH | Cl | O | O—CH₃ | O—CH₃ |
| 4447 | —(CH₂)₄— | N(CH₃)—OH | Cl | O | O—CH₃ | O—CH₃ |
| 4448 | —(CH₂)₄— | NH—O—CH₃ | Cl | O | O—CH₃ | O—CH₃ |
| 4449 | —(CH₂)₄— | NH—O—CH₂—CH=CH₂ | Cl | O | O—CH₃ | O—CH₃ |
| 4450 | —(CH₂)₄— | NH—O—CH₂—C≡CH | Cl | O | O—CH₃ | O—CH₃ |
| 4451 | —(CH₂)₄— | NH—O—CH₂Ph | Cl | O | O—CH₃ | O—CH₃ |
| 4452 | —(CH₂)₄— | NH—O—CH₂Ph-2Cl | Cl | O | O—CH₃ | O—CH₃ |
| 4453 | —(CH₂)₄— | NH—O—CH₂Ph-3Cl | Cl | O | O—CH₃ | O—CH₃ |
| 4454 | —(CH₂)₄— | NH—O—CH₂Ph-4Cl | Cl | O | O—CH₃ | O—CH₃ |
| 4455 | —(CH₂)₄— | NH—O—CH₂Ph-2CH₃ | Cl | O | O—CH₃ | O—CH₃ |
| 4456 | —(CH₂)₄— | NH—O—CH₂Ph-3CH₃ | Cl | O | O—CH₃ | O—CH₃ |
| | | NH—O—CH₂Ph-4CH₃ | | | | |

-continued

| No. | | | | | | | |
|---|---|---|---|---|---|---|---|
| 4457 | —(CH₂)₄— | Cl | O | NH—O—CH₂—CO₂H | O—CH₃ | O—CH₃ | |
| 4458 | —(CH₂)₄— | Cl | O | NH—O—CH₂—CO₂CH₃ | O—CH₃ | O—CH₃ | |
| 4459 | —(CH₂)₄— | Cl | O | NH—OCH(CH₃)—CO₂H | O—CH₃ | O—CH₃ | |
| 4460 | —(CH₂)₄— | Cl | O | NH—OCH(CH₃)—CO₂C₃H₅ | O—CH₃ | O—CH₃ | |
| 4461 | —(CH₂)₄— | Cl | O | NH—O—CO—CH₃ | O—CH₃ | O—CH₃ | |
| 4462 | —(CH₂)₄— | Cl | O | NH—O—CO—C₂H₅ | O—CH₃ | O—CH₃ | |
| 4463 | —(CH₂)₄— | Cl | O | NH—O—CO—n-C₃H₇ | O—CH₃ | O—CH₃ | |
| 4464 | —(CH₂)₄— | Cl | O | NH—O—CO—i-C₃H₇ | O—CH₃ | O—CH₃ | |
| 4465 | —(CH₂)₄— | Cl | O | NH—O—CO—n-C₄H₉ | O—CH₃ | O—CH₃ | |
| 4466 | —(CH₂)₄— | Cl | O | NH-2-thiadiazolyl | O—CH₃ | O—CH₃ | |
| 4467 | —(CH₂)₄— | Cl | O | NH-2-thiadiazolyl-5CF₃ | O—CH₃ | O—CH₃ | |
| 4468 | —(CH₃)₄— | Cl | O | NH-2-pyridyl | O—CH₃ | O—CH₃ | |
| 4469 | —(CH₂)₄— | Cl | O | NH-3-pyridyl | O—CH₃ | O—CH₃ | |
| 4470 | —(CH₂)₄— | Cl | O | NH-4-pyridyl | O—CH₃ | O—CH₃ | |
| 4471 | —(CH₂)₄— | Cl | O | NH-1-pyroridinyl | O—CH₃ | O—CH₃ | |
| 4472 | —(CH₂)₄— | Cl | O | NH-2-benzothiazolyl | O—CH₃ | O—CH₃ | |
| 4473 | —(CH₂)₄— | Cl | O | NH—NH-2-pyridyl | O—CH₃ | O—CH₃ | |
| 4474 | —(CH₂)₄— | Cl | O | NH—NH-2-benzothiazolyl | O—CH₃ | O—CH₃ | |
| 4475 | —(CH₂)₄— | Cl | N—O—CH₃ | O—CH₃ | O—CH₃ | O—CH₃ | |
| 4476 | —(CH₂)₄— | Cl | N—O—CH₂—CH=CH₂ | O—CH₃ | O—CH₃ | O—CH₃ | |
| 4477 | —(CH₃)₄— | Cl | N—O—CH₂—C≡CH | O—CH₃ | O—CH₃ | O—CH₃ | |
| 4478 | —(CH₂)₄— | Cl | N—O—CH₂—Ph | O—CH₃ | O—CH₃ | O—CH₃ | |
| 4479 | —(CH₂)₄— | Cl | N—O—CH₂—CO₂H | O—CH₃ | O—CH₃ | O—CH₃ | |
| 4480 | —(CH₂)₄— | Cl | N—O—CH₂—CO₂CH₃ | O—CH₃ | O—CH₃ | O—CH₃ | |
| 4481 | —(CH₂)₄— | Cl | N—O—CH₂—CO—CH₃ | O—CH₃ | O—CH₃ | O—CH₃ | |
| 4482 | —(CH₂)₄— | Cl | N—O—CH₂—CO—C₂H₅ | O—CH₃ | O—CH₃ | O—CH₃ | |
| 4483 | —(CH₂)₄— | Cl | N—O—CH₂—CO—n-C₃H₇ | O—CH₃ | O—CH₃ | O—CH₃ | |
| 4484 | —(CH₂)₄— | Cl | N—O—CH₂—CO—i-C₃H₇ | O—CH₃ | O—CH₃ | O—CH₃ | |
| 4485 | —(CH₂)₄— | Cl | N—O—CH₂—CO—n-C₄H₉ | O—CH₃ | O—CH₃ | O—CH₃ | |
| 4486 | —(CH₃)₄— | Cl | N—O—CH₂—CO—i-C₄H₉ | O—CH₃ | O—CH₃ | O—CH₃ | |
| 4487 | —(CH₂)₄— | Cl | N—O—CH₂—CO—s-C₄H₇ | O—CH₃ | O—CH₃ | O—CH₃ | |
| 4488 | —(CH₂)₄— | Cl | N—O—CH₂—CO—t-C₄H₇ | O—CH₃ | O—CH₃ | O—CH₃ | |
| 4489 | —(CH₂)₄— | Cl | N—O—CH₂—CO—Ph | O—CH₃ | O—CH₃ | O—CH₃ | |
| 4490 | —(CH₂)₄— | Cl | s | O—CH₃ | O—CH₃ | O—CH₃ | |
| 4491 | —(CH₂)₄— | Cl | s | O—CH₃ | O—CH₃ | O—CH₃ | |
| 4492 | —(CH₂)₄— | Cl | s | O—CH₃ | O—CH₃ | O—CH₃ | |
| 4493 | —(CH₂)₄— | Cl | s | O—CH₃ | O—CH₃ | O—CH₃ | |
| 4494 | —(CH₂)₄— | Cl | s | O—CH₃ | O—CH₃ | O—CH₃ | |
| 4495 | —(CH₃)₄— | Cl | s | O—CH₃ | O—CH₃ | O—CH₃ | |
| 4496 | —(CH₂)₄— | Cl | s | O—CH₃ | O—CH₃ | O—CH₃ | |
| 4497 | —(CH₂)₄— | Cl | O | NH₂ | O—CH₃ | O—CH₃ | |
| 4498 | —(CH₂)₄— | Cl | O | NH₂ | O—CH₃ | O—CH₃ | |
| 4499 | —(CH₂)₄— | Cl | O | NH—CH₃ | O—CH₃ | O—CH₃ | |
| 4500a | —(CH₂)₄— | Cl | O | NH—C₂H₅ | O—CH₃ | O—CH₃ | cis |
| 4500b | —(CH₂)₄— | Cl | O | NH—C₂H₅ | O—CH₃ | O—CH₃ | trans |
| 4501 | —(CH₂)₄— | Cl | O | NH-n-C₃H₇ | O—CH₃ | O—CH₃ | |
| 4502a | —(CH₂)₄— | Cl | O | NH—OH | O—CH₃ | O—CH₃ | cis |
| 4502b | —(CH₂)₄— | Cl | O | NH—O—CH₃ | O—CH₃ | O—CH₃ | trans |
| 4503 | —(CH₂)₄— | Cl | O | NH—O—CH₂-Ph | O—CH₃ | O—CH₃ | |
| 4504 | —(CH₂)₄— | Cl | O | NH—O—CH₂—CO₂CH₃ | O—CH₃ | O—CH₃ | |
| 4505 | —(CH₃)₄— | Cl | O | S—CH₃ | O—CH₃ | O—CH₃ | |
| 4506a | —(CH₂)₄— | Cl | O | S—C₂H₅ | O—CH₃ | O—CH₃ | cis |
| 4506b | —(CH₂)₄— | Cl | O | S—C₂H₅ | O—CH₃ | O—CH₃ | trans |
| 4507 | —(CH₂)₄— | Cl | O | S-n-C₃H₇ | O—CH₃ | O—CH₃ | |
|  | —(CH₂)₄— | Cl | O | S-i-C₃H₇ | O—CH₃ | O—CH₃ | |
|  | —(CH₂)₄— | Cl | O | S-i-C₃H₇ | O—CH₃ | O—CH₃ | |
|  | —(CH₂)₄— | Cl | O | S-n-C₄H₉ | O—CH₃ | O—CH₃ | |
|  | —(CH₂)₄— | Cl | O | S-n-C₄H₉ | O—CH₃ | O—CH₃ | |
|  | —(CH₂)₄— | Cl | O | S-i-C₄H₉ | O—CH₃ | O—CH₃ | |
|  | —(CH₂)₄— | Cl | O | S-s-C₄H₉ | O—CH₃ | O—CH₃ | |
|  | —(CH₂)₄— | Cl | O | S-t-C₄H₉ | O—CH₃ | O—CH₃ | |
|  | —(CH₂)₄— | Cl | O | S—CH₂—CH=CH₂ | O—CH₃ | O—CH₃ | |

-continued

| | | | | | | |
|---|---|---|---|---|---|---|
| 4508a | —(CH₂)₄— | Cl | O | S—CH₂-Ph | O—CH₃ | O—CH₃ | cis |
| 4508b | —(CH₂)₄— | Cl | O | S—CH₂-Ph | O—CH₃ | O—CH₃ | trans |
| 4509 | —(CH₂)₄— | Cl | O | S—CH₂-Ph-2Cl | O—CH₃ | O—CH₃ | |
| 4510 | —(CH₂)₄— | Cl | O | S—CH₂-Ph-3Cl | O—CH₃ | O—CH₃ | |
| 4511a | —(CH₂)₄— | F | O | S-2-pyridyl | O—CH₃ | O—CH₃ | cis |
| 4511b | —(CH₂)₄— | F | O | S-2-pyridyl | O—CH₃ | O—CH₃ | trans |
| 4512a | —(CH₂)₄— | F | O | S—CH₂-furyl | O—CH₃ | O—CH₃ | cis |
| 4512b | —(CH₂)₄— | F | O | S—CH₂-furyl | O—CH₃ | O—CH₃ | trans |
| 4513 | —(CH₂)₄— | F | O | S-Ph | O—CH₃ | O—CH₃ | |
| 4514 | —(CH₂)₄— | F | O | S-Ph-2Cl | O—CH₃ | O—CH₃ | |
| 4515 | —(CH₂)₄— | F | O | S-Ph-3Cl | O—CH₃ | O—CH₃ | |
| 4516 | —(CH₂)₄— | F | O | S-Ph-4Cl | O—CH₃ | O—CH₃ | |
| 4517 | —(CH₂)₄— | F | O | S-Ph-2-OCH₃ | O—CH₃ | O—CH₃ | |
| 4518 | —(CH₂)₄— | F | O | S-Ph-3-OCH₃ | O—CH₃ | O—CH₃ | |
| 4519 | —(CH₂)₄— | Cl | O | S-Ph-4-OCH₃ | O—CH₃ | O—CH₃ | |
| 4520 | —(CH₂)₄— | Cl | O | S-Ph-2-Br | O—CH₃ | O—CH₃ | |
| 4521 | —(CH₃)₄— | Cl | O | S-Ph-3-Br | O—CH₃ | O—CH₃ | |
| 4522 | —(CH₃)₄— | Cl | O | S-Ph-4-Br | O—CH₃ | O—CH₃ | |
| 4523 | —(CH₂)₄— | Cl | O | S—CH₃ | O—CH₃ | O—CH₃ | |
| 4524 | —(CH₃)₄— | Cl | O | S—C₃H₅ | O—CH₃ | O—CH₃ | |
| 4525 | —(CH₂)₄— | Cl | O | S-n-C₃H₇ | O—CH₃ | O—CH₃ | |
| 4526a | —(CH₂)₄— | Cl | O | S-i-C₃H₇ | O—CH₃ | O—CH₃ | cis |
| 4526b | —(CH₂)₄— | Cl | O | S-i-C₃H₇ | O—CH₃ | O—CH₃ | trans |
| 4527 | —(CH₂)₄— | Cl | O | S-n-C₄H₉ | O—CH₃ | O—CH₃ | |
| 4528 | —(CH₃)₄— | Cl | O | S-i-C₄H₉ | O—CH₃ | O—CH₃ | |
| 4529 | —(CH₂)₄— | Cl | O | S-s-C₄H₉ | O—CH₃ | O—CH₃ | |
| 4530 | —(CH₂)₄— | Cl | O | S-t-C₄H₉ | O—CH₃ | O—CH₃ | |
| 4531 | —(CH₂)₄— | Cl | O | S-n-C₅H₁₁ | O—CH₃ | O—CH₃ | |
| 4532 | —(CH₂)₄— | Cl | O | S—CH₂—CH=CH₂ | O—CH₃ | O—CH₃ | |
| 4533 | —(CH₂)₄— | Cl | O | S—CH₂-Ph | O—CH₃ | O—CH₃ | |
| 4534 | —(CH₃)₄— | Cl | O | S—CH₂-Ph-2Cl | O—CH₃ | O—CH₃ | |
| 4535 | —(CH₂)₄— | Cl | O | S—CH₂-Ph-3Cl | O—CH₃ | O—CH₃ | |
| 4536 | —(CH₃)₄— | Cl | O | S-2-pyridyl | O—CH₃ | O—CH₃ | |
| 4537 | —(CH₂)₄— | Cl | O | S—CH₂-furyl | O—CH₃ | O—CH₃ | |
| 4538 | —(CH₂)₄— | F | O | S-Ph | O—CH₃ | O—CH₃ | |
| 4539 | —(CH₂)₄— | F | O | S-Ph-2Cl | O—CH₃ | O—CH₃ | |
| 4540 | —(CH₂)₃— | F | O | S-Ph-3Cl | O—CH₃ | O—CH₃ | |
| 4541 | —(CH₂)₃— | F | O | S-Ph-4Cl | O—CH₃ | O—CH₃ | |
| 4542 | —(CH₂)₄— | F | O | S-Ph-2-OCH₃ | O—CH₃ | O—CH₃ | |
| 4543 | —(CH₃)₄— | F | O | S-Ph-3-OCH₃ | O—CH₃ | O—CH₃ | |
| 4544 | —(CH₂)₄— | F | O | S-Ph-4-OCH₃ | O—CH₃ | O—CH₃ | |
| 4545 | —(CH₂)₃— | F | O | S-Ph-2-Br | O—CH₃ | O—CH₃ | |
| 4546 | —(CH₃)₄— | F | O | S-Ph-3-Br | O—CH₃ | O—CH₃ | |
| 4547 | —(CH₂)₄— | F | O | S-Ph-4-Br | O—CH₃ | O—CH₃ | |
| 4548 | —(CH₂)₄— | F | O | NH—CO—CH₃ | O—CH₃ | O—CH₃ | |
| 4549 | —(CH₂)₃— | F | O | NH—CO—C₂H₅ | O—CH₃ | O—CH₃ | |
| 4550 | —(CH₃)₄— | F | O | NH—CO—CH₃ | O—CH₃ | O—CH₃ | |
| 4551 | —(CH₂)₃— | F | O | NH—CO—C₂H₅ | O—CH₃ | O—CH₃ | |
| 4552 | —(CH₂)₄— | F | O | NH—CO₂CH₃ | O—CH₃ | O—CH₃ | |
| 4553 | —(CH₃)₄— | F | O | NH—CO₂C₂H₅ | O—CH₃ | O—CH₃ | |
| 4554 | —(CH₂)₄— | F | O | NH—CO₂CH₂CH₃ | O—CH₃ | O—CH₃ | |
| 4555 | —(CH₃)₄— | F | O | NH—CO₂CH₃ | O—CH₃ | O—CH₃ | |
| 4556a | —(CH₂)₄— | F | O | NH—CO₂C₂H₅ | O—CH₃ | O—CH₃ | |
| 4556b | —(CH₂)₄— | F | O | SH | O—CH₃ | O—CH₃ | |
| 4557 | —(CH₂)₄— | F | S | SH | O—CH₃ | O—CH₃ | |
| 4558a | —(CH₂)₄— | F | S | O—CH₃ | O—CH₃ | O—CH₃ | cis |
| 4558b | —(CH₂)₄— | F | S | O—C₂H₅ | O—CH₃ | O—CH₃ | trans |

TABLE 5

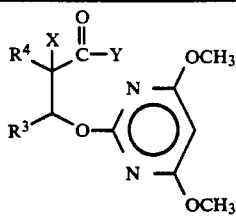

| Compound No. | R³ | R⁴ | X | Y | Remarks |
|---|---|---|---|---|---|
| 5001 | H | CH₃ | F | OH | rac |
| 5002 | H | CH₃ | F | O—CH₃ | |
| 5003 | H | CH₃ | F | O—C₂H₅ | rac |
| 5004 | H | CH₃ | F | O—(CH₂)₂—Cl | |
| 5005 | H | CH₃ | F | O—CH₂—S—CH₃ | |
| 5006 | H | CH₃ | F | O—CH₂-Ph | |
| 5007 | H | CH₃ | F | O-Ph | |
| 5008 | H | CH₃ | F | O—CH₂—CH=CH₂ | |
| 5009 | H | CH₃ | F | O—CH₂—C≡CH | |
| 5010 | H | CH₃ | F | O—CH₂—O—C₂H₅ | |
| 5011 | H | CH₃ | F | NH₂ | |
| 5012 | H | CH₃ | F | NH—CH₃ | |
| 5013 | H | CH₃ | F | N(CH₃)-Ph | |
| 5014 | H | CH₃ | F | NH—OH | |
| 5015 | H | CH₃ | F | N(CH₃)—OH | |
| 5016 | H | CH₃ | F | NH—O—CH₃ | |
| 5017 | H | CH₃ | F | NH—O—CH₂—CH=CH₂ | |
| 5018 | H | CH₃ | F | NH—O—CH₂—C≡CH | |
| 5019 | H | CH₃ | F | NH—O—CH₂-Ph | |
| 5020 | H | CH₃ | F | NH—O—CH₂—CO₂—CH₃ | |
| 5021 | H | CH₃ | F | NH—N(CH₃)₂ | |
| 5022 | H | CH₃ | F | NH-2-pyridyl | |
| 5023 | H | CH₃ | F | N(CH₃)₂ | |
| 5024 | H | CH₃ | F | N₃ | |
| 5025 | H | CH₃ | F | S—CH₃ | |
| 5026 | H | CH₃ | F | S-i-C₃H₇ | |
| 5027 | H | C₂H₅ | F | OH | |
| 5028 | H | C₂H₅ | F | O—CH₃ | |
| 5029 | H | C₂H₅ | F | O—C₂H₅ | |
| 5030 | H | C₂H₅ | F | O—(CH₂)₂—Cl | |
| 5031 | H | C₂H₅ | F | O—CH₂—S—CH₃ | |
| 5032 | H | C₂H₅ | F | O—CH₂-Ph | |
| 5033 | H | C₂H₅ | F | O-Ph | |
| 5034 | H | C₂H₅ | F | O—CH₂—CH=CH₂ | |
| 5035 | H | C₂H₅ | F | O—CH₂—C≡CH | |
| 5036 | H | C₂H₅ | F | NH₂ | |
| 5037 | H | C₂H₅ | F | NH—CH₃ | |
| 5038 | H | C₂H₅ | F | N(CH₃)-Ph | |
| 5039 | H | C₂H₅ | F | NH—OH | |
| 5040 | H | C₂H₅ | F | N(CH₃)—OH | |
| 5041 | H | C₂H₅ | F | NH—O—CH₃ | |
| 5042 | H | C₂H₅ | F | NH—O—CH₂—CH=CH₂ | |
| 5043 | H | C₂H₅ | F | NH—O—CH₂—C≡CH | |
| 5044 | H | C₂H₅ | F | NH—O—CH₂-Ph | |
| 5045 | H | C₂H₅ | F | NH—O—CH₂—CO₂—CH₃ | |
| 5046 | H | C₂H₅ | F | NH—N(CH₃)₂ | |
| 5047 | H | C₂H₅ | F | NH-2-pyridyl | |
| 5048 | H | C₂H₅ | F | N(CH₃)₂ | |
| 5049 | H | C₂H₅ | F | N₃ | |
| 5050 | H | C₂H₅ | F | S—CH₃ | |
| 5051 | H | C₂H₅ | F | S-i-C₃H₇ | |
| 5052 | H | C₃H₇ | F | OH | |
| 5053 | H | C₃H₇ | F | O—CH₃ | |
| 5054 | H | C₃H₇ | F | O—C₂H₅ | |
| 5055 | H | C₃H₇ | F | O—(CH₂)₂—Cl | |
| 5056 | H | C₃H₇ | F | O—CH₂—S—CH₃ | |
| 5057 | H | C₃H₇ | F | O—CH₂-Ph | |
| 5058 | H | C₃H₇ | F | O-Ph | |
| 5059 | H | C₃H₇ | F | O—CH₂—CH=CH₂ | |
| 5060 | H | C₃H₇ | F | O—CH₂—C≡CH | |
| 5061 | H | C₃H₇ | F | O—CH₂—O—C₂H₅ | |
| 5062 | H | C₃H₇ | F | NH₂ | |
| 5063 | H | C₃H₇ | F | NH—CH₃ | |
| 5064 | H | C₃H₇ | F | N(CH₃)-Ph | |
| 5065 | H | C₃H₇ | F | NH—OH | |
| 5066 | H | C₃H₇ | F | N(CH₃)—OH | |
| 5067 | H | C₃H₇ | F | NH—O—CH₃ | |
| 5068 | H | C₃H₇ | F | NH—O—CH₂—CH=CH₂ | |
| 5069 | H | C₃H₇ | F | NH—O—CH₂—C≡CH | |
| 5070 | H | C₃H₇ | F | NH—O—CH₂-Ph | |

TABLE 5-continued

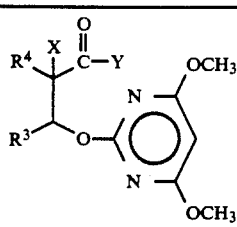

| Compound No. | R³ | R⁴ | X | Y | Remarks |
|---|---|---|---|---|---|
| 5071 | H | C₃H₇ | F | NH—O—CH₂—CO₂—CH₃ | |
| 5072 | H | C₃H₇ | F | NH—N(CH₃)₂ | |
| 5073 | H | C₃H₇ | F | NH-2-pyridyl | |
| 5074 | H | C₃H₇ | F | N(CH₃)₂ | |
| 5075 | H | C₃H₇ | F | N₃ | |
| 5076 | H | C₃H₇ | F | S—CH₃ | |
| 5077 | H | C₃H₇ | F | S-i-C₃H₇ | |
| 5078 | H | i-C₃H₇ | F | OH | |
| 5079 | H | i-C₃H₇ | F | O—CH₃ | |
| 5080 | H | i-C₃H₇ | F | O—C₂H₅ | |
| 5081 | H | i-C₃H₇ | F | O—(CH₂)₂—Cl | |
| 5082 | H | i-C₃H₇ | F | O—CH₂—S—CH₃ | |
| 5083 | H | i-C₃H₇ | F | O—CH₂-Ph | |
| 5084 | H | i-C₃H₇ | F | O-Ph | |
| 5085 | H | i-C₃H₇ | F | O—CH₂—CH=CH₂ | |
| 5086 | H | i-C₃H₇ | F | O—CH₂—C≡CH | |
| 5087 | H | i-C₃H₇ | F | O—CH₂—O—C₂H₅ | |
| 5088 | H | i-C₃H₇ | F | NH₂ | |
| 5089 | H | i-C₃H₇ | F | NH—CH₃ | |
| 5090 | H | i-C₃H₇ | F | N(CH₃)-Ph | |
| 5091 | H | i-C₃H₇ | F | NH—OH | |
| 5092 | H | i-C₃H₇ | F | N(CH₃)—OH | |
| 5093 | H | i-C₃H₇ | F | NH—O—CH₃ | |
| 5094 | H | i-C₃H₇ | F | NH—O—CH₂—CH=CH₂ | |
| 5095 | H | i-C₃H₇ | F | NH—O—CH₂—C≡CH | |
| 5096 | H | i-C₃H₇ | F | NH—O—CH₂-Ph | |
| 5097 | H | i-C₃H₇ | F | NH—O—CH₂—CO₂—CH₃ | |
| 5098 | H | i-C₃H₇ | F | NH—N(CH₃)₂ | |
| 5099 | H | i-C₃H₇ | F | NH-2-pyridyl | |
| 5100 | H | i-C₃H₇ | F | N(CH₃)₂ | |
| 5101 | H | i-C₃H₇ | F | N₃ | |
| 5102 | H | i-C₃H₇ | F | S—CH₃ | |
| 5103 | H | i-C₃H₇ | F | S-i-C₃H₇ | |
| 5104 | CH₃ | H | F | OH | |
| 5105 | CH₃ | H | F | O—CH₃ | |
| 5106 | CH₃ | H | F | O—C₂H₅ | |
| 5107 | CH₃ | H | F | O—(CH₂)₂—Cl | |
| 5108 | CH₃ | H | F | O—CH₂—S—CH₃ | |
| 5109 | CH₃ | H | F | O—CH₂-Ph | |
| 5110 | CH₃ | H | F | O-Ph | |
| 5111 | CH₃ | H | F | O—CH₂—CH=CH₂ | |
| 5112 | CH₃ | H | F | O—CH₂—C≡CH | |
| 5113 | CH₃ | H | F | O—CH₂—O—C₂H₅ | |
| 5114 | CH₃ | H | F | NH₂ | |
| 5115 | CH₃ | H | F | NH—CH₃ | |
| 5116 | CH₃ | H | F | N(CH₃)-Ph | |
| 5117 | CH₃ | H | F | NH—OH | |
| 5118 | CH₃ | H | F | N(CH₃)—OH | |
| 5119 | CH₃ | H | F | NH—O—CH₃ | |
| 5120 | CH₃ | H | F | NH—O—CH₂—CH=CH₂ | |
| 5121 | CH₃ | H | F | NH—O—CH₂—C≡CH | |
| 5122 | CH₃ | H | F | NH—O—CH₂-Ph | |
| 5123 | CH₃ | H | F | NH—O—CH₂—CO₂—CH₃ | |
| 5124 | CH₃ | H | F | NH—N(CH₃)₂ | |
| 5125 | CH₃ | H | F | NH-2-pyridyl | |
| 5126 | CH₃ | H | F | N(CH₃)₂ | |
| 5127 | CH₃ | H | F | N₃ | |
| 5128 | CH₃ | H | F | S—CH₃ | |
| 5129 | CH₃ | H | F | S-i-C₃H₇ | |
| 5130 | CH₃ | F | F | OH | rac |
| 5131 | CH₃ | F | F | O—CH₃ | rac |
| 5132 | CH₃ | F | F | O—C₂H₅ | rac |
| 5133 | CH₃ | F | F | O—(CH₂)₂—Cl | |
| 5134 | CH₃ | F | F | O—CH₂—S—CH₃ | |
| 5135 | CH₃ | F | F | O—CH₂-Ph | |
| 5136 | CH₃ | F | F | O-Ph | |
| 5137 | CH₃ | F | F | O—CH₂—CH=CH₂ | |
| 5138 | CH₃ | F | F | O—CH₂—C≡CH | |
| 5139 | CH₃ | F | F | O—CH₂—O—C₂H₅ | |
| 5140 | CH₃ | F | F | NH₂ | |

TABLE 5-continued

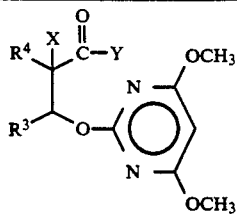

| Compound No. | R³ | R⁴ | X | Y | Remarks |
|---|---|---|---|---|---|
| 5141 | CH₃ | F | F | NH—CH₃ | |
| 5142 | CH₃ | F | F | N(CH₃)-Ph | |
| 5143 | CH₃ | F | F | NH—OH | |
| 5144 | CH₃ | F | F | N(CH₃)—OH | |
| 5145 | CH₃ | F | F | NH—O—CH₃ | |
| 5146 | CH₃ | F | F | NH—O—CH₂—CH=CH₂ | |
| 5147 | CH₃ | F | F | NH—O—CH₂—C≡CH | |
| 5148 | CH₃ | F | F | NH—O—CH₂-Ph | |
| 5149 | CH₃ | F | F | NH—O—CH₂—CO₂—CH₃ | |
| 5150 | CH₃ | F | F | NH—N(CH₃)₂ | |
| 5151 | CH₃ | F | F | NH-2-pyridyl | |
| 5152 | CH₃ | F | F | N(CH₃)₂ | |
| 5153 | CH₃ | F | F | N₃ | |
| 5154 | CH₃ | F | F | S—CH₃ | |
| 5155 | CH₃ | F | F | S-i-C₃H₇ | |
| 5156a | CH₃ | CH₃ | F | OH | erythro |
| 5156b | CH₃ | CH₃ | F | OH | threo |
| 5157a | CH₃ | CH₃ | F | O—CH₃ | erythro |
| 5157b | CH₃ | CH₃ | F | O—CH₃ | threo |
| 5158a | CH₃ | CH₃ | F | O—C₂H₅ | erythro |
| 5158b | CH₃ | CH₃ | F | O—C₂H₅ | threo |
| 5159 | CH₃ | CH₃ | F | O—(CH₂)₂—Cl | |
| 5160 | CH₃ | CH₃ | F | O—CH₂—S—CH₃ | |
| 5161 | CH₃ | CH₃ | F | O—CH₂-Ph | |
| 5162 | CH₃ | CH₃ | F | O-Ph | |
| 5163 | CH₃ | CH₃ | F | O—CH₂—CH=CH₂ | |
| 5164 | CH₃ | CH₃ | F | O—CH₂—C≡CH | |
| 5165 | CH₃ | CH₃ | F | O—CH₂—O—C₂H₅ | |
| 5166 | CH₃ | CH₃ | F | NH₂ | |
| 5167 | CH₃ | CH₃ | F | NH—CH₃ | |
| 5168 | CH₃ | CH₃ | F | N(CH₃)-Ph | |
| 5169 | CH₃ | CH₃ | F | NH—OH | |
| 5170 | CH₃ | CH₃ | F | N(CH₃)—OH | |
| 5171 | CH₃ | CH₃ | F | NH—O—CH₃ | |
| 5172 | CH₃ | CH₃ | F | NH—O—CH₂—CH=CH₂ | |
| 5173 | CH₃ | CH₃ | F | NH—O—CH₂—C≡CH | |
| 5174 | CH₃ | CH₃ | F | NH—O—CH₂-Ph | |
| 5175 | CH₃ | CH₃ | F | NH—O—CH₂—CO₂—CH₃ | |
| 5176 | CH₃ | CH₃ | F | NH—N(CH₃)₂ | |
| 5177 | CH₃ | CH₃ | F | NH-2-pyridyl | |
| 5178a | CH₃ | CH₃ | F | N(CH₃)₂ | erythro |
| 5178b | CH₃ | CH₃ | F | N(CH₃)₂ | threo |
| 5179 | CH₃ | CH₃ | F | N₃ | |
| 5180 | CH₃ | CH₃ | F | S—CH₃ | |
| 5181a | CH₃ | CH₃ | F | S-i-C₃H₇ | erythro |
| 5181b | CH₃ | CH₃ | F | S-i-C₃H₇ | threo |
| 5182a | CH₃ | C₂H₅ | F | OH | erythro |
| 5182b | CH₃ | C₂H₅ | F | OH | threo |
| 5183 | CH₃ | C₂H₅ | F | O—CH₃ | |
| 5184a | CH₃ | C₂H₅ | F | O—C₂H₅ | erythro |
| 5184b | CH₃ | C₂H₅ | F | O—C₂H₅ | threo |
| 5185 | CH₃ | C₂H₅ | F | O—(CH₂)₂—Cl | |
| 5186 | CH₃ | C₂H₅ | F | O—CH₂—S—CH₃ | |
| 5187 | CH₃ | C₂H₅ | F | O—CH₂-Ph | |
| 5188 | CH₃ | C₂H₅ | F | O-Ph | |
| 5189 | CH₃ | C₂H₅ | F | O—CH₂—CH=CH₂ | |
| 5190 | CH₃ | C₂H₅ | F | O—CH₂—C≡CH | |
| 5191 | CH₃ | C₂H₅ | F | O—CH₂—O—C₂H₅ | |
| 5192 | CH₃ | C₂H₅ | F | NH₂ | |
| 5193 | CH₃ | C₂H₅ | F | NH—CH₃ | |
| 5194 | CH₃ | C₂H₅ | F | N(CH₃)-Ph | |
| 5195 | CH₃ | C₂H₅ | F | NH—OH | |
| 5196 | CH₃ | C₂H₅ | F | N(CH₃)—OH | |
| 5197 | CH₃ | C₂H₅ | F | NH—O—CH₃ | |
| 5198 | CH₃ | C₂H₅ | F | NH—O—CH₂—CH=CH₂ | |
| 5199 | CH₃ | C₂H₅ | F | NH—O—CH₂—C≡CH | |
| 5200 | CH₃ | C₂H₅ | F | NH—O—CH₂-Ph | |
| 5201 | CH₃ | C₂H₅ | F | NH—O—CH₂—CO₂—CH₃ | |
| 5202 | CH₃ | C₂H₅ | F | NH—N(CH₃)₂ | |
| 5203 | CH₃ | C₂H₅ | F | NH-2-pyridyl | |

TABLE 5-continued

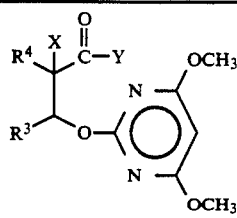

| Compound No. | R³ | R⁴ | X | Y | Remarks |
|---|---|---|---|---|---|
| 5204 | CH₃ | C₂H₅ | F | N(CH₃)₂ | |
| 5205 | CH₃ | C₂H₅ | F | N₃ | |
| 5206 | CH₃ | C₂H₅ | F | S—CH₃ | |
| 5207 | CH₃ | C₂H₅ | F | S-i-C₃H₇ | |
| 5208 | CH₃ | n-C₃H₇ | F | OH | |
| 5209 | CH₃ | n-C₃H₇ | F | O—CH₃ | |
| 5210 | CH₃ | n-C₃H₇ | F | O—C₂H₅ | |
| 5211 | CH₃ | n-C₃H₇ | F | O—(CH₂)₂—Cl | |
| 5212 | CH₃ | n-C₃H₇ | F | O—CH₂—S—CH₃ | |
| 5213 | CH₃ | n-C₃H₇ | F | O—CH₂-Ph | |
| 5214 | CH₃ | n-C₃H₇ | F | O-Ph | |
| 5215 | CH₃ | n-C₃H₇ | F | O—CH₂—CH=CH₂ | |
| 5216 | CH₃ | n-C₃H₇ | F | O—CH₂—C≡CH | |
| 5217 | CH₃ | n-C₃H₇ | F | O—CH₂—O—C₂H₅ | |
| 5218 | CH₃ | n-C₃H₇ | F | NH₂ | |
| 5219 | CH₃ | n-C₃H₇ | F | NH—CH₃ | |
| 5220 | CH₃ | n-C₃H₇ | F | N(CH₃)-Ph | |
| 5221 | CH₃ | n-C₃H₇ | F | NH—OH | |
| 5222 | CH₃ | n-C₃H₇ | F | N(CH₃)—OH | |
| 5223 | CH₃ | n-C₃H₇ | F | NH—O—CH₃ | |
| 5224 | CH₃ | n-C₃H₇ | F | NH—O—CH₂—CH=CH₂ | |
| 5225 | CH₃ | n-C₃H₇ | F | NH—O—CH₂—C≡CH | |
| 5226 | CH₃ | n-C₃H₇ | F | NH—O—CH₂-Ph | |
| 5227 | CH₃ | n-C₃H₇ | F | NH—O—CH₂—CO₂—CH₃ | |
| 5228 | CH₃ | n-C₃H₇ | F | NH—N(CH₃)₂ | |
| 5229 | CH₃ | n-C₃H₇ | F | NH-2-pyridyl | |
| 5230 | CH₃ | n-C₃H₇ | F | N(CH₃)₂ | |
| 5231 | CH₃ | n-C₃H₇ | F | N₃ | |
| 5232 | CH₃ | n-C₃H₇ | F | S—CH₃ | |
| 5233 | CH₃ | n-C₃H₇ | F | S-i-C₃H₇ | |
| 5234 | CH₃ | i-C₃H₇ | F | OH | |
| 5235 | CH₃ | i-C₃H₇ | F | O—CH₃ | |
| 5236 | CH₃ | i-C₃H₇ | F | O—C₂H₅ | |
| 5237 | CH₃ | i-C₃H₇ | F | O—(CH₂)₂—Cl | |
| 5238 | CH₃ | i-C₃H₇ | F | O—CH₂—S—CH₃ | |
| 5239 | CH₃ | i-C₃H₇ | F | O—CH₂-Ph | |
| 5240 | CH₃ | i-C₃H₇ | F | O-Ph | |
| 5241 | CH₃ | i-C₃H₇ | F | O—CH₂—CH=CH₂ | |
| 5242 | CH₃ | i-C₃H₇ | F | O—CH₂—C≡CH | |
| 5243 | CH₃ | i-C₃H₇ | F | O—CH₂—O—C₂H₅ | |
| 5244 | CH₃ | i-C₃H₇ | F | NH₂ | |
| 5245 | CH₃ | i-C₃H₇ | F | NH—CH₃ | |
| 5246 | CH₃ | i-C₃H₇ | F | N(CH₃)-Ph | |
| 5247 | CH₃ | i-C₃H₇ | F | NH—OH | |
| 5248 | CH₃ | i-C₃H₇ | F | N(CH₃)—OH | |
| 5249 | CH₃ | i-C₃H₇ | F | NH—O—CH₃ | |
| 5250 | CH₃ | i-C₃H₇ | F | NH—O—CH₂—CH=CH₂ | |
| 5251 | CH₃ | i-C₃H₇ | F | NH—O—CH₂—C≡CH | |
| 5252 | CH₃ | i-C₃H₇ | F | NH—O—CH₂-Ph | |
| 5253 | CH₃ | i-C₃H₇ | F | NH—O—CH₂—CO₂—CH₃ | |
| 5254 | CH₃ | i-C₃H₇ | F | NH—N(CH₃)₂ | |
| 5255 | CH₃ | i-C₃H₇ | F | NH-2-pyridyl | |
| 5256 | CH₃ | i-C₃H₇ | F | N(CH₃)₂ | |
| 5257 | CH₃ | i-C₃H₇ | F | N₃ | |
| 5258 | CH₃ | i-C₃H₇ | F | S—CH₃ | |
| 5259 | CH₃ | i-C₃H₇ | F | S-i-C₃H₇ | |
| 5260a | CH₃ | CH₂—CH=CH₂ | F | OH | erythro |
| 5260b | CH₃ | CH₂—CH=CH₂ | F | OH | threo |
| 5261a | CH₃ | CH₂—CH=CH₂ | F | O—CH₃ | erythro |
| 5261b | CH₃ | CH₂—CH=CH₂ | F | O—CH₃ | threo |
| 5262a | CH₃ | CH₂—CH=CH₂ | F | O—C₂H₅ | erythro |
| 5262b | CH₃ | CH₂—CH=CH₂ | F | O—C₂H₅ | threo |
| 5263 | CH₃ | CH₂—CH=CH₂ | F | O—(CH₂)₂—Cl | |
| 5264 | CH₃ | CH₂—CH=CH₂ | F | O—CH₂—S—CH₃ | |
| 5265 | CH₃ | CH₂—CH=CH₂ | F | O—CH₂-Ph | |
| 5266 | CH₃ | CH₂—CH=CH₂ | F | O-Ph | |
| 5267 | CH₃ | CH₂—CH=CH₂ | F | O—CH₂—CH=CH₂ | |
| 5268 | CH₃ | CH₂—CH=CH₂ | F | O—CH₂—C≡CH | |
| 5269 | CH₃ | CH₂—CH=CH₂ | F | O—CH₂—O—C₂H₅ | |
| 5270 | CH₃ | CH₂—CH=CH₂ | F | NH₂ | |

TABLE 5-continued

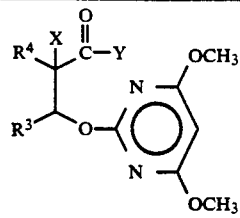

| Compound No. | R³ | R⁴ | X | Y | Remarks |
|---|---|---|---|---|---|
| 5271 | CH₃ | CH₂—CH=CH₂ | F | NH—CH₃ | |
| 5272 | CH₃ | CH₂—CH=CH₂ | F | N(CH₃)-Ph | |
| 5273 | CH₃ | CH₂—CH=CH₂ | F | NH—OH | |
| 5274 | CH₃ | CH₂—CH=CH₂ | F | N(CH₃)—OH | |
| 5275 | CH₃ | CH₂—CH=CH₂ | F | NH—O—CH₃ | |
| 5276 | CH₃ | CH₂—CH=CH₂ | F | NH—O—CH₂—CH=CH₂ | |
| 5277 | CH₃ | CH₂—CH=CH₂ | F | NH—O—CH₂—C≡CH | |
| 5278 | CH₃ | CH₂—CH=CH₂ | F | NH—O—CH₂-Ph | |
| 5279 | CH₃ | CH₂—CH=CH₂ | F | NH—O—CH₂—CO₂—CH₃ | |
| 5280 | CH₃ | CH₂—CH=CH₂ | F | NH—N(CH₃)₂ | |
| 5281 | CH₃ | CH₂—CH=CH₂ | F | NH-2-pyridyl | |
| 5282 | CH₃ | CH₂—CH=CH₂ | F | N(CH₃)₂ | |
| 5283 | CH₃ | CH₂—CH=CH₂ | F | N₃ | |
| 5284 | CH₃ | CH₂—CH=CH₂ | F | S—CH₃ | |
| 5285 | CH₃ | CH₂—CH=CH₂ | F | S-i-C₃H₇ | |
| 5286a | CH₃ | CH₂—C≡CH | F | OH | erythro |
| 5286b | CH₃ | CH₂—C≡CH | F | OH | threo |
| 5287a | CH₃ | CH₂—C≡CH | F | O—CH₃ | erythro |
| 5287b | CH₃ | CH₂—C≡CH | F | O—CH₃ | threo |
| 5288a | CH₃ | CH₂—C≡CH | F | O—C₂H₅ | erythro |
| 5288b | CH₃ | CH₂—C≡CH | F | O—C₂H₅ | threo |
| 5289 | CH₃ | CH₂—C≡CH | F | O—(CH₂)₂—Cl | |
| 5290 | CH₃ | CH₂—C≡CH | F | O—CH₂—S—CH₃ | |
| 5291 | CH₃ | CH₂—C≡CH | F | O—CH₂-Ph | |
| 5292 | CH₃ | CH₂—C≡CH | F | O-Ph | |
| 5293 | CH₃ | CH₂—C≡CH | F | O—CH₂—CH=CH₂ | |
| 5294 | CH₃ | CH₂—C≡CH | F | O—CH₂—C≡CH | |
| 5295 | CH₃ | CH₂—C≡CH | F | O—CH₂—O—C₂H₅ | |
| 5296 | CH₃ | CH₂—C≡CH | F | NH₂ | |
| 5297 | CH₃ | CH₂—C≡CH | F | NH—CH₃ | |
| 5298 | CH₃ | CH₂—C≡CH | F | N(CH₃)-Ph | |
| 5299 | CH₃ | CH₂—C≡CH | F | NH—OH | |
| 5300 | CH₃ | CH₂—C≡CH | F | N(CH₃)—OH | |
| 5301 | CH₃ | CH₂—C≡CH | F | NH—O—CH₃ | |
| 5302 | CH₃ | CH₂—C≡CH | F | NH—O—CH₂—CH=CH₂ | |
| 5303 | CH₃ | CH₂—C≡CH | F | NH—O—CH₂—C≡CH | |
| 5304 | CH₃ | CH₂—C≡CH | F | NH—O—CH₂-Ph | |
| 5305 | CH₃ | CH₂—C≡CH | F | NH—O—CH₂—CO₂—CH₃ | |
| 5306 | CH₃ | CH₂—C≡CH | F | NH—N(CH₃)₂ | |
| 5307 | CH₃ | CH₂—C≡CH | F | NH-2-pyridyl | |
| 5308 | CH₃ | CH₂—C≡CH | F | N(CH₃)₂ | |
| 5309 | CH₃ | CH₂—C≡CH | F | N₃ | |
| 5310 | CH₃ | CH₂—C≡CH | F | S—CH₃ | |
| 5311 | CH₃ | CH₂—C≡CH | F | S-i-C₃H₇ | |
| 5312a | CH₃ | CH₂-Ph | F | OH | erythro |
| 5312b | CH₃ | CH₂-Ph | F | OH | threo |
| 5313a | CH₃ | CH₂-Ph | F | O—CH₃ | erythro |
| 5313b | CH₃ | CH₂-Ph | F | O—CH₃ | threo |
| 5314a | CH₃ | CH₂-Ph | F | O—C₂H₅ | erythro |
| 5314b | CH₃ | CH₂-Ph | F | O—C₂H₅ | threo |
| 5315 | CH₃ | CH₂-Ph | F | O—(CH₂)₂—Cl | |
| 5316 | CH₃ | CH₂-Ph | F | O—CH₂—S—CH₃ | |
| 5317 | CH₃ | CH₂-Ph | F | O—CH₂-Ph | |
| 5318 | CH₃ | CH₂-Ph | F | O-Ph | |
| 5319 | CH₃ | CH₂-Ph | F | O—CH₂—CH=CH₂ | |
| 5320 | CH₃ | CH₂-Ph | F | O—CH₂—C≡CH | |
| 5321 | CH₃ | CH₂-Ph | F | O—CH₂—O—C₂H₅ | |
| 5322 | CH₃ | CH₂-Ph | F | NH₂ | |
| 5323 | CH₃ | CH₂-Ph | F | NH—CH₃ | |
| 5324 | CH₃ | CH₂-Ph | F | N(CH₃)-Ph | |
| 5325 | CH₃ | CH₂-Ph | F | NH—OH | |
| 5326 | CH₃ | CH₂-Ph | F | N(CH₃)—OH | |
| 5327 | CH₃ | CH₂-Ph | F | NH—O—CH₃ | |
| 5328 | CH₃ | CH₂-Ph | F | NH—O—CH₂—CH=CH₂ | |
| 5329 | CH₃ | CH₂-Ph | F | NH—O—CH₂—C≡CH | |
| 5330 | CH₃ | CH₂-Ph | F | NH—O—CH₂-Ph | |
| 5331 | CH₃ | CH₂-Ph | F | NH—O—CH₂—CO₂—CH₃ | |
| 5332 | CH₃ | CH₂-Ph | F | NH—N(CH₃)₂ | |
| 5333 | CH₃ | CH₂-Ph | F | NH-2-pyridyl | |
| 5334 | CH₃ | CH₂-Ph | F | N(CH₃)₂ | |

TABLE 5-continued

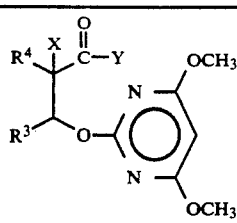

| Compound No. | R³ | R⁴ | X | Y | Remarks |
|---|---|---|---|---|---|
| 5335 | CH₃ | CH₂-Ph | F | N₃ | |
| 5336 | CH₃ | Ph | F | S—CH₃ | |
| 5337 | CH₃ | Ph | F | S-i-C₃H₇ | |
| 5338 | CH₃ | Ph | F | OH | |
| 5339 | CH₃ | Ph | F | O—CH₃ | |
| 5340 | CH₃ | Ph | F | O—C₂H₅ | |
| 5341 | CH₃ | Ph | F | O—(CH₂)₂—Cl | |
| 5342 | CH₃ | Ph | F | O—CH₂—S—CH₃ | |
| 5343 | CH₃ | Ph | F | O—CH₂-Ph | |
| 5344 | CH₃ | Ph | F | O-Ph | |
| 5345 | CH₃ | Ph | F | O—CH₂—CH=CH₂ | |
| 5346 | CH₃ | Ph | F | O—CH₂—C≡CH | |
| 5347 | CH₃ | Ph | F | O—CH₂—O—C₂H₅ | |
| 5348 | CH₃ | Ph | F | NH₂ | |
| 5349 | CH₃ | Ph | F | NH—CH₃ | |
| 5350 | CH₃ | Ph | F | N(CH₃)-Ph | |
| 5351 | CH₃ | Ph | F | NH—OH | |
| 5352 | CH₃ | Ph | F | N(CH₃)—OH | |
| 5353 | CH₃ | Ph | F | NH—O—CH₃ | |
| 5354 | CH₃ | Ph | F | NH—O—CH₂—CH=CH₂ | |
| 5355 | CH₃ | Ph | F | NH—O—CH₂—C≡CH | |
| 5356 | CH₃ | Ph | F | NH—O—CH₂-Ph | |
| 5357 | CH₃ | Ph | F | NH—O—CH₂—CO₂—CH₃ | |
| 5358 | CH₃ | Ph | F | NH—N(CH₃)₂ | |
| 5359 | CH₃ | Ph | F | NH-2-pyridyl | |
| 5360 | CH₃ | Ph | F | N(CH₃)₂ | |
| 5361 | CH₃ | Ph | F | N₃ | |
| 5362 | CH₃ | Ph | F | S—CH₃ | |
| 5363 | CH₃ | Ph | F | S-i-C₃H₇ | |
| 5364 | C₂H₅ | H | F | OH | |
| 5365 | C₂H₅ | H | F | O—CH₃ | |
| 5366 | C₂H₅ | H | F | O—C₂H₅ | |
| 5367 | C₂H₅ | H | F | O—(CH₂)₂—Cl | |
| 5368 | C₂H₅ | H | F | O—CH₂—S—CH₃ | |
| 5369 | C₂H₅ | H | F | O—CH₂-Ph | |
| 5370 | C₂H₅ | H | F | O-Ph | |
| 5371 | C₂H₅ | H | F | O—CH₂—CH=CH₂ | |
| 5372 | C₂H₅ | H | F | O—CH₂—C≡CH | |
| 5373 | C₂H₅ | H | F | O—CH₂—O—C₂H₅ | |
| 5374 | C₂H₅ | H | F | NH₂ | |
| 5375 | C₂H₅ | H | F | NH—CH₃ | |
| 5376 | C₂H₅ | H | F | N(CH₃)-Ph | |
| 5377 | C₂H₅ | H | F | NH—OH | |
| 5378 | C₂H₅ | H | F | N(CH₃)—OH | |
| 5379 | C₂H₅ | H | F | NH—O—CH₃ | |
| 5380 | C₂H₅ | H | F | NH—O—CH₂—CH=CH₂ | |
| 5381 | C₂H₅ | H | F | NH—O—CH₂—C≡CH | |
| 5382 | C₂H₅ | H | F | NH—O—CH₂-Ph | |
| 5383 | C₂H₅ | H | F | NH—O—CH₂—CO₂—CH₃ | |
| 5384 | C₂H₅ | H | F | NH—N(CH₃)₂ | |
| 5385 | C₂H₅ | H | F | NH-2-pyridyl | |
| 5386 | C₂H₅ | H | F | N(CH₃)₂ | |
| 5387 | C₂H₅ | H | F | N₃ | |
| 5388 | C₂H₅ | H | F | S—CH₃ | |
| 5389 | C₂H₅ | H | F | S-i-C₃H₇ | |
| 5390 | C₂H₅ | CH₃ | F | OH | |
| 5391 | C₂H₅ | CH₃ | F | O—CH₃ | |
| 5392 | C₂H₅ | CH₃ | F | O—C₂H₅ | |
| 5393 | C₂H₅ | CH₃ | F | O—(CH₂)₂—Cl | |
| 5394 | C₂H₅ | CH₃ | F | O—CH₂—S—CH₃ | |
| 5395 | C₂H₅ | CH₃ | F | O—CH₂-Ph | |
| 5396 | C₂H₅ | CH₃ | F | O-Ph | |
| 5397 | C₂H₅ | CH₃ | F | O—CH₂—CH=CH₂ | |
| 5398 | C₂H₅ | CH₃ | F | O—CH₂—C≡CH | |
| 5399 | C₂H₅ | CH₃ | F | O—CH₂—O—C₂H₅ | |
| 5400 | C₂H₅ | CH₃ | F | NH₂ | |
| 5401 | C₂H₅ | CH₃ | F | NH—CH₃ | |
| 5402 | C₂H₅ | CH₃ | F | N(CH₃)-Ph | |
| 5403 | C₂H₅ | CH₃ | F | NH—OH | |
| 5404 | C₂H₅ | CH₃ | F | N(CH₃)—OH | |

TABLE 5-continued

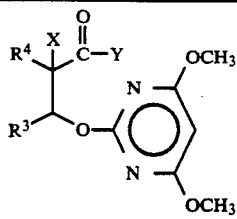

| Compound No. | $R^3$ | $R^4$ | X | Y | Remarks |
|---|---|---|---|---|---|
| 5405 | $C_2H_5$ | $CH_3$ | F | $NH-O-CH_3$ | |
| 5406 | $C_2H_5$ | $CH_3$ | F | $NH-O-CH_2-CH=CH_2$ | |
| 5407 | $C_2H_5$ | $CH_3$ | F | $NH-O-CH_2-C\equiv CH$ | |
| 5408 | $C_2H_5$ | $CH_3$ | F | $NH-O-CH_2\text{-Ph}$ | |
| 5409 | $C_2H_5$ | $CH_3$ | F | $NH-O-CH_2-CO_2-CH_3$ | |
| 5410 | $C_2H_5$ | $CH_3$ | F | $NH-N(CH_3)_2$ | |
| 5411 | $C_2H_5$ | $CH_3$ | F | NH-2-pyridyl | |
| 5412 | $C_2H_5$ | $CH_3$ | F | $N(CH_3)_2$ | |
| 5413 | $C_2H_5$ | $CH_3$ | F | $N_3$ | |
| 5414 | $C_2H_5$ | $CH_3$ | F | $S-CH_3$ | |
| 5415 | $C_2H_5$ | $CH_3$ | F | $S\text{-i-}C_3H_7$ | |
| 5416 | $C_2H_5$ | $C_2H_5$ | F | OH | |
| 5417 | $C_2H_5$ | $C_2H_5$ | F | $O-CH_3$ | |
| 5418 | $C_2H_5$ | $C_2H_5$ | F | $O-C_2H_5$ | |
| 5419 | $C_2H_5$ | $C_2H_5$ | F | $O-(CH_2)_2-Cl$ | |
| 5420 | $C_2H_5$ | $C_2H_5$ | F | $O-CH_2-S-CH_3$ | |
| 5421 | $C_2H_5$ | $C_2H_5$ | F | $O-CH_2\text{-Ph}$ | |
| 5422 | $C_2H_5$ | $C_2H_5$ | F | O-Ph | |
| 5423 | $C_2H_5$ | $C_2H_5$ | F | $O-CH_2-CH=CH_2$ | |
| 5424 | $C_2H_5$ | $C_2H_5$ | F | $O-CH_2-C\equiv CH$ | |
| 5425 | $C_2H_5$ | $C_2H_5$ | F | $O-CH_2-O-C_2H_5$ | |
| 5426 | $C_2H_5$ | $C_2H_5$ | F | $NH_2$ | |
| 5427 | $C_2H_5$ | $C_2H_5$ | F | $NH-CH_3$ | |
| 5428 | $C_2H_5$ | $C_2H_5$ | F | $N(CH_3)\text{-Ph}$ | |
| 5429 | $C_2H_5$ | $C_2H_5$ | F | $NH-OH$ | |
| 5430 | $C_2H_5$ | $C_2H_5$ | F | $N(CH_3)-OH$ | |
| 5431 | $C_2H_5$ | $C_2H_5$ | F | $NH-O-CH_3$ | |
| 5432 | $C_2H_5$ | $C_2H_5$ | F | $NH-O-CH_2-CH=CH_2$ | |
| 5433 | $C_2H_5$ | $C_2H_5$ | F | $NH-O-CH_2-C\equiv CH$ | |
| 5434 | $C_2H_5$ | $C_2H_5$ | F | $NH-O-CH_2\text{-Ph}$ | |
| 5435 | $C_2H_5$ | $C_2H_5$ | F | $NH-O-CH_2-CO_2-CH_3$ | |
| 5436 | $C_2H_5$ | $C_2H_5$ | F | $NH-N(CH_3)_2$ | |
| 5437 | $C_2H_5$ | $C_2H_5$ | F | NH-2-pyridyl | |
| 5438 | $C_2H_5$ | $C_2H_5$ | F | $N(CH_3)_2$ | |
| 5439 | $C_2H_5$ | $C_2H_5$ | F | $N_3$ | |
| 5440 | $C_2H_5$ | $C_2H_5$ | F | $S-CH_3$ | |
| 5441 | $C_2H_5$ | $C_2H_5$ | F | $S\text{-i-}C_3H_7$ | |
| 5442 | $C_2H_5$ | $n\text{-}C_3H_7$ | F | OH | |
| 5443 | $C_2H_5$ | $n\text{-}C_3H_7$ | F | $O-CH_3$ | |
| 5444 | $C_2H_5$ | $n\text{-}C_3H_7$ | F | $O-C_2H_5$ | |
| 5445 | $C_2H_5$ | $n\text{-}C_3H_7$ | F | $O-(CH_2)_2-Cl$ | |
| 5446 | $C_2H_5$ | $n\text{-}C_3H_7$ | F | $O-CH_2-S-CH_3$ | |
| 5447 | $C_2H_5$ | $n\text{-}C_3H_7$ | F | $O-CH_2\text{-Ph}$ | |
| 5448 | $C_2H_5$ | $n\text{-}C_3H_7$ | F | O-Ph | |
| 5449 | $C_2H_5$ | $n\text{-}C_3H_7$ | F | $O-CH_2-CH=CH_2$ | |
| 5450 | $C_2H_5$ | $n\text{-}C_3H_7$ | F | $O-CH_2-C\equiv CH$ | |
| 5451 | $C_2H_5$ | $n\text{-}C_3H_7$ | F | $O-CH_2-O-C_2H_5$ | |
| 5452 | $C_2H_5$ | $n\text{-}C_3H_7$ | F | $NH_2$ | |
| 5453 | $C_2H_5$ | $n\text{-}C_3H_7$ | F | $NH-CH_3$ | |
| 5454 | $C_2H_5$ | $n\text{-}C_3H_7$ | F | $N(CH_3)\text{-Ph}$ | |
| 5455 | $C_2H_5$ | $n\text{-}C_3H_7$ | F | $NH-OH$ | |
| 5456 | $C_2H_5$ | $n\text{-}C_3H_7$ | F | $N(CH_3)-OH$ | |
| 5457 | $C_2H_5$ | $n\text{-}C_3H_7$ | F | $NH-O-CH_3$ | |
| 5458 | $C_2H_5$ | $n\text{-}C_3H_7$ | F | $NH-O-CH_2-CH=CH_2$ | |
| 5459 | $C_2H_5$ | $n\text{-}C_3H_7$ | F | $NH-O-CH_2-C\equiv CH$ | |
| 5460 | $C_2H_5$ | $n\text{-}C_3H_7$ | F | $NH-O-CH_2\text{-Ph}$ | |
| 5461 | $C_2H_5$ | $n\text{-}C_3H_7$ | F | $NH-O-CH_2-CO_2-CH_3$ | |
| 5462 | $C_2H_5$ | $n\text{-}C_3H_7$ | F | $NH-N(CH_3)_2$ | |
| 5463 | $C_2H_5$ | $n\text{-}C_3H_7$ | F | NH-2-pyridyl | |
| 5464 | $C_2H_5$ | $n\text{-}C_3H_7$ | F | $N(CH_3)_2$ | |
| 5465 | $C_2H_5$ | $n\text{-}C_3H_7$ | F | $N_3$ | |
| 5466 | $C_2H_5$ | $n\text{-}C_3H_7$ | F | $S-CH_3$ | |
| 5467 | $C_2H_5$ | $n\text{-}C_3H_7$ | F | $S\text{-i-}C_3H_7$ | |
| 5468 | $C_2H_5$ | $i\text{-}C_3H_7$ | F | OH | |
| 5469 | $C_2H_5$ | $i\text{-}C_3H_7$ | F | $O-CH_3$ | |
| 5470 | $C_2H_5$ | $i\text{-}C_3H_7$ | F | $O-C_2H_5$ | |
| 5471 | $C_2H_5$ | $i\text{-}C_3H_7$ | F | $O-(CH_2)_2-Cl$ | |
| 5472 | $C_2H_5$ | $i\text{-}C_3H_7$ | F | $O-CH_2-S-CH_3$ | |
| 5473 | $C_2H_5$ | $i\text{-}C_3H_7$ | F | $O-CH_2\text{-Ph}$ | |
| 5474 | $C_2H_5$ | $i\text{-}C_3H_7$ | F | O-Ph | |

TABLE 5-continued

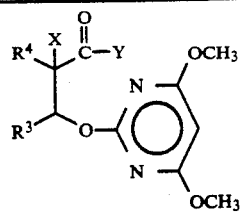

| Compound No. | R³ | R⁴ | X | Y | Remarks |
|---|---|---|---|---|---|
| 5475 | $C_2H_5$ | i-$C_3H_7$ | F | O—$CH_2$—CH=$CH_2$ | |
| 5476 | $C_2H_5$ | i-$C_3H_7$ | F | O—$CH_2$—C≡CH | |
| 5477 | $C_2H_5$ | i-$C_3H_7$ | F | O—$CH_2$—O—$C_2H_5$ | |
| 5478 | $C_2H_5$ | i-$C_3H_7$ | F | $NH_2$ | |
| 5479 | $C_2H_5$ | i-$C_3H_7$ | F | NH—$CH_3$ | |
| 5480 | $C_2H_5$ | i-$C_3H_7$ | F | N($CH_3$)-Ph | |
| 5481 | $C_2H_5$ | i-$C_3H_7$ | F | NH—OH | |
| 5482 | $C_2H_5$ | i-$C_3H_7$ | F | N($CH_3$)—OH | |
| 5483 | $C_2H_5$ | i-$C_3H_7$ | F | NH—O—$CH_3$ | |
| 5484 | $C_2H_5$ | i-$C_3H_7$ | F | NH—O—$CH_2$—CH=$CH_2$ | |
| 5485 | $C_2H_5$ | i-$C_3H_7$ | F | NH—O—$CH_2$—C≡CH | |
| 5486 | $C_2H_5$ | i-$C_3H_7$ | F | NH—O—$CH_2$-Ph | |
| 5487 | $C_2H_5$ | i-$C_3H_7$ | F | NH—O—$CH_2$—$CO_2$—$CH_3$ | |
| 5488 | $C_2H_5$ | i-$C_3H_7$ | F | NH—N($CH_3$)$_2$ | |
| 5489 | $C_2H_5$ | i-$C_3H_7$ | F | NH-2-pyridyl | |
| 5490 | $C_2H_5$ | i-$C_3H_7$ | F | N($CH_3$)$_2$ | |
| 5491 | $C_2H_5$ | i-$C_3H_7$ | F | $N_3$ | |
| 5492 | $C_2H_5$ | i-$C_3H_7$ | F | S—$CH_3$ | |
| 5493 | $C_2H_5$ | i-$C_3H_7$ | F | S-i-$C_3H_7$ | |
| 5494 | n-$C_3H_7$ | H | F | OH | |
| 5495 | n-$C_3H_7$ | H | F | O—$CH_3$ | |
| 5496 | n-$C_3H_7$ | H | F | O—$C_2H_5$ | |
| 5497 | n-$C_3H_7$ | H | F | O—($CH_2$)$_2$—Cl | |
| 5498 | n-$C_3H_7$ | H | F | O—$CH_2$—S—$CH_3$ | |
| 5499 | n-$C_3H_7$ | H | F | O—$CH_2$-Ph | |
| 5500 | n-$C_3H_7$ | H | F | O-Ph | |
| 5501 | n-$C_3H_7$ | H | F | O—$CH_2$—CH=$CH_2$ | |
| 5502 | n-$C_3H_7$ | H | F | O—$CH_2$—C≡CH | |
| 5503 | n-$C_3H_7$ | H | F | O—$CH_2$—O—$C_2H_5$ | |
| 5504 | n-$C_3H_7$ | H | F | $NH_2$ | |
| 5505 | n-$C_3H_7$ | H | F | NH—$CH_3$ | |
| 5506 | n-$C_3H_7$ | H | F | N($CH_3$)-Ph | |
| 5507 | n-$C_3H_7$ | H | F | NH—OH | |
| 5508 | n-$C_3H_7$ | H | F | N($CH_3$)—OH | |
| 5509 | n-$C_3H_7$ | H | F | NH—O—$CH_3$ | |
| 5510 | n-$C_3H_7$ | H | F | NH—O—$CH_2$—CH=$CH_2$ | |
| 5511 | n-$C_3H_7$ | H | F | NH—O—$CH_2$—C≡CH | |
| 5512 | n-$C_3H_7$ | H | F | NH—O—$CH_2$-Ph | |
| 5513 | n-$C_3H_7$ | H | F | NH—O—$CH_2$—$CO_2$—$CH_3$ | |
| 5514 | n-$C_3H_7$ | H | F | NH—N($CH_3$)$_2$ | |
| 5515 | n-$C_3H_7$ | H | F | NH-2-pyridyl | |
| 5516 | n-$C_3H_7$ | H | F | N($CH_3$)$_2$ | |
| 5517 | n-$C_3H_7$ | H | F | $N_3$ | |
| 5518 | n-$C_3H_7$ | H | F | S—$CH_3$ | |
| 5519 | n-$C_3H_7$ | H | F | S-i-$C_3H_7$ | |
| 5520 | n-$C_3H_7$ | F | F | OH | rac |
| 5521 | n-$C_3H_7$ | F | F | O—$CH_3$ | rac |
| 5522 | n-$C_3H_7$ | F | F | O—$CH_3$ | rac |
| 5523 | n-$C_3H_7$ | F | F | O—$C_2H_5$ | |
| 5524 | n-$C_3H_7$ | F | F | O—($CH_2$)$_2$—Cl | |
| 5525 | n-$C_3H_7$ | F | F | O—$CH_2$—S—$CH_3$ | |
| 5526 | n-$C_3H_7$ | F | F | O—$CH_2$-Ph | |
| 5527 | n-$C_3H_7$ | F | F | O-Ph | |
| 5528 | n-$C_3H_7$ | F | F | O—$CH_2$—CH=$CH_2$ | |
| 5529 | n-$C_3H_7$ | F | F | O—$CH_2$—C≡CH | |
| 5530 | n-$C_3H_7$ | F | F | O—$CH_2$—O—$C_2H_5$ | |
| 5531 | n-$C_3H_7$ | F | F | $NH_2$ | |
| 5532 | n-$C_3H_7$ | F | F | NH—$CH_3$ | |
| 5533 | n-$C_3H_7$ | F | F | N($CH_3$)-Ph | |
| 5534 | n-$C_3H_7$ | F | F | NH—OH | |
| 5535 | n-$C_3H_7$ | F | F | N($CH_3$)—OH | |
| 5536 | n-$C_3H_7$ | F | F | NH—O—$CH_3$ | |
| 5537 | n-$C_3H_7$ | F | F | NH—O—$CH_2$—CH=$CH_2$ | |
| 5538 | n-$C_3H_7$ | F | F | NH—O—$CH_2$—C≡CH | |
| 5539 | n-$C_3H_7$ | F | F | NH—O—$CH_2$-Ph | |
| 5540 | n-$C_3H_7$ | F | F | NH—O—$CH_2$—$CO_2$—$CH_3$ | |
| 5541 | n-$C_3H_7$ | F | F | NH—N($CH_3$)$_2$ | |
| 5542 | n-$C_3H_7$ | F | F | NH-2-pyridyl | |
| 5543 | n-$C_3H_7$ | F | F | N($CH_3$)$_2$ | |
| 5544 | n-$C_3H_7$ | F | F | $N_3$ | |

TABLE 5-continued

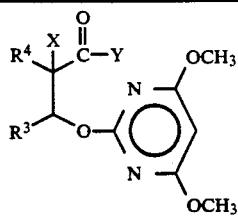

| Compound No. | R³ | R⁴ | X | Y | Remarks |
|---|---|---|---|---|---|
| 5545 | n-C₃H₇ | F | F | S—CH₃ | |
| 5546 | n-C₃H₇ | F | F | S-i-C₃H₇ | |
| 5547 | n-C₃H₇ | CH₃ | F | OH | |
| 5548 | n-C₃H₇ | CH₃ | F | O—CH₃ | |
| 5549 | n-C₃H₇ | CH₃ | F | O—C₂H₅ | |
| 5550 | n-C₃H₇ | CH₃ | F | O—(CH₂)₂—Cl | |
| 5551 | n-C₃H₇ | CH₃ | F | O—CH₂—S—CH₃ | |
| 5552 | n-C₃H₇ | CH₃ | F | O—CH₂-Ph | |
| 5553 | n-C₃H₇ | CH₃ | F | O-Ph | |
| 5554 | n-C₃H₇ | CH₃ | F | O—CH₂—CH=CH₂ | |
| 5555 | n-C₃H₇ | CH₃ | F | O—CH₂—C≡CH | |
| 5556 | n-C₃H₇ | CH₃ | F | O—CH₂—O—C₂H₅ | |
| 5557 | n-C₃H₇ | CH₃ | F | NH₂ | |
| 5558 | n-C₃H₇ | CH₃ | F | NH—CH₃ | |
| 5559 | n-C₃H₇ | CH₃ | F | N(CH₃)-Ph | |
| 5560 | n-C₃H₇ | CH₃ | F | NH—OH | |
| 5561 | n-C₃H₇ | CH₃ | F | N(CH₃)—OH | |
| 5562 | n-C₃H₇ | CH₃ | F | NH—O—CH₃ | |
| 5563 | n-C₃H₇ | CH₃ | F | NH—O—CH₂—CH=CH₂ | |
| 5564 | n-C₃H₇ | CH₃ | F | NH—O—CH₂—C≡CH | |
| 5565 | n-C₃H₇ | CH₃ | F | NH—O—CH₂-Ph | |
| 5566 | n-C₃H₇ | CH₃ | F | NH—O—CH₂—CO₂—CH₃ | |
| 5567 | n-C₃H₇ | CH₃ | F | NH—N(CH₃)₂ | |
| 5568 | n-C₃H₇ | CH₃ | F | NH-2-pyridyl | |
| 5569 | n-C₃H₇ | CH₃ | F | N(CH₃)₂ | |
| 5570 | n-C₃H₇ | CH₃ | F | N₃ | |
| 5571 | n-C₃H₇ | CH₃ | F | S—CH₃ | |
| 5572 | n-C₃H₇ | CH₃ | F | S-i-C₃H₇ | |
| 5573 | n-C₃H₇ | C₂H₅ | F | OH | |
| 5574 | n-C₃H₇ | C₂H₅ | F | O—CH₃ | |
| 5575 | n-C₃H₇ | C₂H₅ | F | O—C₂H₅ | |
| 5576 | n-C₃H₇ | C₂H₅ | F | O—(CH₂)₂—Cl | |
| 5577 | n-C₃H₇ | C₂H₅ | F | O—CH₂—S—CH₃ | |
| 5578 | n-C₃H₇ | C₂H₅ | F | O—CH₂-Ph | |
| 5579 | n-C₃H₇ | C₂H₅ | F | O-Ph | |
| 5580 | n-C₃H₇ | C₂H₅ | F | O—CH₂—CH=CH₂ | |
| 5581 | n-C₃H₇ | C₂H₅ | F | O—CH₂—C≡CH | |
| 5582 | n-C₃H₇ | C₂H₅ | F | O—CH₂—O—C₂H₅ | |
| 5583 | n-C₃H₇ | C₂H₅ | F | NH₂ | |
| 5584 | n-C₃H₇ | C₂H₅ | F | NH—CH₃ | |
| 5585 | n-C₃H₇ | C₂H₅ | F | N(CH₃)-Ph | |
| 5586 | n-C₃H₇ | C₂H₅ | F | NH—OH | |
| 5587 | n-C₃H₇ | C₂H₅ | F | N(CH₃)—OH | |
| 5588 | n-C₃H₇ | C₂H₅ | F | NH—O—CH₃ | |
| 5589 | n-C₃H₇ | C₂H₅ | F | NH—O—CH₂—CH=CH₂ | |
| 5590 | n-C₃H₇ | C₂H₅ | F | NH—O—CH₂—C≡CH | |
| 5591 | n-C₃H₇ | C₂H₅ | F | NH—O—CH₂-Ph | |
| 5592 | n-C₃H₇ | C₂H₅ | F | NH—O—CH₂—CO₂—CH₃ | |
| 5593 | n-C₃H₇ | C₂H₅ | F | NH—N(CH₃)₂ | |
| 5594 | n-C₃H₇ | C₂H₅ | F | NH-2-pyridyl | |
| 5595 | n-C₃H₇ | C₂H₅ | F | N(CH₃)₂ | |
| 5596 | n-C₃H₇ | C₂H₅ | F | N₃ | |
| 5597 | n-C₃H₇ | C₂H₅ | F | S—CH₃ | |
| 5598 | n-C₃H₇ | C₂H₅ | F | S-i-C₃H₇ | |
| 5599 | i-C₃H₇ | H | F | OH | |
| 5600 | i-C₃H₇ | H | F | O—CH₃ | |
| 5601 | i-C₃H₇ | H | F | O—C₂H₅ | |
| 5602 | i-C₃H₇ | H | F | O—(CH₂)₂—Cl | |
| 5603 | i-C₃H₇ | H | F | O—CH₂—S—CH₃ | |
| 5604 | i-C₃H₇ | H | F | O—CH₂-Ph | |
| 5605 | i-C₃H₇ | H | F | O-Ph | |
| 5606 | i-C₃H₇ | H | F | O—CH₂—CH=CH₂ | |
| 5607 | i-C₃H₇ | H | F | O—CH₂—C≡CH | |
| 5608 | i-C₃H₇ | H | F | O—CH₂—O—C₂H₅ | |
| 5609 | i-C₃H₇ | H | F | NH₂ | |
| 5610 | i-C₃H₇ | H | F | NH—CH₃ | |
| 5611 | i-C₃H₇ | H | F | N(CH₃)-Ph | |
| 5612 | i-C₃H₇ | H | F | NH—OH | |
| 5613 | i-C₃H₇ | H | F | N(CH₃)—OH | |
| 5614 | i-C₃H₇ | H | F | NH—O—CH₃ | |

TABLE 5-continued

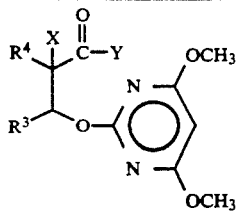

| Compound No. | R³ | R⁴ | X | Y | Remarks |
|---|---|---|---|---|---|
| 5615 | i-C₃H₇ | H | F | NH—O—CH₂—CH=CH₂ | |
| 5616 | i-C₃H₇ | H | F | NH—O—CH₂—C≡CH | |
| 5617 | i-C₃H₇ | H | F | NH—O—CH₂-Ph | |
| 5618 | i-C₃H₇ | H | F | NH—O—CH₂—CO₂—CH₃ | |
| 5619 | i-C₃H₇ | H | F | NH—N(CH₃)₂ | |
| 5620 | i-C₃H₇ | H | F | NH-2-pyridyl | |
| 5621 | i-C₃H₇ | H | F | N(CH₃)₂ | |
| 5622 | i-C₃H₇ | H | F | N₃ | |
| 5623 | i-C₃H₇ | H | F | S—CH₃ | |
| 5624 | i-C₃H₇ | H | F | S-i-C₃H₇ | |
| 5625 | i-C₃H₇ | F | F | OH | rac |
| 5626 | i-C₃H₇ | F | F | O—CH₃ | rac |
| 5627 | i-C₃H₇ | F | F | O—C₂H₅ | rac |
| 5628 | i-C₃H₇ | F | F | O—(CH₂)₂—Cl | |
| 5629 | i-C₃H₇ | F | F | O—CH₂—S—CH₃ | |
| 5630 | i-C₃H₇ | F | F | O—CH₂-Ph | |
| 5631 | i-C₃H₇ | F | F | O-Ph | |
| 5632 | i-C₃H₇ | F | F | O—CH₂—CH=CH₂ | |
| 5633 | i-C₃H₇ | F | F | O—CH₂—C≡CH | |
| 5634 | i-C₃H₇ | F | F | O—CH₂—O—C₂H₅ | |
| 5635 | i-C₃H₇ | F | F | NH₂ | |
| 5636 | i-C₃H₇ | F | F | NH—CH₃ | |
| 5637 | i-C₃H₇ | F | F | N(CH₃)-Ph | |
| 5638 | i-C₃H₇ | F | F | NH—OH | |
| 5639 | i-C₃H₇ | F | F | N(CH₃)—OH | |
| 5640 | i-C₃H₇ | F | F | NH—O—CH₃ | |
| 5641 | i-C₃H₇ | F | F | NH—O—CH₂—CH=CH₂ | |
| 5642 | i-C₃H₇ | F | F | NH—O—CH₂—C≡CH | |
| 5643 | i-C₃H₇ | F | F | NH—O—CH₂-Ph | |
| 5644 | i-C₃H₇ | F | F | NH—O—CH₂—CO₂—CH₃ | |
| 5645 | i-C₃H₇ | F | F | NH—N(CH₃)₂ | |
| 5646 | i-C₃H₇ | F | F | NH-2-pyridyl | |
| 5647 | i-C₃H₇ | F | F | N(CH₃)₂ | |
| 5648 | i-C₃H₇ | F | F | N₃ | |
| 5649 | i-C₃H₇ | F | F | S—CH₃ | |
| 5650 | i-C₃H₇ | F | F | S-i-C₃H₇ | |
| 5651a | i-C₃H₇ | CH₃ | F | OH | erythro |
| 5651b | i-C₃H₇ | CH₃ | F | OH | threo |
| 5652 | i-C₃H₇ | CH₃ | F | O—CH₃ | |
| 5653a | i-C₃H₇ | CH₃ | F | O—C₂H₅ | erythro |
| 5653b | i-C₃H₇ | CH₃ | F | O—C₂H₅ | threo |
| 5654 | i-C₃H₇ | CH₃ | F | O—(CH₂)₂—Cl | |
| 5655 | i-C₃H₇ | CH₃ | F | O—CH₂—S—CH₃ | |
| 5656 | i-C₃H₇ | CH₃ | F | O—CH₂-Ph | |
| 5657 | i-C₃H₇ | CH₃ | F | O-Ph | |
| 5658 | i-C₃H₇ | CH₃ | F | O—CH₂—CH=CH₂ | |
| 5659 | i-C₃H₇ | CH₃ | F | O—CH₂—C≡CH | |
| 5660 | i-C₃H₇ | CH₃ | F | O—CH₂—O—C₂H₅ | |
| 5661 | i-C₃H₇ | CH₃ | F | NH₂ | |
| 5662 | i-C₃H₇ | CH₃ | F | NH—CH₃ | |
| 5663 | i-C₃H₇ | CH₃ | F | N(CH₃)-Ph | |
| 5664 | i-C₃H₇ | CH₃ | F | NH—OH | |
| 5665 | i-C₃H₇ | CH₃ | F | N(CH₃)—OH | |
| 5666 | i-C₃H₇ | CH₃ | F | NH—O—CH₃ | |
| 5667 | i-C₃H₇ | CH₃ | F | NH—O—CH₂—CH=CH₂ | |
| 5668 | i-C₃H₇ | CH₃ | F | NH—O—CH₂—C≡CH | |
| 5669 | i-C₃H₇ | CH₃ | F | NH—O—CH₂-Ph | |
| 5670 | i-C₃H₇ | CH₃ | F | NH—O—CH₂—CO₂—CH₃ | |
| 5671 | i-C₃H₇ | CH₃ | F | NH—N(CH₃)₂ | |
| 5672 | i-C₃H₇ | CH₃ | F | NH-2-pyridyl | |
| 5673 | i-C₃H₇ | CH₃ | F | N(CH₃)₂ | |
| 5674 | i-C₃H₇ | CH₃ | F | N₃ | |
| 5675 | i-C₃H₇ | CH₃ | F | S—CH₃ | |
| 5676 | i-C₃H₇ | CH₃ | F | S-i-C₃H₇ | |
| 5677 | i-C₃H₇ | C₂H₅ | F | OH | |
| 5678 | i-C₃H₇ | C₂H₅ | F | O—CH₃ | |
| 5679 | i-C₃H₇ | C₂H₅ | F | O—C₂H₅ | |
| 5680 | i-C₃H₇ | C₂H₅ | F | O—(CH₂)₂—Cl | |
| 5681 | i-C₃H₇ | C₂H₅ | F | O—CH₂—S—CH₃ | |
| 5682 | i-C₃H₇ | C₂H₅ | F | O—CH₂-Ph | |

TABLE 5-continued

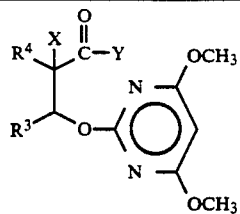

| Compound No. | R³ | R⁴ | X | Y | Remarks |
|---|---|---|---|---|---|
| 5683 | i-C₃H₇ | C₂H₅ | F | O-Ph | |
| 5684 | i-C₃H₇ | C₂H₅ | F | O—CH₂—CH=CH₂ | |
| 5685 | i-C₃H₇ | C₂H₅ | F | O—CH₂—C≡CH | |
| 5686 | i-C₃H₇ | C₂H₅ | F | O—CH₂—O—C₂H₅ | |
| 5687 | i-C₃H₇ | C₂H₅ | F | NH₂ | |
| 5688 | i-C₃H₇ | C₂H₅ | F | NH—CH₃ | |
| 5689 | i-C₃H₇ | C₂H₅ | F | N(CH₃)-Ph | |
| 5690 | i-C₃H₇ | C₂H₅ | F | NH—OH | |
| 5691 | i-C₃H₇ | C₂H₅ | F | N(CH₃)—OH | |
| 5692 | i-C₃H₇ | C₂H₅ | F | NH—O—CH₃ | |
| 5693 | i-C₃H₇ | C₂H₅ | F | NH—O—CH₂—CH=CH₂ | |
| 5694 | i-C₃H₇ | C₂H₅ | F | NH—O—CH₂—C≡CH | |
| 5695 | i-C₃H₇ | C₂H₅ | F | NH—O—CH₂-Ph | |
| 5696 | i-C₃H₇ | C₂H₅ | F | NH—O—CH₂—CO₂—CH₃ | |
| 5697 | i-C₃H₇ | C₂H₅ | F | NH—N(CH₃)₂ | |
| 5698 | i-C₃H₇ | C₂H₅ | F | NH-2-pyridyl | |
| 5699 | i-C₃H₇ | C₂H₅ | F | N(CH₃)₂ | |
| 5700 | i-C₃H₇ | C₂H₅ | F | N₃ | |
| 5701 | i-C₃H₇ | C₂H₅ | F | S—CH₃ | |
| 5702 | i-C₃H₇ | C₂H₅ | F | S-i-C₃H₇ | |
| 5703 | n-C₄H₉ | H | F | OH | |
| 5704 | n-C₄H₉ | H | F | O—CH₃ | |
| 5705 | n-C₄H₉ | H | F | O—C₂H₅ | |
| 5706 | n-C₄H₉ | H | F | O—(CH₂)₂—Cl | |
| 5707 | n-C₄H₉ | H | F | O—CH₂—S—CH₃ | |
| 5708 | n-C₄H₉ | H | F | O—CH₂-Ph | |
| 5709 | n-C₄H₉ | H | F | O—Ph | |
| 5710 | n-C₄H₉ | H | F | O—CH₂—CH=CH₂ | |
| 5711 | n-C₄H₉ | H | F | O—CH₂—C≡CH | |
| 5712 | n-C₄H₉ | H | F | O—CH₂—O—C₂H₅ | |
| 5713 | n-C₄H₉ | H | F | NH₂ | |
| 5714 | n-C₄H₉ | H | F | NH—CH₃ | |
| 5715 | n-C₄H₉ | H | F | N(CH₃)-Ph | |
| 5716 | n-C₄H₉ | H | F | NH—OH | |
| 5717 | n-C₄H₉ | H | F | N(CH₃)—OH | |
| 5718 | n-C₄H₉ | H | F | NH—O—CH₃ | |
| 5719 | n-C₄H₉ | H | F | NH—O—CH₂—CH=CH₂ | |
| 5720 | n-C₄H₉ | H | F | NH—O—CH₂—C≡CH | |
| 5721 | n-C₄H₉ | H | F | NH—O—CH₂-Ph | |
| 5722 | n-C₄H₉ | H | F | NH—O—CH₂—CO₂—CH₃ | |
| 5723 | n-C₄H₉ | H | F | NH—N(CH₃)₂ | |
| 5724 | n-C₄H₉ | H | F | NH-2-pyridyl | |
| 5725 | n-C₄H₉ | H | F | N(CH₃)₂ | |
| 5726 | n-C₄H₉ | H | F | N₃ | |
| 5727 | n-C₄H₉ | H | F | S—CH₃ | |
| 5728 | n-C₄H₉ | H | F | S-i-C₃H₇ | |
| 5729 | n-C₄H₉ | CH₃ | F | OH | |
| 5730 | n-C₄H₉ | CH₃ | F | O—CH₃ | |
| 5731 | n-C₄H₉ | CH₃ | F | O—C₂H₅ | |
| 5732 | n-C₄H₉ | CH₃ | F | O—(CH₂)₂—Cl | |
| 5733 | n-C₄H₉ | CH₃ | F | O—CH₂—S—CH₃ | |
| 5734 | n-C₄H₉ | CH₃ | F | O—CH₂-Ph | |
| 5735 | n-C₄H₉ | CH₃ | F | O-Ph | |
| 5736 | n-C₄H₉ | CH₃ | F | O—CH₂—CH=CH₂ | |
| 5737 | n-C₄H₉ | CH₃ | F | O—CH₂—C≡CH | |
| 5738 | n-C₄H₉ | CH₃ | F | O—CH₂—O—C₂H₅ | |
| 5739 | n-C₄H₉ | CH₃ | F | NH₂ | |
| 5740 | n-C₄H₉ | CH₃ | F | NH—CH₃ | |
| 5741 | n-C₄H₉ | CH₃ | F | N(CH₃)-Ph | |
| 5742 | n-C₄H₉ | CH₃ | F | NH—OH | |
| 5743 | n-C₄H₉ | CH₃ | F | N(CH₃)—OH | |
| 5744 | n-C₄H₉ | CH₃ | F | NH—O—CH₃ | |
| 5745 | n-C₄H₉ | CH₃ | F | NH—O—CH₂—CH=CH₂ | |
| 5746 | n-C₄H₉ | CH₃ | F | NH—O—CH₂—C≡CH | |
| 5747 | n-C₄H₉ | CH₃ | F | NH—O—CH₂-Ph | |
| 5748 | n-C₄H₉ | CH₃ | F | NH—O—CH₂—CO₂—CH₃ | |
| 5749 | n-C₄H₉ | CH₃ | F | NH—N(CH₃)₂ | |
| 5750 | n-C₄H₉ | CH₃ | F | NH-2-pyridyl | |
| 5751 | n-C₄H₉ | CH₃ | F | N(CH₃)₂ | |
| 5752 | n-C₄H₉ | CH₃ | F | N₃ | |

TABLE 5-continued

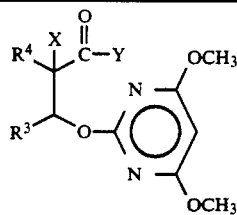

| Compound No. | R³ | R⁴ | X | Y | Remarks |
|---|---|---|---|---|---|
| 5753 | n-C₄H₉ | CH₃ | F | S—CH₃ | |
| 5754 | n-C₄H₉ | CH₃ | F | S-i-C₃H₇ | |
| 5755 | Ph | H | F | OH | |
| 5756 | Ph | H | F | O—CH₃ | |
| 5757 | Ph | H | F | O—C₂H₅ | |
| 5758 | Ph | H | F | O—(CH₂)₂—Cl | |
| 5759 | Ph | H | F | O—CH₂—S—CH₃ | |
| 5760 | Ph | H | F | O—CH₂-Ph | |
| 5761 | Ph | H | F | O-Ph | |
| 5762 | Ph | H | F | O—CH₂—CH=CH₂ | |
| 5763 | Ph | H | F | O—CH₂—C≡CH | |
| 5764 | Ph | H | F | O—CH₂—O—C₂H₅ | |
| 5765 | Ph | H | F | NH₂ | |
| 5766 | Ph | H | F | NH—CH₃ | |
| 5767 | Ph | H | F | N(CH₃)-Ph | |
| 5768 | Ph | H | F | NH—OH | |
| 5769 | Ph | H | F | N(CH₃)—OH | |
| 5770 | Ph | H | F | NH—O—CH₃ | |
| 5771 | Ph | H | F | NH—O—CH₂—CH=CH₂ | |
| 5772 | Ph | H | F | NH—O—CH₂—C≡CH | |
| 5773 | Ph | H | F | NH—O—CH₂-Ph | |
| 5774 | Ph | H | F | NH—O—CH₂—CO₂—CH₃ | |
| 5775 | Ph | H | F | NH—N(CH₃)₂ | |
| 5776 | Ph | H | F | NH-2-pyridyl | |
| 5777 | Ph | H | F | N(CH₃)₂ | |
| 5778 | Ph | H | F | N₃ | |
| 5779 | Ph | H | F | S—CH₃ | |
| 5780 | Ph | H | F | S-i-C₃H₇ | |
| 5781a | Ph | CH₃ | F | OH | erythro |
| 5781b | Ph | CH₃ | F | OH | threo |
| 5782 | Ph | CH₃ | F | O—CH₃ | |
| 5783a | Ph | CH₃ | F | O—C₂H₅ | erythro |
| 5783b | Ph | CH₃ | F | O—C₂H₅ | threo |
| 5784 | Ph | CH₃ | F | O—(CH₂)₂—Cl | |
| 5785 | Ph | CH₃ | F | O—CH₂—S—CH₃ | |
| 5786 | Ph | CH₃ | F | O—CH₂-Ph | |
| 5787 | Ph | CH₃ | F | O-Ph | |
| 5788 | Ph | CH₃ | F | O—CH₂—CH=CH₂ | |
| 5789 | Ph | CH₃ | F | O—CH₂—C≡CH | |
| 5790 | Ph | CH₃ | F | O—CH₂—O—C₂H₅ | |
| 5791 | Ph | CH₃ | F | NH₂ | |
| 5792 | Ph | CH₃ | F | NH—CH₃ | |
| 5793 | Ph | CH₃ | F | N(CH₃)-Ph | |
| 5794 | Ph | CH₃ | F | NH—OH | |
| 5795 | Ph | CH₃ | F | N(CH₃)—OH | |
| 5796 | Ph | CH₃ | F | NH—O—CH₃ | |
| 5797 | Ph | CH₃ | F | NH—O—CH₂—CH=CH₂ | |
| 5798 | Ph | CH₃ | F | NH—O—CH₂—C≡CH | |
| 5799 | Ph | CH₃ | F | NH—O—CH₂—Ph | |
| 5800 | Ph | CH₃ | F | NH—O—CH₂—CO₂—CH₃ | |
| 5801 | Ph | CH₃ | F | NH—N(CH₃)₂ | |
| 5802 | Ph | CH₃ | F | NH-2-pyridyl | |
| 5803 | Ph | CH₃ | F | N(CH₃)₂ | |
| 5804 | Ph | CH₃ | F | N₃ | |
| 5805 | Ph | CH₃ | F | S—CH₃ | |
| 5806 | Ph | CH₃ | F | S-i-C₃H₇ | |
| 5807 | CF₃ | F | F | OH | rac |
| 5808 | CF₃ | F | F | O—CH₃ | rac |
| 5809 | CF₃ | F | F | O—C₂H₅ | rac |
| 5810 | CF₃ | F | F | O—(CH₂)₂—Cl | |
| 5811 | CF₃ | F | F | O—CH₂—S—CH₃ | |
| 5812 | CF₃ | F | F | O—CH₂-Ph | |
| 5813 | CF₃ | F | F | O-Ph | |
| 5814 | CF₃ | F | F | O—CH₂—CH=CH₂ | |
| 5815 | CF₃ | F | F | O—CH₂—C≡CH | |
| 5816 | CF₃ | F | F | O—CH₂—O—C₂H₅ | |
| 5817 | CF₃ | F | F | NH₂ | |
| 5818 | CF₃ | F | F | NH—CH₃ | |
| 5819 | CF₃ | F | F | N(CH₃)-Ph | |
| 5820 | CF₃ | F | F | NH—OH | |

TABLE 5-continued

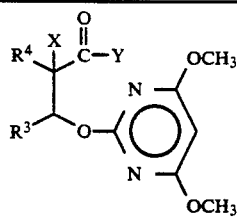

| Compound No. | R³ | R⁴ | X | Y | Remarks |
|---|---|---|---|---|---|
| 5821 | CF₃ | F | F | N(CH₃)—OH | |
| 5822 | CF₃ | F | F | NH—O—CH₃ | |
| 5823 | CF₃ | F | F | NH—O—CH₂—CH=CH₂ | |
| 5824 | CF₃ | F | F | NH—O—CH₂—C≡CH | |
| 5825 | CF₃ | F | F | NH—O—CH₂-Ph | |
| 5826 | CF₃ | F | F | NH—O—CH₂—CO₂—CH₃ | |
| 5827 | CF₃ | F | F | NH—N(CH₃)₂ | |
| 5828 | CF₃ | F | F | NH-2-pyridyl | |
| 5829 | CF₃ | F | F | N(CH₃)₂ | |
| 5830 | CF₃ | F | F | N₃ | |
| 5831 | CF₃ | F | F | S—CH₃ | |
| 5832 | CF₃ | F | F | S-i-C₃H₇ | |
| 5833 | CF₃ | CH₃ | F | OH | mixture |
| 5834 | CF₃ | CH₃ | F | O—CH₃ | |
| 5835 | CF₃ | CH₃ | F | O—C₂H₅ | mixture |
| 5836 | CF₃ | CH₃ | F | O—(CH₂)₂—Cl | |
| 5837 | CF₃ | CH₃ | F | O—CH₂—S—CH₃ | |
| 5838 | CF₃ | CH₃ | F | O—CH₂-Ph | |
| 5839 | CF₃ | CH₃ | F | O-Ph | |
| 5840 | CF₃ | CH₃ | F | O—CH₂—CH=CH₂ | |
| 5841 | CF₃ | CH₃ | F | O—CH₂—C≡CH | |
| 5842 | CF₃ | CH₃ | F | O—CH₂—O—C₂H₅ | |
| 5843 | CF₃ | CH₃ | F | NH₂ | |
| 5844 | CF₃ | CH₃ | F | NH—CH₃ | |
| 5845 | CF₃ | CH₃ | F | N(CH₃)-Ph | |
| 5846 | CF₃ | CH₃ | F | NH—OH | |
| 5847 | CF₃ | CH₃ | F | N(CH₃)—OH | |
| 5848 | CF₃ | CH₃ | F | NH—O—CH₃ | |
| 5849 | CF₃ | CH₃ | F | NH—O—CH₂—CH=CH₂ | |
| 5850 | CF₃ | CH₃ | F | NH—O—CH₂—C≡CH | |
| 5851 | CF₃ | CH₃ | F | NH—O—CH₂-Ph | |
| 5852 | CF₃ | CH₃ | F | NH—O—CH₂—CO₂—CH₃ | |
| 5853 | CF₃ | CH₃ | F | NH—N(CH₃)₂ | |
| 5854 | CF₃ | CH₃ | F | NH-2-pyridyl | |
| 5855 | CF₃ | CH₃ | F | N(CH₃)₂ | |
| 5856 | CF₃ | CH₃ | F | N₃ | |
| 5857 | CF₃ | CH₃ | F | S—CH₃ | |
| 5858 | CF₃ | CH₃ | F | S-i-C₃H₇ | |
| 5859 | CF₃ | CH₂—CH=CH₂ | F | OH | |
| 5860 | CF₃ | CH₂—CH=CH₂ | F | O—CH₃ | |
| 5861 | CF₃ | CH₂—CH=CH₂ | F | O—C₂H₅ | |
| 5862 | CF₃ | CH₂—CH=CH₂ | F | O—(CH₂)₂—Cl | |
| 5863 | CF₃ | CH₂—CH=CH₂ | F | O—CH₂—S—CH₃ | |
| 5864 | CF₃ | CH₂—CH=CH₂ | F | O—CH₂-Ph | |
| 5865 | CF₃ | CH₂—CH=CH₂ | F | O-Ph | |
| 5866 | CF₃ | CH₂—CH=CH₂ | F | O—CH₂—CH=CH₂ | |
| 5867 | CF₃ | CH₂—CH=CH₂ | F | O—CH₂—C≡CH | |
| 5868 | CF₃ | CH₂—CH=CH₂ | F | O—CH₂—O—C₂H₅ | |
| 5869 | CF₃ | CH₂—CH=CH₂ | F | NH₂ | |
| 5870 | CF₃ | CH₂—CH=CH₂ | F | NH—CH₃ | |
| 5871 | CF₃ | CH₂—CH=CH₂ | F | N(CH₃)-Ph | |
| 5872 | CF₃ | CH₂—CH=CH₂ | F | NH—OH | |
| 5873 | CF₃ | CH₂—CH=CH₂ | F | N(CH₃)—OH | |
| 5874 | CF₃ | CH₂—CH=CH₂ | F | NH—O—CH₃ | |
| 5875 | CF₃ | CH₂—CH=CH₂ | F | NH—O—CH₂—CH=CH₂ | |
| 5876 | CF₃ | CH₂—CH=CH₂ | F | NH—O—CH₂—C≡CH | |
| 5877 | CF₃ | CH₂—CH=CH₂ | F | NH—O—CH₂-Ph | |
| 5878 | CF₃ | CH₂—CH=CH₂ | F | NH—O—CH₂—CO₂—CH₃ | |
| 5879 | CF₃ | CH₂—CH=CH₂ | F | NH—N(CH₃)₂ | |
| 5880 | CF₃ | CH₂—CH=CH₂ | F | NH-2-pyridyl | |
| 5881 | CF₃ | CH₂—CH=CH₂ | F | N(CH₃)₂ | |
| 5882 | CF₃ | CH₂—CH=CH₂ | F | N₃ | |
| 5883 | CF₃ | CH₂—CH=CH₂ | F | S—CH₃ | |
| 5884 | CF₃ | CH₂—CH=CH₂ | F | S-i-C₃H₇ | |
| 5885 | CF₃ | CH₂—C≡CH | F | OH | |
| 5886 | CF₃ | CH₂—C≡CH | F | O—CH₃ | |
| 5887 | CF₃ | CH₂—C≡CH | F | O—C₂H₅ | |
| 5888 | CF₃ | CH₂—C≡CH | F | O—(CH₂)₂—Cl | |
| 5889 | CF₃ | CH₂—C≡CH | F | O—CH₂—S—CH₃ | |
| 5890 | CF₃ | CH₂—C≡CH | F | O—CH₂-Ph | |

TABLE 5-continued

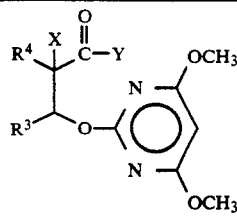

| Compound No. | R³ | R⁴ | X | Y | Remarks |
|---|---|---|---|---|---|
| 5891 | $CF_3$ | $CH_2-C\equiv CH$ | F | O-Ph | |
| 5892 | $CF_3$ | $CH_2-C\equiv CH$ | F | $O-CH_2-CH=CH_2$ | |
| 5893 | $CF_3$ | $CH_2-C\equiv CH$ | F | $O-CH_2-C\equiv CH$ | |
| 5894 | $CF_3$ | $CH_2-C\equiv CH$ | F | $O-CH_2-O-C_2H_5$ | |
| 5895 | $CF_3$ | $CH_2-C\equiv CH$ | F | $NH_2$ | |
| 5896 | $CF_3$ | $CH_2-C\equiv CH$ | F | $NH-CH_3$ | |
| 5897 | $CF_3$ | $CH_2-C\equiv CH$ | F | $N(CH_3)$-Ph | |
| 5898 | $CF_3$ | $CH_2-C\equiv CH$ | F | NH-OH | |
| 5899 | $CF_3$ | $CH_2-C\equiv CH$ | F | $N(CH_3)$-OH | |
| 5900 | $CF_3$ | $CH_2-C\equiv CH$ | F | $NH-O-CH_3$ | |
| 5901 | $CF_3$ | $CH_2-C\equiv CH$ | F | $NH-O-CH_2-CH=CH_2$ | |
| 5902 | $CF_3$ | $CH_2-C\equiv CH$ | F | $NH-O-CH_2-C\equiv CH$ | |
| 5903 | $CF_3$ | $CH_2-C\equiv CH$ | F | $NH-O-CH_2$-Ph | |
| 5904 | $CF_3$ | $CH_2-C\equiv CH$ | F | $NH-O-CH_2-CO_2-CH_3$ | |
| 5905 | $CF_3$ | $CH_2-C\equiv CH$ | F | $NH-N(CH_3)_2$ | |
| 5906 | $CF_3$ | $CH_2-C\equiv CH$ | F | NH-2-pyridyl | |
| 5907 | $CF_3$ | $CH_2-C\equiv CH$ | F | $N(CH_3)_2$ | |
| 5908 | $CF_3$ | $CH_2-C\equiv CH$ | F | $N_3$ | |
| 5909 | $CF_3$ | $CH_2-C\equiv CH$ | F | $S-CH_3$ | |
| 5910 | $CF_3$ | $CH_2-C\equiv CH$ | F | $S-i-C_3H_7$ | |
| 5911 | $CF_3$ | $CH_2$-Ph | F | OH | |
| 5912 | $CF_3$ | $CH_2$-Ph | F | $O-CH_3$ | |
| 5913 | $CF_3$ | $CH_2$-Ph | F | $O-C_2H_5$ | |
| 5914 | $CF_3$ | $CH_2$-Ph | F | $O-(CH_2)_2-Cl$ | |
| 5915 | $CF_3$ | $CH_2$-Ph | F | $O-CH_2-S-CH_3$ | |
| 5916 | $CF_3$ | $CH_2$-Ph | F | $O-CH_2$-Ph | |
| 5917 | $CF_3$ | $CH_2$-Ph | F | O-Ph | |
| 5918 | $CF_3$ | $CH_2$-Ph | F | $O-CH_2-CH=CH_2$ | |
| 5919 | $CF_3$ | $CH_2$-Ph | F | $O-CH_2-C\equiv CH$ | |
| 5920 | $CF_3$ | $CH_2$-Ph | F | $O-CH_2-O-C_2H_5$ | |
| 5921 | $CF_3$ | $CH_2$-Ph | F | $NH_2$ | |
| 5922 | $CF_3$ | $CH_2$-Ph | F | $NH-CH_3$ | |
| 5923 | $CF_3$ | $CH_2$-Ph | F | $N(CH_3)$-Ph | |
| 5924 | $CF_3$ | $CH_2$-Ph | F | NH-OH | |
| 5925 | $CF_3$ | $CH_2$-Ph | F | $N(CH_3)$-OH | |
| 5926 | $CF_3$ | $CH_2$-Ph | F | $NH-O-CH_3$ | |
| 5927 | $CF_3$ | $CH_2$-Ph | F | $NH-O-CH_2-CH=CH_2$ | |
| 5928 | $CF_3$ | $CH_2$-Ph | F | $NH-O-CH_2-C\equiv CH$ | |
| 5929 | $CF_3$ | $CH_2$-Ph | F | $NH-O-CH_2$-Ph | |
| 5930 | $CF_3$ | $CH_2$-Ph | F | $NH-O-CH_2-CO_2-CH_3$ | |
| 5931 | $CF_3$ | $CH_2$-Ph | F | $NH-N(CH_3)_2$ | |
| 5932 | $CF_3$ | $CH_2$-Ph | F | NH-2-pyridyl | |
| 5933 | $CF_3$ | $CH_2$-Ph | F | $N(CH_3)_2$ | |
| 5934 | $CF_3$ | $CH_2$-Ph | F | $N_3$ | |
| 5935 | $CF_3$ | $CH_2$-Ph | F | $S-CH_3$ | |
| 5936 | $CF_3$ | $CH_2$-Ph | F | $S-i-C_3H_7$ | |
| 5937 | $CH_3$ | $CF_3$ | F | OH | |
| 5938 | $CH_3$ | $CF_3$ | F | OH | |
| 5939 | $CH_3$ | $CF_3$ | F | $O-CH_3$ | |
| 5940 | $CH_3$ | $CF_3$ | F | $O-CH_3$ | |
| 5941 | $CH_3$ | $CF_3$ | F | $O-C_2H_5$ | |
| 5942 | $CH_3$ | $CF_3$ | F | $O-C_2H_5$ | |
| 5943 | $CH_3$ | $CF_3$ | F | $O-(CH_2)_2-Cl$ | |
| 5944 | $CH_3$ | $CF_3$ | F | $O-CH_2-S-CH_3$ | |
| 5945 | $CH_3$ | $CF_3$ | F | $O-CH_2$-Ph | |
| 5946 | $CH_3$ | $CF_3$ | F | O-Ph | |
| 5947 | $CH_3$ | $CF_3$ | F | $O-CH_2-CH=CH_2$ | |
| 5948 | $CH_3$ | $CF_3$ | F | $O-CH_2-C\equiv CH$ | |
| 5949 | $CH_3$ | $CF_3$ | F | $O-CH_2-O-C_2H_5$ | |
| 5950 | $CH_3$ | $CF_3$ | F | $NH_2$ | |
| 5951 | $CH_3$ | $CF_3$ | F | $NH-CH_3$ | |
| 5952 | $CH_3$ | $CF_3$ | F | $N(CH_3)$-Ph | |
| 5953 | $CH_3$ | $CF_3$ | F | NH-OH | |
| 5954 | $CH_3$ | $CF_3$ | F | $N(CH_3)$-OH | |
| 5955 | $CH_3$ | $CF_3$ | F | $NH-O-CH_3$ | |
| 5956 | $CH_3$ | $CF_3$ | F | $NH-O-CH_2-CH=CH_2$ | |
| 5957 | $CH_3$ | $CF_3$ | F | $NH-O-CH_2-C\equiv CH$ | |
| 5958 | $CH_3$ | $CF_3$ | F | $NH-O-CH_2$-Ph | |
| 5959 | $CH_3$ | $CF_3$ | F | $NH-O-CH_2-CO_2-CH_3$ | |
| 5960 | $CH_3$ | $CF_3$ | F | $NH-N(CH_3)_2$ | |

TABLE 5-continued

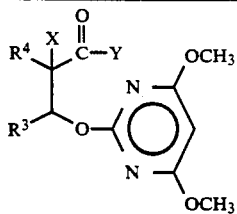

| Compound No. | R³ | R⁴ | X | Y | Remarks |
|---|---|---|---|---|---|
| 5961 | CH₃ | CF₃ | F | NH-2-pyridyl | |
| 5962 | CH₃ | CF₃ | F | N(CH₃)₂ | |
| 5963 | CH₃ | CF₃ | F | S—CH₃ | |
| 5964 | CH₃ | CF₃ | F | S-i-C₃H₇ | |
| 5965 | CO₂H | CH₃ | F | OH | mixture |
| 5966 | CO₂—CH₃ | CH₃ | F | O—CH₃ | |
| 5967 | CO₂—C₂H₅ | CH₃ | F | O—C₂H₅ | mixture |

TABLE 6

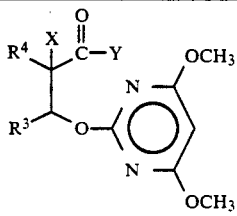

| Compound No. | R₃ | R₄ | X | Y | Remarks |
|---|---|---|---|---|---|
| 6001 | —CH₂—O—CH₂— | | F | OH | mixture |
| 6002 | —CH₂—O—CH₂— | | F | O—CH₃ | |
| 6003 | —CH₂—O—CH₂— | | F | O—C₂H₅ | mixture |
| 6004 | —CH₂—O—CH₂— | | F | O-i-C₃H₇ | |
| 6005 | —CH₂—O—CH₂— | | F | O—(CH₂)₂—Cl | |
| 6006 | —CH₂—O—CH₂— | | F | O—CH₂—S—CH₃ | |
| 6007 | —CH₂—O—CH₂— | | F | O—CH₂—Ph | |
| 6008 | —CH₂—O—CH₂— | | F | O—Ph | |
| 6009 | —CH₂—O—CH₂— | | F | O—CH₂—CH=CH₂ | |
| 6010 | —CH₂—O—CH₂— | | F | O—CH₂—C≡CH | |
| 6011 | —CH₂—O—CH₂— | | F | O—CH₂—O—C₂H₅ | |
| 6012 | —CH₂—O—CH₂— | | F | NH₂ | |
| 6013 | —CH₂—O—CH₂— | | F | NH—CH₃ | |
| 6014 | —CH₂—O—CH₂— | | F | N(CH₃)—Ph | |
| 6015 | —CH₂—O—CH₂— | | F | NH—OH | |
| 6016 | —CH₂—O—CH₂— | | F | N(CH₃)—OH | |
| 6017 | —CH₂—O—CH₂— | | F | NH—O—CH₃ | |
| 6018 | —CH₂—O—CH₂— | | F | NH—O—CH₂—CH=CH₂ | |
| 6019 | —CH₂—O—CH₂— | | F | NH—O—CH₂—C≡CH | |
| 6020 | —CH₂—O—CH₂— | | F | NH—O—CH₂—Ph | |
| 6021 | —CH₂—O—CH₂— | | F | NH—O—CH₂—CO₂—CH₃ | |
| 6022 | —CH₂—O—CH₂— | | F | NH—N(CH₃)₂ | |
| 6023 | —CH₂—O—CH₂— | | F | NH-2-pyridyl | |
| 6024 | —CH₂—O—CH₂— | | F | NH-2-thiadiazoly | |
| 6025 | —CH₂—O—CH₂— | | F | N₃ | |
| 6026 | —CH₂—O—CH₂— | | F | S—CH₃ | |
| 6027 | —CH₂—O—CH₂— | | F | S—C₂H₅ | |
| 6028 | —(CH₂)₂—O— | | F | OH | |
| 6029 | —(CH₂)₂—O— | | F | O—CH₃ | |
| 6030 | —(CH₂)₂—O— | | F | O—C₂H₅ | |
| 6031 | —(CH₂)₂—O— | | F | O-i-C₃H₇ | |
| 6032 | —(CH₂)₂—O— | | F | O—(CH₂)₂—Cl | |
| 6033 | —(CH₂)₂—O— | | F | O—CH₂—S—CH₃ | |
| 6034 | —(CH₂)₂—O— | | F | O—CH₂—Ph | |
| 6035 | —(CH₂)₂—O— | | F | O—Ph | |
| 6036 | —(CH₂)₂—O— | | F | O—CH₂—CH=CH₂ | |
| 6037 | —(CH₂)₂—O— | | F | O—CH₂—C≡CH | |
| 6038 | —(CH₂)₂—O— | | F | O—CH₂—O—C₂H₅ | |
| 6039 | —(CH₂)₂—O— | | F | NH₂ | |
| 6040 | —(CH₂)₂—O— | | F | NH—CH₃ | |
| 6041 | —(CH₂)₂—O— | | F | N(CH₃)—Ph | |
| 6042 | —(CH₂)₂—O— | | F | NH—OH | |
| 6043 | —(CH₂)₂—O— | | F | N(CH₃)OH | |
| 6044 | —(CH₂)₂—O— | | F | NH—O—CH₃ | |
| 6045 | —(CH₂)₂—O— | | F | NH—O—CH₂—CH=CH₂ | |

TABLE 6-continued

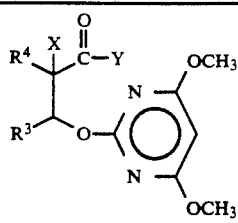

| Compound No. | R₃ | R₄ | X | Y | Remarks |
|---|---|---|---|---|---|
| 6046 | —(CH₂)₂—O— | | F | NH—O—CH₂—C≡CH | |
| 6047 | —(CH₂)₂—O— | | F | NH—O—CH₂—Ph | |
| 6048 | —(CH₂)₂—O— | | F | NH—O—CH₂—CO₂—CH₃ | |
| 6049 | —(CH₂)₂—O— | | F | NH—N(CH₃)₂ | |
| 6050 | —(CH₂)₂—O— | | F | NH-2-pyridyl | |
| 6051 | —(CH₂)₂—O— | | F | NH-2-thiadiazoly | |
| 6052 | —(CH₂)₂—O— | | F | N₃ | |
| 6053 | —(CH₂)₂—O— | | F | S—CH₃ | |
| 6054 | —(CH₂)₂—O— | | F | S—C₂H₅ | |
| 6055 | —CH₂—O—(CH₂)₂— | | F | OH | |
| 6056 | —CH₂—O—(CH₂)₂— | | F | O—CH₃ | |
| 6057 | —CH₂—O—(CH₂)₂— | | F | O—C₂H₅ | |
| 6058 | —CH₂—O—(CH₂)₂— | | F | O-i-C₃H₇ | |
| 6059 | —CH₂—O—(CH₂)₂— | | F | O—(CH₂)₂—Cl | |
| 6060 | —CH₂—O—(CH₂)₂— | | F | O—CH₂—S—CH₃ | |
| 6061 | —CH₂—O—(CH₂)₂— | | F | O—CH₂—Ph | |
| 6062 | —CH₂—O—(CH₂)₂— | | F | O—Ph | |
| 6063 | —CH₂—O—(CH₂)₂— | | F | O—CH₂—CH=CH₂ | |
| 6064 | —CH₂—O—(CH₂)₂— | | F | O—CH₂—C≡CH | |
| 6065 | —CH₂—O—(CH₂)₂— | | F | O—CH₂—O—C₂H₅ | |
| 6066 | —CH₂—O—(CH₂)₂— | | F | NH₂ | |
| 6067 | —CH₂—O—(CH₂)₂— | | F | NH—CH₃ | |
| 6068 | —CH₂—O—(CH₂)₂— | | F | N(CH₃)—Ph | |
| 6069 | —CH₂—O—(CH₂)₂— | | F | NH—OH | |
| 6070 | —CH₂—O—(CH₂)₂— | | F | N(CH₃)—OH | |
| 6071 | —CH₂—O—(CH₂)₂— | | F | NH—O—CH₃ | |
| 6072 | —CH₂—O—(CH₂)₂— | | F | NH—O—CH₂—CH=CH₂ | |
| 6073 | —CH₂—O—(CH₂)₂— | | F | NH—O—CH₂—C≡CH | |
| 6074 | —CH₂—O—(CH₂)₂— | | F | NH—O—CH₂—Ph | |
| 6075 | —CH₂—O—(CH₂)₂— | | F | NH—O—CH₂—CO₂—CH₃ | |
| 6076 | —CH₂—O—(CH₂)₂— | | F | NH—N(CH₃)₂ | |
| 6077 | —CH₂—O—(CH₂)₂— | | F | NH-2-pyridyl | |
| 6078 | —CH₂—O—(CH₂)₂— | | F | NH-2-thiadiazoly | |
| 6079 | —CH₂—O—(CH₂)₂— | | F | N₃ | |
| 6080 | —CH₂—O—(CH₂)₂— | | F | S—CH₃ | |
| 6081 | —CH₂—O—(CH₂)₂— | | F | S—C₂H₅ | |
| 6082a | —(CH₂)₂—O—CH₂— | | F | OH | cis |
| 6082b | —(CH₂)₂—O—CH₂— | | F | OH | trans |
| 6083 | —(CH₂)₂—O—CH₂— | | F | O—CH₃ | |
| 6084a | —(CH₂)₂—O—CH₂— | | F | O—C₂H₅ | cis |
| 6084b | —(CH₂)₂—O—CH₂— | | F | O—C₂H₅ | trans |
| 6085a | —(CH₂)₂—O—CH₂— | | F | O-i-C₃H₇ | cis |
| 6085b | —(CH₂)₂—O—CH₂— | | F | O-i-C₃H₇ | trans |
| 6086 | —(CH₂)₂—O—CH₂— | | F | O—(CH₂)₂—Cl | |
| 6087 | —(CH₂)₂—O—CH₂— | | F | O—CH₂—S—CH₃ | |
| 6088 | —(CH₂)₂—O—CH₂— | | F | O—CH₂—Ph | |
| 6089 | —(CH₂)₂—O—CH₂— | | F | O—Ph | |
| 6090a | —(CH₂)₂—O—CH₂— | | F | O—CH₂—CH=CH₂ | cis |
| 6090b | —(CH₂)₂—O—CH₂— | | F | O—CH₂—CH=CH₂ | trans |
| 6091a | —(CH₂)₂—O—CH₂— | | F | O—CH₂—C≡CH | cis |
| 6091b | —(CH₂)₂—O—CH₂— | | F | O—CH₂—C≡CH | trans |
| 6092 | —(CH₂)₂—O—CH₂— | | F | O—CH₂—O—C₂H₅ | |
| 6093 | —(CH₂)₂—O—CH₂— | | F | NH₂ | |
| 6094 | —(CH₂)₂—O—CH₂— | | F | NH—CH₃ | |
| 6095 | —(CH₂)₂—O—CH₂— | | F | N(CH₃)—Ph | |
| 6096 | —(CH₂)₂—O—CH₂— | | F | NH—OH | |
| 6097 | —(CH₂)₂—O—CH₂— | | F | N(CH₃)—OH | |
| 6098 | —(CH₂)₂—O—CH₂— | | F | NH—O—CH₃ | |
| 6099 | —(CH₂)₂—O—CH₂— | | F | NH—O—CH₂—CH=CH₂ | |
| 6100 | —(CH₂)₂—O—CH₂— | | F | NH—O—CH₂—C≡CH | |
| 6101 | —(CH₂)₂—O—CH₂— | | F | NH—O—CH₂—Ph | |
| 6102 | —(CH₂)₂—O—CH₂— | | F | NH—O—CH₂—CO₂—CH₃ | |
| 6103 | —(CH₂)₂—O—CH₂— | | F | NH—N(CH₃)₂ | |
| 6104 | —(CH₂)₂—O—CH₂— | | F | NH-2-pyridyl | |
| 6105 | —(CH₂)₂—O—CH₂— | | F | NH-2-thiadiazoly | |
| 6106 | —(CH₂)₂—O—CH₂— | | F | N₃ | |
| 6107 | —(CH₂)₂—O—CH₂— | | F | S—CH₃ | |
| 6108 | —(CH₂)₂—O—CH₂— | | F | S—C₂H₅ | |
| 6109 | —(CH₂)₃—O— | | F | OH | |

TABLE 6-continued

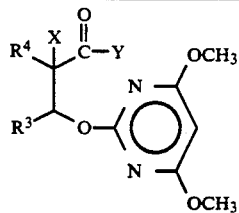

| Compound No. | R3 | R4 | X | Y | Remarks |
|---|---|---|---|---|---|
| 6110 | —(CH$_2$)$_3$—O— | | F | O—CH$_3$ | |
| 6111 | —(CH$_2$)$_3$—O— | | F | O—C$_2$H$_5$ | |
| 6112 | —(CH$_2$)$_3$—O— | | F | O-i-C$_3$H$_7$ | |
| 6113 | —(CH$_2$)$_3$—O— | | F | O—(CH$_2$)$_2$—Cl | |
| 6114 | —(CH$_2$)$_3$—O— | | F | O—CH$_2$—S—CH$_3$ | |
| 6115 | —(CH$_2$)$_3$—O— | | F | O—CH$_2$—Ph | |
| 6116 | —(CH$_2$)$_3$—O— | | F | O—Ph | |
| 6117 | —(CH$_2$)$_3$—O— | | F | O—CH$_2$—CH=CH$_2$ | |
| 6118 | —(CH$_2$)$_3$—O— | | F | O—CH$_2$—C≡CH | |
| 6119 | —(CH$_2$)$_3$—O— | | F | O—CH$_2$—O—C$_2$H$_5$ | |
| 6120 | —(CH$_2$)$_3$—O— | | F | NH$_2$ | |
| 6121 | —(CH$_2$)$_3$—O— | | F | NH—CH$_3$ | |
| 6122 | —(CH$_2$)$_3$—O— | | F | N(CH$_3$)—Ph | |
| 6123 | —(CH$_2$)$_3$—O— | | F | NH—OH | |
| 6124 | —(CH$_2$)$_3$—O— | | F | N(CH$_3$)—OH | |
| 6125 | —(CH$_2$)$_3$—O— | | F | NH—O—CH$_3$ | |
| 6126 | —(CH$_2$)$_3$—O— | | F | NH—O—CH$_2$—CH=CH$_2$ | |
| 6127 | —(CH$_2$)$_3$—O— | | F | NH—O—CH$_2$—C≡CH | |
| 6128 | —(CH$_2$)$_3$—O— | | F | NH—O—CH$_2$—Ph | |
| 6129 | —(CH$_2$)$_3$—O— | | F | NH—O—CH$_2$—CO$_2$—CH$_3$ | |
| 6130 | —(CH$_2$)$_3$—O— | | F | NH—N(CH$_3$)$_2$ | |
| 6131 | —(CH$_2$)$_3$—O— | | F | NH-2-pyridyl | |
| 6132 | —(CH$_2$)$_3$—O— | | F | NH-2-thiadiazoly | |
| 6133 | —(CH$_2$)$_3$—O— | | F | N$_3$ | |
| 6134 | —(CH$_2$)$_3$—O— | | F | S—CH$_3$ | |
| 6135 | —(CH$_2$)$_3$—O— | | F | S—C$_2$H$_5$ | |
| 6136a | —CH$_2$—S—CH$_2$— | | F | OH | cis |
| 6136b | —CH$_2$—S—CH$_2$— | | F | OH | trans |
| 6137a | —CH$_2$—S—CH$_2$— | | F | O—CH$_3$ | cis |
| 6137b | —CH$_2$—S—CH$_2$— | | F | O—CH$_3$ | trans |
| 6138 | —CH$_2$—S—CH$_2$— | | F | O—C$_2$H$_5$ | |
| 6139 | —CH$_2$—S—CH$_2$— | | F | O-i-C$_3$H$_7$ | |
| 6140 | —CH$_2$—S—CH$_2$— | | F | O—(CH$_2$)$_2$—Cl | |
| 6141 | —CH$_2$—S—CH$_2$— | | F | O—CH$_2$—S—CH$_3$ | |
| 6142 | —CH$_2$—S—CH$_2$— | | F | O—CH$_2$—Ph | |
| 6143 | —CH$_2$—S—CH$_2$— | | F | O—Ph | |
| 6144 | —CH$_2$—S—CH$_2$— | | F | O—CH$_2$—CH≡CH$_2$ | |
| 6145 | —CH$_2$—S—CH$_2$— | | F | O—CH$_2$—C≡CH | |
| 6146 | —CH$_2$—S—CH$_2$— | | F | O—CH$_2$—O—C$_2$H$_5$ | |
| 6147 | —CH$_2$—S—CH$_2$— | | F | NH$_2$ | |
| 6148 | —CH$_2$—S—CH$_2$— | | F | NH—CH$_3$ | |
| 6149 | —CH$_2$—S—CH$_2$— | | F | N(CH$_3$)—Ph | |
| 6150 | —CH$_2$—S—CH$_2$— | | F | NH—OH | |
| 6151 | —CH$_2$—S—CH$_2$— | | F | N(CH$_3$)—OH | |
| 6152 | —CH$_2$—S—CH$_2$— | | F | NH—O—CH$_3$ | |
| 6153 | —CH$_2$—S—CH$_2$— | | F | NH—O—CH$_2$—CH=CH$_2$ | |
| 6154 | —CH$_2$—S—CH$_2$— | | F | NH—O—CH$_2$—C≡CH | |
| 6155 | —CH$_2$—S—CH$_2$— | | F | NH—O—CH$_2$—Ph | |
| 6156 | —CH$_2$—S—CH$_2$— | | F | NH—O—CH$_2$—CO$_2$—CH$_3$ | |
| 6157 | —CH$_2$—S—CH$_2$— | | F | NH—N(CH$_3$)$_2$ | |
| 6158 | —CH$_2$—S—CH$_2$— | | F | NH-2-pyridyl | |
| 6159 | —CH$_2$—S—CH$_2$— | | F | NH-2-tiadiazoly | |
| 6160 | —CH$_2$—S—CH$_2$— | | F | N$_3$ | |
| 6161 | —CH$_2$—S—CH$_2$— | | F | S—CH$_3$ | |
| 6162 | —CH$_2$—S—CH$_2$— | | F | S—C$_2$H$_5$ | |
| 6163 | —(CH$_2$)$_2$—S— | | F | OH | |
| 6164 | —(CH$_2$)$_2$—S— | | F | O—C$_2$H$_5$ | |
| 6165 | —(CH$_2$)$_2$—S— | | F | O-i-C$_3$H$_7$ | |
| 6166 | —(CH$_2$)$_2$—S— | | F | O—(CH$_2$)$_2$—Cl | |
| 6167 | —(CH$_2$)$_2$—S— | | F | O—CH$_2$—S—CH$_3$ | |
| 6168 | —(CH$_2$)$_2$—S— | | F | O—CH$_2$—Ph | |
| 6169 | —(CH$_2$)$_2$—S— | | F | O—Ph | |
| 6170 | —(CH$_2$)$_2$—S— | | F | O—CH$_2$—CH=CH$_2$ | |
| 6171 | —(CH$_2$)$_2$—S— | | F | O—CH$_2$—C≡CH | |
| 6172 | —(CH$_2$)$_2$—S— | | F | O—CH$_2$—O—C$_2$H$_5$ | |
| 6173 | —(CH$_2$)$_2$—S— | | F | NH$_2$ | |
| 6174 | —(CH$_2$)$_2$—S— | | F | NH—CH$_3$ | |
| 6175 | —(CH$_2$)$_2$—S— | | F | N(CH$_3$)—Ph | |
| 6176 | —(CH$_2$)$_2$—S— | | F | NH—OH | |

TABLE 6-continued

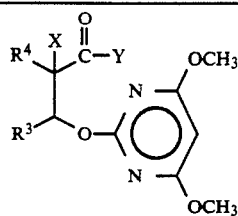

| Compound No. | R₃ | R₄ | X | Y | Remarks |
|---|---|---|---|---|---|
| 6177 | —(CH₂)₂—S— | | F | N(CH₃)—OH | |
| 6178 | —(CH₂)₂—S— | | F | NH—O—CH₃ | |
| 6179 | —(CH₂)₂—S— | | F | NH—O—CH₂—CH=CH₂ | |
| 6180 | —(CH₂)₂—S— | | F | NH—O—CH₂—C≡CH | |
| 6181 | —(CH₂)₂—S— | | F | NH—O—CH₂—Ph | |
| 6182 | —(CH₂)₂—S— | | F | NH—O—CH₂—CO₂—CH₃ | |
| 6183 | —(CH₂)₂—S— | | F | NH—N(CH₃)₂ | |
| 6184 | —(CH₂)₂—S— | | F | NH-2-pyridyl | |
| 6185 | —(CH₂)₂—S— | | F | NH-2-thiadiazoly | |
| 6186 | —(CH₂)₂—S— | | F | N₃ | |
| 6187 | —(CH₂)₂—S— | | F | S—CH₃ | |
| 6188 | —(CH₂)₂—S— | | F | S—C₂H₅ | |
| 6189 | —CH₂—S—(CH₂)₂— | | F | OH | |
| 6190 | —CH₂—S—(CH₂)₂— | | F | O—CH₃ | |
| 6191 | —CH₂—S—(CH₂)₂— | | F | O—C₂H₅ | |
| 6192 | —CH₂—S—(CH₂)₂— | | F | O-i-C₃H₇ | |
| 6193 | —CH₂—S—(CH₂)₂— | | F | O—(CH₂)₂—Cl | |
| 6194 | —CH₂—S—(CH₂)₂— | | F | O—CH₂—S—CH₃ | |
| 6195 | —CH₂—S—(CH₂)₂— | | F | O—CH₂—Ph | |
| 6196 | —CH₂—S—(CH₂)₂— | | F | O—Ph | |
| 6197 | —CH₂—S—(CH₂)₂— | | F | O—CH₂—CH=CH₂ | |
| 6198 | —CH₂—S—(CH₂)₂— | | F | O—CH₂—C≡CH | |
| 6199 | —CH₂—S—(CH₂)₂— | | F | O—CH₂—O—C₂H₅ | |
| 6200 | —CH₂—S—(CH₂)₂— | | F | NH₂ | |
| 6201 | —CH₂—S—(CH₂)₂— | | F | NH—CH₃ | |
| 6202 | —CH₂—S—(CH₂)₂— | | F | N(CH₃)—Ph | |
| 6203 | —CH₂—S—(CH₂)₂— | | F | NH—OH | |
| 6204 | —CH₂—S—(CH₂)₂— | | F | N(CH₃)—OH | |
| 6205 | —CH₂—S—(CH₂)₂— | | F | NH—O—CH₃ | |
| 6206 | —CH₂—S—(CH₂)₂— | | F | NH—O—CH₂—CH=CH₂ | |
| 6207 | —CH₂—S—(CH₂)₂— | | F | NH—O—CH₂—C≡CH | |
| 6208 | —CH₂—S—(CH₂)₂— | | F | NH—O—CH₂—Ph | |
| 6209 | —CH₂—S—(CH₂)₂— | | F | NH—O—CH₂—CO₂—CH₃ | |
| 6210 | —CH₂—S—(CH₂)₂— | | F | NH—N(CH₃)₂ | |
| 6211 | —CH₂—S—(CH₂)₂— | | F | NH-2-pyridyl | |
| 6212 | —CH₂—S—(CH₂)₂— | | F | NH-2-thiadiazoly | |
| 6213 | —CH₂—S—(CH₂)₂— | | F | N₃ | |
| 6214 | —CH₂—S—(CH₂)₂— | | F | S—CH₃ | |
| 6215 | —CH₂—SO(CH₂)₂— | | F | S—C₂H₅ | |
| 6216a | —(CH₂)₂—S—CH₂— | | F | OH | cis |
| 6216b | —(CH₂)₂—S—CH₂— | | F | OH | trans |
| 6217a | —(CH₂)₂—S—CH₂— | | F | O—CH₃ | cis |
| 6217b | —(CH₂)₂—S—CH₂— | | F | O—CH₃ | trans |
| 6218 | —(CH₂)₂—S—CH₂— | | F | O—C₂H₅ | |
| 6219 | —(CH₂)₂—S—CH₂— | | F | O-i-C₃H₇ | |
| 6220 | —(CH₂)₂—S—CH₂— | | F | O—(CH₂)₂—Cl | |
| 6221 | —(CH₂)₂—S—CH₂— | | F | O—CH₂—S—CH₃ | |
| 6222 | —(CH₂)₂—S—CH₂— | | F | O—CH₂—Ph | |
| 6223 | —(CH₂)₂—S—CH₂— | | F | O—Ph | |
| 6224 | —(CH₂)₂—S—CH₂— | | F | O—CH₂—CH=CH₂ | |
| 6225 | —(CH₂)₂—S—CH₂— | | F | O—CH₂—C≡CH | |
| 6226 | —(CH₂)₂—S—CH₂— | | F | O—CH₂—O—C₂H₅ | |
| 6227 | —(CH₂)₂—S—CH₂— | | F | NH₂ | |
| 6228 | —(CH₂)₂—S—CH₂— | | F | NH—CH₃ | |
| 6229 | —(CH₂)₂—S—CH₂— | | F | N(CH₃)—Ph | |
| 6230 | —(CH₂)₂—S—CH₂— | | F | NH—OH | |
| 6231 | —(CH₂)₂—S—CH₂— | | F | N(CH₃)—OH | |
| 6232 | —(CH₂)₂—S—CH₂— | | F | NH—O—CH₃ | |
| 6233 | —(CH₂)₂—S—CH₂— | | F | NH—O—CH₂—CH=CH₂ | |
| 6234 | —(CH₂)₂—S—CH₂— | | F | NH—O—CH₂—C≡CH | |
| 6235 | —(CH₂)₂—S—CH₂— | | F | NH—O—CH₂—Ph | |
| 6236 | —(CH₂)₂—S—CH₂— | | F | NH—O—CH₂—CO₂—CH₃ | |
| 6237 | —(CH₂)₂—S—CH₂— | | F | NH—N(CH₃)₂ | |
| 6238 | —(CH₂)₂—S—CH₂— | | F | NH-2-pyridyl | |
| 6239 | —(CH₂)₂—S—CH₂— | | F | NH-2-thiadiazoly | |
| 6240 | —(CH₂)₂—S—CH₂— | | F | N₃ | |
| 6241 | —(CH₂)₂—S—CH₂— | | F | S—CH₃ | |
| 6242 | —(CH₂)₂—S—CH₂— | | F | S—C₂H₅ | |
| 6243 | —(CH₂)₃—S— | | F | OH | |

TABLE 6-continued

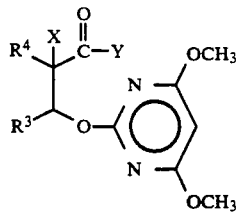

| Compound No. | R₃ | R₄ | X | Y | Remarks |
|---|---|---|---|---|---|
| 6244 | —(CH₂)₃—S— | | F | O—CH₃ | |
| 6245 | —(CH₂)₃—S— | | F | O—C₂H₅ | |
| 6246 | —(CH₂)₃—S— | | F | O-i-C₃H₇ | |
| 6247 | —(CH₂)₃—S— | | F | O—(CH₂)₂—Cl | |
| 6248 | —(CH₂)₃—S— | | F | O—CH₂—S—CH₃ | |
| 6249 | —(CH₂)₃—S— | | F | O—CH₂—Ph | |
| 6250 | —(CH₂)₃—S— | | F | O—Ph | |
| 6251 | —(CH₂)₃—S— | | F | O—CH₂—CH=CH₂ | |
| 6252 | —(CH₂)₃—S— | | F | O—CH₂—C≡CH | |
| 6253 | —(CH₂)₃—S— | | F | O—CH₂—O—C₂H₅ | |
| 6254 | —(CH₂)₃—S— | | F | NH₂ | |
| 6255 | —(CH₂)₃—S— | | F | NH—CH₃ | |
| 6256 | —(CH₂)₃—S— | | F | N(CH₃)—Ph | |
| 6257 | —(CH₂)₃—S— | | F | NH—OH | |
| 6258 | —(CH₂)₃—S— | | F | N(CH₃)—OH | |
| 6259 | —(CH₂)₃—S— | | F | NH—O—CH₃ | |
| 6260 | —(CH₂)₃—S— | | F | NH—O—CH₂—CH=CH₂ | |
| 6261 | —(CH₂)₃—S— | | F | NH—O—CH₂—C≡CH | |
| 6262 | —(CH₂)₃—S— | | F | NH—O—CH₂—Ph | |
| 6263 | —(CH₂)₃—S— | | F | NH—O—CH₂—CO₂—CH₃ | |
| 6264 | —(CH₂)₃—S— | | F | NH—N(CH₃)₂ | |
| 6265 | —(CH₂)₃—S— | | F | NH-2-pyridyl | |
| 6266 | —(CH₂)₃—S— | | F | NH-2-thiadiazoly | |
| 6267 | —(CH₂)₃—S— | | F | N₃ | |
| 6268 | —(CH₂)₃—S— | | F | S—CH₃ | |
| 6269 | —(CH₂)₃—S— | | F | S—C₂H₅ | |
| 6270 | —CH₂—N—CH₂— | | F | OH | |
| 6271 | —CH₂—NH—CH₂— | | F | O—CH₃ | |
| 6272 | —CH₂—NH—CH₂— | | F | O—C₂H₅ | |
| 6273 | —CH₂—NH—CH₂— | | F | O-i-C₃H₇ | |
| 6274 | —CH₂—NH—CH₂— | | F | O—(CH₂)₂—Cl | |
| 6275 | —CH₂—NH—CH₂— | | F | O—CH₂—S—CH₃ | |
| 6276 | —CH₂—NH—CH₂— | | F | O—CH₂—Ph | |
| 6277 | —CH₂—NH—CH₂— | | F | O—Ph | |
| 6278 | —CH₂—NH—CH₂— | | F | O—CH₂—CH=CH₂ | |
| 6279 | —CH₂—NH—CH₂— | | F | O—CH₂—C≡CH | |
| 6280 | —CH₂—NH—CH₂— | | F | O—CH₂—O—C₂H₅ | |
| 6281 | —CH₂—NH—CH₂— | | F | NH₂ | |
| 6282 | —CH₂—NH—CH₂— | | F | NH—CH₃ | |
| 6283 | —CH₂—NH—CH₂— | | F | N(CH₃)—Ph | |
| 6284 | —CH₂—NH—CH₂— | | F | NH—OH | |
| 6285 | —CH₂—NH—CH₂— | | F | N(CH₃)—OH | |
| 6286 | —CH₂—NH—CH₂— | | F | NH—O—CH₃ | |
| 6287 | —CH₂—NH—CH₂— | | F | NH—O—CH₂—CH=CH₂ | |
| 6288 | —CH₂—NH—CH₂— | | F | NH—O—CH₂—C≡CH | |
| 6289 | —CH₂—NH—CH₂— | | F | NH—O—CH₂—Ph | |
| 6290 | —CH₂—NH—CH₂— | | F | NH—O—CH₂—CO₂—CH₃ | |
| 6291 | —CH₂—NH—CH₂— | | F | NH—N(CH₃)₂ | |
| 6292 | —CH₂—NH—CH₂— | | F | NH-2-pyridyl | |
| 6293 | —CH₂—NH—CH₂— | | F | NH-2-thiadiazoly | |
| 6294 | —CH₂—NH—CH₂— | | F | N₃ | |
| 6295 | —CH₂—NH—CH₂— | | F | S—CH₃ | |
| 6296 | —CH₂—NH—CH₂— | | F | S—C₂H₅ | |
| 6297 | —(CH₂)₂—NH— | | F | OH | |
| 6298 | —(CH₂)₂—NH— | | F | O—CH₃ | |
| 6299 | —(CH₂)₂—NH— | | F | O—C₂H₅ | |
| 6300 | —(CH₂)₂—NH— | | F | O-i-C₃H₇ | |
| 6301 | —(CH₂)₂—NH— | | F | O—(CH₂)₂—Cl | |
| 6302 | —(CH₂)₂—NH— | | F | O—CH₂—S—CH₃ | |
| 6303 | —(CH₂)₂—NH— | | F | O—CH₂—Ph | |
| 6304 | —(CH₂)₂—NH— | | F | O—Ph | |
| 6305 | —(CH₂)₂—NH— | | F | O—CH₂—CH—CH₂ | |
| 6306 | —(CH₂)₂—NH— | | F | O—CH₂—C≡CH | |
| 6307 | —(CH₂)₂—NH— | | F | O—CH₂—O—C₂H₅ | |
| 6308 | —(CH₂)₂—NH— | | F | NH₂ | |
| 6309 | —(CH₂)₂—NH— | | F | NH—CH₃ | |
| 6310 | —(CH₂)₂—NH— | | F | N(CH₃)—Ph | |
| 6311 | —(CH₂)₂—NH— | | F | NH—OH | |
| 6312 | —(CH₂)₂—NH— | | F | N(CH₃)—OH | |

TABLE 6-continued

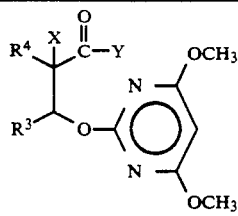

| Compound No. | R₃ | R₄ | X | Y | Remarks |
|---|---|---|---|---|---|
| 6313 | —(CH₂)₂—NH— | | F | NH—O—CH₃ | |
| 6314 | —(CH₂)₂—NH— | | F | NH—O—CH₂—CH=CH₂ | |
| 6315 | —(CH₂)₂—NH— | | F | NH—O—CH₂—C≡CH | |
| 6316 | —(CH₂)₂—NH— | | F | NH—O—CH₂—Ph | |
| 6317 | —(CH₂)₂—NH— | | F | NH—O—CH₂—CO₂—CH₃ | |
| 6318 | —(CH₂)₂—NH— | | F | NH—N(CH₃)₂ | |
| 6319 | —(CH₂)₂—NH— | | F | NH-2-pyridyl | |
| 6320 | —(CH₂)₂—NH— | | F | NH-2-thiadiazoly | |
| 6321 | —(CH₂)₂—NH— | | F | N₃ | |
| 6322 | —(CH₂)₂—NH— | | F | S—CH₃ | |
| 6323 | —(CH₂)₂—NH— | | F | S—C₂H₅ | |
| 6324 | —CH₂—NH—(CH₂)₂— | | F | OH | |
| 6325 | —CH₂—NH—(CH₂)₂— | | F | O—CH₃ | |
| 6326 | —CH₂—NH—(CH₂)₂— | | F | O—C₂H₅ | |
| 6327 | —CH₂—NH—(CH₂)₂— | | F | O-i-C₃H₇ | |
| 6328 | —CH₂—NH—(CH₂)₂— | | F | O—(CH₂)₂—Cl | |
| 6329 | —CH₂—NH—(CH₂)₂— | | F | O—CH₂—S—CH₃ | |
| 6330 | —CH₂—NH—(CH₂)₂— | | F | O—CH₂—Ph | |
| 6331 | —CH₂—NH—(CH₂)₂— | | F | O—Ph | |
| 6332 | —CH₂—NH—(CH₂)₂— | | F | O—CH₂—CH=CH₂ | |
| 6333 | —CH₂—NH—(CH₂)₂— | | F | O—CH₂—C≡CH | |
| 6334 | —CH₂—NH—(CH₂)₂— | | F | O—CH₂—O—C₂H₅ | |
| 6335 | —CH₂—NH—(CH₂)₂— | | F | NH₂ | |
| 6336 | —CH₂—NH—(CH₂)₂— | | F | NH—CH₃ | |
| 6337 | —CH₂—NH—(CH₂)₂— | | F | N(CH₃)—Ph | |
| 6338 | —CH₂—NH—(CH₂)₂— | | F | NH—OH | |
| 6339 | —CH₂—NH—(CH₂)₂— | | F | N(CH₃)—OH | |
| 6340 | —CH₂—NH—(CH₂)₂— | | F | NH—O—CH₃ | |
| 6341 | —CH₂—NH—(CH₂)₂— | | F | NH—O—CH₂—CH=CH₂ | |
| 6342 | —CH₂—NH—(CH₂)₂— | | F | NH—O—CH₂—C≡CH | |
| 6343 | —CH₂—NH—(CH₂)₂— | | F | NH—O—CH₂—Ph | |
| 6344 | —CH₂—NH—(CH₂)₂— | | F | NH—O—CH₂—CO₂—CH₃ | |
| 6345 | —CH₂—NH—(CH₂)₂— | | F | NH—N(CH₃)₂ | |
| 6346 | —CH₂—NH—(CH₂)₂— | | F | NH-2-pyridyl | |
| 6347 | —CH₂—NH—(CH₂)₂— | | F | NH-2-thiadiazoly | |
| 6348 | —CH₂—NH—(CH₂)₂— | | F | N₃ | |
| 6349 | —CH₂—NH—(CH₂)₂— | | F | S—CH₃ | |
| 6350 | —CH₂—NH—(CH₂)₂— | | F | S—C₂H₅ | |
| 6351 | —(CH₂)₂—NH—CH₂— | | F | OH | |
| 6352 | —(CH₂)₂—NH—CH₂— | | F | O—CH₃ | |
| 6353 | —(CH₂)₂—NH—CH₂— | | F | O—C₂H₅ | |
| 6354 | —(CH₂)₂—NH—CH₂— | | F | O-i-C₃H₇ | |
| 6355 | —(CH₂)₂—NH—CH₂— | | F | O—(CH₂)₂—Cl | |
| 6356 | —(CH₂)₂—NH—CH₂— | | F | O—CH₂—S—CH₃ | |
| 6357 | —(CH₂)₂—NH—CH₂— | | F | O—CH₂—Ph | |
| 6358 | —(CH₂)₂—NH—CH₂— | | F | O—Ph | |
| 6359 | —(CH₂)₂—NH—CH₂— | | F | O—CH₂—CH=CH₂ | |
| 6360 | —(CH₂)₂—NH—CH₂— | | F | O—CH₂—C≡CH | |
| 6361 | —(CH₂)₂—NH—CH₂— | | F | O—CH₂—O—C₂H₅ | |
| 6362 | —(CH₂)₂—NH—CH₂— | | F | NH₂ | |
| 6363 | —(CH₂)₂—NH—CH₂— | | F | NH—CH₃ | |
| 6364 | —(CH₂)₂—NH—CH₂— | | F | N(CH₃)—Ph | |
| 6365 | —(CH₂)₂—NH—CH₂— | | F | NH—OH | |
| 6366 | —(CH₂)₂—NH—CH₂— | | F | N(CH₃)—OH | |
| 6367 | —(CH₂)₂—NH—CH₂— | | F | NH—O—CH₃ | |
| 6368 | —(CH₂)₂—NH—CH₂— | | F | NH—O—CH₂—CH=CH₂ | |
| 6369 | —(CH₂)₂—NH—CH₂— | | F | NH—O—CH₂—C≡CH | |
| 6370 | —(CH₂)₂—NH—CH₂— | | F | NH—O—CH₂—Ph | |
| 6371 | —(CH₂)₂—NH—CH₂— | | F | NH—O—CH₂—CO₂—CH₃ | |
| 6372 | —(CH₂)₂—NH—CH₂— | | F | NH—N(CH₃)₂ | |
| 6373 | —(CH₂)₂—NH—CH₂— | | F | NH-2-pyridyl | |
| 6374 | —(CH₂)₂—NH—CH₂— | | F | NH-2-thiadiazoly | |
| 6375 | —(CH₂)₂—NH—CH₂— | | F | N₃ | |
| 6376 | —(CH₂)₂—NH—CH₂— | | F | S—CH₃ | |
| 6377 | —(CH₂)₂—NH—CH₂— | | F | S—C₂H₅ | |
| 6378 | —(CH₂)₃—NH— | | F | OH | |
| 6379 | —(CH₂)₃—NH— | | F | O—CH₃ | |
| 6380 | —(CH₂)₃—NH— | | F | O—C₂H₅ | |
| 6381 | —(CH₂)₃—NH— | | F | O-i-C₃H₇ | |

TABLE 6-continued

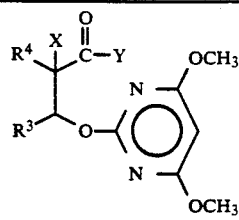

| Compound No. | R$_3$ | R$_4$ | X | Y | Remarks |
|---|---|---|---|---|---|
| 6382 | —(CH$_2$)$_3$—NH— | | F | O—(CH$_2$)$_2$—Cl | |
| 6383 | —(CH$_2$)$_3$—NH— | | F | O—CH$_2$—S—CH$_3$ | |
| 6384 | —(CH$_2$)$_3$—NH— | | F | O—CH$_2$—Ph | |
| 6385 | —(CH$_2$)$_3$—NH— | | F | O—Ph | |
| 6386 | —(CH$_2$)$_3$—NH— | | F | O—CH$_2$—CH=CH$_2$ | |
| 6387 | —(CH$_2$)$_3$—NH— | | F | O—CH$_2$—C≡CH | |
| 6388 | —(CH$_2$)$_3$—NH— | | F | O—CH$_2$—O—C$_2$H$_5$ | |
| 6389 | —(CH$_2$)$_3$—NH— | | F | NH$_2$ | |
| 6390 | —(CH$_2$)$_3$—NH— | | F | NH—CH$_3$ | |
| 6391 | —(CH$_2$)$_3$—NH— | | F | N(CH$_3$)—Ph | |
| 6392 | —(CH$_2$)$_3$—NH— | | F | NH—OH | |
| 6393 | —(CH$_2$)$_3$—NH— | | F | N(CH$_3$)—OH | |
| 6394 | —(CH$_2$)$_3$—NH— | | F | NH—O—CH$_3$ | |
| 6395 | —(CH$_2$)$_3$—NH— | | F | NH—O—CH$_2$—CH=CH$_2$ | |
| 6396 | —(CH$_2$)$_3$—NH— | | F | NH—O—CH$_2$—C≡CH | |
| 6397 | —(CH$_2$)$_3$—NH— | | F | NH—O—CH$_2$—Ph | |
| 6398 | —(CH$_2$)$_3$—NH— | | F | NH—O—CH$_2$—CO$_2$—CH$_3$ | |
| 6399 | —(CH$_2$)$_3$—NH— | | F | NH—N(CH$_3$)$_2$ | |
| 6400 | —(CH$_2$)$_3$—NH— | | F | NH-2-pyridyl | |
| 6401 | —(CH$_2$)$_3$—NH— | | F | NH-2-thiadiazoly | |
| 6402 | —(CH$_2$)$_3$—NH— | | F | N$_3$ | |
| 6403 | —(CH$_2$)$_3$—NH— | | F | S—CH$_3$ | |
| 6404 | —(CH$_2$)$_3$—NH— | | F | S—C$_2$H$_5$ | |
| 6405 | | —CH$_2$—N(CO$_2$CH$_3$)—(CH$_2$)$_2$— | F | OH | |
| 6406 | | —CH$_2$—N(CO$_2$CH$_3$)—(CH$_2$)$_2$— | F | O—CH$_3$ | |
| 6407 | | —CH$_2$—N(CO$_2$CH$_3$)—(CH$_2$)$_2$— | F | O—C$_2$H$_5$ | |
| 6408 | | —CH$_2$—N(CO$_2$CH$_3$)—(CH$_2$)$_2$— | F | O-i-C$_3$H$_7$ | |
| 6409 | | —CH$_2$—N(CO$_2$CH$_3$)—(CH$_2$)$_2$— | F | O—(CH$_2$)$_2$—Cl | |
| 6410 | | —CH$_2$—N(CO$_2$CH$_3$)—(CH$_2$)$_2$— | F | O—CH$_2$—S—CH$_3$ | |
| 6411 | | —CH$_2$—N(CO$_2$CH$_3$)—(CH$_2$)$_2$— | F | O—CH$_2$—Ph | |
| 6412 | | —CH$_2$—N(CO$_2$CH$_3$)—(CH$_2$)$_2$— | F | O—Ph | |
| 6413 | | —CH$_2$—N(CO$_2$CH$_3$)—(CH$_2$)$_2$— | F | O—CH$_2$—CH=CH$_2$ | |
| 6414 | | —CH$_2$—N(CO$_2$CH$_3$)—(CH$_2$)$_2$— | F | O—CH$_2$—C≡CH | |
| 6415 | | —CH$_2$—N(CO$_2$CH$_3$)—(CH$_2$)$_2$— | F | O—CH$_2$—O—C$_2$H$_5$ | |
| 6416 | | —CH$_2$—N(CO$_2$CH$_3$)—(CH$_2$)$_2$— | F | NH$_2$ | |
| 6417 | | —CH$_2$—N(CO$_2$CH$_3$)—(CH$_2$)$_2$— | F | NH—CH$_3$ | |
| 6418 | | —CH$_2$—N(CO$_2$CH$_3$)—(CH$_2$)$_2$— | F | N(CH$_3$)—Ph | |
| 6419 | | —CH$_2$—N(CO$_2$CH$_3$)—(CH$_2$)$_2$— | F | NH—OH | |
| 6420 | | —CH$_2$—N(CO$_2$CH$_3$)—(CH$_2$)$_2$— | F | N(CH$_3$)—OH | |
| 6421 | | —CH$_2$—N(CO$_2$CH$_3$)—(CH$_2$)$_2$— | F | NH—O—CH$_3$ | |
| 6422 | | —CH$_2$—N(CO$_2$CH$_3$)—(CH$_2$)$_2$— | F | NH—O—CH$_2$—CH=CH$_2$ | |
| 6423 | | —CH$_2$—N(CO$_2$CH$_3$)—(CH$_2$)$_2$— | F | NH—O—CH$_2$—C≡CH | |
| 6424 | | —CH$_2$—N(CO$_2$CH$_3$)—(CH$_2$)$_2$— | F | NH—O—CH$_2$—Ph | |
| 6425 | | —CH$_2$—N(CO$_2$CH$_3$)—(CH$_2$)$_2$— | F | NH—O—CH$_2$—CO$_2$—CH$_3$ | |
| 6426 | | —CH$_2$—N(CO$_2$CH$_3$)—(CH$_2$)$_2$— | F | NH—N(CH$_3$)$_2$ | |
| 6427 | | —CH$_2$—N(CO$_2$CH$_3$)—(CH$_2$)$_2$— | F | NH-2-pyridyl | |
| 6428 | | —CH$_2$—N(CO$_2$CH$_3$)—(CH$_2$)$_2$— | F | NH-2-thiadiazoly | |
| 6429 | | —CH$_2$—N(CO$_2$CH$_3$)—(CH$_2$)$_2$— | F | N$_3$ | |
| 6430 | | —CH$_2$—N(CO$_2$CH$_3$)—(CH$_2$)$_2$— | F | S—CH$_3$ | |
| 6431 | | —CH$_2$—N(CO$_2$CH$_3$)—(CH$_2$)$_2$— | F | S—C$_2$H$_5$ | |
| 6432 | | —CH$_2$—N(COCH$_3$)—(CH$_2$)$_2$— | F | OH | |
| 6433 | | —CH$_2$—N(COCH$_3$)—(CH$_2$)$_2$— | F | O—CH$_3$ | |
| 6434 | | —CH$_2$—N(COCH$_3$)—(CH$_2$)$_2$— | F | O—C$_2$H$_5$ | |
| 6435 | | —CH$_2$—N(COCH$_3$)—(CH$_2$)$_2$— | F | O-i-C$_3$H$_7$ | |
| 6436 | | —CH$_2$—N(COCH$_3$)—(CH$_2$)$_2$— | F | O—(CH$_2$)$_2$—Cl | |
| 6437 | | —CH$_2$—N(COCH$_3$)—(CH$_2$)$_2$— | F | O—CH$_2$—S—CH$_3$ | |
| 6438 | | —CH$_2$—N(COCH$_3$)—(CH$_2$)$_2$— | F | O—CH$_2$—Ph | |
| 6439 | | —CH$_2$—N(COCH$_3$)—(CH$_2$)$_2$— | F | O—Ph | |
| 6440 | | —CH$_2$—N(COCH$_3$)—(CH$_2$)$_2$— | F | O—CH$_2$—CH—CH$_2$ | |
| 6441 | | —CH$_2$—N(COCH$_3$)—(CH$_2$)$_2$— | F | O—CH$_2$—C≡CH | |
| 6442 | | —CH$_2$—N(COCH$_3$)—(CH$_2$)$_2$— | F | O—CH$_2$—O—C$_2$H$_5$ | |
| 6443 | | —CH$_2$—N(COCH$_3$)—(CH$_2$)$_2$— | F | NH$_2$ | |
| 6444 | | —CH$_2$—N(COCH$_3$)—(CH$_2$)$_2$— | F | NH—CH$_3$ | |
| 6445 | | —CH$_2$—N(COCH$_3$)—(CH$_2$)$_2$— | F | N(CH$_3$)Ph | |
| 6446 | | —CH$_2$—N(COCH$_3$)—(CH$_2$)$_2$— | F | NH—OH | |
| 6447 | | —CH$_2$—N(COCH$_3$)—(CH$_2$)$_2$— | F | N(CH$_3$)—OH | |
| 6448 | | —CH$_2$—N(COCH$_3$)—(CH$_2$)$_2$— | F | NH—O—CH$_3$ | |
| 6449 | | —CH$_2$—N(COCH$_3$)—(CH$_2$)$_2$— | F | NH—O—CH$_2$—CH=CH$_2$ | |
| 6450 | | —CH$_2$—N(COCH$_3$)—(CH$_2$)$_2$— | F | NH—O—CH$_2$—C≡CH | |

TABLE 6-continued

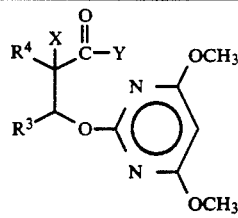

| Compound No. | R₃ | R₄ | X | Y | Remarks |
|---|---|---|---|---|---|
| 6451 | —CH₂—N(COCH₃)—(CH₂)₂— | | F | NH—O—CH₂—Ph | |
| 6452 | —CH₂—N(COCH₃)—(CH₂)₂— | | F | NH—O—CH₂—CO₂—CH₃ | |
| 6453 | —CH₂—N(COCH₃)—(CH₂)₂— | | F | NH—N(CH₃)₂ | |
| 6454 | —CH₂—N(COCH₃)—(CH₂)₂— | | F | NH-2-pyridyl | |
| 6455 | —CH₂—N(COCH₃)—(CH₂)₂— | | F | NH-2-thiadiazoly | |
| 6456 | —CH₂—N(COCH₃)—(CH₂)₂— | | F | N₃ | |
| 6457 | —CH₂—N(COCH₃)—(CH₂)₂— | | F | S—CH₃ | |
| 6458 | —CH₂—N(COCH₃)—(CH₂)₂— | | F | S—C₂H₅ | |
| 6459a | —(CH₂)₂—N(CO₂CH₃)—CH₂— | | F | OH | cis |
| 6459b | —(CH₂)₂—N(CO₂CH₃)—CH₂— | | F | OH | trans |
| 6460a | —(CH₂)₂—N(CO₂CH₃)—CH₂— | | F | O—CH₃ | cis |
| 6460b | —(CH₂)₂—N(CO₂CH₃)—CH₂— | | F | O—CH₃ | trans |
| 6461 | —(CH₂)₂—N(CO₂CH₃)—CH₂— | | F | OC₂H₅ | |
| 6462 | —(CH₂)₂—N(CO₂CH₃)—CH₂— | | F | O-i-C₃H₇ | |
| 6463 | —(CH₂)₂—N(CO₂CH₃)—CH₂— | | F | O—(CH₂)₂—Cl | |
| 6464 | —(CH₂)₂—N(CO₂CH₃)—CH₂— | | F | O—CH₂—S—CH₃ | |
| 6465 | —(CH₂)₂—N(CO₂CH₃)—CH₂— | | F | O—CH₂—Ph | |
| 6466 | —(CH₂)₂—N(CO₂CH₃)—CH₂— | | F | O—Ph | |
| 6467 | —(CH₂)₂—N(CO₂CH₃)—CH₂— | | F | O—CH₂—CH=CH₂ | |
| 6468 | —(CH₂)₂—N(CO₂CH₃)—CH₂— | | F | O—CH₂—C≡CH | |
| 6469 | —(CH₂)₂—N(CO₂CH₃)—CH₂— | | F | O—CH₂—O—C₂H₅ | |
| 6470 | —(CH₂)₂—N(CO₂CH₃)—CH₂— | | F | NH₂ | |
| 6471 | —(CH₂)₂—N(CO₂CH₃)—CH₂— | | F | NH—CH₃ | |
| 6472 | —(CH₂)₂—N(CO₂CH₃)—CH₂— | | F | N(CH₃)—Ph | |
| 6473 | —(CH₂)₂—N(CO₂CH₃)—CH₂— | | F | NH—OH | |
| 6474 | —(CH₂)₂—N(CO₂CH₃)—CH₂— | | F | N(CH₃)—OH | |
| 6475 | —(CH₂)₂—N(CO₂CH₃)—CH₂— | | F | NH—O—CH₃ | |
| 6476 | —(CH₂)₂—N(CO₂CH₃)—CH₂— | | F | NH—O—CH₂—CH=CH₂ | |
| 6477 | —(CH₂)₂—N(CO₂CH₃)—CH₂— | | F | NH—O—CH₂—C≡CH | |
| 6478 | —(CH₂)₂—N(CO₂CH₃)—CH₂— | | F | NH—O—CH₂—Ph | |
| 6479 | —(CH₂)₂—N(CO₂CH₃)—CH₂— | | F | NH—O—CH₂—CO₂—CH₃ | |
| 6480 | —(CH₂)₂—N(CO₂CH₃)—CH₂— | | F | NH—N(CH₃)₂ | |
| 6481 | —(CH₂)₂—N(CO₂CH₃)—CH₂— | | F | NH-2-pyridyl | |
| 6482 | —(CH₂)₂—N(CO₂CH₃)—CH₂— | | F | NH-2-thiadiazoly | |
| 6483 | —(CH₂)₂—N(CO₂CH₃)—CH₂— | | F | N₃ | |
| 6484 | —(CH₂)₂—N(CO₂CH₃)—CH₂— | | F | S—CH₃ | |
| 6485 | —(CH₂)₂—N(CO₂CH₃)—CH₂— | | F | S—C₂H₅ | |
| 6486 | —(CH₂)₂—N(COCH₃)—CH₂— | | F | OH | |
| 6487 | —(CH₂)₂—N(COCH₃)—CH₂— | | F | O—CH₃ | |
| 6488 | —(CH₂)₂—N(COCH₃)—CH₂— | | F | O—C₂H₅ | |
| 6489 | —(CH₂)₂—N(COCH₃)—CH₂— | | F | O-i-C₃H₇ | |
| 6490 | —(CH₂)₂—N(COCH₃)—CH₂— | | F | O—(CH₂)₂—Cl | |
| 6491 | —(CH₂)₂—N(COCH₃)—CH₂— | | F | O—CH₂—S—CH₃ | |
| 6492 | —(CH₂)₂—N(COCH₃)—CH₂— | | F | O—CH₂—Ph | |
| 6493 | —(CH₂)₂—N(COCH₃)—CH₂— | | F | O—Ph | |
| 6494 | —(CH₂)₂—N(COCH₃)—CH₂— | | F | O—CH₂—CH=CH₂ | |
| 6495 | —(CH₂)₂—N(COCH₃)—CH₂— | | F | O—CH₂—C≡CH | |
| 6496 | —(CH₂)₂—N(COCH₃)—CH₂— | | F | O—CH₂—O—C₂H₅ | |
| 6497 | —(CH₂)₂—N(COCH₃)—CH₂— | | F | NH₂ | |
| 6498 | —(CH₂)₂—N(COCH₃)—CH₂— | | F | NH—CH₃ | |
| 6499 | —(CH₂)₂—N(COCH₃)—CH₂— | | F | N(CH₃)—Ph | |
| 6500 | —(CH₂)₂—N(COCH₃)—CH₂— | | F | NH—OH | |
| 6501 | —(CH₂)₂—N(COCH₃)—CH₂— | | F | N(CH₃)—OH | |
| 6502 | —(CH₂)₂—N(COCH₃)—CH₂— | | F | NH—O—CH₃ | |
| 6503 | —(CH₂)₂—N(COCH₃)—CH₂— | | F | NH—O—CH₂—CH=CH₂ | |
| 6504 | —(CH₂)₂—N(COCH₃)—CH₂— | | F | NH—O—CH₂—C≡CH | |
| 6505 | —(CH₂)₂—N(COCH₃)—CH₂— | | F | NH—O—CH₂—Ph | |
| 6506 | —(CH₂)₂—N(COCH₃)—CH₂— | | F | NH—O—CH₂—CO₂—CH₃ | |
| 6507 | —(CH₂)₂—N(COCH₃)—CH₂— | | F | NH—N(CH₃)₂ | |
| 6508 | —(CH₂)₂—N(COCH₃)—CH₂— | | F | NH-2-pyridyl | |
| 6509 | —(CH₂)₂—N(COCH₃)—CH₂— | | F | NH-2-thiadiazoly | |
| 6510 | —(CH₂)₂—N(COCH₃)—CH₂— | | F | N₃ | |
| 6511 | —(CH₂)₂—N(COCH₃)—CH₂— | | F | S—CH₃ | |
| 6512 | —(CH₂)₂—N(COCH₃)—CH₂— | | F | S—C₂H₅ | |
| 6513 | —(CH₂)₃—N(CO₂CH₃)— | | F | OH | |
| 6514 | —(CH₂)₃—N(CO₂CH₃)— | | F | O—CH₃ | |
| 6515 | —(CH₂)₃—N(CO₂CH₃)— | | F | O—C₂H₅ | |
| 6516 | —(CH₂)₃—N(CO₂CH₃)— | | F | O-i-C₃H₇ | |
| 6517 | —(CH₂)₃—N(CO₂CH₃)— | | F | O—(CH₂)₂—Cl | |

TABLE 6-continued

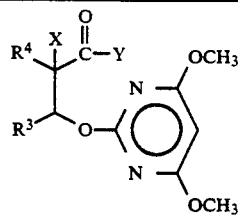

| Compound No. | R3 | R4 | X | Y | Remarks |
|---|---|---|---|---|---|
| 6518 | —(CH2)3—N(CO2CH3)— | | F | O—CH2—S—CH3 | |
| 6519 | —(CH2)3—N(CO2CH3)— | | F | O—CH2—Ph | |
| 6520 | —(CH2)3—N(CO2CH3)— | | F | O—Ph | |
| 6521 | —(CH2)3—N(CO2CH3)— | | F | O—CH2—CH=CH2 | |
| 6522 | —(CH2)3—N(CO2CH3)— | | F | O—CH2—C≡CH | |
| 6523 | —(CH2)3—N(CO2CH3)— | | F | O—CH2—O—C2H5 | |
| 6524 | —(CH2)3—N(CO2CH3)— | | F | NH2 | |
| 6525 | —(CH2)3—N(CO2CH3)— | | F | NH—CH3 | |
| 6526 | —(CH2)3—N(CO2CH3)— | | F | N(CH3)—Ph | |
| 6527 | —(CH2)3—N(CO2CH3)— | | F | NH—OH | |
| 6528 | —(CH2)3—N(CO2CH3)— | | F | N(CH3)—OH | |
| 6529 | —(CH2)3—N(CO2CH3)— | | F | NH—O—CH3 | |
| 6530 | —(CH2)3—N(CO2CH3)— | | F | NH—O—CH2—CH=CH2 | |
| 6531 | —(CH2)3—N(CO2CH3)— | | F | NH—O—CH2—C≡CH | |
| 6532 | —(CH2)3—N(CO2CH3)— | | F | NH—O—CH2—Ph | |
| 6533 | —(CH2)3—N(CO2CH3)— | | F | NH—O—CH2—CO2—CH3 | |
| 6534 | —(CH2)3—N(CO2CH3)— | | F | NH—N(CH3)2 | |
| 6535 | —(CH2)3—N(CO2CH3)— | | F | NH-2-pyridyl | |
| 6536 | —(CH2)3—N(CO2CH3)— | | F | NH-2-thiadiazoly | |
| 6537 | —(CH2)3—N(CO2CH3)— | | F | N3 | |
| 6538 | —(CH2)3—N(CO2CH3)— | | F | S—CH3 | |
| 6539 | —(CH2)3—N(CO2CH3)— | | F | S—C2H5 | |
| 6540 | —(CH2)3—N(COCH3)— | | F | OH | |
| 6541 | —(CH2)3—N(COCH3)— | | F | O—CH3 | |
| 6542 | —(CH2)3—N(COCH3)— | | F | O—C2H5 | |
| 6543 | —(CH2)3—N(COCH3)— | | F | O-i-C3H7 | |
| 6544 | —(CH2)3—N(COCH3)— | | F | O—(CH2)2—Cl | |
| 6545 | —(CH2)3—N(COCH3)— | | F | O—CH2—S—CH3 | |
| 6546 | —(CH2)3—N(COCH3)— | | F | O—CH2—Ph | |
| 6547 | —(CH2)3—N(COCH3)— | | F | O—Ph | |
| 6548 | —(CH2)3—N(COCH3)— | | F | O—CH2—CH=CH2 | |
| 6549 | —(CH2)3—N(COCH3)— | | F | O—CH2—C≡CH | |
| 6550 | —(CH2)3—N(COCH3)— | | F | O—CH2—O—C2H5 | |
| 6551 | —(CH2)3—N(COCH3)— | | F | NH2 | |
| 6552 | —(CH2)3—N(COCH3)— | | F | NH—CH3 | |
| 6553 | —(CH2)3—N(COCH3)— | | F | N(CH3)—Ph | |
| 6554 | —(CH2)3—N(COCH3)— | | F | NH—OH | |
| 6555 | —(CH2)3—N(COCH3)— | | F | N(CH3)—OH | |
| 6556 | —(CH2)3—N(COCH3)— | | F | NH—O—CH3 | |
| 6557 | —(CH2)3—N(COCH3)— | | F | NH—O—CH2—CH=CH2 | |
| 6558 | —(CH2)3—N(COCH3)— | | F | NH—O—CH2—C≡CH | |
| 6559 | —(CH2)3—N(COCH3)— | | F | NH—O—CH2—Ph | |
| 6560 | —(CH2)3—N(COCH3)— | | F | NH—O—CH2—CO2—CH3 | |
| 6561 | —(CH2)3—N(COCH3)— | | F | NH—N(CH3)2 | |
| 6562 | —(CH2)3—N(COCH3)— | | F | NH-2-pyridyl | |
| 6563 | —(CH2)3—N(COCH3)— | | F | NH-2-thiadiazoly | |
| 6564 | —(CH2)3—N(COCH3)— | | F | N3 | |
| 6565 | —(CH2)3—N(COCH3)— | | F | S—CH3 | |
| 6566 | —(CH2)3—N(COCH3)— | | F | S—C2H5 | |

TABLE 7

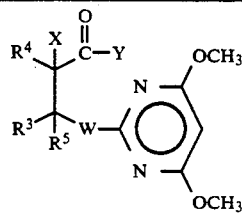

| Compound No. | R5 | R3 | R4 | X | W | Y | Remarks |
|---|---|---|---|---|---|---|---|
| 7001 | | | =CH—(CH2)3— | F | S | H | |
| 7002 | | | =CH—(CH2)3— | F | S | OH | |

TABLE 7-continued

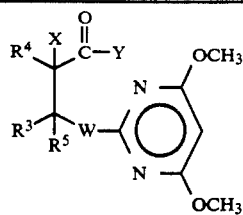

| Compound No. | R⁵ | R³ | R⁴ | X | W | Y | Remarks |
|---|---|---|---|---|---|---|---|
| 7003 | | =CH—(CH₂)₃— | | F | S | O—CH₃ | |
| 7004 | | =CH—(CH₂)₃— | | F | S | O—C₂H₅ | |
| 7005 | | =CH—(CH₂)₃— | | F | S | O-n-C₃H₇ | |
| 7006 | | =CH—(CH₂)₃— | | F | S | O-i-C₃H₇ | |
| 7007 | | =CH—(CH₂)₃— | | F | S | O-n-C₄H₉ | |
| 7008 | | =CH—(CH₂)₃— | | F | S | O-i-C₄H₉ | |
| 7009 | | =CH—(CH₂)₃— | | F | S | O-s-C₄H₉ | |
| 7010 | | =CH—(CH₂)₃— | | F | S | O-t-C₄H₉ | |
| 7011 | | =CH—(CH₂)₃— | | F | S | O—(CH₂)₂—Cl | |
| 7012 | | =CH—(CH₂)₃— | | F | S | O—CH₂—S—CH₃ | |
| 7013 | | =CH—(CH₂)₃— | | F | S | O—CH₂—Ph | |
| 7014 | | =CH—(CH₂)₃— | | F | S | O—Ph | |
| 7015 | | =CH—(CH₂)₃— | | F | S | O—CH₂—CH=CH₂ | |
| 7016 | | =CH—(CH₂)₃— | | F | S | O—CH₂—C≡CH | |
| 7017 | | =CH—(CH₂)₃— | | F | S | O—CH₂—O—C₂H₅ | |
| 7018 | CH₃ | —(CH₂)₄— | | F | O | OH | |
| 7019 | CH₃ | —(CH₂)₄— | | F | O | O—CH₃ | |
| 7020 | CH₃ | —(CH₂)₄— | | F | O | O—C₂H₅ | |
| 7021 | CH₃ | CH₃ | CH₃ | F | O | OH | |
| 7022 | CH₃ | CH₃ | CH₃ | F | O | O—CH₃ | |
| 7023 | CH₃ | CH₃ | CH₃ | F | O | O—C₂H₅ | |
| 7024 | =CH—CH₃ | | CH₃ | F | O | OH | |
| 7025 | =CH—CH₃ | | CH₃ | F | O | O—CH₃ | |
| 7026 | =CH—CH₃ | | CH₃ | F | O | O—CH₃ | |

TABLE 8

| Compound No. | ¹H-NMR(δ ppm, CDCl₃) and/or Physical data |
|---|---|
| 1002a | mp 77–79° C. |
| 1002a1 | [α]$_D^{30}$ = +18.5° (C=0.029, iPrOH) (60% enantiomeric excess) |
| 1002a2 | [α]$_D^{30}$ = −14.2° (c=0.049, iPrOH) (70% enantiomeric excess) |
| 1002b | mp 122–124° C. |
| 1002b1 | [α]$_D^{30}$ = +36.6° (c=0.071, iPrOH) (99% enantiomeric excess) |
| 1002b2 | [α]$_D^{30}$ = −38.6° (c=0.083, iPrOH) (87% enantiomeric excess) |
| 1003a | 1.7–2.73(6H, m), 3.55(3H, s), 3.88(6H, s), 5.23–5.57(1H, m), 5.63(1H, s) |
| 1003b | 1.53–2.77(6H, m), 3.71(3H, s), 3.87(6H, s), 5.3–5.76(1H, m), 5.63(1H, s) |
| 1004b | 1.22(3H, t, J=7Hz), 1.53–2.69(6H, m), 3.88(6H, s), 4.17(2H, q, J=7Hz), 5.27–5.90(1H, m), 5.63(1H, s) mp 39.4–42.0° C. |
| 1006a | 1.08(3H, d, J=6Hz), 1.17(3H, d, J=6Hz), 1.74–2.74(6H, m), 3.91(6H, s), 4.92(1H, sep, J=6Hz), 5.66(1H, s), 5.27–5.86(1H, m) |
| 1006b | 1.16(3H, d, J=6.2Hz), 1.26(3H, d, J=6.2Hz), 1.51–2.68(6H, m), 3.89(6H, s), 5.03(1H, sep), 5.66(1H, s), 5.31–5.95(1H, m) |
| 1007b | 0.67–2.67(13H, m), 3.90(6H, s), 4.12(2H, t, J=6Hz), 5.33–5.92(1H, m), 5.66((1H, s) |
| 1009b | 0.67–1.33(6H, m), 1.43–2.57(8H, m), 3.90(6H, s), 4.67–5.13(1H, m), 5.33–5.93(1H.m), 5.67(1H, s) |
| 1010a | 1.37(9H, s), 1.67–2.67(6H, m), 3.92(6H, s), 5.67(1H, s), 5.23–5.82(1H, m) mp 77.0–79.9° C. |
| 1010b | 1.43(9H, s), 1.53–2.58(6H, m), 3.89(6H, s), 5.38–5.93(1H, m), 5.66(1H, s) |
| 1011a | 1.70–2.77(6H, m), 3.60(2H, t, J=6Hz), 3.90(6H, s), 4.25(2H, t, J=6Hz), 5.69(1H, s), 5.30–5.87(1H, m) |
| 1011b | 1.41–2.74(6H, m), 3.63(2H, t, J=6Hz), 3.87(6H, s), 4.37(2H, t, J=6Hz), 5.64(1H, s), 5.26–6.01(1H, m) |
| 1012a | 2.14(3H, s), 1.73–2.73(6H, m), 3.88(6H, s), 5.02(2H, s)5.63(1H, s) 5.27–5.79(1H, m) |
| 1012b | 2.17(3H, s), 1.53–2.70(6H, m), 3.89(6H, s), 5.17(2H, s), 5.66(1H, s) 5.32–5.90(1H, m) |

TABLE 8-continued

| Compound No. | $^1$H-NMR($\delta$ ppm, CDCl$_3$) and/or Physical data |
|---|---|
| 1013a | 1.60-2.67(6H, m), 3.85(6H, s), 4.91(1H, s), 5.00(1H, s), 5.33-5.83 (1H, m), 5.62(1H, s), 7.24(5H, s) |
| 1013b | 1.64-2.67(6H, m), 3.69(6H, s), 5.16(2H, s)5.62(1H, s), 5.34-5.92 (1H, m), 7.07-7.42(5H, m) |
| 1023a | 1.69-2.79(6H, m), 3.92(6H, s), 5.69(1H, s), 5.42-5.97(1H, m), 6.64-7.45(5H, m) |
| 1023b | 1.60-2.82(6H, m), 3.81(6H, s), 5.37-6.03(1H, m), 5.66(1H, s), 6.83-7.50(5H, m) mp.53.0-55.5° C. |
| 1024a | 1.67-2.77(6H, m), 3.93(6H, s), 5.72(1H, s), 5.43-6.03(1H, m), 6.87-7.53(4H, m) |
| 1024b | 1.70-2.91(6H, m), 3.89(6H, s), 5.46-6.13(1H, m), 5.70(1H, s), 6.93-7.50(5H, m) |
| 1033a | 1.70-2.67(6H, m), 3.89(6H, s), 4.33-4.55(2H, m), 4.97-5.41(2H, m), 5.67(1H, s), 5.43-6.03(2H, m) |
| 1033b | 1.83-2.70(6H, m), 3.88(6H, s), 4.53-4.73(2H, m), 5.00-5.42(2H, m), 5.61(1H, s), 5.50-6.10(2H, m) |
| 1034a | 2.35(1H, t, J=2.4Hz), 1.53-2.77(6H, m), 3.93(6H, s), 4.52(2H, d, J=2.4Hz), 5.64(1H, s), 5.30-5.80(1H, m) |
| 1034b | 1.64-2.57(6H, m), 2.43(1H, t, J=2.4Hz), 3.88(6H, s), 4.72(2H, d, J=2.4Hz), 5.30-5.87(1H, m), 5.64(1H, s) |
| 1038b | white powder |
| 1039b | white powder |
| 1040b | white powder |
| 1041b | white powder |
| 1042b | 1.40-2.67(6H, m), 1.70(3H, s), 1.77(3H, s), 3.91(6H, s), 5.37-5.97(1H, m), 5.67(1H, s) |
| 1043b | 1.37-2.64(6H, m), 1.70(3H, s), 3.89(6H, s), 4.54(2H, s), 4.90(2H, bs) 5.30-5.95(1H, m), 5.63(1H, s) |
| 1069a | 1.67-2.67(6H, m), 3.89(6H, s), 5.57(1H, s), 5.40-5.90(1H, m), 7.17-7.77(5H, m), 8.11(1H, s) mp 114.0-115.5° C. |
| 1069b | 1.47-2.80(6H, m), 3.87(6H, s), 5.62(1H, s), 5.34-6.07(1H, m), 7.14-7.80(5H, m), 8.26(1H, s) |
| 1075a | 1.26(3H, t, J=7Hz), 2.00(3H, s), 1.66-2.53(6H, m), 3.88(6H, s), 4.11(2H, q, J=7Hz), 5.62(1H, s), 5.29-5.79(1H, m) |
| 1076b | 1.57-2.60(6H, m), 2.82(4H, s), 3.86(6H, s), 5.67(1H, s), 5.43-6.03(1H, m) |
| 1081 | 0.93 and 1.02(3H, d, J=3.6Hz and J=2Hz), 1.02-2.63(5H, m), 3.71 (6H, s), 4.78-5.62(1H, m), 5.51(1H, s) |
| 1082 | 1.06-1.39(6H, m), 1.43-2.9(5H, m), 3.9(6H, s), 3.87-4.47(2H, m) 4.92-5.77(1H, m), 5.65(1H, s) |
| 1180a | mp 179-181° C. |
| 1180a1 | $[\alpha]_D^{30}$ = +71.6° (c=0.046, iPrOH) (96% enantiomeric excess) |
| 1180a2 | $[\alpha]_D^{30}$ = −63.5° (c=0.060, iPrOH) (86% enantiomeric excess) |
| 1180b | mp 157.5-160° C. |
| 1180b1 | $[\alpha]_D^{30}$ = +5.0° (c=0.092, iPrOH) (100% enantiomeric excess) |
| 1180b2 | $[\alpha]_D^{30}$ = −5.0° (c=0.10, iPrOH) (100% enantiomeric excess) |
| 1181a | 1.0-2.67(8H, m), 3.63(3H, s), 3.88(6H, s), 5.43-5.77(1H, m), 5.77(1H, s) |
| 1181b | 1.0-2.5(8H, m), 3.67(3H, s), 3.88(6H, s), 5.42-5.73(1H, m), 5.63 (1H, s) |
| 1182a | 1.17(3H, t, J=7Hz), 1.30-2.30(8H, m), 3.90(6H, s), 4.10(2H, q, J=7Hz), 5.22-5.70(1H, m), 5.65(1H, s) |
| 1182b | 1.17(3H, t, J=7Hz), 1.33-2.42(8H, m), 3.90(6H, s), 4.15(2H, q, J=7Hz), 5.02-5.42(1H, m), 5.63(1H, s) mp 107.5-110.0° C. |
| 1183b | 0.85(3H, t, J=6.4Hz), 1.19-2.38(11H, m), 3.89(6H, s), 4.05(2H, t, J=6.4Hz), 5.04-5.75(1H, m), 5.63(1H, s) mp 69.6-71.3° C. |
| 1184a | 1.12(3H, d, J=6Hz), 1.15(3H, d, J=6Hz), 1.37-2.27(8H, m), 3.87(6H, s), 4.95(1H, sep, J=6Hz), 5.50-5.80(1H, m), 5.83(1H, s) |
| 1184b | 1.12(3H, d, J=6Hz), 1.18(3H, d, J=6Hz), 1.37-2.37(8H, m), 3.88(6H, s), 5.0(1H, sep, J=6Hz), 5.07-5.40(1H, m), 5.63(1H, s) |
| 1185b | 0.60-2.40(15H, m), 3.93(6H, s), 4.10(2H, t, J=6Hz), 5.06-5.83(1H, m), 5.66(1H, s) |
| 1186b | 0.85(6H, d, J=6Hz), 1.20-2.47(9H, m), 3.89(1H, d, J=6Hz), 3.90(1H, d, J=6Hz), 3.90(6H, s), 5.03-5.80(1H, m), 5.63(1H, s) mp 56.3-57.0° C. |
| 1187b | 0.70-1,25(6H, m), 1.36-2.36(10H, m), 3.89(6H, s), 4.70-5.76(2H, m), 5.66(1H, s) |
| 1188b | 1.33(9H, s), 1.40-2.33(8H, m), 3.87(6H, s), 5.00-5.35(1H, m), 5.63(1H, s) mp 143.5-146.5° C. |
| 1189a | 1.33-2.30(8H, m), 3.60(2H, t, J=6Hz), 3.90(6H, s), 4.30(2H, t, J=6Hz), 5.23-5.70(1H, m), 5.67(1H, s) |

TABLE 8-continued

| Compound No. | $^1$H-NMR($\delta$ ppm, CDCl$_3$) and/or Physical data |
|---|---|
| 1189b | 1.07–2.57(8H, m), 3.47–3.80(2H, m), 3.88(6H, s), 4.23–4.53(2H, m), 5.00–5.53(1H, m), 5.65(1H, s) |
| 1190a | 1.23–2.33(8H, m), 2.17(3H, s), 3.90(6H, s), 5.10(1H, s), 5.17(1H, s) 5.32–5.63(1H, m), 5.67(1H, s) |
| 1190b | 1.00–2.33(8H, m), 2.13(3H, s), 3.90(6H, s), 5.17(2H, s), 5.27–5.53 (1H, m), 5.67(1H, s) |
| 1191a | 1.10–2.38(8H, m), 3.85(6H, s), 4.93(1H, d, J=12Hz), 5.17(1H, d, J=12Hz) 5.30–5.72(1H, m), 5.62(1H, s), 7.20(5H, s) |
| 1191b | 1.10–2.43(8H, m), 3.83(6H, s), 5.05(1H, d, J=12Hz), 5.15(1H, d, J=12Hz), 5.23–5.80(1H, m), 5.62(1H, s), 7.18(5H, s) |
| 1201a | 1.17–3.07(8H, m), 3.90(6H, s), 5.40–5.83(1H, m), 5.67(1H, s), 6.77–7.67(5H, m) |
| 1201b | 1.17–2.73(8H, m), 3.90(6H, s), 5.07–5.57(1H, m), 5.87(1H, s), 6.73–7.73(5H, m) mp 129.0–131.6° C. |
| 1202a | 1.17–2.50(8H, m), 3.90(6H, s), 5.33–5.83(1H, m), 5.68(1H, s), 6.73–7.57(4H, m) |
| 1202b | 1.17–2.73(8H, m), 3.90(6H, s), 5.17–6.00(1H, m), 5.70(1H, s), 6.77–7.60(4H, m) mp 137.5–139.5° C. |
| 1211a | 1.12–2.35(8H, m), 3.88(6H, s), 4.33–4.63(2H, m), 4.93–5.43(2H, m), 5.63(1H, s), 5.52–6.17(2H, m) |
| 1211b | 1.00–2.50(8H, m), 3.90(6H, s), 4.32–4.62(2H, m), 4.97–5.43(2H, m), 5.63(1H, s), 5.47–6.13(2H, m) mp 41.0–42.5° C. |
| 1212a | 0.77–2.33(8H, m), 2.40(1H, t, J=2Hz), 3.93(6H, s), 4.63(2H, d, J=2Hz) 5.33–5.77(1H, m), 5.67(1H, s) |
| 1212b | 1.33–2.50(8H, m), 2.35(1H, t, J=2Hz), 3.90(6H, s), 4.65(2H, d, J=2Hz) 5.07–5.57(1H, m), 5.97(1H, s) |
| 1215b | white powder |
| 1216b | white powder |
| 1220b | 1.69(3H, s), 1.72(3H, s), 1.13–2.43(8H, m), 3.89(6H, s), 5.06–5.79(1H, m), 5.66(1H, s) mp 109.3–112.1° C. |
| 1222b | 1.10–2.44(12H, m), 3.89(6H, s), 4.50–5.00(1H, m), 5.05–5.84(1H, m), 5.64(1H, s) mp 74.4–76.2° C. |
| 1223b | 1.06–2.42(14H, m), 3.91(6H, s), 4.11(2H, q, J=6.6Hz), 4.84–5.89((2H, m), 5.65(1H, s) |
| 1224b | 0.93–2.53(8H, m), 1.23(3H, t, J=7Hz), 3.90(6H, s), 4.17(2H, q, J=7Hz), 4.63(2H, s), 5.05–5.87(1H, m), 5.67(1H, s) mp 81.6–84.6° C. |
| 1225b | 1.39–2.46(8H, m), 2.13(3H, s), 3.88(6H, s), 4.63(2H, s), 5.08–5.82(1H, m), 5.67(1H, s) mp 106.6–107.9° C. |
| 1226b | 1.20–2.41(8H, m), 3.88(6H, s), 4.48(2H, q, J=8Hz, ), 5.06–5.81(1H, m), 5.65(1H, s) mp 75.1–77.4° C. |
| 1227b | 1.27–2.41(8H, m), 3.88(6H, s), 4.74(2H, s), 5.00–5.75(1H, m) 5.66(1H, s) mp 94.7–96.2° C. |
| 1228b | 1.34–2.46(8H, m), 3.91(6H, s), 4.69(2H, s), 5.33(1H, s), 5.46(1H, s) 5.09–5.81(1H, m), 5.67(1H, s) mp 52.3–54.8° C. |
| 1229b | 1.16–2.41(8H, m), 3.86(6H, s), 4.54(2H, dd, J=8Hz, 12Hz), 5.00–5.78(1H, m), 5.65(1H, s), 5.78–6.42(2H, m) mp 59.3–61.6° C. |
| 1230b | 1.12–2.39(8H, m), 3.91(6H, s), 4.62(2H, q, J=2.4Hz), 5.09–5.84(1H, m), 5.65(1H, s) |
| 1231b | 1.13–2.38(8H, m), 3.89(6H, s), 5.03(1H, s), 5.08(1H, s), 5.17–5.83(1H, s), 5.66(1H, s), 6.26(2H, m), 7.25(1H, m) |
| 1232b | 1.21–2.49(9H, m), 2.44(2H, dt, J=3Hz, 6.4Hz), 3.90(6H, s), 4.21(2H, t, J=6.4Hz), 5.04–5.76(1H, m), 5.66(1H, s) |
| 1233b | 1.19–2.36(16H, m), 3.92(6H, s), 5.00–5.76(1H, m), 5.17(1H, m), 5.67(1H, s) mp 91.5–93.9° C. |
| 1234b | 1.33–2.40(8H, m), 3.37(2H, t, J=6Hz), 3.88(6H, s), 4.37(2H, t, J=6Hz), 5.02–5.37(1H, m), 5.63(1H, s) |
| 1235b | 1.24–2.41(8H, m), 3.29–3.58(2H, m), 3.89(6H, s), 4.24(2H, t, J=6Hz), 5.05–5.78(1H, m), 5.65(1H, s) |
| 1236b | 1.40–2.42(18H, m), 3.90(6H, s), 4.58–5.00(1H, m), 5.08–5.82(1H, m), 5.66(1H, s) |
| 1237b | 0.09–0.65(4H, m), 0.72–1.30(1H, m), 1.32–2.42(8H, m), 3.89(6H, s), 3.99(2H, d, J=2Hz), 5.09–5.85(1H, m), 5.65(1H, s) mp 73.6–75.5° C. |
| 1238b | 1.00–2.40(11H, m), 3.92(6H, s), 4.30–4.77(2H, m), 5.00–6.03(3H, m), 5.67(1H, s) |
| 1239b | 1.03–2.43(14H, m), 3.90(6H, s), 4.37–4.75(2H, m), 4.93–5.83(2H, m), 5.65(1H, s) |
| 1240b | 0.77–2.50(8H, m), 3.87(6H, s), 4.73(2H, s), 4.90–5.87(1H, m), |

TABLE 8-continued

| Compound No. | $^1$H-NMR($\delta$ ppm, CDCl$_3$) and/or Physical data |
|---|---|
| | 5.63(1H, s) |
| 1241b | 1.10-2.63(8H, m), 3.80(6H, s), 4.60-4.83(2H, m), 4.93-5.77(1H, m), 5.57(1H, s), 6.08(1H, dt, J=16Hz, 6Hz), 6.52(1H, d, J=16Hz), 7.23(5H, s) mp.71.2-73.2° C. |
| 1242b | 0.93-2.57(8H, m), 3.33(3H, s), 3.37(3H, s), 4.02(6H, s), 5.07-5.97(1H, m) 4.22(1H, d, J=6Hz), 4.23(1H, d, J=6Hz), 4.58(1H, dd, J=6Hz, 6Hz), 5.78(1H, s) mp 68.6-70.0° C. |
| 1243b | 1.17-2.40(8H, m), 3.91(6H, s), 4.11(2H, s), 4.47-4.69(1H, m), 4.81-5.01(1H, m), 5.10-5.84(1H, m), 5.68(1H, s) mp 108.7-111.1° C. |
| 1244b | 1.28-2.33(14H, m), 3.87(6H, s), 5.06-6.03(4H, m), 5.62(1H, s) |
| 1245b | 1.17-2.37(8H, m), 3.86(6H, s), 5.00-5.77(1H, m), 5.20(1H, s), 5.26(1H, s), 5.61(1H, s), 6.70-7.33(3H, m) |
| 1246b | 1.10(3H, t, J=7Hz), 1.10-2.87(8H, m), 3.55(2H, q, J=7Hz), 3.87(6H, s), 4.87-5.78(1H, m), 5.27(2H, s), 5.63(1H, s) |
| 1247b | 0.73-2.57(8H, m), 3.87(6H, s), 4.90-5.53(1H, m), 5.67(1H, s), 7.23-7.80(5H, m), 8.33(1H, s) mp 128.5-129.0° C. |
| 1248b | 0.93-2.60(8H, m), 1.97(3H, s), 2.00(3H, s), 3.88(6H, s), 5.03-5.83(1H, m), 5.63(1H, s) |
| 1249b | 0.85-2.58(10H, m), 1.12(3H, t, J=7Hz), 1.95(3H, s), 3.88(6H, s), 5.05-5.85(1H, m), 5.65(1H, s) mp 89.4-91.3° C. |
| 1250b | 0.73-2.57(16H, m), 0.93(6H, t, J=7Hz), 3.90(6H, s), 5.00-5.87(1H, m), 5.63(1H, s) |
| 1251b | 0.95-2.63(8H, m), 1.24(6H, d, J=7Hz), 1.27(6H, d, J=7Hz), 2.75(1H, sep, J=7Hz), 2.98(1H, sep, J=7Hz), 3.95(6H, s), 4.88-5.90(1H, m), 5.73(1H, s) mp 133.2-135.9° C. |
| 1252b | 0.93-2.87(18H, m), 3.87(6H, s), 4.87-5.83(1H, m), 5.63(1H, s) mp 106.3-108.6° C. |
| 1253b | 0.93-2.46(8H, m), 1.29(3H, t, J=6.4Hz), 2.02(3H, s), 3.89(6H, s), 4.14(2H, q, J=6.4Hz), 5.06-5.76(1H, m), 5.60(1H, s) mp 93.2-95.5° C. |
| 1276a | 0.90(3H, d, J=7Hz), 1.05-2.81(7H, m), 3.87(6H, s), 5.29-5.68(1H, m), 5.62(1H, s), 8.12(1H, s) (axial methyl group) |
| 1276b | 0.77-1.22(3H, m), 1.2-2.47(7H, m), 3.87(6H, s), 5.0-5.73(1H, m), 5.63(1H, s) (equatrial methyl group) |
| 1278a | 0.93(3H, d, J=6.4Hz), 1.07(3H, t, J=7.2Hz), 1.27-2.49(7H, m), 3.88-4.12(2H, m), 3.9(6H, s), 5.55-5.61(1H, m), 5.68(1H, s) (axial methyl group) |
| 1278b | 1.03(3H, d, J=4.4Hz), 1.12-2.27(7H, m), 3.9(6H, s), 4.26-4.43(2H, m) 5.41-5.49(1H, m), 5.68(1H, s) (equatrial methyl group) |
| 1295a | 0.95(9H, s), 1.08(3H, t, J=7Hz), 0.78-2.55(7H, m), 3.88(6H, s), 4.0 (2H, q, J=7Hz), 5.35-5.74(1H, m), 5.64(1H, s) (equatrial t-butyl group) |
| 1411a | 1.40-2.83(10H, m), 3.88(6H, s), 4.18(1H, s), 4.82-5.62(1H, m), 5.67(1H, s) mp 177.5-179.0° C. |
| 1411b | 1.43-2.52(10H, m), 3.87(6H, s), 5.02-5.63(1H, m), 5.65(1H, s), 7.58(1H, s) mp 113.0-115.5° C. |
| 1412a | 1.15-2.70(10H, m), 3.85(3H, s), 3.88(6H, s), 5.08-5.93(1H, m), 5.67(1H, s) |
| 1412b | 1.47-2.47(10H, m), 3.70(3H, s), 3.87(6H, s), 5.08-5.78(1H, m), 5.63(1H, s) mp 85.5-86.0° C. |
| 1413a | 1.27-2.73(10H, m), 1.32(3H, t, J=7Hz), 3.88(6H, s), 4.30(2H, q, J=7Hz), 5.03-5.56(1H, m), 5.65(1H, s) |
| 1413b | 1.57-2.43(10H, m), 1.17(3H, t, J=7Hz), 3.90(6H, s), 4.17(2H, q, J=7Hz), 5.07-5.43(1H, m), 5.43(1H, s) |
| 1427a | 1.35-2.40(12H, m), 3.88(6H, s), 4.63(1H, s), 5.53-6.00(1H, m), 5.68(1H, s) mp 179-180.5° C. |
| 1428a | 1.0-2.77(12H, m), 3.83(3H, s), 3.90(6H, s), 5.07-6.02(1H, m), 5.48(1H, s) mp 90.5-92.0° C. |
| 1454b | 1.42-2.47(8H, m), 3.88(6H, s), 5.20-5.80(1H, m), 5.65(1H, S) 7.15(1H, s) |
| 1455b | 1.18(3H, t, J=7.0Hz), 1.33-2.37(8H, m), 3.90(6H, s), 4.13(2H, q, J=7.0Hz), 5.52-5.82(1H, m), 5.65(1H, s) |
| 1467b | 1.07-2.40(8H, m), 2.42(1H, t, J=2.5Hz), 3.91(6H, s), 4.71(2H, d, J=2.5Hz), 5.57-5.85(1H, m), 5.67(1H, s) |
| 1496 | 1.1-3.3(9H, m), 3.75(3H, s), 3.90(6H, s), 5.78(1H, s) |
| 1563a | 1.35-2.73(6H, m), 3.93(6H, s), 4.03-4.77(1H, m), 4.63(2H, s), 5.9 (1H, s), 7.67(1H, s) |

TABLE 8-continued

| Compound No. | $^1$H-NMR($\delta$ ppm, CDCl$_3$) and/or Physical data |
|---|---|
| 1563b | 1,35–2.82(6H, m), 3.9(6H, s), 3.93–4.79(1H, m), 4.62(2H, s), 5.9(1H, s) 8.9(1H, s) |
| 1564b | 1.3–2.58(6H, m), 3.77(3H, s), 3.93(6H, s), 4.04–4.79(1H, m), 4.55(2H, s), 5.87(1H, s) |
| 1580a | 1.11–2.75(8H, m), 3.59–4.86(1H, m), 3.92(6H, s), 4.71(2H, d, J=8Hz), 5.88(1H, s) |
| 1580b | 1.08–2.37(8H, m), 3.52–4.38(1H, m) 3.88(6H, s), 4.75(2H, s) 5.81 (1H, s) |
| 1582a | 0.95–2.73(8H, m), 1.28(3H, t, J=7Hz), 3.57–4.72(1H, m), 3.9(6H, s), 4.21(2H, q, J=7Hz), 4.57(2H, s), 5.9(1H, s) |
| 1582b | 0.8–2.36(8H, m), 1.28(3H, t, J=7Hz), 3.55–4.83(1H, m), 3.91(6H, s), 4.2(2H, q, J=7Hz), 4.52(2H, s), 5.88(1H, s) |

TABLE 9

| Compound No. | $^1$H-NMR($\delta$ ppm, CDCl$_3$) and/or Physical data |
|---|---|
| 2021a | 6.16(1H, s), 5.3–5.8(1H, m), 3.91(3H, s), 3.54(3H, s), 2.29 (3H, s), 1.6–2.5(6H, m) |
| 2021b | 6.16(1H, s), 5.3–5.8(1H, m), 3.91(3H, s), 3.75(3H, s), 2.32 (3H, s), 1.6–2.5(6H, m) |
| 2039 | 5.84(1H × 2, s), 5.1–5.6(1H × 2, m), 3.94(3H × 2, s), 3.80(3H, s), 3.66(3H, s), 1.4–2.5(6H × 2, 2) |
| 2057a | 6.34(1H, s), 5.3–5.8(1H, m), 3.92(3H, s), 3.59(3H, s), 1.7–2.2(6H, m) |
| 2057b | 6.33(1H, s), 5.3–5.8(1H, m), 3.92(3H, s), 3.77(3H, s), 1.7–2.5(6H, m) |
| 2058a | 6.35(1H, s), 5.3–5.7(1H, m), 4.11(2H, q, J=7Hz), 3.93(3H, s), 1.5–2.3(8H, m), 1.21(3H, t, J=7Hz) |
| 2093a | 6.32(1H, s), 5.3–5.7(1H, m), 4.34(2H, q, J=7Hz), 3.63(3H, s), 1.7–2.5(6H, m), 1.37(3H, t, J=7Hz) |
| 2093b | 6.32(1H, s), 5.2–5.7(1H, m), 4.35(2H, q, J=7Hz), 3.81(3H, s), 1.6–2.6(6H, m), 1.36(3H, t, J=7Hz) |
| 2111a | 5.3–5.7(1H, m), 5.64(1H, s), 4.34(2H, q, J=7Hz), 3.88(3H, s), 3.56(3H, s), 1.6–2.5(6H, m), 1.34(3H, t, J=7Hz) |
| 2111b | 5.3–5.7(1H, m), 5.63(1H, s), 4.20(2H, q, J=7Hz), 3.88(3H, s), 3.74(3H, s), 1.6–2.5(6H, m), 1.34(3H, t, J=7Hz) |
| 2128b | 5.61(1H, s), 5.2–5.6(1H, m), 4.28(4H, q, J=7Hz), 1.7–2.5 (6H, m), 1.34(6H, t, J=7Hz) |
| 2129a | 5.3–5.7(1H, m), 5.58(1H, s), 4.29(4H, q, J=7Hz), 3.55(3H, s), 1.6–2.5(6H, m), 1.34(6H, t, J=7Hz) |
| 2129b | 5.3–5.7(1H, m), 5.57(1H, s), 4.25(4H, q, J=7Hz), 3.72(3H, s), 1.6–2.5(6H, m), 1.34(6H, t, J=7Hz) |
| 2142b | 5.0–5.9(4H, m), 5.61(1H, s), 4.61(2H, m), 4.27(4H, q, J=7Hz), 1.6–2.5(6H, m), 1.35(6H, t, J=7Hz) |
| 2143b | 5.2–5.7(1H, m), 5.61(1H, s), 4.75(2H, d, J=2Hz), 4.26(4H, q, J=7Hz), 2.44(1H, t, J=2Hz), 1.5–2.4(6H, m), 1.34(6H, t, J=7Hz) |
| 2147a | 5.3–5.7(1H, m), 5.62(1H, s), 4.22(4H, t, J=6Hz), 3.60(3H, s), 1.2–2, 4(10H, m), 1.01(6H, t, J=7Hz) |
| 2147b | 5.3–5.8(1H, m), 5.60(1H, s), 4.16(4H, t, J=6Hz), 3.73(3H, s), 1.3–2.6(10H, m), 0.98(6H, t, J=7Hz) mp 40–40.5° C. |
| 2164a | 5.3–5.6(1H, m), 5.55(1H, s), 5.20(2H, sep, J=6Hz), 1.7–2.6 (6H, m), 1.32(12H, d, J=6Hz) |
| 2164b | 5.54(1H, s), 5.1–5.4(1H, m), 5.17(2H, sep, J=6Hz), 1.7–2.6 (6H, m), 1.29(12H, d, J=6Hz) |
| 2165a | 5.3–5.7(1H, m), 5.54(1H, s), 5.24(2H, sep, J=6Hz), 3.61(3H, s), 1.6–2.5(6H, m), 1.32(12H, d, J=6Hz) |
| 2165b | 5.3–5.6(1H, m), 5.55(1H, s), 5.29(2H, sep, J=6Hz), 3.74(3H, s), 1.6–2.5(6H, m), 1.36(12H, d, J=6Hz) mp 66–67° C. |
| 2183b | 7.38(2H, t, $J_{CF}$=82Hz), 6.02(1H, s), 5.2–5.7(1H, m), 3.77(3H, s), 1.6–2.7(6H, m) |
| 2344a | 6.34(1H, s), 5.10–5.60(1H, m), 3.95(3H, s), 1.26–2.30(8H, m) |
| 2344b | 6.32(1H, s), 5.00–5.70(1H, m), 3.92(3H, s), 1.25–2.45(8H, m) |
| 2345a | 6.34(1H, s), 5.25–5.65(1H, m), 3.96(3H.s), 3.70(3H, s), 1. 30–2.30 (8H, m) |
| 2345b | 6.37(1H, s), 5.1–5.8(1H, m), 3.95(3H, s), 3.74(3H, s), 1.4–2.3(8H, m) |
| 2346a | 6.32(1H, s), 5.3–5.6(1H, m), 4.12(2H, q, J=7Hz), 3.94(3H, s), 1.4–2.3(8H, m), 1.21(3H, t, J=7Hz) |
| 2346b | 6.32(1H, s), 5.1–5.8(1H, m), 4.14(2H, q, J=7Hz), 3.91(3H, s), 1.4–2.3(8H, m), 1.17(3H, t, J=7Hz) |
| 2348a | 6.34(1H, s), 5.30–5.65(1H, m), 4.97(1H, sep, J=7Hz), 3.93(3H, s), 1.40–2.30(8H, m), 1.17(3H, d, J=7Hz), 1.15(3H, d, J=7Hz) |
| 2351a | 6.31(1H, s), 4.65–5.70(2H, m), 3.92(6H, s), 0.63–2.24(16H, m) |
| 2351b | 6.34(1H, s), 4.66–5.85(2H, m), 3.93(6H, s), 0.49–2.29(16H, m) |
| 2353a | 6.34(1H, s), 5.26–5.62(1H, m), 4.10–4.42(2H, m), 3.93(6H, s), 3.57(2H, t, J= |

TABLE 9-continued

| Compound No. | $^1$H-NMR($\delta$ ppm, CDCl$_3$) and/or Physical data |
|---|---|
| | 7Hz), 1.17-2.35(8H, m) |
| 2380a | 6.33(1H, s), 5.2-5.5(1H, m), 4.28(2H, q, J=7Hz), 1.6-2.3 (8H, m), 1.37(3H, t, J=7Hz) |
| 2382a | 6.31(1H, s), 5.3-5.7(1H, m), 4.37(2H, q, J=7Hz), 4.13(2H, q, J=7Hz), 1.5-2.3(8H, m), 1.37(3H, t, J=7Hz), 1.15(3H, t, J=7Hz) |
| 2382b | 6.28(1H, s), 5.0-5.5(1H, m), 4.37(2H, q, J=7Hz), 4.14(2H, q, J=7Hz), 1.5-2.3(8H, m), 1.34(3H, t, J=7Hz), 1.16(3H, t, J=7Hz) |
| 2416a | 5.4-5.7(1H, m), 5.61(1H, s), 4.27(4H, q, J=7Hz), 1.5-2.3 (8H, m), 1.33(6H, t) mp 136.5-137.5° C. |
| 2418a | 5.58(1H, s), 5.3-5.6(1H, m), 4.28(4H, q, J=7Hz), 4.07(1H, q, J=7Hz), 4.04(1H, q, J=7Hz), 1.5-1.9(8H, m), 1.34(6H, t, J=7Hz), 1.14(3H, t, J=7Hz) |
| 2418b | 5.4-5.7(1H, m), 5.60(1H, s), 4.29(4H, q, J=7Hz), 4.12(2H, q, J=7Hz), 1.5-2.3(8H, m), 1.33(6H, t, J=7Hz), 1.14(3H, t, J=7Hz) |
| 2434b | 5.64(1H, s), 5.0-5.5(1H, m), 4.17(4H, t, J=6Hz), 1.3-2.1 (12H, m), 0.98(6H, t, J=7Hz) |
| 2436a | 5.4-5.7(1H, m), 5.59(1H, s), 4.17(4H, t, J=6Hz), 4.09(2H, q, J=7Hz), 1.2-2.3(12H, m), 1.15(3H, t, J=7Hz), 0.98(6H, t, J=7Hz) |
| 2436b | 5.62(1H, s), 5.0-5.5(1H, m), 4.22(4H, t, J=6Hz), 4.15(2H, q, J=7Hz), 1.3-2.3(12H, m), 1.17(3H, t, J=7Hz), 0.98(6H, t, J=7Hz) |
| 2489a | 6.16(1H, s), 5.25-5.70(1H, m), 3.91(3H, s), 3.65(3H, s), 2.49(3H, s), 1.37-2.25(8H, m) |
| 2508a | 6.81(1H, s), 5.30-5.70(1H, s), 4.17(1H, q, J=7Hz), 4.10(1H, q, J=7Hz), 2.51(3H, s), 1.40-2.25(8H, m), 1.19(3H, t, J=7Hz) |
| 2508b | 6.79(1H, s), 5.10-5.70(1H, m), 4.16(2H, q, J=7Hz), 2.52(3H, s), 1.20(3H, t, J=7Hz), 1.40-2.35(8H, m) |
| 2560a | 5.30(1H, s), 5.25-5.60(1H, m), 4.05(1H, q, J=7Hz), 4.01(1H, q, J=7Hz), 2.99(6H, s), 1.35-2.20(8H, m), 1.13(3H, t, J=7Hz) |
| 2560b | 5.33(1H, s), 5.10-5.65(1H, m), 4.12(2H, q, J=7Hz), 3.88(3H, s), 3.01(6H, s), 1.40-2.30(8H, m), 1.16(3H, t, J=7Hz) |

TABLE 10

| Compound No. | $^1$H-NMR($\delta$ ppm, CDCl$_3$) and/or Physical data |
|---|---|
| 3003a | 5.4-5.9(1H, m), 4.00(6H, s), 3.68(3H, s), 1.7-2.6(6H, m) |
| 3003b | 5.4-5.9(1H, m), 4.00(6H, s), 3.72(3H, s), 1.7-2.6(6H, m) |
| 3077a | 6.29(1H, s), 5.3-5.9(1H, m), 3.68(3H, s), 2.49(3H, s), 1.6-2.6(6H, m) |
| 3077b | 6.42(1H, s), 5.3-5.9(1H, m), 3.81(3H, s), 2.49(3H, s), 1.7-2.6(6H, m) |
| 3292b | 6.35(1H, s), 5.4-5.9(1H, m), 2.49(3H, s), 1.3-2.4(8H, m) |
| 3294a | 6.36(1H, s), 5.3-5.7(1H, m), 4.16(2H, q, J=7Hz), 2.49(3H, s), 1.4-2.2(8H, m), 1.22(3H, t, J=7Hz) |
| 3294b | 6.39(1H, s), 5.1-5.9(1H, m), 4.17(2H, q, J=7Hz), 2.51(3H, s), 1.3-2.4(8H, m), 1.19(3H, t, J=7Hz) |
| 3310a | 5.70(1H, s), 5.25-5.75(1H, m), 3.90(3H, s), 2.52(3H, s), 1.25-2.30(8H, m) |
| 3312b | 5.69(1H, s), 5.05-5.70(1H, m), 4.15(2H, q, J=7Hz), 3.89(3H, s), 2.50(3H, s), 1.20-2.35(8H, m), 1.16(3H, t) |
| 3330a | 6.83(1H, s), 5.30-5.55(1H.m), 4.22(2H.q.J=7Hz), 3.33(3H, s), 1.30-2.40(m, 8H), 1.28(3H, t) |
| 3366a | 6.38(1H, s), 5.20-5.70(1H, m), 3.96(3H, s), 3.73(3H, s), 1.20-2.30(8H, m) |
| 3379a | 6.30(1H, s), 5.25-5.65(1H, m), 4.64(2H, d, J=3Hz), 3.93(3H, s), 2.36(1H, t, J=3Hz), 1.25-2.45(8H, m) |
| 3379b | 6.38(1H, s), 5.15-5.80(1H, m), 4.69(2H, d, J=3Hz), 4.00(3H, s), 2.38(1H, t, J=3Hz), 1.26-2.60(8H, m) |

TABLE 11

| Compound No. | $^1$H-NMR($\delta$ ppm, CDCl$_3$) and/or Physical data |
|---|---|
| 4001b | 1.61-2.73(6H, m), 3.90(6H, s), 5.63(1H, s), 5.27-5.90(1H, m), 5.90-6.57(2H, br) mp 163.2-165.0° C. |
| 4002b | 1.54-1.70(6H, m), 3.79(3H, d, J=5Hz), 3.90(6H, s), 5.64(1H, s), 5.27-5.97(1H, m), 6.20-6.67(1H, bs) mp 129.0-131.5° C. |
| 4003a | 1.01(3H, t, J=7Hz), 1.60-2.50(6H, m), 3.20(2H, q, J=7Hz), 3.90(6H, s), 5.63(1H, s), 5.20-5.84(1H, m), 6.22(1H, bs) mp 118.3-119.5° C. |
| 4003b | 1.06(3H, t, J=7.6Hz), 1.53-2.70(6H, m), 3.26(2H, q, J=7.6Hz), 3.92(6H, s), 5.64(1H, s), 5.30-5.96(1H, m), 6.45(1H, bs) |
| 4009a | 1.25(9H, s), 1.50-2.50(6H, m), 3.90(6H, s), 5.65(1H, s), 5.17-5.83(1H, m), 6.00(1H, bs) |
| 4009b | 1.28(9H, s), 1.61-2.68(6H, m), 3.94(6H, s), 5.64(1H, s), 5.31-6.0(1H, m), 6.23(1H, bs) |
| 4010b | 1.67-2.67(6H, m), 2.73-3.20(6H, m), 3.87(6H, s), 5.62(1H, s), 5.47-6.05(1H, m) |
| 4013b | 1.57-2.73(6H, m), 3.81(6H, s), 5.61(1H, s), 5.40-6.03(1H, m), 7.00-7.63(5H, m), 7.88-8.23(1H, bs) mp 154.0-157.5° C.. |
| 4035b | 1.64-2.72(6H, m), 3.88(6H, s), 5.30-6.00(1H, m), 5.61(1H, s), |

TABLE 11-continued

| Compound No. | $^1$H-NMR($\delta$ ppm, CDCl$_3$) and/or Physical data |
|---|---|
| | 9.09(1H, bs) |
| 4036b | 1.63-2.87(6H, m), 3.38(3H, d, J=3Hz), 3.88(6H, s), 5.73(1H, s), 5.40-6.00(1H, m), 8.17-8.55(1H, bs) mp 124.0-127.5° C. |
| 4037b | 1.59-2.82(6H, m), 3.67(3H, s), 3.92(6H, s), 5.66(1H, s), 5.29-5.99 (1H, m), 5.29-5.99(1H, m), 8.96-9.24(1H, bs) mp 114.5-117.5° C. |
| 4040b | 1.65-2.75(6H, m), 3.91(6H, s), 4.80(2H, s), 5.31-5.98(1H, m), 5.68 (1H, s), 7.21-7.40(5H, m), 8.80(1H, bs) |
| 4048b | 1.70-2.77(6H, m), 3.76(3H, s)3.94(6H, s), 4.41(2H, s), 5.70(1H, s), 5.33-6.00(1H, m), 9.43-9.73(1H, bs) mp 68.0-70.2° C. |
| 4071b | 1.68-2.72(6H, m), 2.48(6H, s), 3.91(6H, s), 5.65(1H, s), 5.35-6.05 (1H, s), 7.05-7.18(1H, m) |
| 4079b | 1.61-2.69(6H, m), 3.89(6H, s), 5.66(1H, s), 5.33-5.89(1H, m) |
| 4095b | 1.67-2.57(6H, m), 3.63(3H, s), 3.90(6H, s), 4.49(2H, s), 5.65(1H, s), 5.47-6.14(1H, m), 7.72(1H, bs) |
| 4096b | 1.56-2.59(6H, m), 3.69(3H, s), 3.92(6H, s), 4.10(3H, s), 4.44(2H, s), 5.66(1H, s), 5.39-5.92(1H, m) mp 72.5-74.0° C. |
| 4228a | 1.08(3H, t, J=7Hz), 1.71-2.55(6H, m), 2.74(2H, q, J=7Hz), 3.92(6H, s), 5.61(1H, s), 5.33-5.85(1H, m) |
| 4228b | 1.20(3H, t, J=7.6Hz), 1.60-2.56(6H, m), 2.77(2H, q, J=7.6Hz), 3.90(6H, s), 5.65(1H, s), 5.30-5.90(1H, m) |
| 4230a | 1.11(3H, d, J=8Hz), 1.24(3H, d, J=8Hz), 1.62-2.75(6H, m), 3.48(1H, sep, J=8Hz), 3.59(6H, s), 5.64(1H, s), 5.32-5.88(1H, m) |
| 4230b | 1.20(3H, d, J=7Hz), 1.30(3H, d, J=7Hz), 1.67-2.53(6H, m), 3.50(1H, sep, J=7Hz), 3.88(6H, s), 5.63(1H, s), 5.33-5.90(1H, m) |
| 4234b | 1.41(9H, s), 1.97-2.83(6H, m), 3.88(6H, s), 5.62(1H, s), 5.37-5.95(1H, m) mp 81.5-83.2° C. |
| 4239a | 1.72-2.72(6H, m), 3.93(6H, s), 5.65(1H, s), 5.40-5.93(1H, m), 7.03-7.77(3H, m), 8.52(1H, m) mp 92.0-94.5° C. |
| 4239b | 1.54-2.70(6H, m), 3.75(6H, s), 5.66(1H, s), 5.30-5.90(1H, m), 7.05-7.84(3H, m), 8.57(1H, m) |
| 4275b | 1.00-2.83(8H, m), 3.90(6H, s), 4.93-5.83(1H, m), 5.63(1H, s), 6.00(1H, bs), 6.53(1H, bs) |
| 4276a | 1.00-2.67(8H, m), 2.87(3H, d, J=6Hz), 3.90(6H, s), 4.97-5.63 (1H, m), 5.68(1H, s), 6.50(1H, bs) mp 147.2-149.5° C. |
| 4276b | 1.02-2.65(8H, m), 2.82(3H, d, J=6Hz), 3.90(6H, s), 4.95-5.85(1H, m), 5.65(1H, s), 6.53(1H, bs) |
| 4277a | 1.22(3H, t, J=7Hz), 1.32-2.50(8H, m), 3.17(1H, q, J=7Hz), 3.28(1H, q, J=7Hz), 3.87(6H, s), 4.87-5.60(1H, m), 5.63(1H, s), 6.43(1H, bs) mp 99.5-100.5° C. |
| 4277b | 1.07(3H, t, J=6Hz), 1.17-2.48(8H, m), 3.15(1H, q, J=6Hz), 3.27(1H, q, J=6Hz), 3.87(1H, s), 4.92-5.37(1H, m), 5.60(1H, s), 6.47(1H, bs) mp 130.5-133.5° C. |
| 4283a | 1.40(9H, s), 1.52-2.52(8H, m), 3.88(6H, s), 5.02-5.48(1H, m), 5.65(1H, s), 6.15(1H, bs) |
| 4283b | 1.28(9H, s), 1.37-2.53(8H, m), 3.87(6H, s), 4.93-5.33(1H, m), 5.62(1H, s), 6.30(1H, bs) |
| 4287b | 1.10-2.70(8H, m), 3.87(6H, s), 5.03-5.97(1H, m), 5.60(1H, s), 6.87-7.70(5H, m), 7.87-8.53(1H, m) mp 189.9-193.6° C. |
| 4293b | 1.35(3H, t, J=7Hz), 1.41-2.53(8H, m), 3.87(6H, s), 3.95(2H, q, J=7Hz), 5.00-5.93(1H, m), 5.58(1H, s), 6.74(2H, d, J=9Hz), 7.32(2H, d, J=9Hz), 8.09(1H, bs) mp 152.5-155.3° C. |
| 4295b | 1.32-2.53(8H, m), 3.90(6H, s), 5.07-5.90(1H, m), 5.62(1H, s), 7.27-7.95(4H, m), 8.43(1H, m) |
| 4297b | 1.16-2.40(8H, m), 3.26(3H, s), 3.93(6H, s), 5.13-5.86(1H, m), 5.68(1H, s), 7.13-7.53(5H, m) |
| 4305b | 1.31-2.41(8H, m), 3.88(6H, s), 4.33(1H, s), 4.42(1H, s), 5.05-5.81 (1H, m), 5.63(1H, s), 6.17(2H, m), 7.22(1H, m) |
| 4309b | 1.25-2.38(8H, m), 3.85(6H, s), 5.00-5.73(1H, m), 5.61(1H, s), 9.22(1H, bs) mp 184.2-187.4° C. |
| 4311b | 1.26-2.48(8H, m), 3.68(3H, s), 3.92(6H, s), 5.05-5.81(1H, m), 5.68(1H, s), 9.32(1H, bs) |
| 4314b | 1.20-2.40(8H, m), 3.87(6H, s), 4.76(1H, s), 4.78(1H, s), 5.00-5.77 (1H, m), 5.64(1H, s), 7.20-7.53(5H, m), 8.88(1H, bs) |
| 4322b | 1.33-2.80(8H, m), 3.83(3H, s), 3.92(6H, s), 4.43(2H, s), 5.00-5.93 (1H, m), 5.72(1H, s), 9.67(1H, bs) |
| 4325b | 1.30-2.50(8H, m), 2.22(3H, s), 3.92(6H, s), 5.03-5.83(1H, m), 5.68(1H, s), 9.98(1H, bs) mp 158.2-160.3° C. |
| 4332b | 1.28(9H, s), 1.44-2.44(8H, m), 3.91(6H, s), 5.01-5.74(1H, m), 5.65(1H, s), 9.78(1H, bs) |

TABLE 11-continued

| Compound No. | $^1$H-NMR($\delta$ ppm, CDCl$_3$) and/or Physical data |
|---|---|
| | mp 170.6–173.9° C. |
| 4344b | 1.33–2.57(8H, m), 2.47(3H, s), 3.90(6H, s), 5.03–5.80(1H, m), 5.63(1H, s), 7.25(1H, d, J=8Hz), 7.62(1H, d, J=8Hz) |
| | mp 166.1–168.3° C. |
| 4346b | 1.21(3H, t, J=7.8Hz), 1.38–2.48(8H, m), 3.91(6H, s), 4.14(2H, q, J=7.8Hz), 5.10–5.91(1H, m), 5.67(1H, s), 6.98(1H, bs), 8.55(1H, bs) |
| 4347b | 1.27(3H, t, J=7Hz), 1.19–2.47(8H, m), 3.04(3H, s), 3.37(3H, s), 3.86(6H, s), 4.13(2H, q, J=7Hz), 4.99–5.84(1H, m), 5.62(1H, s) |
| 4348b | 1.27(3H, t, J=7Hz), 1.33–2.76(8H, m), 3.55(2H, s), 3.92(6H, s), 4.19(2H, q, J=7Hz), 5.01–5.79(1H, m), 5.67(1H, s), 8.33(1H, bs) |
| | mp 116.8–118.5° C. |
| 4350b | 1.26(3H, t, J=6.6Hz), 1.32–2.52(8H, m), 3.86(6H, s), 3.82–4.44(4H, m), 5.06–5.82(1H, m), 5.63(1H, s), 7.09(1H, bs) |
| | mp 159.1–161.3° C. |
| 4351b | 0.73(6H, t, J=7Hz), 1.33–2.70(12H, m), 3.74(3H, s), 3.90(6H, s), 4.95–5.76(1H, m), 5.63(1H, s), 7.45(1H, bs) |
| | mp 106.2–108.7° C. |
| 4352b | 1.22–2.43(8H, m), 3.91(6H, s), 4.92–5.75(1H, m), 5.66(1H, s), |
| 4353b | 1.43–2.46(8H, m), 3.85(6H, s), 5.12–5.86(1H, m), 5.57(1H, s), 6.90(1H, d, J=3.6Hz), 7.58(1H, d, J=3.6Hz), 10.96(1H, bs) |
| | mp 181.0–181.3° C. |
| 4354b | 1.34–2.37(8H, m), 3.83(6H, s), 5.14–5.74(1H, m), 5.57(1H, s), 8.76(1H, s) |
| | mp 215.2–215.8° C. |
| 4355b | 1.40–2.50(8H, m), 3.86(6H, s), 5.00–5.83(1H, m), 5.59(1H, s), |
| | mp 164.2–165.0° C. |
| 4356b | 1.36–2.49(8H, m), 3.83(6H, s), 5.00–5.91(1H, m), 5.56(1H, s), 6.81–7.11(1H, m), 7.39–7.78(1H, m), 7.93–8.31(2H, m), 8.78(1H, bs) |
| | mp 148.6–149.2° C. |
| 4358b | 1.37–2.40(8H, m), 3.84(6H, s), 5.00–5.83(1H, m), 5.56(1H, s), 7.20–7.51(2H, m), 8.25–8.58(2H, m) |
| | mp 145.1–148.5° C. |
| 4359b | 1.14–2.44(14H, m), 2.48–2.91(4H, m), 3.90(6H, s), 5.01–5.81(1H, m), 5.66(1H, s), 7.25(1H, bs) |
| | mp 182.2–183.0° C. |
| 4360b | 1.40–2.67(8H, m), 3.88(6H, s), 5.05–5.91(1H, m), 5.59(1H, s), 7.03–7.99(4H, m), 10.15(1H, bs) |
| 4361b | 1.33–2.46(8H, m), 3.89(6H, s), 5.01–5.76(1H, m), 5.64(1H, s), 6.53–6.79(2H, m), 7.11–7.44(1H, m), 7.96–8.13(1H, m) |
| | mp 196.5–198.9° C. |
| 4379b | 1.25–2.63(8H, m), 3.88(6H, s), 5.01–5.84(1H, m), 5.68(1H, s), 7.30(2H, bs) |
| | mp 189.1–192.6° C. |
| 4396b | 1.04–2.38(8H, m), 3.47(3H, s), 3.49(3H, s), 3.91(6H, s), 5.68(1H, s), 5.76–5.79(1H, m) |
| 4500a | 1.17(3H, t, J=7Hz), 1.35–2.23(8H, m), 2.82(2H, q, J=7Hz), 3.87(6H, s), 5.20–5.67(1H, m), 5.62(1H, s) |
| 4500b | 1.13(3H, t, J=7Hz), 1.37–2.37(8H, m), 2.82(2H, q, J=7Hz), 3.90(6H, s), 4.97–5.40(1H, m), 5.63(1H, s) |
| | mp 75.0–77.0° C. |
| 4502b | 1.15(3H, d, J=7Hz), 1.27(3H, d, J=7Hz), 1.33–2.04(8H, m), 3.52(1H, sep, J=7Hz), 3.90(6H, s), 4.97–5.37(1H, m), 5.60(1H, s) |
| | mp 82.0–83.0° C. |
| 4506a | 1.42(9H, s), 1.47–2.23(8H, m), 3.90(6H, s), 5.27–5.70(1H, m), 5.63(1H, s) |
| 4508b | 1.20–2.37(8H, m), 3.87(6H, m), 4.03(2H, s), 5.03–5.87(1H, m), 5.63(1H, s), 7.10(5H, s) |
| 4511a | 1.30–2.35(8H, m), 3.90(6H, s), 5.13–5.82(1H, m), 5.70(1H, s), 7.17–8.00(3H, m), 8.58(1H, m) |
| 4511b | 1.00–2.50(8H, m), 3.87(6H, s), 4.90–5.60(1H, m), 5.67(1H, s), 7.00–7.87(3H, m), 8.40–8.73(1H, m) |
| | mp 115.0–118.5° C. |
| 4512b | 0.86–2.36(8H, m), 3.86(6H, s), 4.05(2H, s), 5.06–5.81(1H, m), 5.63(1H, s), 6.00–6.34(2H, m), 7.15–7.36(1H, m) |
| 4526b | 1.04–2.18(8H, m), 1.17(3H, d, J=7Hz), 1.26(3H, d, J=7Hz), 3.43–3.47(1H, m), 3.91(6H, s), 5.63–5.67(1H, m), 5.67(1H, s) |
| 4556b | 1.08–2.78(8H, m), 3.73(1H, s), 3.93(6H, s), 5.10–5.82(1H, m), 5.68(1H, s) |
| 4558a | 0.87–3.03(8H, m), 1.27(3H, t, J=7Hz), 4.00(6H, s), 4.17(1H, q, J=7Hz), 4.23(1H, q, J=7Hz), 5.37–5.80(1H, m), 5.77(1H, s) |
| 4558b | 1.00–2.60(8H, m), 1.23(3H, t, J=7Hz), 3.97(6H, s), 4.22(2H, q, J=7Hz), 5.03–5.87(1H, m), 5.73(1H, s) |

TABLE 12

| Compound No. | $^1$H-NMR($\delta$ ppm, CDCl$_3$) and/or Physical data |
|---|---|
| 5001 | 1.68(3H, d, J=21Hz), 3.87(6H, s), 4.62(2H, d, J=21Hz), 5.67(1H, s), |

TABLE 12-continued

| Compound No. | $^1$H-NMR($\delta$ ppm, CDCl$_3$) and/or Physical data |
|---|---|
| | 8.55(1H, s) <br> mp 120.0–122.50° C. |
| 5003 | 1.3(3H, t, J=7Hz), 1.68(3H, d, J=21Hz), 3.92(6H, s), 4.28(2H, q, J=7Hz), 4.67(2H, d, J=21Hz), 5.7(1H, s) |
| 5130 | 1.54(3H, d, J=7Hz), 3.9(6H, s), 5.23–6.02(1H, m), 5.72(1H, s), 11(1H, s) <br> mp 124.0–126.0° C. |
| 5132 | 1.25(3H, t, J=7Hz), 1.52(3H, d, J=6.4Hz), 3.95(6H, s), 4.28(2H, q, J=7Hz 5.33–6.13(1H, m), 5.75(1H, s) <br> mp 36.0–37.0° C. |
| 5156a | 1.48(3H, d, J=6.4Hz), 1.7(3H, d, J=20Hz), 3.95(6H, s), 5.26–5.98(1H, m) 5.73(1H, s) <br> mp 129.0–130.0° C. |
| 5156b | 1.45(3H, d, J=6Hz), 1.63(3H, d, J=21.2Hz), 3.88(6H, s), 5.08–5.87(1H, s), 5.67(1H, s), 10.6(1H, s) <br> mp 141.5–144.2° C. |
| 5157b | 1.44(3H, d, J=6Hz), 1.63(3H, d, J=21Hz), 3.73(3H, s), 3.9(6H, s) 5.12–5.9(1H, m), 5.67(1H, S) <br> mp 94.7–97.1° C. |
| 5158a | 1.4(3H, t, J=7Hz), 1.38(3H, d, J=6Hz), 1.63(3H, d, J=20.2Hz), 3.92(6H, s), 4.24(2H, q, J=7Hz), 5.2–5.97(1H, m), 5.68(1H, s) |
| 5158b | 1.22(3H, t, J=7Hz), 1.45(3H, d, J=6Hz), 1.61(3H, d, J=21.6Hz), 3.93(6H, s), 4.22(2H, q, J=7Hz), 5.03–5.88(1H, m), 5.67(1H, s) <br> mp 49.8–51.0° C. |
| 5178b | 1.43(3H, d, J=6Hz), 1.63(3H, d, J=22Hz), 2.70–3.57(6H, m), 3.88(6H, s), 5.22–6.13(1H, m), 5.65(1H, s) |
| 5181b | 1.25(3H, d, J=6Hz), 1.3(3H, d, J=6Hz), 1.44(3H, d, J=6Hz), 1.55(3H, d, J=21Hz), 3.55–3.6(1H, m), 3.9(6H, s), 5.5–5.59(1H, m), 5.69(1H, s) |
| 5182a | 1.03(3H, t, J=7Hz), 1.53(3H, d, J=4.4Hz), 1.63–2.53(2H, m), 3.93(6H, s) 5.05–6.03(1H, m), 5.72(1H, s), 9.38(1H, s) <br> mp 147.0–148.5° C. |
| 5182b | 0.97(3H, t, J=7Hz), 1.44(3H, d, J=6Hz), 1.5–2.31(2H, m), 3.88(6H, s), 5.12–5.84(1H, m), 5.68(1H, s), 8.87(1H, s) <br> mp 81.5–82.5° C. |
| 5184a | 0.94(3H, t, J=7.3Hz), 1.32(3H, t, J=7Hz), 1.38(3H, d, J=6Hz), 1.48–2.45(2H, m), 3.91(6H, s), 4.27(2H, q, J=7Hz), 5.07–5.98(1H, s), 5.68(1H, s) |
| 5260a | 1.47(3H, d, J=6.4Hz), 2.33–3.07(2H, m), 3.92(6H, s), 4.94–5.35(2H, m), 5.35–6.02(1H, m), 5.35–6, 02(1H, m), 5.72(1H, s), 8.2(1H, s) <br> mp 148.0–150.5° C. |
| 5260b | 1.47(3H, d, J=6.4Hz), 2.23–3.03(2H, m), 3.88(6H, s), 4.86–5.43(2H, m) 5.33–6.23(1H, m), 5.33–6, 23(1H, m), 5.70(1H, s), 9.37(1H, s) <br> mp 106.0–109.0° C. |
| 5262a | 1.28(3H, t, J=7Hz), 1.39(3H, d, J=6.4Hz), 2.1–3.3(2H, m), 3.88(6H, s) 4.23(2H, q, J=7Hz), 4.83–5.27(2H, m, ), 5.27–6.13(1H, m), 5.27–6.13(1H, m), 5.97(1H, s) |
| 5262b | 1.19(3H, t, J=7Hz), 1.43(3H, d, J=6.4Hz), 2.33–3.01(2H, m), 3.85(6H, s) 4.15(2H, q, J=7Hz), 4.82–5.30(2H, m, ), 5.3–6.15(1H, m), 5.30–6.15(1H, m), 5.62(1H, s) |
| 5286a | 1.47(3H, d, J=6Hz), 1.95–2.27(1H, m), 2.6-–3.43(2H, m), 3.93(6H, s) 5.23–6.1(1H, m), 5.75(1H, s) <br> mp 164.5–165.0° C. |
| 5286b | 1.47(3H, d, J=6Hz), 2, 28–2.39(1H, m), 2.58–3.43(2H, m), 3.93(6H, s) 5.27–6.02(1H, m), 5.75(1H, s) <br> mp 139.0–142.0° C. |
| 5288a | 1.33(3H, t, J=7Hz), 1.43(3H, d, J=6Hz), 1.93–2.1(1H, m), 2.57–3.2(2H, m, ), 3.91(6H, s), 4.31(2H, q, J=7Hz), 5.2–6.03(1H, m), 5.68(1H, s) |
| 5288b | 1.25(3H, t, J=7Hz), 1.45(3H, d, J=6Hz), 1.93–2.14(1H, m), 2.50–3.23(2H, m, ), 3.91(6H, s), 4.27(2H, q, J=7Hz), 5.2–5–98(1H, m), 5.67(1H, s) <br> mp 91.7–94.0° C. |
| 5312a | 1.48(3H, d, J=6Hz), 2.6–3.62(2H, m), 3.87(6H, s), 5.3–6.07(1H, m), 5.72(1H, s), 7.21(5H, s), 8.37(1H, s) <br> mp 79.1–80.3° C. |
| 5312b | 1.06(3H, d, J=6Hz), 2.42–3.11(2H, m), 3.38(6H, s), 4.72–5.4(1H, m), 5.23(1H, s), 6.75(5H, s), 7.68(1H, s) <br> mp 112.0–113.5° C. |
| 5314a | 1.05(3H, t, J=7Hz), 1.43(3H, d, J=6.4Hz), 2.37–3.67(2H, m), 3.93(6H, s), 3.95(2H, q, J=7Hz), 5.22–6.05(1H, m), 5.85(1H, s), 7.18(5H, s) <br> mp 48.0–48.5° C. |
| 5314b | 1.02(3H, t, J=7Hz), 1.52(3H, d, J=6.4Hz), 3.37–3.5 (2H, m), 3.85(6H, s), 3.98(2H, q, J=7Hz), 5.2 –5.96(1H, m), 5.65(1H, s), 7.16(5H, s) <br> mp 81.4–83.3° C. |
| 5520 | 0.58–1.03(3H, m), 0.98–2.05(4H, m), 3.8(6H, s), 5.37–5.97(1H, m), 5.62(1H, s), 9.2(1H, s) <br> mp 105.0–106.0° C. |
| 5523 | 0.47–1.23(3H, m), 0.47–2.06(4H, m), 1.13(3H, t, J=7Hz), 3.85(6H, s), 4.13(2H, q, J=7Hz), 5.33–6.1(1H, m), 5.63(1H, s) |

TABLE 12-continued

| Compound No. | ¹H-NMR(δ ppm, CDCl₃) and/or Physical data |
|---|---|
| 5625 | 0.75-1.42(6H, m), 1.90-2.57(1H, m), 3.89(6H, s), 5.26-5.9(1H, m), 5.7(1H, s), 7.51(1H, s) |
| 5627 | 0.73-1.47(6H, m), 1.18(3H, t, J=7Hz), 1.93-2.7(1H, m), 3.9(6H, s), 4.15(2H, q, J=7Hz), 5.3-5.91(1H, m), 5.66(1H, s) |
| 5651a | 1.04(6H, d, J=7Hz), 1.6(3H, d, J=21.8Hz), 1.77-2.43(1H, m), 3.95(6H, s), 5.35-5.97(1H, m), 5.71(1H, s), 10.8(1H, s)<br>mp 103.0-105.0° C. |
| 5651b | 1.05(6H, d, J=7Hz), 1.66(3H, d, J=21.4Hz), 2.07-2.48(1H, m), 3.88(6H, s), 5.28-5.80(1H, m), 5.67(1H, s), 10.6(1H, s)<br>mp 118.0-121.5° C. |
| 5653a | 0.65-1.38(6H, m), 1.3(3H, t, J=7Hz), 1.55(3H, d, J=22Hz) 1.9-2.42(1H, m), 3.93(6H, s), 4.23(2H, q, J=7Hz), 5.35-5.93(1H, m) 5.68(1H, s) |
| 5653b | 1.08(6H, d, J=7Hz), 1.12(3H, t, J=7Hz), 1.63(3H, d, J=21.2Hz) 1.95-2.46(1H, m), 3.94(6H, s), 4.1(2H, q, J=7Hz), 5.3-5.8(1H, m) 5.66(1H, s) |
| 5781a | 1.77(3H, d, J=21.6Hz), 3.8(6H, s), 5.62(1H, s), 6.27(1H, d, J=21Hz), 7.0-7.67(5H, m)<br>mp 148.0-149.5° C. |
| 5781b | 1.47(3H, d, J=21Hz), 3.81(6H, s), 6.2(1H, d, J=24.4Hz), 7.16-7.67(5H, m), 10.7(1H, s)<br>mp 113.0-114.0° C. |
| 5783a | 1.13(3H, t, J=7Hz), 1.74(3H, d, J=21.4Hz), 3.87(6H, s), 4.12(2H, q, J=7Hz), 5.62(1H, s), 6.27(1H, d, J=21.4Hz), 7.07-7.64(5H, m) |
| 5783b | 1.23(3H, t, J=7Hz), 1.45(3H, d, J=20.8Hz), 3.79(6H, s), 4.23(2H, q, J=7Hz), 5.56(1H, s), 6.15(1H, d, J=24Hz), 7.05-7.62(5H, m)<br>mp 97.6-99.8° C. |
| 5833 | 1.48-1.98(3H, m), 3.88 and 3.92(6H, s), 5.72 and 5.78(1H, s) 8.27(1H, s) |
| 5835 | 1.06-1.44(3H, m), 1.46-2.03(3H, m), 3.94(6H, s), 3.95-4.48(2H, m), 5.77 and 5.79(1H, s), 5.87-6.72(1H, m) |
| 5965 | 1.42(3H, d, J=22.6Hz), 3.53(6H, s), 4.92(2H, s), 5.03-5.7(1H, s), 5.41(1H, s)<br>mp 186.5-189.0° C. |
| 5967 | 1.23(3H, t, J=7Hz), 1.31(3H, t, J=7Hz), 1.79(3H, d, J=21.4Hz), 3.88(6H, s), 4.24(2H, q, J=7Hz), 4.31(2H, q, J=7Hz), 5.03-6.02(1H, m), 5.72(1H, s)<br>mp 63.7-64.8° C. |

TABLE 13

| Compound No. | ¹H-NMR(δ ppm, CDCl₃) and/or Physical data |
|---|---|
| 6001 | 3.93(6H, s), 4.12-4.36(4H, .m), 5.64-5.69(1H, m), 5.77(1H, s) |
| 6002 | 3.22-4.52(4H, m), 3.81(3H, s), 3.85(6H, s), 5.42-5.94(1H, m), 5.7(1H, s) |
| 6082a | 1.95-2.43(2H, m), 3.3-4.6(4H, m), 3.88(6H, s), 5.25-5.72(1H, m), 5.67(1H, s), 7.68(1H, s) |
| 6082b | 1.9-2.4(2H, m), 3.28-4.43(4H, m), 3.87(6H, s), 5.07-5.92(1H, m), 5.68(1H, s), 7.42(1H, s) |
| 6084a | 1.14(3H, t, J=7.2Hz), 2.01-2.33(2H, m), 3.79-4.32(4H, m), 3.91(6H, S) 4.07(2H, q, J=7.2Hz), 5.61-5.63(1H, m), 5.72(1H, s) |
| 6084b | 1.19(3H, t, J=7.2Hz), 2.21-2.28(2H, m), 3.6-4.21(4H, m), 3.91(6H, S) 4.05(2H, q, J=7.2Hz), 5.6-5.72(1H, m), 5.71(1H, s) |
| 6085b | 1, 1(3H, d, J=1.6Hz), 1.2(3H, d, J=1.6Hz), 1.8-2.47(2H, m), 3.3-4.4(4H, m), 3.88(6H, s), 4.75-6.0(2H, m), 5.67(1H, s) |
| 6090b | 1.87-2.47(2H, m), 3.32-4.27(4H, m), 4.38-4.72(2H, m), 3.90(6H, s), 4.92-6.05(1H, m), 5.68(1H, s) |
| 6091b | 1.83-2.48(2H, m), 2.25-2.48(1H, m), 3.28-4.43(4H, m), 3.9(6H, s), 4.53-4.75(2H, m), 5.18-6.0(1H, m), 5.67(1H, s) |
| 6136b | 2.83-3.8(4H, m), 3.9(6H, s), 5.02-6.04(1H, m), 5.7(1H, s), 8.48(1H, s) |
| 6137a | 3.15-3.88(4H, m), 3.68(3H, s), 3.91(6H, s), 5.71(1H, s), 5.82-6.1(1H, s) |
| 6137b | 2.87-4.4(4H, m), 3.69(3H, s), 3.9(6H, s), 5.72(1H, s), 5.28-6.05(1H, s) |
| 6216a | 2.12-3.73(6H, m), 3.85(6H, s), 5.23-5.77(1H, m), 5.65(1H, s), 6.77(1H, s) |
| 6217a | 2.34-3.7(6H, m), 3.67(3H, s), 3.9(6H, s), 5.59-5.62(1H, m), 5.72(1H, s) |
| 6217b | 2.26-3.7(6H, m), 3.78(3H, s), 3.92(6H, s), 5.49-5.57(1H, m), 5.72(1H, s) |
| 6459a | 1.83-2.34(2H, m), 2.67-4.77(4H, m), 3.72(3H, s), 3.9(6H, s), 5.35-5.8(1H, m), 5.72(1H, s) |
| 6459b | 1.67-2.34(2H, m), 2.45-4.93(4H, m), 3.67(3H, s), 3.88(6H, s), 5.08-5.9(1H, m), 5.69(1H, s), 9.3(1H, s) |
| 6460a | 1.78-2.29(2H, m), 3.0-4.67(4H, m), 3.63(3H, s), 3.7(3H, s), 3.88(6H, s) 5.4-5.77(1H, m), 5.68(1H, s) |
| 6460b | 1.73-2.35(2H, m), 2.67-4.77(4H, m), 3.72(3H, s), 3.72(3H, s), 3.9(6H, s), 5.03-5.9(1H, m), 5.68(1H, s) |

TABLE 13-continued

| Compound No. | $^1$H-NMR($\delta$ ppm, CDCl$_3$) and/or Physical data |
|---|---|
| 7004 | 1.23(3H, t, J=7Hz), 1.58–2.62(6H, m), 3.83(6H, s), 4.17(2H, q, J=7Hz), 5.69(1H, s), 5.82–6.06(1H, m) |

TABLE 14

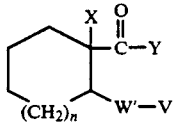

| Compound No. | n | X | W' | Y | V | Remarks |
|---|---|---|---|---|---|---|
| 1 | 0 | F | O | OH | H | |
| 2a | 0 | F | O | O—CH$_3$ | H | cis |
| 2b | 0 | F | O | O—CH$_3$ | H | trans |
| 3a | 0 | F | O | O—CH$_3$ | COCH$_3$ | cis |
| 3b | 0 | F | O | O—CH$_3$ | COCH$_3$ | trans |
| 4a | 0 | F | O | O—CH$_3$ | COPh | cis |
| 4b | 0 | F | O | O—CH$_3$ | COPh | trans |
| 5a | 0 | F | O | O—CH$_3$ | Ms | cis |
| 5b | 0 | F | O | O—CH$_3$ | Ms | trans |
| 6a | 0 | F | O | O—CH$_3$ | Ts | cis |
| 6b | 0 | F | O | O—CH$_3$ | Ts | trans |
| 7 | 0 | F | O | O—C$_2$H$_5$ | H | |
| 8 | 0 | F | O | O—C$_2$H$_5$ | COCH$_3$ | |
| 9 | 0 | F | O | O—C$_2$H$_5$ | COPh | |
| 10 | 0 | F | O | O—C$_2$H$_5$ | Ms | |
| 11 | 0 | F | O | O—C$_2$H$_5$ | Ts | |
| 12a | 0 | F | O | OH | CH$_3$ | cis |
| 12b | 0 | F | O | OH | CH$_3$ | trans |
| 13a | 0 | F | O | O—CH$_3$ | CH$_3$ | cis |
| 13b | 0 | F | O | O—CH$_3$ | CH$_3$ | trans |
| 14 | 0 | F | O | O—C$_2$H$_5$ | CH$_3$ | |
| 15 | 0 | F | O | O-n-C$_3$H$_7$ | CH$_3$ | |
| 16 | 0 | F | O | O-i-C$_3$H$_7$ | CH$_3$ | |
| 17 | 0 | F | O | O-n-C$_4$H$_9$ | CH$_3$ | |
| 18 | 0 | F | O | O-i-C$_4$H$_9$ | CH$_3$ | |
| 19 | 0 | F | O | O-s-C$_4$H$_9$ | CH$_3$ | |
| 20a | 0 | F | O | O-t-C$_4$H$_9$ | CH$_3$ | cis |
| 20b | 0 | F | O | O-t-C$_4$H$_9$ | CH$_3$ | trans |
| 21 | 0 | F | O | NH$_2$ | CH$_3$ | |
| 22 | 0 | F | O | NH—CH$_3$ | CH$_3$ | |
| 23a | 0 | F | O | NH—C$_2$H$_5$ | CH$_3$ | cis |
| 23b | 0 | F | O | NH—C$_2$H$_5$ | CH$_3$ | trans |
| 24 | 0 | F | O | NH-n-C$_3$H$_7$ | CH$_3$ | |
| 25 | 0 | F | O | NH-i-C$_3$H$_7$ | CH$_3$ | |
| 26 | 0 | F | O | NH-n-C$_4$H$_9$ | CH$_3$ | |
| 27 | 0 | F | O | NH-i-C$_4$H$_9$ | CH$_3$ | |
| 28 | 0 | F | O | NH-s-C$_4$H$_9$ | CH$_3$ | |
| 29a | 0 | F | O | NH-t-C$_4$H$_9$ | CH$_3$ | cis |
| 29b | 0 | F | O | NH-t-C$_4$H$_9$ | CH$_3$ | trans |
| 30a | 0 | F | O | N(CH$_3$)$_2$ | CH$_3$ | cis |
| 30b | 0 | F | O | N(CH$_3$)$_2$ | CH$_3$ | trans |
| 31 | 0 | F | O | S—CH$_3$ | CH$_3$ | |
| 32a | 0 | F | O | S—C$_2$H$_5$ | CH$_3$ | cis |
| 32b | 0 | F | O | S—C$_2$H$_5$ | CH$_3$ | trans |
| 33 | 0 | F | O | S-n-C$_3$H$_7$ | CH$_3$ | |
| 34 | 0 | F | O | S-i-C$_3$H$_7$ | CH$_3$ | |
| 35 | 0 | F | O | S-n-C$_4$H$_9$ | CH$_3$ | |
| 36 | 0 | F | O | S-i-C$_4$H$_9$ | CH$_3$ | |
| 37 | 0 | F | O | S-s-C$_4$H$_9$ | CH$_3$ | |
| 38a | 0 | F | O | S-t-C$_4$H$_9$ | CH$_3$ | cis |
| 38b | 0 | F | O | S-t-C$_4$H$_9$ | CH$_3$ | trans |
| 39a | 0 | F | O | OH | CH$_2$Ph | cis |
| 39b | 0 | F | O | OH | CH$_2$Ph | trans |
| 40a | 0 | F | O | O—CH$_3$ | CH$_2$Ph | cis |
| 40b | 0 | F | O | O—CH$_3$ | CH$_2$Ph | trans |
| 41 | 0 | F | O | O—C$_2$H$_5$ | CH$_2$Ph | |
| 42 | 0 | F | O | O-n-C$_3$H$_7$ | CH$_2$Ph | |
| 43 | 0 | F | O | O-i-C$_3$H$_7$ | CH$_2$Ph | |
| 44 | 0 | F | O | O-n-C$_4$H$_9$ | CH$_2$Ph | |
| 45 | 0 | F | O | O-i-C$_4$H$_9$ | CH$_2$Ph | |
| 46 | 0 | F | O | O-s-C$_4$H$_9$ | CH$_2$Ph | |
| 47 | 0 | F | O | O-t-C$_4$H$_9$ | CH$_2$Ph | |
| 48a | 0 | F | O | O—CH$_2$Ph | CH$_2$Ph | cis |
| 48b | 0 | F | O | O—CH$_2$Ph | CH$_2$Ph | trans |

TABLE 14-continued

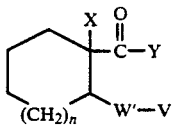

| Compound No. | n | X | W' | Y | V | Remarks |
|---|---|---|---|---|---|---|
| 49 | 0 | F | O | NH$_2$ | CH$_2$Ph | |
| 50 | 0 | F | O | NH—CH$_3$ | CH$_2$Ph | |
| 51 | 0 | F | O | NH—C$_2$H$_5$ | CH$_2$Ph | |
| 52 | 0 | F | O | NH-n-C$_3$H$_7$ | CH$_2$Ph | |
| 53 | 0 | F | O | NH-i-C$_3$H$_7$ | CH$_2$Ph | |
| 54 | 0 | F | O | NH-n-C$_4$H$_9$ | CH$_2$Ph | |
| 55 | 0 | F | O | NH-i-C$_4$H$_9$ | CH$_2$Ph | |
| 56 | 0 | F | O | NH-s-C$_4$H$_9$ | CH$_2$Ph | |
| 57 | 0 | F | O | NH-t-C$_4$H$_9$ | CH$_2$Ph | |
| 58 | 0 | F | O | N(CH$_3$)$_2$ | CH$_2$Ph | |
| 59 | 0 | F | O | S—CH$_3$ | CH$_2$Ph | |
| 60 | 0 | F | O | S—C$_2$H$_5$ | CH$_2$Ph | |
| 61 | 0 | F | O | S-n-C$_3$H$_7$ | CH$_2$Ph | |
| 62 | 0 | F | O | S-i-C$_3$H$_7$ | CH$_2$Ph | |
| 63 | 0 | F | O | S-n-C$_4$H$_9$ | CH$_2$Ph | |
| 64 | 0 | F | O | S-i-C$_4$H$_9$ | CH$_2$Ph | |
| 65 | 0 | F | O | S-s-C$_4$H$_9$ | CH$_2$Ph | |
| 66 | 0 | F | O | S-t-C$_4$H$_9$ | CH$_2$Ph | |
| 67 | 1 | F | O | OH | H | |
| 68 | 1 | F | O | O—CH$_3$ | H | |
| 69 | 1 | F | O | O—CH$_3$ | COCH$_3$ | |
| 70 | 1 | F | O | O—CH$_3$ | COPh | |
| 71 | 1 | F | O | O—CH$_3$ | Ms | |
| 72 | 1 | F | O | O—CH$_3$ | Ts | |
| 73a | 1 | F | O | O—C$_2$H$_5$ | H | cis |
| 73b | 1 | F | O | O—C$_2$H$_5$ | H | trans |
| 74a | 1 | F | O | O—C$_2$H$_5$ | COCH$_3$ | cis |
| 74b | 1 | F | O | O—C$_2$H$_5$ | COCH$_3$ | trans |
| 75a | 1 | F | O | O—C$_2$H$_5$ | COPh | cis |
| 75b | 1 | F | O | O—C$_2$H$_5$ | COPh | trans |
| 76a | 1 | F | O | O—C$_2$H$_5$ | Ms | cis |
| 76b | 1 | F | O | O—C$_2$H$_5$ | Ms | trans |
| 77a | 1 | F | O | O—C$_2$H$_5$ | Ts | cis |
| 77b | 1 | F | O | O—C$_2$H$_5$ | Ts | trans |
| 78 | 1 | F | O | OH | CH$_3$ | |
| 79 | 1 | F | O | O—CH$_3$ | CH$_3$ | |
| 80a | 1 | F | O | O—C$_2$H$_5$ | CH$_3$ | cis |
| 80b | 1 | F | O | O—C$_2$H$_5$ | CH$_3$ | trans |
| 81 | 1 | F | O | O-n-C$_3$H$_7$ | CH$_3$ | |
| 82 | 1 | F | O | O-i-C$_3$H$_7$ | CH$_3$ | |
| 83 | 1 | F | O | O-n-C$_4$H$_9$ | CH$_3$ | |
| 84 | 1 | F | O | O-i-C$_4$H$_9$ | CH$_3$ | |
| 85 | 1 | F | O | O-s-C$_4$H$_9$ | CH$_3$ | |
| 86 | 1 | F | O | O-t-C$_4$H$_9$ | CH$_3$ | |
| 87 | 1 | F | O | NH$_2$ | CH$_3$ | |
| 88 | 1 | F | O | NH—CH$_3$ | CH$_3$ | |
| 89 | 1 | F | O | NH—C$_2$H$_5$ | CH$_3$ | |
| 90 | 1 | F | O | NH-n-C$_3$H$_7$ | CH$_3$ | |
| 91 | 1 | F | O | NH-i-C$_3$H$_7$ | CH$_3$ | |
| 92 | 1 | F | O | NH-n-C$_4$H$_9$ | CH$_3$ | |
| 93 | 1 | F | O | NH-i-C$_4$H$_9$ | CH$_3$ | |
| 94 | 1 | F | O | NH-s-C$_4$H$_9$ | CH$_3$ | |
| 95 | 1 | F | O | NH-t-C$_4$H$_9$ | CH$_3$ | |
| 96 | 1 | F | O | N(CH$_3$)$_2$ | CH$_3$ | |
| 97 | 1 | F | O | S—CH$_3$ | CH$_3$ | |
| 98 | 1 | F | O | S—C$_2$H$_5$ | CH$_3$ | |
| 99 | 1 | F | O | S-n-C$_3$H$_7$ | CH$_3$ | |
| 100 | 1 | F | O | S-i-C$_3$H$_7$ | CH$_3$ | |
| 101 | 1 | F | O | S-n-C$_4$H$_9$ | CH$_3$ | |
| 102 | 1 | F | O | S-i-C$_4$H$_9$ | CH$_3$ | |
| 103 | 1 | F | O | S-s-C$_4$H$_9$ | CH$_3$ | |
| 104 | 1 | F | O | S-t-C$_4$H$_9$ | CH$_3$ | |
| 105a | 1 | F | O | OH | CH$_2$Ph | cis |
| 105b | 1 | F | O | OH | CH$_2$Ph | trans |
| 106 | 1 | F | O | O—CH$_3$ | CH$_2$Ph | |
| 107a | 1 | F | O | O—C$_2$H$_5$ | CH$_2$Ph | cis |
| 107b | 1 | F | O | O—C$_2$H$_5$ | CH$_2$Ph | trans |
| 108 | 1 | F | O | O-n-C$_3$H$_7$ | CH$_2$Ph | |
| 109 | 1 | F | O | O-i-C$_3$H$_7$ | CH$_2$Ph | |
| 110 | 1 | F | O | O-n-C$_4$H$_9$ | CH$_2$Ph | |
| 111 | 1 | F | O | O-i-C$_4$H$_9$ | CH$_2$Ph | |
| 112 | 1 | F | O | O-s-C$_4$H$_9$ | CH$_2$Ph | |
| 113 | 1 | F | O | O-t-C$_4$H$_9$ | CH$_2$Ph | |

TABLE 14-continued

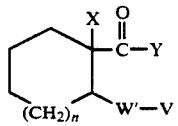

| Compound No. | n | X | W' | Y | V | Remarks |
|---|---|---|---|---|---|---|
| 114 | 1 | F | O | O—CH$_2$Ph | CH$_2$Ph | |
| 115 | 1 | F | O | NH$_2$ | CH$_2$Ph | |
| 116 | 1 | F | O | NH—CH$_3$ | CH$_2$Ph | |
| 117a | 1 | F | O | NH—C$_2$H$_5$ | CH$_2$Ph | cis |
| 117b | 1 | F | O | NH—C$_2$H$_5$ | CH$_2$Ph | trans |
| 118 | 1 | F | O | NH-n-C$_3$H$_7$ | CH$_2$Ph | |
| 119 | 1 | F | O | NH-i-C$_3$H$_7$ | CH$_2$Ph | |
| 120 | 1 | F | O | NH-n-C$_4$H$_9$ | CH$_2$Ph | |
| 121 | 1 | F | O | NH-i-C$_4$H$_9$ | CH$_2$Ph | |
| 122 | 1 | F | O | NH-s-C$_4$H$_9$ | CH$_2$Ph | |
| 123a | 1 | F | O | NH-t-C$_4$H$_9$ | CH$_2$Ph | cis |
| 123b | 1 | F | O | NH-t-C$_4$H$_9$ | CH$_2$Ph | trans |
| 124 | 1 | F | O | N(CH$_3$)$_2$ | CH$_2$Ph | |
| 125 | 1 | F | O | S—CH$_3$ | CH$_2$Ph | |
| 126 | 1 | F | O | S—C$_2$H$_5$ | CH$_2$Ph | |
| 127 | 1 | F | O | S-n-C$_3$H$_7$ | CH$_2$Ph | |
| 128 | 1 | F | O | S-i-C$_3$H$_7$ | CH$_2$Ph | |
| 129 | 1 | F | O | S-n-C$_4$H$_9$ | CH$_2$Ph | |
| 130 | 1 | F | O | S-i-C$_4$H$_9$ | CH$_2$Ph | |
| 131 | 1 | F | O | S-s-C$_4$H$_9$ | CH$_2$Ph | |
| 132 | 1 | F | O | S-t-C$_4$H$_9$ | CH$_2$Ph | |
| 133 | 2 | F | O | OH | H | |
| 134a | 2 | F | O | OCH$_3$ | H | cis |
| 134b | 2 | F | O | OCH$_3$ | H | trans |
| 135 | 2 | F | O | OCH$_3$ | COCH$_3$ | |
| 136 | 2 | F | O | OCH$_3$ | COPh | |
| 137 | 2 | F | O | OCH$_3$ | Ms | |
| 138 | 2 | F | O | OCH$_3$ | Ts | |
| 139 | 2 | F | O | O—C$_2$H$_5$ | H | |
| 140 | 2 | F | O | O—C$_2$H$_5$ | COCH$_3$ | |
| 141 | 2 | F | O | O—C$_2$H$_5$ | COPh | |
| 142 | 2 | F | O | O—C$_2$H$_5$ | Ms | |
| 143 | 2 | F | O | O—C$_2$H$_5$ | Ts | |
| 144 | 2 | F | O | OH | CH$_2$Ph | |
| 145 | 2 | F | O | O—CH$_3$ | CH$_2$Ph | |
| 146 | 2 | F | O | O—C$_2$H$_5$ | CH$_2$Ph | |
| 147 | 3 | F | O | OH | H | |
| 148 | 3 | F | O | O—CH$_3$ | H | |
| 149 | 3 | F | O | O—CH$_3$ | COCH$_3$ | |
| 150 | 3 | F | O | O—CH$_3$ | COPh | |
| 151 | 3 | F | O | O—CH$_3$ | Ms | |
| 152 | 3 | F | O | O—CH$_3$ | Ts | |
| 153 | 3 | F | O | O—C$_2$H$_5$ | H | |
| 154 | 3 | F | O | O—C$_2$H$_5$ | COCH$_3$ | |
| 155 | 3 | F | O | O—C$_2$H$_5$ | COPh | |
| 156 | 3 | F | O | O—C$_2$H$_5$ | Ms | |
| 157 | 3 | F | O | O—C$_2$H$_5$ | Ts | |
| 158 | 3 | F | O | OH | CH$_2$Ph | |
| 159 | 3 | F | O | O—CH$_3$ | CH$_2$Ph | |
| 160 | 3 | F | O | O—C$_2$H$_5$ | CH$_2$Ph | |
| 161 | 0 | F | S | OH | H | |
| 162 | 0 | F | S | O—CH$_3$ | H | |
| 163 | 1 | F | S | OH | H | |
| 164 | 1 | F | S | O—CH$_3$ | H | |
| 165 | 0 | Cl | O | OH | H | |
| 166 | 0 | Cl | O | O—C$_2$H$_5$ | H | |
| 167 | 1 | Cl | O | OH | H | |
| 168 | 1 | Cl | O | O—C$_2$H$_5$ | H | |
| 169 | 1 | Br | O | O—C$_2$H$_5$ | H | |

TABLE 15

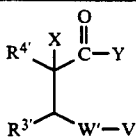

| Compound No. | R³' R⁴' | X | Y | W' | V |
|---|---|---|---|---|---|
| 201 | —CH(CH₃)—(CH₂)₂— | F | OH | O | H |
| 202 | —CH(CH₃)—(CH₂)₂— | F | O—C₂H₅ | O | H |
| 203 | —C(CH₃)₂—(CH₂)₂— | F | OH | O | H |
| 204 | —C(CH₃)₂—(CH₂)₂— | F | O—C₂H₅ | O | H |
| 205 | —(CH₂)₂—C(CH₃)₂— | F | OH | O | H |
| 206 | —(CH₂)₂—C(CH₃)₂— | F | O—C₂H₅ | O | H |
| 207 | —(CH₂)₂—CH(CH₃)—CH₂— | F | OH | O | H |
| 208 | —(CH₂)₂—CH(CH₃)—CH₂— | F | O—C₂H₅ | O | H |
| 209 | —(CH₂)₂—CH(t-C₄H₉)—CH₂— | F | OH | O | H |
| 210 | —(CH₂)₂—CH(t-C₄H₉)—CH₂— | F | O—C₂H₅ | O | H |
| 211 | —C(CH₃)₂—(CH₂)₃— | F | OH | O | H |
| 212 | —C(CH₃)₂—(CH₂)₃— | F | O—C₂H₅ | O | H |
| 213 | —(CH₂)₃—C(CH₃)₂— | F | OH | O | H |
| 214 | —(CH₂)₃—C(CH₃)₂— | F | O—C₂H₅ | O | H |
| 215 | —(CH₂)₃—CH(OH)— | F | OH | O | H |
| 216 | —(CH₂)₃—CH(OH)— | F | O—C₂H₅ | O | H |
| 217 | —(CH₂)₃—CH(OCH₃)— | F | OH | O | H |
| 218 | —(CH₂)₃—CH(OCH₃)— | F | O—C₂H₅ | O | H |
| 219 | —(CH₂)₃—C(=O)— | F | OH | O | H |
| 220 | —(CH₂)₃—C(=O)— | F | O—C₂H₅ | O | H |
| 221 | —(CH₂)₂—CH(OH)—CH₂— | F | OH | O | H |
| 222 | —(CH₂)₂—CH(OH)—CH₂— | F | O—C₂H₅ | O | H |
| 223 | —(CH₂)₂—CH(OCH₃)—CH₂— | F | OH | O | H |
| 224 | —(CH₂)₂—CH(OCH₃)—CH₂— | F | O—C₂H₅ | O | H |
| 225 | —(CH₂)₂—C(=O)—CH₂— | F | OH | O | H |
| 226 | —(CH₂)₂—C(=O)—CH₂— | F | O—C₂H₅ | O | H |
| 227 | —(CH₂)₂—O— | F | OH | O | H |
| 228 | —(CH₂)₂—O— | F | O—CH₃ | O | H |
| 229 | —(CH₂)₂—S— | F | OH | O | H |
| 230 | —(CH₂)₂—S— | F | O—CH₃ | O | H |
| 231 | —CH₂—O—CH₂ | F | OH | O | H |
| 232 | —CH₂—O—CH₂ | F | O—CH₃ | O | H |
| 233 | —CH₂—S—CH₂ | F | OH | O | H |
| 234 | —CH₂—S—CH₂ | F | O—CH₃ | O | H |
| 235 | —(CH₂)₃—O— | F | OH | O | H |
| 236 | —(CH₂)₃—O— | F | O—C₂H₅ | O | H |
| 237 | —(CH₂)₃—S— | F | OH | O | H |
| 238 | —(CH₂)₃—S— | F | O—C₂H₅ | O | H |
| 239 | —(CH₂)₃—N(CO₂CH₃)— | F | OH | O | H |
| 240 | —(CH₂)₃—N(CO₂CH₃)— | F | O—C₂H₅ | O | H |
| 241 | —(CH₂)₂—O—CH₂— | F | OH | O | H |
| 242 | —(CH₂)₂—O—CH₂— | F | O—C₂H₅ | O | H |
| 243 | —(CH₂)₂—S—CH₂— | F | OH | O | H |
| 244 | —(CH₂)₂—S—CH₂— | F | O—CH₃ | O | H |
| 245 | —(CH₂)₂—N(CO₂CH₃)—CH₂— | F | OH | O | H |
| 246 | —(CH₂)₂—N(CO₂CH₃)—CH₂— | F | O—CH₃ | O | H |
| 247 | —CH₂—O—(CH₂)₂— | F | OH | O | H |
| 248 | —CH₂—O—(CH₂)₂— | F | O—C₂H₅ | O | H |
| 249 | —CH₂—S—(CH₂)₂— | F | OH | O | H |
| 250 | —CH₂—S—(CH₂)₂— | F | O—C₂H₅ | O | H |
| 251 | —CH₂—N(CO₂CH₃)—(CH₂)₂— | F | OH | O | H |
| 252 | —CH₂—N(CO₂CH₃)—(CH₂)₂— | F | O—C₂H₅ | O | H |

TABLE 16

| Compound No. | ¹H-NMR (δ ppm, CDCl₃) and/or physical data |
|---|---|
| 2a | 1.33–3.03(6H, m), 3.82(3H, s), 4.07–4.60(1H, m) Mass/m/Z=162 (M⁺) |
| 2b | 1.30–2.90(6H, m), 3.80(3H, s), 4.03–4.63(1H, m) |
| 3a | 1.50–2.93(6H, m), 2.02(3H, s), 3.77(3H, s), 5.00–5.50(1H, m), Mass/m/Z=204(M⁺) |
| 3b | 1.37–2.73(6H, m), 2.03(3H, s), 3.77(3H, s), 4.80–5.47(1H, m), Mass/m/Z=204(M⁺) |
| 4a | 1.47–3.03(6H, m)3, 73(3H, s), 5.20–5.73(1H, m), 7.20–8.22(5H, m) |
| 4b | 1.37–2.77(6H, m), 3.80(3H, s), 5.03–5.77(1H, m), 7.22–8.25(5H, m) |
| 5a | 1.52–2.63(6H, m), 3.00(3H, s), 3.81(3H, s), 4.80–5.28(1H, m) |
| 5b | 1.38–2.63(6H, m), 3.01(3H, s), 3.82(3H, s) 4.63–5.47(1H, m) |
| 6a | 1.37–2.37(6H, m), 2.46(3H, s), 3.70(3H, s), 4.27–5.17(1H, m), 7.00–8, 20(5H, m) |
| 6b | 1.30–2.37(6H, m), 2.43(3H, s), 3.63(3H, s), 3.93–5.00(1H, m), 6.93–7.93(5H, m) |
| 12a | 1.43–2.80(6H, m), 3.40(3H, s), 3.63–4.57(1H, m) 8.90(1H, s) |
| 12b | 1.43–2.60(6H, m), 3.43(3H, s), 3.77–4.67(1H, m) 8.47(1H, s) |
| 13a | 1.50–2.82(6H, m), 3.31(3H, s), 3.80(3H, s) 3.90–4.55(1H, m), Mass/m/Z=176(M⁺) |
| 13b | 1.42–2.68(6H, m), 3.35(3H, s), 3.80(3H, s), |

TABLE 16-continued

| Compound No. | $^1$H-NMR ($\delta$ ppm, CDCl$_3$) and/or physical data |
|---|---|
| | 4.03–5.00(1H, m) |
| 20a | 1.47–2.80(6H, m), 1.53(9H, s), 3.37(3H, s), 3.57–4.37(1H, m) |
| 23b | 1.17(3H, t, J=6.6Hz), 1.50–2.70(6H, m), 3.36(2H, q, J=6.6Hz), 3.37(3H, s), 3.72–4.53(1H, m) |
| 29a | 1.43–2.57(6H, m), 1.39(9H, s), 3.37(3H, s), 3.83–4.28(1H, m), Mass/m/Z=217(M$^+$) |
| 29b | Mass/m/Z=217(M$^+$) |
| 30a | Mass/m/Z=189(M$^+$) |
| 30b | 1.43–2.60(6H, m), 2.60–3.12(6H, m), 3.39(3H, s), 3.93–4.57(1H, m), Mass/m/Z=189(M$^+$) |
| 32a | 1.33–2.62(6H, m), 1.28(3H, t, J=7.0Hz), 2.93(2H, q, J=7.0Hz), 3.35(3H, s), 3.57–4.30(1H, m), Mass/m/Z=206(M$^+$) |
| 32b | Mass/m/Z=206(M$^+$) |
| 38b | 1.30–2.60(6H, m), 1.48(9H, s), 3.33(3H, s), 3.42–4.37(1H, m) |
| 39a | 1.48–2.80(6H, m), 3.80–4.38(1H, m), 4.58(2H, s), 7.25(5H, s), 7.87(1H, s) |
| 39b | 1.50–2.65(6H, m), 4.00–4.47(1H, m), 4.57(2H, s), 7.33(5H, s), 7.55(1H, s) |
| 40a | 1.57–2.87(6H, m), 3.75(3H, s), 3.90–4.40(1H, m), 4.45(2H, s), 7.23(5H, s) |
| 40b | 1.59–2.43(6H, m), 3.75(3H, s), 3.77–4.43(1H, M), 4.50(2H, s), 7.25(5H, s), Mass/m/Z=252(M$^+$) |
| 48b | 1.47–2.57(6H, m), 4.40(2H, s), 5.18(2H, s), 7.20(5H, s), 7.29(5H, s) |
| 73a | 1.33(3H, t, J=7Hz), 1, 10–2.50(8H, m), 2.83–3.17(1H, bs), 3.67–4.17(1H, m), 4.23(2H, q, J=7Hz), Mass/m/Z=190(m$^+$) |
| 73b | Mass/m/Z=190(M$^+$) |
| 74a | 1.28(3H, t, J=7Hz), 1.33–2.13(8H, m), 2.03(3H, s), 4.20(2H, q, J=7Hz), 4.87–5.32(1H, m) |
| 74b | 1.27(3H, t, J=7Hz), 1.17–2.23(8H, m), 2.02(3H, s), 4.18(2H, q, J=7Hz), 4.70–5.30(1H, m) |
| 75a | 1.18(3H, t, J=7Hz), 1.37–2.28(8H, m), 4.17(2H, q, J=7Hz), 5.13–5.57(1H, m), 7.17–7.70(3H, m), 7.80–8.23(2H, m), Mass/m/Z=294(M$^+$) |
| 75b | 1.12(3H, t.J=7Hz), 1.18–2.38(8H, m), 4.12(2H, q, J=7Hz), 4.85–5.62(1H, m), 7.07–7.62((3H, m), 7.70–8.20(2H, m), Mass/m/Z=294(M$^+$) |
| 76a | 1.32(3H, t, J=7Hz), 1.28–2.52(8H, m), 3.00(3H, s), 4.25(2, t, J=7Hz), 4.48–5.05(1H, m) |
| 76b | 1.30(3H, t, J=7Hz), 1.30–2.33(8H, m), 2.95(3H, s), 4.23(2H, q, J=7Hz), 4.53–5.37(1H, m) |
| 77a | 1.23(3H, t, J=7Hz), 1.18–2.22(8H, m), 2.42(3H, s), 4.08(2H, q, J=7Hz), 4.50–4.93(1H, m), 6.90–7.37(2H, m), 7.56–7.88(2H, m), Mass/m/Z=344(M$^+$) |
| 77b | 1.22(3H, t, J=7Hz), 1.20–2.33(8H, m), 2.40(3H, m), 4.03(2H, q, J=7Hz), 4.50–5.30(1H, m), 6.95–7.37(2H, m), 7.53–7.83(2H, m), Mass/m/Z=344(M$^+$) |
| 80a | Mass/m/Z=204(M$^+$) |
| 80b | Mass/m/Z=204(M$^+$) |
| 105a | 0.80–2.85(8H, m), 3.28–4.12(iH, m), 4.60(1H, s), 7.27(5H, s) |
| 107b | 1.25(3H, t, J=7Hz), 1.23–2.30(8H, m), 3.23–4.00(1H, m), 4.18(2H, q, J=7Hz), 4.43(1H, q, J=12Hz), 4.60(1H, q, J=12Hz, ), 7.23(5H, s) |
| 117a | 1.10(3H, t, J=7Hz), O.72–2.45(8H, m), 2.95–4.00(3H, m), 4.60(2H, s), 6.08–6.77(1, bs), 7.27(5H, s) |
| 123a | 0.88–2.50(8H, m), 1.32(9H, s), 3.23–3.97(1H, m), 4.60(2H, s), 5.93–6.53(1H, bs), 7.27(5H, s) |
| 134a | 0.98–2.62(10H, m), 3.80(3H, s), 3.88–4.35(1H,m) |
| 134b | 1.18–2.75(10H, m), 3.78(3H, s), 3.90–4.40(1H, m) |
| 153 | 1.35–2.87(12H, m), 1.30(3H, t, J=7.0Hz), 3.80–4.40(1H, m), 4.25(2H,q, J=7.0Hz) |
| 164 | Mass/m/Z=192(M$^+$) |
| 168 | 0.84–3.02(8H, m), 1.3(3H, t, J=7Hz), 3.25–4.48(1H.m), 4.25(2H, q, J=7Hz |
| 242 | 1.3(3H, t.J=7Hz), 1.5–217(2H, m), 2.17, 2.67(1H, m), 3.22–4.53(5H, m) 4.24(2H, q, J=7Hz)ppm |

Process for synthesis of compound represented by the formula (II)

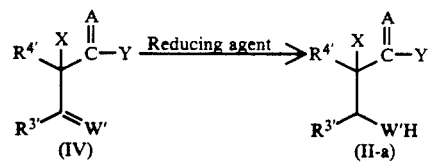

(wherein R$^{3'}$, R$^{4'}$, X, A and Y are as defined hereinbefore, and W' represents an oxygen atom or sulfur atom).

In the above reaction formula of the Process B-1, a compound represented by the formula (II-a) can be prepared by reacting a halogenated ketone derivative or halogenated thione derivative of the formula (IV) with a reducing agent without any solvents or in the presence of a suitable solvent in the temperature range of −78° C. to the boiling point of the solvent for 1 to 24 hours using a suitable base.

When a solvent is used in this reaction, examples thereof include, for example, alcoholic solvents such as methanol, ethanol and isopropyl alcohol, hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc.

Further, examples of the reducing agent include organotin compounds such as triphenyltin hydride, diphenyltin hydride, tri-n-butyltin hydride and di-nbutyltin hydride metal hydrogen complexes and their related compounds such as lithium tri-tert-butylaluminum hydride, sodium borohydride, sodium trimethoxyborohydride, sodium borohydride sulfur, sodium cyanoborohydride, lithium borohydride, calcium triethylborohydride, potassium borohydride, potassium triisopropoxy borohydride, potassium tri-sec-butylborohydride, zinc borohydride, tetramethylammonium borohydride and tetran-butylammonium cyanoborohydride, diborane and borane complexes such as a dimethylamine-borane complex, a trimethylamine-borane borane complex, a triethylamineborane complex, a tert-butylamine-borane complex, a pyridine-borane complex, a dimethylsulfide-borane complex, a morpholine-borane complex and a 1,4-oxathiane-borane complex, aklylborances such as dicylohexylborane and 9-boradicyclo[3,3,1]nonane, metal alkoxides such as aluminum isopropoxide and aluminum tert-butoxide, catalytically hydrogenating catalysts such as palladium carbon, platinum oxide and Raney nickel, etc.

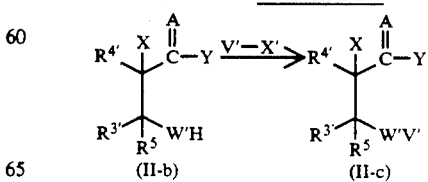

(wherein R$^{3'}$, R$^{4'}$, R$^5$, X, A and Y are as defined hereinbefore, and W' represents an oxygen atom or sulfur atom, V' has the same meaning as the above V but a hydrogen atom is excluded, and X' represents a halogen atom).

In the above reaction formula of the Process B-2, a compound represented by the formula (II-c) can be prepared by reacting a halogenated alcohol or thiol derivative of the formula (II-b) with a compound represented by V'-X' without any solvents or in the presence of a suitable solvent in the temperature range of −78° C. to the boiling point of the solvent for 1 to 24 hours using a suitable base.

When a solvent is used in this reaction, examples thereof include, for example, hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc.

Further, examples of the base include carbonates such as sodium carbonate and potassium carbonate, metal hydroxides such as sodium hydroxide and potassium hydroxide, metal alcoholates such as sodium methylate and sodium ethylate, alkali metal hydrides such as sodium hydride and potassium hydride, and lithium amides such as lithium diethylaminde, lithium diisopropylamide and lithium bis(trimethylsilyl)amide

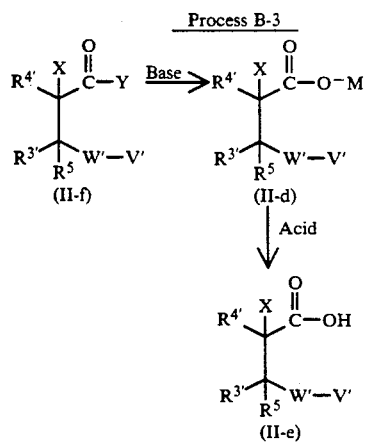

(wherein $R^{3'}$, $R^{4'}$, $R^5$, X, Y and V' are as defined hereinbefore, W' represents an oxygen atom or sulfur atom and M represents a cation of an alkyl metal or alkaline earth metal).

In the above reaction formula of the Process B-3, a compound represented by the formula (II-d) can be prepared by reacting a compound represented by the formula (II-f) with a suitable base in the presence of a suitable solvent in the temperature range of room temperature to the boiling point of the solvent for 1 to 24 hours. Further, a compound represented by the formula (II-e) can be prepared by treating a compound represented by the formula (II-d) with an acid. Examples of the solvent use in this reaction include alcoholic solvents such as methanol, ethanol and isopropyl alcohol, hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc. Further, examples of the base include carbonate salts such as sodium carbonate, potassium carbonate, sodium bicarbonate and potassium bicarbonate, metal hydroxides such as sodium hydroxide and potassium hydroxide, metal alcoholates such as sodium methylate and sodium ethylate, alkali metal hydrides such as sodium hydride and potassium hydride.

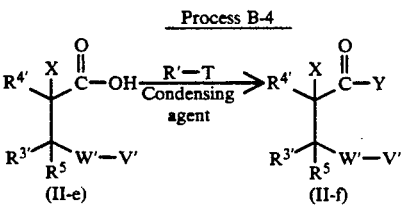

(wherein $R^{3'}$, $R^{4'}$, $R^5$, X, Y and V' are as defined hereinbefore, and W' represents an oxygen atom or sulfur atom, R' represents a group which is allowed to convert to Y through this reaction and T represents a hydroxyl group, mercapto group, amino group or halogen atom).

In the above reaction formula of the Process B-4, a compound represented by the formula (II-f) can be prepared by reacting a carboxylic acid of the formula (II-e) with a suitable alkyl halide, alcohol mercaptane or amine (R-T) without any solvents or in the presence of a suitable solvent in the temperature range of under ice cooling to the boiling point of the solvent for 1 to 24 hours using a suitable condensing agent. Examples of the solvent use in this reaction include hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc.

Further, examples of the condensing agent include, carbonate salts such as sodium carbonate, potassium carbonate, sodium bicarbonate and potassium bicarbonate, metal hydroxides such as sodium hydroxide and potassium hydroxide, metal alcoholates such as sodium methylate and sodium ethylate, alkali metal hydrides such as sodium hydride and potassium hydride, organic bases such as diazabicycloundecene, and dehydrating agents such as dicyclohexylcarbodiimide.

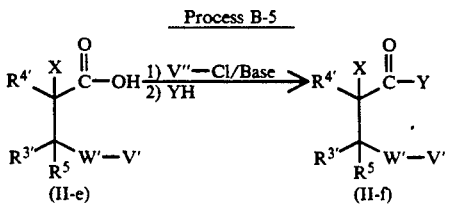

(wherein $R^{3'}$, $R^{4'}$, $R^5$, X, Y and V' are as defined hereinbefore, and W' represents an oxygen atom or sulfur atom, and V''' represents a lower alkoxycarbonyl group, lower alkylsulfonyl group, or optionally substituted arylsulfonyl group).

In the above reaction formula of the Process B-5, a compound represented by the formula (II-f) can be prepared by reacting a carboxylic acid of the formula (II-e) with a suitable activating agent represented by V'''-Cl to give an active intermediate and reacting the intermediate with a corresponding alcohol, amine or thiol in the absence or presence of a catalyst. Examples of the solvent use in the reaction include hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc. Examples of the base include organic bases such as pyridine and triethylamine, and examples of the activating agent include alkyl chloroformates such as methyl chloroformate and ethyl chloroformate, arylsulfonyl chloride such as benzenesulfonyl chloride and toluenesulfonyl chloride, etc. Examples of the catalyst include dimethylaminopyridine, 4-pyrrolidinopyridine, etc.

Process for the synthesis of compound represented by the formula (I)

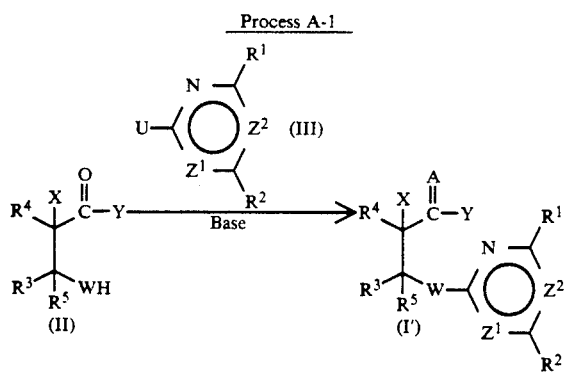

(wherein X, A, W, Y, $R^1$, $R^2$, $R^3$, $R^4$, $R^5$, $Z^1$ and $Z^2$ are as defined hereinbefore, and U represents a halogen atom, lower alkylsulfonyl group or arylalkylsulfonyl group).

In the above reaction formula of the process A-1, a compound represented by the formula (I') can be prepared by reacting a halogenated alcohol, halogenated thiol or halogenated enethiol derivative of the formula (II) with a substituted pyrimidine or triazine of the formula (III) without any solvents or in the presence of a suitable solvent in the temperature range of −78° C. to the boiling point of the solvent for 1 to 24 hours using a suitable base.

When a solvent is used in this reaction, examples thereof include, for example, hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc.

Further, examples of the base include carbonate salts such as sodium carbonate and potassium carbonate, metal hydroxides such as sodium hydroxide and potassium hydroxide, metal alcoholates such as sodium methylate and sodium ethylate, alkali metal hydrides such as sodium hydride and potassium hydride, and lithium amides such as lithium diethylamide, lithium diisopropylamide and lithium bis(trimethylsilyl)amide.

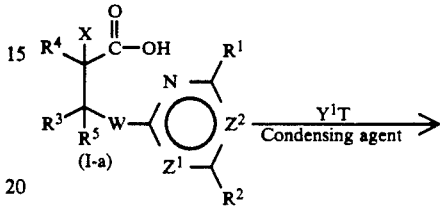

wherein X, A, W, Y, $R^1$, $R^2$, $R^3$, $R^4$, $R^5$, $Z^1$ and $Z^2$ are as defined hereinbefore, $Y^1$ represents a lower alkyl, lower alkenyl, lower alkynyl, aryl, aralkyl, lower cycloalkyl, lower cycloalkenyl, pyridyl, furylmethyl, furyl, thienyl or group N

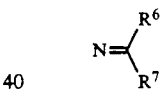

(wherein $R^6$ and $R^7$ are as defined herein before) each optionally substituted with halogen atom(s), lower alkyl, hydroxyl, lower alkoxy, lower alkylthio, lower alkoxycarbonyl, lower alkylcarbonyl, cyano, nitro or azido, and T represents a hydroxyl group, mercapto group or halogen atom].

In the above reaction formula of the Process A-2, a compound represented by the formula (I-b) can be prepared by reacting a carboxylic acid of the formula (I-a) with a compound $Y^1T$ which has a halogen atom, hydroxyl group or mercapto group in the presence of a suitable condensing agent without any solvents or in the presence of a suitable solvent in the temperature range of under ice cooling to the boiling point of the solvent for 1 to 24 hours. Examples of the solvent used in the reaction include hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc. Further, examples of the condensing agent include carbonate salts such as sodium carbonate, potassium carbonate, sodium bicarbonate and potassium bicarbonate, metal hydroxides such as sodium hydroxide and potassium hydroxide, metal alcoholates such as sodium methylate and sodium ethylate, alkali metal hydrides such as sodium hydride and potassium hydride, organic bases such as diazabicycloundecene, and dehydrating and condensing agents such as dicylohexylcarbodiimide.

Process A-3

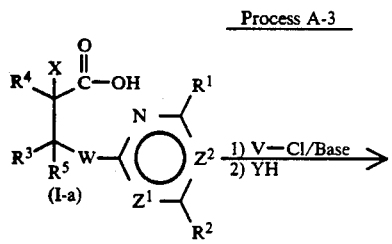

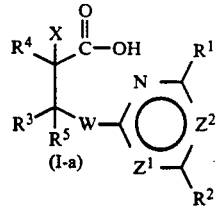

(wherein X, W, Y, $R^1$, $R^2$, $R^3$, $R^4$, $R^5$, $Z^1$ and $Z^2$ are as defined hereinbefore, and V represents a lower alkoxycarbony, lower alkylsulfonyl or optionally substituted arylsulfonyl group).

In the above reaction formula of the Process A-3, a compound represented by the formula (I-c) can be prepared by reacting a carboxylic acid of the formula (I-a) with a suitable activating agent represented by V-Cl in the presence of a suitable base to give first an active intermediate and then reacting the intermediate with a corresponding alcohol, amine or thiol in the presence or absence of a catalyst. Examples of the solvent use in the reaction include hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc. Examples of the base include organic bases such as pyridine and triethylamine. Examples of the activating agent include alkyl chloroformates such as methyl chloroformate and ethyl chloroformate, and arylsulfonyl chlorides such as benzenesulfonyl chloride and toluenesulfonyl chloride. Examples of the catalyst include dimethylaminopyridine 4-pyrrolidinopyridine, etc.

-continued
Process A-4

(wherein X, W, Y, $R^1$, $R^2$, $R^3$, $R^4$, $R^5$, $Z^1$ and $Z^2$ are as defined hereinbefore, and M represents a cation of an alkali metal or alkaline earth metal).

In the above reaction formula of the Process A-4, a compound represented by the formula (I-f) can be prepared by reacting a compound represented by the formula (I-d) with a suitable base in the presence of a suitable solvent in the temperature range of room temperature to boiling point of the solvent for 1 to 24 hours. Further, a compound represented by the formula (I-a) can be prepared by treating a compound represented by the formula (I-f) with an acid. Examples of the solvent use in the reaction include alcoholic solvents such as methanol, ethanol and isopropyl alcohol, hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc. Further, examples of the base include carbonate salts such as sodium carbonate potassium bicarbonate, metal hydroxides such as sodium hydroxide and potassium hydroxide, metal alcoholates such as sodium methylate and sodium ethylate, alkali metal hydrides such as sodium hydride and potassium hydride, etc.

When in the general formula (I) A represents an oxygen atom and Y represents $$-N\begin{matrix}R^8\\R^9\end{matrix}$$

and particularly $R^8$ represents a hydrogen atom, a substituent $R^{12}$ can be introduced by the following process A-5.

Process A-4

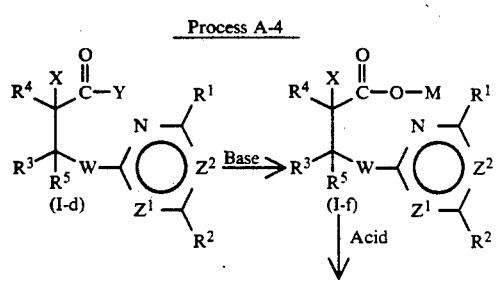

Process A-5

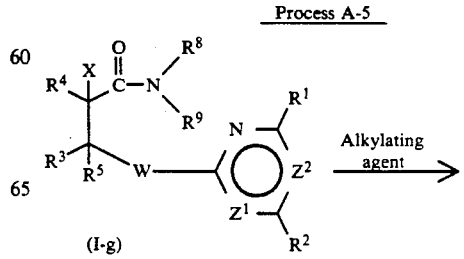

-continued

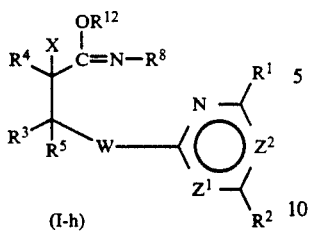

(I-h)

(wherein X, W, A, $Z^1$, $Z^2$, $R^1$, $R^2$, $R^3$, $R^4$, $R^5$, $R^8$ and $R^9$ are as defined hereinbefore, and $R^{12}$ represents a lower alkyl group).

In the above reaction formula of the process A-5, a compound represented by the formula (I-h) can be prepared by reacting an amide derivative of the formula (I-g) with an alkylating agent without any solvents or in the presence of a suitable solvent in the temperature range of −78° C. to the boiling point of the solvent for 1 to 48 hours, if necessary using a suitable base.

When a solvent is used in this reaction, examples thereof include, for example, hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, acetonitrile, water, etc. Further, examples of the base include carbonate salts such as sodium hydroxide and potassium hydroxide, metal alcoholates such as sodium methylate and sodium ethylate, alkali metal hydrides such as sodium hydride and potassium hydride, and lithium amides such as lithium diethylamide, lithium diisopropylamide and lithium bis(trimethylsilyl)amide.

Further, examples of the alkylating agent include lower alkyl halides such as methyl iodide, methyl bromide, ethyl iodide and ethyl bromide, diazoalkanes such as diazomethane and diazoethane, sulfonic acid esters such as methyl trifluoromethanesulfonate, ethyl trifluoromethanesulfonate and methyl fluorosulfonate, and alkyloxonium salts such as trimethyloxonium tetrafluroborate and triethyloxonium tetrafluoroborate.

Process A-6

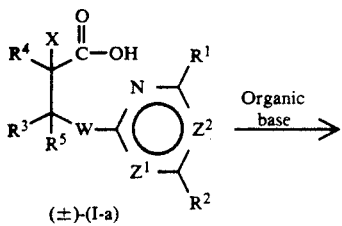

(±)-(I-a) →Organic base→

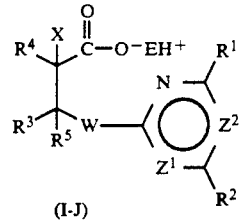

(I-J)

↓ Acid

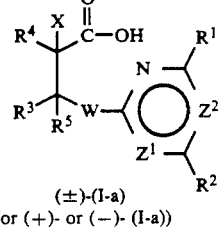

(±)-(I-a)
(or (+)- or (−)- (I-a))

(wherein $R^3$, $R^5$, $R^6$, X, W, $Z^1$, $Z^2$, $R^1$ and $R^2$ are as defined hereinbefore, and E represents an organic amine in the form of a racemic compound or optically active compound).

In the above reaction formula of the Process A-6, a salt of the formula (I-j) can be prepared by reacting a compound of the formula (±)-(I-a) with a suitable organic base E in the presence of a suitable solvent in the temperature range of room temperature to the boiling point of the solvent. This salt can be reconverted to (±)-(I-a) by reaction with a suitable acid.

Further, an optically active salt (I-j) can be prepared by reacting a racemic compound represented by the above formula (±)-(I-a) with a suitable optically active amine E in the presence of a suitable solvent in the temperature range of room temperature to the boiling point of the solvent to give a diasteromer mixture and recrystallizing this mixture in a suitable solvent in the temperature range of room temperature to the boiling point of the solvent, followed by purification. Further, (+)- or (−)- (I-a) can be prepared by decomposing this salt with a suitable acid in the presence of a suitable solvent in the temperature range of room temperature to the boiling point of the solvent.

When a solvent is used in this reaction, examples thereof include hydrocarbonic solvents such as benzene, toluene and xylene, halogenated hydrocarbonic solvents such as dichloromethane and chloroform, etherial solvents such as diethyl ether, diisopropyl ether, tetrahydrofuran and 1,4-dioxane, ketonic solvents such as acetone and methyl ethyl ketone, ester solvents such as methyl acetate and ethyl acetate, aprotic polar solvents such as dimethylformamide, dimethylsulfoxide and dimethylacetamide, alcoholic solvents such as methyl alcohol, ethyl alcohol, n-propyl alcohol, isopropyl alcohol and tert-butyl alcohol, acetonitrile, water, etc.

Further, examples of the amine include ammonia, alkylamines such as methylamine, ethylamine, 1-propylamine, isopropylamine, n-butylamine, sec-butylamine, iso-butylamine, tert-butylamine, n-hexylamine, n-octylamine, n-nonylamine and n-decylamine, and organic amines in (+) form or (−) form such as brucine, cinchonidine, dehydroabiethylamine, 1-phenylethylamine, morphine, deoxyephedrine, strychnine, quinine, amphetamine, threo-2-amino-1-paranitrophenyl-1,3-propanediol and 1-(1-naphthyl)ethylamine.

Further, examples of the acid include mineral acids such as hydrochloric acid, sulfuric acid and phosphoric acid.

Process A-7

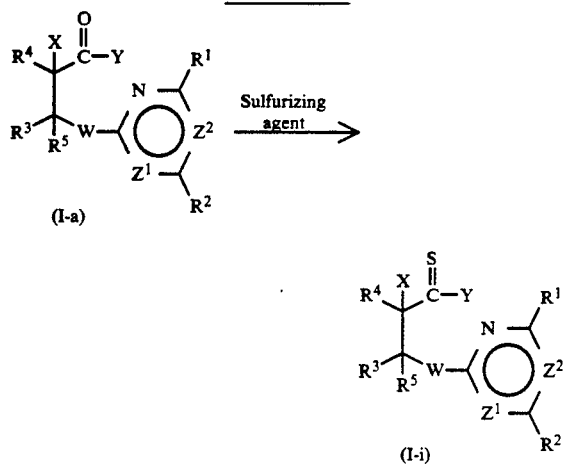

(wherein $R^1$, $R^2$, $R^3$, $R^4$, $R^5$, X, W, $Z^1$, $Z^2$ are as defined hereinbefore).

In the above reaction formula of the Process A-7, a compound represented by the formula (I-i) can be prepared by reacting a compound of the formula (I-a) with a suitable sulfurizing agent without any solvents on in the presence of a suitable solvent in the temperature range of room temperature to the boiling point of the solvent for 1 to 24 hours.

When a solvent is used in this reaction, examples thereof include, for example, hydrocarbonic solvents such as benzene, toluene and xylene, organic bases such as pyridine and triethylamine, halogenated hydrocarbonic solvents such as dichloromethane and chloroform, etherial solvents such as diethyl ether, diisopropyl ether, tetrahydrofuran and 1,4-dioxane, acetonitrile, water, etc.

Further, examples of the sulfurizing agent include Lawesson's reagent, phosphorus pentasulfide, hydrogen sulfide, etc.

EXAMPLE 1

Preparation of 1-fluoro-2-hydroxy-1-cyclopentanecarboxylic acid methyl ester in cis form (compound number 2a)

First, methyl 1-fluoro-2-oxocyclopentanecarboxylate was prepared from methyl 2-oxocyclopentanecarboxylate referring to the process described in Tetrahedron Letters 27 (37), 4465-4468 (1986). Then, 2.3 g (0.032 mol) of trimethylamine-borane complex and 5.0 g (0.031 mol) of the methyl 1-fluoro-2-oxocyclopentanecarboxylate were added to 50 ml of dry diglyme, the resulting solution was cooled to 0° C., and while it as stirred in the stream of nitrogen, 0.8 ml of boron trifluoride etherate was added dropwise. The resulting solution was stirred at room temperature for 1 hour and then poured into a saturated aqueous sodium bicarbonate solution, followed by extraction with ether. The ether layer was washed with water and dried over anhydrous magnesium sulfate, and the solvent was distilled away to obtain 4.5 g (yield: 89%) of the objective methyl 1-fluoro-2-hydroxycyclopentanecarboxylate in cis form (compound number 2a; the substance such that the substituent at the 2-position is supposed to take cis configuration when the methoxycarbonyl group at the 1-position is taken as a standard) which contains almost no the same in trans form.

$^1$H-NMR ($\delta$, CDCl$_3$): 1.33-3.03 (6H,m), 3.82 (3H,S), 4.07-4.60 (1H,m) ppm

EXAMPLE 2

Preparation of 1-fluoro-2-hydroxy-1-cyclopentanecarboxylic acid methyl ester in trans form (compound number 2b)

3.1 ml (0.031 mol) of dimethylsulfide-borone complex was added to 50 ml of dry tetrahydrofuran at room temperature in the stream of nitrogen. The resulting solution was cooled to 0° C. and 5.0 g (0.031 mol) of 1-fluoro-2-oxocyclopentanecarboxylic acid methyl ester synthesized according to the literature shown in Example 1 was added dropwise. The mixture was stirred at room temperature for 1 hour, the solvent was distilled away under reduced pressure, and the remaining liquid was poured into water, followed by extraction with ethyl acetate. The ethyl acetate layer was washed with water and dried over anhydrous magnesium sulfate, and the solvent was distilled away to obtain 3.7 g (yield: 73%) of a stereoisomer mixture comprising methyl 1-fluoro-2-oxocyclopentanecarboxylate in cis form (compound number 2a; the substance such that the substituent at the 2-position is supposed to take cis configuration when the methoxycarbonyl group at the 1-position is taken as a standard) and same in the trans form (compound 2b; the substance such that the substituent at the 2-position is supposed to take trans configuration when the methoxycarbonyl group at the 1-position is taken at a standard). As a result of analysis by gas chromatography, the formation ratio of cis/trans was 9/91. This mixture was further purified by silica gel column chromatography (developing solvent: hexane/ethyl acetate=10/1) to obtain 3.3 g (yield: 65%) of the objective methyl 1-fluoro-2-hycroxycyclopentanecarboxylate in trans form (compound number 2b).

$^1$H-NMR ($\delta$, CDCl$_3$): 1.30-2.90 (6H,m), 3.80 (3H,S), 4.03-4.63 (1H,m) ppm

EXAMPLE 3

Preparation of 1-fluoro-2-hydroxy-1-cyclohexanecarboxylic acid ethyl ester cis form and trans form (compound numbers 73a and 73b)

3.1 ml (0.031 mol) of dimethyl sulfide-borone complex was added to 50 ml of dry tetrahydrofuran at room temperature in the stream of nitrogen. The resulting solution was cooled to 0° C. and 5.8 g (0.031 mol) of 1-fluoro-2-oxocyclohexanecarboxylic acid ethyl ester synthesized according to the process of Example 1 was added dropwise. The mixture was stirred at room temperature for 1 hour, the solvent was distilled away under reduced pressure, the remaining liquid was poured into water, and the mixture was extracted with ethyl acetate. The ethyl acetate layer was washed with water and dried over anhydrous magnesium sulfate, and the solvent was distilled away to obtain 4.3 g (yield: 85%) of a stereoisomer mixture comprising 1-fluoro-2-hydroxycyclohexanecarboxylic acid ethyl ester in cis form (compound number 73a; the substance such that the substituent at the 2-position is supposed to take cis configuration when the ethoxycarbonyl group at the 1-position is taken as a standard) and the same in trans form (compound number 73b; the substance such that the substituent at the 2-position is supposed to take trans configuration when the ethoxycarbonyl group at the 1-position is taken as a standard). This mixutre was further purified by silica gel column chromatography (developing solvent: hexane/ethyl acetate=10:1) to obtain 1.6 g (yield: 27.2%) of the objective 1-fluoro-2-hydroxycyclohexanecarboxylic acid ethyl ester in cis form (compound number 73a) and 2.4 g (yield: 40.7%) of the same in trans form (compound number 73b).

EXAMPLE 4

Preparation of 1-fluoro-2-hydroxy-1-cycloheptanecarboxylic acid methyl ester in cis form and trans form (compound numbers 134a and 134b)

First, a raw material 1-fluoro-2-oxocycloheptanecarboxylic acid methyl ester was synthesized as follows referring to the process of the literature shown in Example 1. 0.88 g (22 mmol) of sodium hydride (60% suspension in mineral oil) was added to 45 ml of dry tetrahydrofuran, and while the mixture was stirred in the range of −5° C. to 0° C., 3.4 g (20 mmol) of 2-oxocycloheptanecarboxylic acid methyl ester was added dropwise. At the time when the generation of hydrogen gas ceased, 5.8 g (20 mmol) of N-fluoro-2,4,6-trimethylpyridinium triflate was added, the temperature of the mixture was allowed to get back to room temperature, and stirring was continued for further 2 hours. The tetrahydrofuran was distilled away, the contents were poured into a 1N diluted aqueous hydrochloric acid water, and the mixture was extracted with ethyl acetate. The ethyl acetate layer was thoroughly washed with a diluted aqueous hydrochloric acid solution, and further successively washed with saturated saline, a saturated aqueous sodium bicarbonate solution and saturated saline. After drying with anhydrous magnesium sulfate, the solvent was distilled away to obtain 2.63 g (yield: 70%) of the raw material 1-fluoro-2-oxo-1-cycloheptanecarboxylic acid methyl ester.

25 ml of methanol was cooled to 5° C. and 70 mg (1.8 mmol) of sodium hydroxide and 0.14 g (3.7 mmol) of sodium borohydride were added. To the resulting solution was added dropwise in the range of 5° C. to 10° C. 10 ml of a methanol solution of 2.5 g (13.3 mmol) of the 1-fluoro2-oxo-1-cycloheptanecarboxylic acid methyl ester. After stirring at room temperature for 2 hours, the contents were poured into saturated saline, followed by extraction with ethyl acetate. The extract was successively washed with diluted hydrochloric acid, saline, a saturated sodium bicarbonate solution and saline. The ethyl acetate layer was dried over anhydrous sodium sulfate and the solvent was distilled away to obtain 2.3 g of the crude product. The crude product was purified by silica gel column chromatography (developing solvent: hexane/isopropyl alcohol=99/1) to obtain 1.4 g (yield: 55.4%) of 1-fluoro-2-hydroxycycloheptanecarboxylic acid methyl ester in cis form (compound number 134a; the substance such that the substituent at the 2-position is supposed to take cis configuration when the methoxycarbonyl group at the 1-position is taken as a standard):

$^1$H-NMR ($\delta$, CDCl$_3$): 0.98–2.62 (10H,m), 3.80 (3H,S), 3.88–4.35 (1H,m) ppm and 0.6 g (yield: 23.7%) of the same in trans form (compound number 134b; the substance such that the substituent at the 2-position is supposed to take trans configuration when the methoxycarbonyl group at the 1-position is taken as a standard):

$^1$H-NMR ($\delta$, CDCl$_3$): 1.18–2.75 (10H,m), 3.78 (3H,S), 3.90–4.40 (1H,m) ppm

EXAMPLE 5

Preparation of 1-fluoro-2-hydroxy-1-cyclooctanecarboxylic acid ethyl ester (compound number 153)

2-Oxo-1-cyclooctanecarboxylic acid ethyl ester was synthesized from cyclooctanone according to the process disclosed in Organic Synthesis, collective volume 5, page 198 (1973). The obtained compound was fluorinated and reduced in the same manner as in Example 4 to obtain a mixture of 1-fluoro-2 hydroxycyclooctanecarboxylic acid ethyl ester in cis form (the substance such that the substituent at the 2-position is supposed to take cis configuration when the methoxycarbonyl group at the 1-position is taken as a standard) and the same in trans form (the substance such that the substituent at the 2-position is supposed to take trans configuration when the methoxycarbonyl group at the 1-position is taken as a standard).

$^1$H-NMR ($\delta$, CDCl$_3$): 1.35–2.87 (12H,m), 1.30 (3H,t,J=7.0Hz), 3.80–4.40 (1H,m), 4.25 (2H q,J=7.0Hz) ppm

EXAMPLE 6

Preparation of 2-acetoxy-1-fluoro-1-cyclopentanecarboxylic acid methyl ester in cis form (compound number 3a)

0.32 g (3 mmol) of acetic anhydride and a catalytic amount of concentrated sulfuric acid were added at room temperature to 0.5 g (3 mmol) of 1-fluoro-2-hydroxycyclopentanecarboxylic acid methyl ester in cis form (compound number 2a) synthesized in Example 1, and the mixture was stirred for 5 hours. The reaction solution was poured into ice water and extracted with ethyl acetate, and the extract was successively washed with saturated saline, a saturated aqueous sodium bicarbonate solution and saturated saline. The ethyl acetate layer was dried over anhydrous magnesium sulfate and the solvent was distilled away to obtain 0.45 g (yield: 72%) of the objective 2-acetoxy-1-fluoro-1-cyclopentanecarboxylic acid methyl ester in cis form (compound number 3a).

$^1$H-NMR ($\delta$, CDCl$_3$): 1.50–2.93 (6H,m), 2.02 (3H,S), 3.77 (3H,s), 5.00–5.50 (1H,m) ppm

EXAMPLE 7

Preparation of 2-benzoyloxy-1-fluoro-1-cyclopentanecarboxylic acid methyl ester in cis form (compound number 4a)

.045 g (3 mmol) of benzoyl chloride was added under ice cooling to a mixture of 0.5 g (3 mmol) of the 1-fluoro-2-hydroxy-1-cyclopentanecarboxylic acid methyl ester in cis form (compound number 2a) synthesized in Example 1 and 2 ml of pyridine, the temperature of the mixture was brought back to room temperature, and the mixture was stirred for 5 hours. The reaction solution was poured into a diluted aqueous hydrochloric acid solution and extracted with ethyl acetate and the extract was successively washed with saturated saline, a saturated aqueous sodium bicarbonate solution and saturated saline. The ethyl acetate layer was dried over anhydrous magnesium sulfate and the solvent was distilled away to obtain 0.68 g (yield: 84%) of the objective 2-benzoyloxy-1-fluoro-cyclopentanecarboxylic acid methyl ester in cis form (compound number 4a).

$^1$H-NMR ($\delta$, CDCl$_3$): 1.47–3.03 (6H,m), 3.73 (3H,S), 5.20–5.73 (1H,s), 7.20–8.22 (5H,m) ppm

EXAMPLE 8

Preparation of 1-fluoro-2-methanesulfonyloxy-1-cyclopentanecarboxylic acid methyl ester in cis form (compound number 5a)

0.36 g (3 mmol) of methanesulfonyl chloride was added under ice cooling to a mixture of 0.5 g (3 mmol) of 1-fluoro-2-hydroxy-1-cyclopentanecarboxylic acid methyl ester in cis form (compound number 2a) synthesized in Example 1 and 2 ml of pyridine, and the mixture was stirred at 0° C. for 5 hours. The reaction solution was poured into a ice water and extracted with ether, and the ether layer was washed with cold water. The ether layer was dried over anhydrous magnesium sulfate and the solvent was distilled away to obtain 0.59 g (yield: 80%) of the desired 2-methanesulfonyloxy-1-fluoro-1-cyclopentanecarboxylic acid methyl ester in cis form (compound number 5a).

$^1$H-NMR ($\delta$, CDCl$_3$): 1.52–2.63 (6H,m), 3.00 (3H,s), 3.81 (3H,s), 4.80–5.28 (1H,m) ppm

EXAMPLE 9

Preparation of 1-fluoro-2-paratoluenesulfonyloxy-1-cyclopentanecarboxylic acid methyl ester in cis form (compound number 6a)

0.56 g (3 mmol) of paratoluenesulfonyl chloride was added under ice cooling to a mixture of 0.5 g (3 mmol) of 1-fluoro-2-hydroxy-1-cyclopentanecarboxylic acid methyl ester in cis form (compound number 2a) synthesized in Example 1 and 2 ml of pyridine, the temperature of the resulting mixture was brought back to room temperature, and mixture was stirred for 5 hours. The reaction solution was poured into a ice water and extracted with ether, and the extract was washed with cold water. The ether layer was dried over anhydrous magnesium sulfate and the solvent was distilled away to obtain 0.77 g (yield: 79%) of the objective 2-paratoluenesulfonyloxy-1-fluoro-1-cyclopentanecarboxylic acid methyl ester in cis form (compound number 6a).

$^1$H-NMR ($\delta$, CDCl$_3$): 1.37–2.37 (6H,m), 2.46 (3H,s), 3.70 (3H,s), 4.27–5.17 (1H,m), 7.00–8.20 (5H,m) ppm

EXAMPLE 10

Preparation of 1-fluoro-2-methoxy-1-cyclopentanecarboxylic acid methyl ester in trans form (compound number 13b)

0.12 g (3 mmol) of sodium hydride (60% suspension in mineral oil) was added to 5 ml of dry dimethylsulfoxide, and the mixture was cooled to 5° C. To the resulting solution was added dropwise 5 ml of the dimethylsulfoxide solution of 0.5 g (3 mmol) of 1-fluoro-2-hydroxy-1-cyclopentanecarboxylic acid methyl ester in trans form (compound number 2b) synthesized in Example 2, then 0.47 g (3.3 mmol) of methyl iodide was added. The temperature of the mixture was brought back to room temperature, and the mixture was stirred for 2 hours. The reaction solution was poured into a diluted aqueous hydrochloric acid solution and extracted with ethyl acetate, and the extract was successively washed with saturated saline, a saturated aqueous sodium bicarbonate solution and saturated saline. The ethyl acetate layer was dried over anhydrous magnesium sulfate, and the solvent was distilled away to obtain 0.33 g (yield: 62%) of the objective 2-methoxy-1-fluoro-1-cyclopentanecarboxylic acid methyl ester in trans form (compound number 13b).

$^1$H-NMR ($\delta$, CDCl$_3$): 1.42–2.68 (6H,m), 3.35 (3H,s), 3.80 (3H,s), 4.03–5.00 (1H,m) ppm

EXAMPLE 11

Preparation of 1-fluoro-2-methoxy-1-cyclopentanecarboxylic acid in trans form (compound number 12b)

0.35 g (2 mmol) of 1-fluoro-2-methoxy-1-cyclopentanecarboxylic acid methyl ester in trans form (compound number 13b) synthesized in Example 10 was dissolved in 5 ml of methanol, and 8 ml of a 5% aqueous potassium hydroxide solution was added, and mixture was stirred at room temperature for 2 hours. The reaction solution was poured into a diluted aqueous hydrochloric acid solution and extracted with ether, and ether layer was dried over anhydrous magnesium sulfate, and the solvent was distilled away to obtain 0.26 g (yield: 81%) of the objective 2-methoxy-1-fluoro-1-cyclopentanecarboxylic acid in trans form (compound number 12b).

$^1$H-NMR ($\delta$, CDCl ): 1.43–2.60 (6H,m), 3.43 (3H,s), 3.77–4.67 (1H,m), 8.47 (1H,s) ppm

EXAMPLE 12

Preparation of 1-fluoro-2-methoxy-1-cyclopentanecarboxylic acid tertiary butyl ester in cis form (compound number 20a)

The 1-fluoro-2-hydroxy 1-cyclopentanecarboxylic acid methyl ester in cis form (compound number 2a) synthesized in Example 1 was methylated in the same manner as in Example 10 and further hydrolyzed in the same manner as in Example 11 to obtain 1-fluoro-2-methoxy-1-cyclopentanecarboxylic acid in cis form (compound number 12a). 0.4 g (2.7 mmol) of this carboxylic acid, 0.20 g (2.7 mmol) of tertiary butyl alcohol, 0.56 g (3.7 mmol) of dicyclohexylcarbodiimide and 15 mg of 4,4-dimethylaminopyridine were mixed in 5 ml of ether and stirred at room temperature for 2 hours. The reaction solution was filtered, ether was added to the filtrate, and the mixture was successively washed with a diluted hydrochloric acid solution, saturated saline, a saturated aqueous sodium bicarbonate solution and saturated saline. The ether layer was dried over anhydrous magnesium sulfate, and the solvent was distilled away to obtain 0.31 g (yield: 56%) of the objective 2-methoxy-1-fluoro-1-cyclopentanecarboxylic acid tertiary butyl ester in cis form (compound number 20a).

$^1$H-NMR ($\delta$, CDCl$_3$): 1.47–2.80 (6H,m), 1.53 (9H,s), 3.37 (3H,s), 3.57–4.37 (1H,m) ppm

EXAMPLE 13

Preparation of 1-fluoro-2-methoxy-1-cyclopentanecarboxylic acid tertiary butylamide in cis form (compound number 29a)

0.4 g (2.7 mmol) of 1-fluoro-2-methoxy-1-cyclopentanecarboxylic acid in cis form (compound number 12a) disclosed in Example 12 and 0.27 g (2.7 mmol) of triethylamine were dissolved in 10 ml of tetrahydrofuran, and the solution was cooled to 0° C. 0.29 g (2.7 mmol) of ethyl chlorocarbonate was added dropwise, the mixture was stirred at 0° C. for 1 hour, 0.24 g (3.2 mmol) of tertiary butylamine was add, and the mixture was further stirred at room temperature for 1 hour. The reaction mixture was poured into water and extracted with ether, and the extract was washed with saturated saline. The ether layer was dried over anhydrous magnesium sulfate, and the solvent was distilled away to obtain 0.3 g (yield: 55%) of the objective 1-fluoro-2-methoxy-1-cyclopentanecarboxylic acid tertiary butylamide in cis form (compound number 29a).

$^1$H-NMR ($\delta$, CDCl$_3$): 1.43–2.57 (6H,m), 1.39 (9H,s), 3.37 (3H,s), 3.83–4.28 (1H,m) ppm

EXAMPLE 14

Preparation of 1-fluoro-2-methoxy-1-cyclopentanecarboxylic acid tertiary butyl thiol ester in trans form (compound number 38b)

0.4 g (2.7 mmol) of 1-fluoro-2-methoxy-1-cyclopentanecarboxylic acid in trans form (compound number 12b) synthesized in Example 11 and 0.24 g (2.7 mmol) of tertiary butyl thiol were dissolved in 5 ml of ether, 0.56 g (2.7 mmol) of dicyclohexylcarbodiimide and 15 mg of 4,4-dimethylaminopyridine were added, and the mixture was stirred at room temperature for 2 hours. The reaction solution was filtered, ether was added to the filtrate, and the mixture was successively washed with a diluted aqueous hydrochloric acid solution, saturated saline, a saturated aqueous sodium bicarbonate solution and saturated saline. The ether layer was dried over anhydrous magnesium sulfate, and the solvent was distilled away to obtain 0.48 g (yield: 83%) of the objective 2-methoxy-1-fluoro-1-cyclopentanecarboxylic acid tertiary butyl thiol ester in trans form (compound number 38b).

$^1$H-NMR ($\delta$, CDCl$_3$): 1.30–2.60 (6H,m), 1.48 (9H,s), 3.33 (3H,s), 3.42–4.37 (1H,m) ppm

EXAMPLE 15

Preparation of 2-benzyloxy-1-fluoro-1-cyclohexanecarboxylic acid ethyl ester in trans form (compound number 107b)

0.5 g (3 mmol) of 1-fluoro-2-hydroxy-1-cyclohexanecarboxylic acid ethyl ester in trans form (compound number 73b) synthesized in Example 3 was dissolved in 5 ml of tetrahydrofuran, the mixture was cooled to 0° C., and 0.12 g (3 mmol) of sodium hydride (60% suspension in mineral oil) was added. At the time when the generation of hydrogen gas ceased, 11 mg (3 mmol) of tetra-n-butylammonium iodide and 0.52 g (3 mmol) of benzyl bromide were successively added. After stirring at room temperature for 5 hours, the reaction solution was poured into a diluted aqueous hydrochloric acid solution and extracted with ethyl acetate. The ethyl acetate layer was successively washed with saturated saline, a saturated aqueous sodium bicarbonate solution and saline and dried over anhydrous magnesium sulfate, and the solvent was distilled away to obtain 0.3 g (yield: 36%) of the objective 2-benzyloxy-1-fluoro-1-cyclohexanecarboxylic acid ethyl ester in trans form (compound number 107b).

$^1$H-NMR ($\delta$, CDCl$_3$): 1.25 (3H,t,J=7Hz), 1.23–2.30 (8H,m), 3.23–4.00 (1H,m), 4.18 (2H,q,J=7Hz), 4.43 (1H,d,J=12Hz), 4.60 (1H,d,J=12Hz), 7.23 (5H,s) ppm

EXAMPLE 16

Preparation of 2-benzyloxy-1-fluoro-1-cyclo hexanecarboxylic acid in cis form (compound number 105a)

The 1-fluoro-2-hydroxy-1-cyclohexanecarboxylic acid ethyl ester in cis form (compound number 73a) synthesized in Example 3 was benzylated in the same manner as in Example 15 to obtain 2-benzyloxy-1-fluoro1-cyclohexanecarboxylic acid ethyl ester in cis form (compound number 107a). The compound hydrolyzed in the same manner as in Example 11 to obtain the objective 2-benzyloxy-1-fluoro-1-cyclohexanecarboxylic acid in cis form (compound number 105a).

$^1$H-NMR ($\delta$, CDCl$_3$): 0.80–2.85 (8H,m), 3.28–4.12 (1H,m), 4.60 (1H,s), 7.27 (5H,s) ppm

EXAMPLE 17

Preparation of ethyl 1-chloro-2-hydroxy-1-cyclohexanecarboxylate (compound number 168)

First, ethyl 1-chloro-2-oxocyclohexanecarboxylate was prepared from ethyl 2-oxocyclohexanecarboxylate referring to the process described in Organic Synthesis volume 4, page 162. 17 g (0.1 mol) of ethyl 2-oxocyclohexanecarboxylate was dissolved in 50 ml of carbon tetrachloride, and to the solution was added dropwise 14.8 g (0.11 mol) of sulfuryl chloride dissolved in 15 ml of carbon tetrachloride at 0° C. After stirring at room temperature for 2 hours, the reaction solution was poured into 100 ml of ice water, the mixture was extracted three times with 50 ml each of carbon tetrachloride, and the extract was washed twice with 75 ml each of saturated aqueous sodium bicarbonate and once with 75 ml of saturated saline and dried over anhydrous magnesium sulfate. The solvent was distilled away to obtain 18 g (yield: 88%) of ethyl 1-chloro-2-oxocyclohexanecarboxylate. 1.22 ml (2 mmol) of dimethyl sulfide borane was dissolved in 40 ml of tetrahydrofuran, and 2.5 g (12 mmol) of ethyl 1-chloro-2-oxocyclohexanecarboxylate was added dropwise at −5° C. to 0° C. After stirring at 0° C. for 1 hour, the solvent was distilled away under reduced pressure and the reaction solution was poured into 50 ml of ice water. The mixture was extracted three times with 50 ml each of ethyl acetate, and the resulting organic layer was washed once with 75 ml of saturated saline and dried over anhydrous magnesium sulfate. The solvent was distilled away to obtain 2.2 g of a stereoisomer mixture of ethyl 1-chloro-2-hydroxy-1-cyclohexanecarboxylate.

$^1$H-NMR: 0.84–3.02 (8H,m), 1.3 (3H,t,J=7Hz), 3.25–4.4.8 (1H,m), 4.25 (2H,q,J=7Hz) ppm

EXAMPLE 18

Preparation of methyl 1-fluoro-2-mercapto1-cyclohexanecarboxylate (compound number 164)

First, ethyl 1-fluoro-2-oxocyclohexanecarboxylate was synthesized according to the process described in Example 1. Then, referring to the process described in Comptes Rendus Hebdomadaire des Seances de l'Academie des Sciences Serie C No. 279, pages 529 to 531 (1974), 5.3 g (30 mmol) of this ester was dissolved in 50 ml of methanol was carried out at −78° C. for 2 hours and at −10° C. for 2 hours while hydrogen sulfide and hydrogen chloride were blown into the solution at the same time. The reaction solution was poured into ice water and extracted with ether. The ether layer was washed with saturated saline and the solvent was distilled away to obtain 4.0 g of the crude product of methyl 1-fluoro-2-mercapto-2-cyclohexenecarboxylate. This was dissolved in 30 ml of methanol, 200 mg (5 mmol) of sodium hydroxide was added, and the mixture was cooled to 0° C. 740 mg (20 mmol) of sodium borohydride was added and reaction was carried out at 0° C. for 2 hours. The reaction solution was poured into saturated saline and extracted with ether. The solvent was distilled away and the resulting product was purified by silica gel column chromatography (developing solvent: hexane/ethyl acetate =20/1) to obtain 580 mg (yield: 10%) of the objective methyl 1-fluoro-2-mercapto-1-cyclohexanecarboxylate.

Mass / M/z= 192 (M+)

EXAMPLE 19

Preparation of 3-ethoxycarbonyl-3-fluoro4-hydroxy-tetrahydro-4H-pyran (compound number 242)

First, 3-ethoxycarbonyl-tetrahydro-4H-pyran4-one was synthesized referring the process described in Japan Laid-Open Patent Publication No. 32080/90. Then this ester was fluorinated in the same manner as in Example 4 to prepare 3-ethoxycarbony-3-fluoro-tetrahydro-4H-pyran-4-one which was then reduced in the same manner as in the same example to prepare 3-ethoxycarbonyl-3-fluoro-4-hydroxytetrahydro-4H-pyran.

$^1$H-NMR: 1.3 (3H,t,J=7Hz), 1.5–2.17 (2H,m), 2.17–2.67 (1H,m), 3.22–4.53 (5H,m), 4.24 (2H,q,J=7Hz) ppm

EXAMPLE 20

Preparation of methyl 1-fluoro-2-(4,6-dimethoxypyrimidinyl-2-oxy)-1-cyclopentanecarboxylate in trans form (compound number 1003b)

1.55 g (9.6 mmol) of methyl 1-fluoro-2-hydroxycyclopentanecarboxylate in trans form prepared according to Example 1 was dissolved in 40 ml of dimethylformamide, to the solution were added 0.38 g (9.6 mmol) of sodium hydride (60% suspension in mineral oil) and 2.0 g (9.6 mmol) of 4,6-dimethoxy-2-methylsulfonylpyrimidine, and the mixture was stirred at room temperature for 5 hours. The reaction solution was poured in 150 ml of water and extracted three times with 50 ml each of ethyl acetate, and obtained organic layer was washed with water and dried over anhydrous magnesium sulfate. The solvent was distilled away to obtain 2.6 g of the crude product. This was purified by silica gel chromatography (developing solvent: hexane/ethyl acetate =10/1) to obtain 0.6 g (yield: 20.9%) of a substance supposed to be the desired methyl 1-fluoro-2-(4,6-dimethoxypyrimidinyl-2-oxy)-1-cyclopentanecarboxylate in trans form (compound number 1003b) (wherein the substituent at the 2-position takes trans configuration when the methoxycarbonyl group at the 1-position is taken as a standard).

$^1$H-NMR (δ, CDCl$_3$): 1.53–2.77 (m,6H), 3.71 (s,3H), 3.87 (s,6H), 5.3–5.76 (m,1H), 5.63 (s,1H) ppm

EXAMPLE 21

Preparation of ethyl 3-(4,6-dimethoxy-2-fluoro-2-methylbutylate in erythro from and threo form (compound numbers 5158a and 5158b)

First, ethyl 2-fluoro-2-methylacetoacetate was prepared from ethyl 2-methylacetoacetate referring to the process described in Tetrahedron Letters 27 (No. 37), 4456–4468 (1986). This compound was reduced, referring to the process described in Journal of Organic Chemistry 27, 4141 (1962), to prepare a stereoisomer mixture of ethyl 2-fluoro-3-hydroxy-2-methylbutylate. 1.6 g (10 mmol) of this alcohol was dissolved in 40 ml of dimethylformamide, to the solution were added 0.4 g (10 mmol) of sodium hydride (60% suspension in mineral oil) and 2.2 g (10 mmol) of 4,6-dimethoxy-2-methylsulfonylpyrimidine, and the mixture was stirred at room temperature for 3 hours. The reaction solution was poured into 150 ml of water and extracted three times with 50 ml each of ethyl acetate, and the obtained organic layer was washed with water and dried over anhydrous magnesium sulfate. The solvent was distilled to obtain 1.9 g of the crude product. This was purified by silica gel chromatography (developing solvent: hexane/ethyl acetate=10/1) to obtain 0.9 g (yield: 30%) of a substance supposed to be the objective ethyl 3-(4,6-dimethoxypyrimidinyl-2-oxy)-2-fluoro-2-methylbutyrate in erythro form (compound number 5158a), $^1$H-NMR (δ, CDCl$_3$): 1.40 (3H,t,J=7.0Hz), 1.38 (3H,d,J=6.0Hz), 1.63 (3H,d,J=20.2Hz), 3.92 (6H,s), 4.24 (2H,d,J=7.0Hz), 5.20–5.97 (1H,m), 5.68 (1H,s) ppm and 0.8 g (yield: 26%) of the same in threo form (compound number 5158b), $^1$H-NMR (δ, CDCl$_3$): 1.22 (3H,t,J=7.0Hz), 1.45 (3H,d,J=6.0Hz), 1.61 (3H,d,J=21.6Hz), 3.93 (6H,s), 4.22 (2H,d,J=7.0Hz), 5.03–5.88 (1H,m), 5.67 (1H,s) ppm.

EXAMPLE 22

Preparation of 4-(4,6-dimethoxypyrimidinyl-2-oxy)-3-ethoxycarbonyl-3-fluorotetrahydro-4H-pyran in cis form (compound number 6084a) and in trans form (compound number 6084b)

1.9 g (10 mmol) of a stereoisomer mixture of 3-ethoxycarbonyl-3-fluorotetrahydro-4H-4-hydroxy-pyran prepared in Example 19 was dissolved in 40 ml of dimethylformamide, to the solution were added 0.4 g (10 mmol) of sodium hydride (60% suspension in mineral oil) and 2.2 g (10 mmol) of 4,6-dimethoxy-2-methylsulfonylpyrimidine, and the mixture was stirred at 0° C. for 1 hour and at room temperature for 3 hours. The reaction solution was poured into 150 ml of water and extracted three times with 50 ml each of ethyl acetate, and the resulting organic layer was washed with water and dried over anhydrous magnesium sulfate. The solvent was distilled away to obtain 2.3 g of the crude product. This crude product was purified by silica gel chromatography (developing solvent: hexane/ethyl acetate=10/1) to obtain 1.1 g (yield: 34%) of the objective 4-(4,6-dimethoxypyrimidinyl-2-oxy)-3-ethoxycarbonyl-3-fluorotetrahydro-4H-pyran in cis form (compound number 6084a, the substance such that the substituent at the 2-position is supposed to take trans configuration when the ethoxycarbonyl group at the 1-position is taken as a standard), $^1$H-NMR (δ, CDCl$_3$): 1.14 (3H,t,J=7.2Hz), 2.01–2.33 (2H,m), 3.79–4.32 (4H,m), 3.91 (6H,s), 4.07 (2H,q,J=7.2Hz), 5.61–5.63 (1H,m), 5.72 (1H,s) ppm and 0.78 g (yield: 24%) of the same in trans form (compound number 6084b, the substance such the substituent at the 2-position is supposed to take trans configuration when the ethoxycarbonyl group at the 1-position is taken as a standard), $^1$H-NMR (δ, CDCl$_3$): 1.19 (3H,t,J=7.2Hz), 2.21–2.28 (2H,m), 3.6–4.21 (4H,m), 3.91 (6H,s), 4.05 (2H,q,J=7.2Hz), 5.6–5.72 (1H,m), 5.71 (1H,s) ppm.

EXAMPLE 23

Preparation of ethyl 1-chloro-2-(4,6-dimethoxypyrimidinyl-2-oxy)-1-cyclohexanecarbonylate in trans form (compound number 1455b)

2.1 g (10 mmol) of ethyl 1-chloro-2-hydroxyl-cyclohexanecarboxylate synthesized according to Example 17 was dissolved in 30 ml of dimethylformamide, to the solution were added 0.4 g (10 mmol) of sodium hydride (60% suspension in mineral oil) and 2.2 g (10 mmol) of 4,6-dimethoxy-2-methylsulfonylpyrimidine, and the mixture was stirred at room temperature for 2 hours. The reaction solution was poured into 150 ml of water and extracted three times with 50 ml each of ethyl acetate, the obtained organic layer was washed with water and dried over anhydrous magnesium sulfate, and the solvent was distilled away to obtain 2.9 g of the crude product. The crude product was purified by silica gel chromatography (developing solvent: hexane/ethyl acetate=12/1) to obtain 0.33 g (yield: 10%) of a substance (compound number 1455b) supposed to be the objective ethyl 1-chloro-2-(4,6-dimethoxypyrimidinyl-2-oxy)-1-cyclohexanecarbonylate in trans form (wherein the substituent at the 2-position takes trans configuration when the ethoxycarbonyl group at the 1-position is taken as a standard).

EXAMPLE 24

Preparation of methyl 1-fluoro-2-(4,6-dimethoxypyrimidinyl-2-thio)-1-cyclohexanecarboxylate (compound number 1496)

In 10 ml of dimethylformamide were dissolved 192 mg (1 mmol) of methyl 1-fluoro-2-mercaptocyclohexanecarboxylate synthesized according to Example 18 and 218 mg (1 mmol) of 4,6-diethoxy-2-methylsulfonylpyrimidine, to the solution was added 166 mg (1.2 mmol) of potassium carbonate, and the mixture was stirred at room temperature for 5 hours. The reaction solution was poured into water and extracted three times with 30 ml of ethyl acetate, and the obtained organic layer was washed with water and dried over anhydrous magnesium sulfate. The solvent was distilled away to obtain 350 mg of the crude product. This was purified by silica gel chromtography (developing solvent: hexane/ethyl acetate=10/1) to obtain 257 mg (yield: 78%) the objective methyl 1-fluoro-2-(4,6-dimethoxypyrmidinyl-2-thio)-1-cyclohexanecarboxylate (compound number 1496), $^1$H-NMR (δ, CDCl$_3$): 5.78 (s,1H), 3.90 (s,6H), 3.75 (s,3H), 1.1–3.3 (m,9H) ppm.

EXAMPLE 25

Preparation of 1-fluoro-2-(4,6-dimethoxypyrimidinyl-2-oxy)-1-cyclopentanecarboxylic acid in trans form (compound number 1002b)

0.6 g (2 mmol) of methyl 1-fluoro-2-(4,6-dimethoxypyrimidinyl-2-oxy)-1-cyclopentanecarboxylate in trans form (compound number 1003b) synthesized according to Example 20 was dissolved in a mixed solution of 5 ml of methanol and 10 ml of water, 0.34 g of potassium hydroxide was added, and the mixture was stirred at 40° C. for 1 hour. The methanol was distilled away, 30 ml of water was added to the reaction solution, and the mixture was acidified with diluted hydrochloric acid and extracted three times with 30 ml each of ethyl acetate. The ethyl acetate layer was dried over anhydrous magnesium sulfate and the solvent was distilled away to obtain 0.27 g (yield: 47.2%) of the desired 1-fluoro2-(4,6-dimethoxypyrimidinyl-2-oxy)-1-cyclopentanecarboxylic acid in trans form (compound number 1002b). Melting point 122°–124° C.

EXAMPLE 26

Preparation of 1-fluoro-2-(4,6-dimethoxypyrimidinyl-2-oxy)-1-cyclohexanecarboxylic acid isopropylamine salt in trans form (compound number 1218b)

Ethyl 1-fluoro-2-hydroxy-cyclohexanecarboxylate synthesized according to Example 3 was converted successively according to the process of Examples 20 and 21 to obtain 1-fluoro-2-(4,6-dimethoxypyrimidinyl-2-oxy)-1-cyclohexanecarboxylic acid in trans form (compound number 1180b). To 5 ml of the ethanol solution of 0.4 g (1.34 mmol) of this compound was added at room temperature 0.88 g (1.5 mmol) of isopropylamine, and the mixture was stirred for 30 minutes and concentrated under reduced pressure to obtain 0.48 g (yield: 99%) of the objective 1-fluoro-2-(4,6-dimethoxypyrimidinyl-2-oxy)1-cyclohexanecarboxylic acid isopropylamine salt in trans form (compound number 1218b).

EXAMPLE 27

Preparation of 1-fluoro-2-(4,6-dimethoxypyrimidinyl-2-oxy)-1-cyclopentanecarboxylic acid isopropyl ester in trans form (compound number 1006b)

0.12 g (1.74 mmol) of isopropyl alcohol was added to 10 ml of an ether solution of 0.5 g (1.74 mmol) of 1-fluoro-2-(4,6-dimethoxypyrimidinyl-2-oxy)-1-cyclopentanecarboxylic acid (compound number 1002b) synthesized according to Example 25, and then 0.4 g (1.93 mmol) of dicyclohexylcarbodiimide and 20 mg of 4,4-dimethylaminopyridine were added at room temperature. After stirring for 2 hours, the reaction solution was filtered and the filtrate was concentrated to obtain the crude product. The crude product was purified by silica gel column chromatography (developing solvent: hexane/ethyl acetate=4/1) to obtain 0.4 g (yield: 70%) of the objective 1-fluoro-2-(4,6-dimethoxypyrimidinyl2-oxy)-1-cyclopentanecarboxylic acid isopropyl ester in trans form (compound number 1006b).

$^1$H-NMR (δ, CDCl$_3$): 1.16 (3H,d,J=6.2Hz), 1.26 (3H,d,J=6.2Hz), 1.51–2.68 (6H,m), 3.89 (6H,s), 5.03 (1H,sep), 5.66 (1H,s), 5.31–5.95 (1H,m) ppm

EXAMPLE 28

Preparation of
1-fluoro-2-(4,6-dimethoxypyrimidinyl-2-oxy)-1-cyclopentanecarboxylic acid ethanethiol ester in trans form (compound number 4228b)

0.14 ml (1.74 mmol) of ethanethiol was added to 10 ml of an ether solution of 0.5 g (1.74 mmol) of 1-fluoro-2-(4,6-dimethoxypyrimidinyl-2-oxy)-1-cyclopentanecarboxylic acid (compound number 1002b) synthesized according to Example 25, and then 0.4 g (1.93 mmol) of dicyclohexylcarbodiimide and 20 mg of 4,4-dimethylaminopyridine were added at room temperature. After stirring for 2 hours, the reaction solution was filtered and the filtrate was concentrated to obtain the crude product. This was purified by silica gel column chromatography (developing solvent: hexane/ethyl acetate =9/1) to obtain 0.3 g (yield: 52%) of the objective 1-fluoro-2-(4,6-dimethoxypyrimidinyl-2-oxy)-1-cyclopentanecarboxylic acid ethanethiol ester in trans form (compound number 4228b).

EXAMPLE 29

Preparation of N,N-dimethyl,
1-fluoro-2-(4,6-dimethoxypyrimidinyl-2-oxy)-1-cyclopentanecarboxylic amide in trans form (compound number 4010b)

6 ml of an tetrahydrofuran solution of 0.4 g (1.4 mmol) of 1-fluoro-2-(4,6-dimethoxypyrimidinyl-2-oxy)-1-cyclopentanecarboxylic acid (compound number 1002b) was cooled to 0° C., and 0.19 ml (1.4 mmol) of triethylamine and 0.13 ml (1.4 mmol) of ethyl chlorocarbonate were added. After stirring at 0° C. for 1 hour, 0.15 g of a 50% aqueous dimethylamine solution was added and the mixture was further stirred for 2 hours. Water was added to the reaction solution, the mixture was extracted with ether and the ether layer was successively washed with diluted hydrochloric acid and saturated saline. The ether layer was dried over anhydrous sodium sulfate, the solvent was distilled away and the crude product was purified by silica gel column chromatography (developing solvent: hexane/ethyl acetate=1/9) to obtain 0.29 g (yield: 68%) of the objective N,N-dimethyl, 1-fluoro-2-(4,6-dimethoxypyrimidinyl-2-oxy)1-cyclopentanecarboxamide in trans form (compound number 4010b).

$^1$H-NMR ($\delta$, CDCl$_3$): 1.67–2.67 (6H,m), 2.73–3.20 (6H,m), 3.87 (6H,s), 5.62 (1H,s), 5.47–6.05 (1H,m) ppm

EXAMPLE 30

Preparation of methyl
O-methoxycarbonylmethyl-1-fluoro-2-(4,6-dimethoxypyrimidinyl-2-oxy)-1-cyclopentanehydroxymate (compound number 4096b)

0.8 ml of triethylamine was added to 10 ml of a tetrahydrofuran solution of 0.8 g (2.8 mmol) of 1-fluoro-2-(4,6-dimethoxypyrimidinyl-2-oxy)-1-cyclopentanecarboxylic acid (compound number 1002b) synthesized according to Example 25, the mixture was cooled to 0° C., and 0.26 ml (2.8 mmol) of ethyl chloroformate was added dropwise. After stirring for 1 hour, 0.36 g (3.4 mmol) of methyl aminooxyacetate was added and the mixture was further stirred for 2 hours. The reaction solution was poured into saturated saline and extracted with ether, the ether layer was successively washed with a diluted aqueous hydrochloric acid solution and saturated saline and dried over anhydrous sodium sulfate, and the solvent was distilled away to obtain the crude product. This was purified by silica gel column chromatography (developing solvent: hexane/ethyl acetate=4/1) to obtain 0.66 g (yield: 63%) of the objective N-methoxycarbonylmethoxy, 1-fluoro-2-(4,6-dimethoxypyrimidinyl-2-oxy)-1-cyclopentanecarboxamide (compound number 4048b).

$^1$H-NMR ($\delta$, CDCl$_3$): 1.70–2.77 (6H,m), 3.36 (3H,s), 3.94 (6H,s), 4.41 (2H,s), 5.70 (1H,s), 5.33–6.00 (1H,m), 9.43–9.73 (1H,bs) ppm Melting point: 68°–70.2° C.

Then, to 10 ml of an ether solution of 0.66 g (1.7 mmol) of this amide (compound number 4048b) was added under ice cooling an ether solution containing 1.5 equivalent amount of diazomethane, and the mixture was stirred for 1 hour. The excessive diazomethane was decomposed by the addition of acetic acid to the reaction solution, the solvent was distilled away, and the resulting crude product was purified by silica gel column chromatography (developing solvent: hexane/ethyl acetate =9/1) to obtain 0.67 g (yield: 97%) of the objective methyl O-methoxycarbonylmethyl-1-fluoro-2-(4,6-dimethoxypyrimidinyl-2-oxy)-1-cyclopentanehydroxymate (compound number 4096b).

$^1$H-NMR ($\delta$, CDCl$_3$): 1.56–2.59 (6H,m), 3.69 (3H,s), 3.92 (6H,s), 4.10 (3H,s), 4.44 (2H,s), 5.66 (1H,s), 5.39–5.92 (1H,m) ppm Melting point: 72°–74.0° C.

EXAMPLE 31

Preparation of
1-fluoro-2-(4,6-dimethoxypyrimidinyl-2-oxy)-1-cyclohexanethiocarboxamide in trans form (compound number 4379b)

Ethyl 1-fluoro-2-hydroxy-cyclohexanecarboxylate synthesized in Example 3 was successively converted according to the processes of Examples 20, 21 and 29 to obtain 1-fluoro-2-(4,6-dimethoxypyrimidinyl-2-oxy)-1-cyclohexanecarboxamide acid in trans form (compound number 4275b). To 5 ml of an ethylene glycol dimethyl ether solution of 0.32 g (1.07 mmol) of this compound was added 0.24 g (0.59 mmol) of Lawesson's reagent, and the mixture was refluxed with heating for 2 hours. The reaction solution was cooled to room temperature, poured into water and extracted with chloroform, the chloroform layer was dried over anhydrous sodium sulfate, the solvent was distilled away, and the crude product was purified by silica gel column chromatography (developing solvent: hexane/ethyl acetate=4/1) to obtain 0.05 g (yield: 15%) of the objective 1-fluoro-2-(4,6-dimethoxypyrimidinyl-2-oxy)-1-cyclohexanethiocarboxamide in trans form (compound number 4379b).

$^1$H-NMR ($\delta$, CDCl$_3$): 1.00–2.83 (8H,m), 3.90 (6H,s), 4.93–5.83 (1H,m), 5,63 (1H,s), 6.00 (1H,bs), 6.53 (1H,bs) ppm

EXAMPLE 32

Preparation of ethyl
2-(4,6-dimethoxypyrimidin-2-yl)-thio-1-fluoro-2-cyclohexenecarboxylate (compound number 7004)

Referring to the process described in Bulletin des Societe Chimiques Belges volume 87, page 223 (1978), 5.4 g (30 mmol) of ethyl 1-fluoro-2-oxocyclohexanecarboxylate was dissolved in 50 ml of toluene, to this was added 6.0 g (15 mmol) of Lawesson's reagent, and reaction was carried out at 100° C. for 5 hours. 100 ml of hexane was added, the precipitate was filtered out and the solvent was distilled away. The filtrate was purified by silica gel column chromatography (developing solvent: hexane / ethyl acetate=15/1) to obtain 1.1 g (yield: 18 % of ethyl 1-fluoro-2-mercapto-2-cyclohexenecarboxylate.

204 mg (1 mmol) of this ethyl 1-fluoro-2-mercaptocyclohexenecarboxylate and 218 mg (1 mmol) of 4,6-dimethoxy-2-methylsulfonylpyrimidine were dissolved in 10 ml of dimethylformamide, 166 mg (1.2 mmol) of potassium carbonate was added to the solution and the mixture was stirred at room temperature for 5 hours. The reaction solution was poured into 50 ml of water and extracted three times with 30 ml each of ethyl acetate, and the obtained organic layer was washed with water and dried over anhydrous magnesium sulfate. The solvent was distilled away to obtain 350 mg of the crude product. The crude product was purified by silica gel column chromatography (hexane: ethyl acetate=9:1) to obtain 240 mg (yield: 70%) of the objective ethyl 2-(4,6-dimethoxypyrimidine-2-yl)-thio-1-fluoro-2-cyclohexcarboxylate (compound number 7004).

EXAMPLE 33

Preparation of (+) and (−)-1-fluoro-2-(4,6-dimethoxypyrimidinyl-2-oxy)-1-cyclopentanecarboxylic acid in trans form (compound numbers 1002b1 and 1002b2) and their methyl esters (compound numbers 1003b1 and 1003b2)

In 40 ml of isopropyl alcohol was dissolved 6.15 g (21.5 mmol) of 1-fluoro-2-(4,6-dimethoxypyrimidinyl-2-oxy)-1-cyclopentanecarboxylic acid (compound number 1002b) synthesized according to Example 25, 7 g (21.5 mmol) of quinine was added, and the formed salt was dissolved under reflux with heating. After being left at room temperature overnight, the reaction solution was filtered to obtain 10.65 g of a salt (named the first crystals). This salt was then twice recrystallized from isopropyl alcohol to obtain 4.4 g of pure quinine salt of (+)-1-fluoro 2-(4,6-dimethoxypyrimidinyl-2-oxy)-1-cyclopentenecarboxylic acid in trans form. 3.54 g of this salt wad dissolved in 40 ml of 1N hydrochloric acid, 50 ml of ether was added and the mixture was stirred for 1 hours. The ether layer was separated and dried over anhydrous magnesium sulfate and the solvent was distilled away to prepare 1.49 g (24.2%) of the objective (+)-1-fluoro-2-(4,6-dimethoxypyrimidinyl-2-oxy)-1-cyclopentanecarboxylic acid in trans form (compound number 1002 bl). [

$\alpha]_D = +36.62°$ (c=0.071, i-Pr-OH)

The mother liquor after the recrystallization of the first crystals was then concentrated, and 3.53 g of the deposited the quinine salt of (−)-1-fluoro-2-(4,6-dimethoxypyrimidinyl-2-oxy)-1-cyclopentanecarboxylic acid in trans form (compound number 1002b2) was decomposed in the same manner as above to prepare 1.09 g (17.7%) of the objective (−)-1-fluoro-2-(4,6-dimethoxypyrimidinyl-2-oxy)-1-cyclopentanecarboxylic acid in trans form (compound number 1002b2).

$[\alpha]_D^{30} = -38.55°$ (c=0.083, i-Pr-OH)

1.49 g of the thus obtained optically active carboxylic acid in (+) from (compound number 1002bl) was dissolved in 20 ml of ether, and a necessary amount of an ether solution of diazomethane was added under ice cooling to methylate the carboxylic acid. The excessive diazomethane was decomposed with acetic acid and the solvent was distilled away to obtain 1.5 g (95.6%) of the object (+)-1-fluoro-2-(4,6-dimethoxypyrimidinyl-2-oxy)-1-cyclopentanecarboxylic acid methyl ester in trans form (compound number 1003bl).

Analysis with an optical isomer-separating column (CHIRALCEL OD; manufactured by Daisel Co.) (solvent system: hexane/isopropyl alcohol=9/1, flow rate: 2 ml/min, detection wavelength: 254 nm) revealed that the ester was excessive in antipode by 99%.

Further 1.09 g of (−)-1-fluoro-2-(4,6-dimethoxypyrimidinyl-2-oxy)-1-cyclopentanecarboxylic acid in trans form (compound number 1002b2) was methylated in the same manner as in the (+) form compound to obtain 1.11 g (yield: 96.4%) of (−)-1-fluoro-2-(4,6-dimethoxypyrimidinyl-2-oxy)-1-cyclopentanecarboxylic acid methyl ester in trans form (compound number 1003b2). The analysis of this ester under the same conditions as in the (+) form compound revealed that the ester was excessive in antitope by 86.8%.

The halogen-containing compounds represented by the formula (I) of this invention have an excellent activity as a hebicide. When used as herbicides, the compounds represented by the formula (I) are mixed with agriculturally and forticulturally acceptable carrier(s) or diluent(s), additive(s) and auxiliary(ies) and the like by a method known per se and formulated into preparation forms usually used for pesticides, such as, for example, dusts, granules, wettable powders, emulsifiable concentrate liquids and flowables. Further, other pesticides such as, for example, fungicides, insecticides, acaricides, other herbicides, plant growth regulators, fertilizers or soil-improving agents can be mixed therewith or used together. Particularly by using the compounds represented by the formula (I) in a state such that they are mixed with other herbicides, the amounts of the chemicals to be used can be reduced and labors can be reduced, and further, the enlargement of weeding spectrum due to the synergism of both chemicals and a still higher effect due to potentiation can also be expected.

The following can, for example, be mentioned as specific examples of other herbicides usable in a state such that they are mixed with the compounds of the invention represented by the formula (I) (the words in the parentheses denote common names unless otherwise defined).

Carbamate herbicides

Methyl 3,4-dichlorophenylcarbamate (Swep), isopropyl 3-chlorophenylcarbamate (Chloroproham), S-(p-chlorobenzyl)-N,N-diethylthiocarbamate (Benthiocarb), S-ethyl N,N-hexamethylenethiocarbamate (Molinate), S-(1-methyl-1-phenylethyl) piperidine-1-carbothioate (Dimepiperate), S-benzyl N-ethyl-N-(1,2-dimethylpropyl) thiolcarbamate (Esprocarb), 3-(methoxycarbonylaminophenyl N-(3-methylphenyl) carbamate (Phenmedipham), ethyl 3-phenylcarbamoyloxyphenylcarbamate (Desmedipham), etc.

Urea herbicides 1-(α, α-Dimethylbenzyl-3-(4-methylphenyl)urea Dymron), 3-(3,4-dichlorophenyl)-1,1-dimethylurea (Diuron), 1,1-dimethyl-3-(α,α,α-trifluoro-m-tolyl)urea (Fluometuron), 3-[4-(4-chlorophenoxy)phenyl)-1,1- dimethylurea (Chloroxuron), 3-(3,4-dichlorophenyl)-1-methoxy-1-methylurea (Linuron), 3-(4-chlorophenyl)-1-methoxy-1-methylurea (Monolinuron), 3-(4-bromo-3-chlorophenyl)-1-methoxy-1-methylurea (Chlorbromron), 1-( ,-dimethylbenzyl)-3-(2-chlorobenzyl)urea (Code number JC-940), etc.

Haloaceta amide herbicides

2-Chloro-2',6'-dimethyl-N-methoxymethyla cetanilide (Alachlor), N-butoxymethyl-2-chloro-2',6'-diethlacetanilide (Butachlor), 2-chloro-2',6'-diethyl-N-(2-propoxyethyl) acetanilide (Pretilachlor), 2-chloro-N-isopropylacetanilide (Propachlor), etc.

Amide herbicides

3',4'-Dichloropropionanilide (Propanil), 2-bromo-N-(1,1-dimethylbenzyl)-3,3-dimethylbutanamide (Bromobutide), 2-benzothiazol-2-yloxy-N-methylacetanilide (Mefenacet), N,N-dimethyldiphenylacetamide (Diphenamide), etc.

Dinitrophenyl herbicides 4,6-dinitro-o-cresol (DNOC), 2-tert-butyl-4,6-dinitrophenol (Dinoterb), 2-sec-butyl-4,6-dinitrophenol (Dinoseb), N,N-diethyl-2,6-dinitro-4-trifluoromethyl-m-phenylenediamine (Dinitramine), $\alpha,\alpha,\alpha$-trifluoro-2,6-dinitro-N,N-dipropyl-p-toluidine (Trifluralin), 4-methyl-sulfonyl-2,6-dinitro-N,N-dipropylaniline (Nitralin), N-(1-ethylpropyl)-2,6-dinitro-3,4-xylidine (Pendimethalin), etc.

Phenoxy herbicides 2,4-Dichlorophenoxyacetic acid (2,4-D), 2,4,5-trichlorophenoxyacetic acid (2,4,5-T), 4-chloro-o-tolyloxacetic acid (MCPA), 4-(4-chloro-o-tolyloxy) butyric acid (MCPB), 2,4-dichlorophenoxy butyric acid (2,4-DB), 2,(4-chloro-o-tolyloxy) propionic acid (Mecoprop), 2-(2,4-dichlorophenoxy) propionic acid (Dichlorprop), (RS)-2-[4-(2,4-dichlorophenoxy)phenoxy propionic acid (Diclofop) and its esters, (RS)-2-[4-(5-trifluoromethyl-2-pyridyloxy)phenoxy] acid (Fluazifop) and its esters, 2-(2,4-dichloro-3-methylphenoxy) propionanilide (Cromeprop), S-ethyl 4-chloro-2-methylphenoxy-thioacetate (Phenothiol), 2-(2-naphthoxy) propionanilide (Naproanilide), etc.

Carboxylic acid herbicides 2,2-Dichporopropionic acid (Dalapone), trichloroacetic acid (TCA), 2,3,6-trichlorobenzoic acid (2,3,6-TBA), 3,6-dichloro-o-anisic acid (Dicamba), 3-amino-2,5-dichlorobenzoic acid (Chloromben), etc.

Organic phosphorus herbicides

O-Ethyl O-(2-nitro-5-methylphenyl)-N-sec-butylphosphoroamidethioate (Butamifos), O,O-diisopropyl S-(2-benzenesulfonylaminoethyl)phosphorodithioate (SAP), S-(2-methylpiperidin-1-yl)carbonylmethyl O,O-dipropylphosphorodithioate (Piperophos), etc.

Benzonitrile herbicides 2,6-Dichlorobenzonitrile (Dichlobenil), 3,5-dibromo-4-hydroxybenzonitrile (Bromoxynil), 4-hydroxy-3,5-diiodobenzonitrile (Ioxynil), etc.

Diphenyl ether herbicides 2,4-Dichlorophenyl 4-nitrophenyl ether (Nitrofen), 2,4,6-trichlorophenyl 4'-nitrophenyl ether (Chlornitrofen), 2,4-dichlorophenyl 3-methoxy-4-nitrophenyl ether (Chlomethoxynil), methyl 5-(2,4-dichlorophenoxy)-2-nitrobenzoate (Bifenox), 4-nitrophenyl $\alpha,\alpha$,-trifluoro-2-nitro-p-tolyl ether (Fluorodifen), 2-chloro-4-trifluoromethylphenyl 3-ethoxy-4-nitrophenyl ether (Oxygluorfen), 5-(2-chloro-$\alpha,\alpha,\alpha$-trifluoro-p-tolyloxy)-2-nitrobenzoic acid (Acifluorfen), etc.

Triazine herbicides

4-Amino-3-methyl-6-phenyl-1-1,2,4-triazin-5-(4H)-one (Metribuzin), 2-chloro-4,6-bis-(ethylamino)1,3,5-triazine (Simazine), 2-chloro-4-ethylamino-6-isopropylamino-1,3,5-triazine (Atrazine), 2,4-bis(ethylamino)-6-methylthio-1,3,5-triazine (Simetryne), 2,4-bis(isopropylamino)-6-methylthio-1,3,5-ethylamino-6-methylthio-1,3,5-triazone (Dimethametryne), etc.

Sulfonylurea herbicides

2-Chloro-N-4-methoxy-6-methyl-1,3,5-triazin-yl) aminocarbonyl] benzenesulfonamide (Chlorsulfuron), methyl 2-{((4,6-dimethoxypyrimidin-2-yl) aminocabonyl) aminosulfonyl] methyl)benzoate (Bensulfuron methyl), Ethyl 2-[((4-chloro-6-methoxypyrimidin-2-yl) aminocarbonyl)aminosulfonyl)benzoate (Chlorimuron ethyl), etc.

Diazine herbicides 4-(2,4-Dichlorobenzoyl)-1,3-dimethylpyrazol-5-yl-p-toluenesulfonate (Pyrazolate), 1,3-dimethyl-4-(2,4-dichlorobenzoyl)-5-phenacyloxypyrazole (Pyrazoxyfen), 1,3-dimethyl-4-(2,4-dichloro-3-methyl-benzoyl)-5-(4-methylphenacyloxy) pyrazole (Benzofenap), etc.

Other herbicides 3,6-Dichloropyridine-2-carboxylic acid (Clopyralid), 4-amino-3,5,6-trichloropyridine-2-carboxylic acid (Picloram), 5-amino-4-chloro-2-phenylpyridazin-3(2H)-one (Chloridazon),3-cyclohexyl-1,5,6,7-tetrahydrocyclo pentenopyrimidine-2,4(3H)-dione (Lenacil), 5-bromo-3-sec-butyl-6-methyluracil (Bromacil), 3-tert-butyl-5-chloro-6-methyluracil (Terbacil), 3-isopropyl-(1H)-2,1,3 benzothiadiazin-4(3H)-one 2,2-dioxide (Bentazone), N-1-naphthylphthalamic acid (Naptalam), etc.

As the agriculturally and horticulturally acceptable carrier(s) or diluents(s) used in the formulation of the compund(s) of this invention alone or in mixing with other herbicide(s) solid or liquid carrier(s) usually used in agriculture is (are) used. Examples of the solid carriers include inorganic matters such as clays represented by the Kaolinite group, montmorillonite group, illite group and attapulgite group, talc, diatom earth, magnesium lime, apatite, zeolite, silicic anhydride and synthesized calcium silicate; vegetable organic matters such as soybean meal, tobacco meal, walnut meal, wheat flour, wood meal, starch and crystalline cellulose; synthetic and natural high molecular compounds such as coumarone resins, petroleum resins, alkyd resins, polyvinyl chloride, polyalkylene glycol, ketone resins, ester gum, copal gum and dammar gun; and further waxes such as carnauba wax and beeswax and urea, etc.

Examples of suitable liquid carriers include paraffin and naphthene hydrocarbons such as kerosene, mineral oil, spindle oil and white oil; aromatic hydrocarbons such as toluene, xylene, ethylbenzene, cumene and methyl naphthalene; ethers such as dioxane and tetrahydrofuran; ketones such as methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, n-hexanol, ethylene glycol, diethylene glycol, cyclohexanol and benzyl alcohol; ether alcohols such as ethylene glycol ethyl ether, ethylene glycol phenyl ether, diethylene glycol ethyl ether and diethylene glycol butyl ether; polar solvents such as dimethylformamide and dimethylsulfoxide; water, etc.

In addition, surfactants and other auxiliaries can be used for purposes of emulsification, dispersion, wetting, spreading, binding, regulation of disintegration, stabilization of the effective ingredient, improvement of fluidity, rust inhibition and the like on the compounds of the invention. Any of nonionic, anionic, cationic and amphoteric surfactants can be used as the surfactants, but usually nonionic and/or anionic compounds are used.

Examples of suitable nonionic surfactants include compounds obtained by addition polymerizing ethylene oxide with a higher alcohol such as lauryl alcohol, stearyl alcohol or oleyl alcohol; compounds obtained by addition polymerizing ethylene oxide with an alkylphenol such as isooctylphenol or nonylphenol; compounds obtained by addition polymerizing ethylene oxide with an alkylnaphthol such as butylnaphthol or octylnaphthol; compounds obtained by addition polymerizing ethylene oxide with a higher fatty acid such as palmitic acid, stearic acid or oleic acid; higher fatty acid esters of polyhydric alcohols such as sorbitan and compounds obtained by addition polymerizing ethylene oxide with such a higher fatty acid ester; compounds obtained by block addition polymerizing ethylene oxide with propylene oxide; etc.

Examples of suitable anionic surfactants include alkyl sulfate ester salts such as sodium lauryl sulfate and amine salts of oleyl alcohol sulfuric acid ester; alkylsulfonate salts such as sodium 2-ethylhexenesulfonate; arylsulfonate salts such as sodium isopropylnaphthalenesulfonate, sodium methylenebisnaphthalenesulfonate, sodium ligninsulfonate and sodium dodecylbenzenesulfonate; etc.

Further, the herbicide of the invention can contain, for purposes of improving the properties of the preparations and enhancing its herbicidal effect, a high molecular compound such as casein, gelatin, albumin, glue, sodium alginate, carboxymethylcellulose, methyl-cellulose, hydroxyethylcellulose or polyvinyl alcohol and other auxiliaries.

The above carriers and various auxiliaries can be used alone or in combination according to their purposes taking the application forms and places of the preparations into account.

The content of the compound of the invention represented by the formula (I) amount of the active ingredient in the thus obtained preparations varies depending on the preparation form, but is usually 0.1 to 99% by weight, particularly preferably 1 to 80% by weight.

In case of dust, it usually contains 1 to 25% by weight of the effective ingredient compound and the remaining part is the solid carrier.

In case of wettable powder, it usually contains, for example, 25 to 90% by weight of the active ingredient compound and the remaining part is the solid carrier and the dispersing and wetting agents, and if necessary, a protective colloid agent and an antifoaming agent are added.

In case of granules, they usually contain, for example, 1 to 35% by weight of the active ingredient compound and most of the remaining part are the solid carrier, the surfactant, etc. The effective ingredient compound is either uniformly mixed with the solid carrier or uniformly adhering or adsorbed on the surface of the solid carrier, and the diameter of the grains is about 0.2 to 1.5 mm.

In case of emulsifiable concentrate, it usually contains, for example, 5 to 60% by weight of the active ingredient compound and the remaining part is the liquid carrier, and if necessary, a rust inhibitor is added.

In case of flowables, they usually contain, for example 5 to 50% by weight of the active ingredient compound and 3 to 10% by weight of the dispersing and wetting agents, and the remaining part is water, and if necessary, a protective colloid agent, an antiseptic, an antifoaming agent, etc. can be added.

The halogen-containing compounds of the invention represented by the formula (I) can be applied as such or in an optional preparation form as abovementioned.

The herbicide of the invention can be applied for the extermination on control of various weeds from before generation to growth phase growing in paddy fields and farmlands. The amount of the herbicide to be applied is on the order of 0.001 to 5 kg, preferably on the order of 0.01 to 1 kg per 1 ha as the amount of the compound represented by the formula (I) (the amount of the active ingredient), and can appropriately be selected and changed depending on the kind and growth stage of objective weeds, application place, application time, weather, etc.

Several embodiments of preparations wherein the compounds of this invention are used are denoted below. "Part" in the following preparation examples is based on weight.

PREPARATION EXAMPLE 1

Granules

| Compound number 1182b | 5 parts |
| --- | --- |
| Bentonite | 40 parts |
| Talc | 52 parts |
| Sodium lignisulfonate | 2 parts |
| Polyoxyethylene alkyl aryl ether | 1 part |

The above components were sufficiently mixed, kneaded with the addition of a suitable amount of water and granuled by a granulator to obtain 100 parts of granules.

PREPARATION EXAMPLE 2

Wettable powder

| Compound number 1182b | 20 parts |
| --- | --- |
| Diatom earth | 60 parts |
| White carbon | 15 parts |
| Sodium lignisulfonate | 3 parts |
| Sodium dialkylnaphthalenesulfonate | 2 parts |

The above components were mixed, and then uniformly mixed and pulverized by a jet mill to obtain 100 parts of wettable powder.

PREPARATION EXAMPLE 3

Emulsifiable concentrate

| Compound number 1182b | 30 parts |
| --- | --- |
| Xylene | 55 parts |
| Cyclohexanone | 10 parts |

-continued

| | |
|---|---|
| Calcium dodecylbenzenesulfonate | 3 parts |
| Polyoxyethylene alkyl aryl ether | 2 parts |

The above components were uniformly mixed and dissolved to obtain 100 parts of an emulsion.

Herbicides using compounds of this invention could be each prepared according to the above preparation examples.

The halogen-containing compounds of the invention represented by the formula (I) are novel compunds not disclosed in literatures. The compounds of the invention represented by the formula (I) have their characteristic in that they take a structure wherein the α-halogenated carboxylic acid derivative part having a relatively simple structure and the pyrimidine ring or triazine ring part to which specific substituents bind at the 4-position and 6-position bind through an oxygen atom, sulfur atom or —OCH$_2$—, and it is considered that the excellent herbicidal effect is mainfested due to the structural characteristic.

The compounds and herbicide of this invention can exterminate and/or prevent various weeds from before generation to the growth phase which grow in agricultural lands. For example, the compounds and herbicide of the invention can exterminate and/or prevent weeds in paddy fields such as barnyardagrass (*Echinochloa crus-galli*), Japanese bulrush (*Scirpus juncoides*), "mizugayatruri"-(*cyperus serotinus*), monochoria (*Monochoria vaginalis*), common flase pimpernel (*Lindernia pyxidaria*), waterwort (*Elatine triandra*), indian toothcup (*Rotala indica*), needle spikerush (*Eleocharis acicularis*) and "urikawa" (*segittaria pygmoea*), and various weeds in farmlands such as crabgrass (*Digitaria sanquinalis*), giant foxtail (*Setaria faberi*), goosegrass (*Eleusine indica*), ricegrass paspalum (*Paspalum orbiculare*) water foxtail (*Alopecurus aegualis*), common chickweed (*Stellaria media*), various species of Polygonum, various species of Amaranthus, velvetleaf (*Abutilon theophrasti*), common lambsquarters (*Chenopodium album*), prickly sida (*Sida spinosa*), various species of Ipomoea, common cocklebur (*Xanthium strumarium*), common ragweed (*Ambrosia artemisialfolia*), sheherd'-spurse (*Capsella bursa-pastoris*), flexuous bittercress (*Cardamine flexuosa*), hairy beggarticks (*Bidens pilosa*), catchweed bedstraw (*Galium aparine*), wild mustard (*Brassica kaber*), various species of Ipomoea, jimson-weed (*Datura stramonium*), wild sunflower and wild buckwheat (*Polygonum convolvulus*). Further, the compounds and herbicide of this invention can be used not only in paddy fields and farmlands but also in fruit farms, lawns, and non-crop lands.

Moreover, the compounds of this invention have selectivity on some kinds of crops, and particularly do not give such phytotoxicity as practically becomes a problem on crops such as cotton, soybean and maize.

The herbicidal effects of the compounds and herbicide of this invention and described below according to test examples.

TEST EXAMPLE 1

Foliar application test in a upland field

Plowed field soil was packed into four-sided port (30×30×12 cm), a predetermiend amount each of the seeds of the various crops and various weeds shown in Table 17 were sown respectively, and the respective plants were grown in a greenhouse up to 1.5 to 3 leaf stage. Wettable powders were prepared according to Preparation example 2 using the compounds of this invention shown in Table 17 respectively. A dilution of each wettable powder with water was evenly applied on the foliages of each plant in the application amount corresponding to 500 l/ha so that the active ingredient amount indicated in Table 17 was given. 21 days after the application, herbicidal effects on the various weeds and the degree of phytotoxicity on the various crops were evaluated according to the following criterion. The results are shown in Table 17.

| Rating | Herbicidal effect: weeding rate (%) based on the non-treated group | Phytotoxicity on crop: phytotoxicity rate (%) based on the non-control group |
|---|---|---|
| 0 | 0 | the same as left |
| 1 | above - 10 | |
| 2 | above - 20 | |
| 3 | above - 30 | |
| 4 | above - 40 | |
| 5 | above - 50 | |
| 6 | above - 60 | |
| 7 | above - 70 | |
| 8 | above - 80 | |
| 9 | above - 90 | |
| 10 | above - 100 (withered) | |

TABLE 17

Foliar application test in upland field

| Compound No. | Amount of active ingredient (g/ha) | Herbicidal effect | | | | | | | | Phytotoxicity | | |
|---|---|---|---|---|---|---|---|---|---|---|---|---|
| | | barnyard grass | giant foxtail | slender Amaranth | velvet-leaf | tall morning-glory | cocklebur | wild mustard | wild sunflower | maize | soybean | cotton |
| 1004b | 50 | 10 | 10 | 10 | 10 | 10 | 10 | 10 | 10 | — | — | 0 |
| 4228b | 50 | 10 | 10 | 10 | 10 | 10 | 10 | 10 | 10 | — | — | 0 |
| 1182b | 50 | 10 | 10 | 10 | 10 | 10 | 10 | 10 | 10 | 0 | — | — |
| 1184b | 50 | 10 | 9 | 10 | 10 | 9 | 10 | 10 | 10 | 0 | — | — |
| 1411b | 50 | — | — | 10 | 10 | 9 | 10 | 9 | 10 | 1 | — | — |
| 2039 | 50 | 10 | 10 | 10 | 10 | 10 | 10 | 10 | 10 | — | — | 0 |
| 2057b | 50 | 10 | 10 | 10 | 10 | 10 | 10 | 10 | 10 | 0 | — | — |
| 3003b | 50 | 10 | 10 | 10 | 10 | 10 | 10 | 10 | 10 | 0 | 0 | 0 |
| 1187b | 50 | 10 | 9 | 10 | 10 | 10 | 10 | 10 | 10 | 0 | — | — |
| 1234b | 50 | 10 | 9 | 10 | 10 | 10 | 10 | 10 | 10 | 1 | — | — |
| 4512b | 50 | 10 | 9 | 10 | 10 | 10 | 10 | 10 | 10 | 1 | — | — |

TEST EXAMPLE 2

Pre-emergence soil application test in upland filed

Plowed field soil was packed into four-sided ports (30×30×12 cm), a predetermined amount each of the seeds of the various crops and various weeds shown in Table 18 were sown respectively, and covered with the soil so that the height of the covering soil became 1 cm. Wettable powders were prepared according to Preparation example 2 using the compounds of this invention shown in Table 18 respectively. A dilution of each wettable powder was evenly applied on the soil surface in the application amount corresponding to 500 1/ha so that the active ingredient amount indicated in Table 18 was given. 21 days after the application, herbicidal effects on the various weeds and the degree of phytotoxicity on the various crops were evaluated according to the criterion in Test example 1. The results are shown in Table 18.

| Evaluation criterion (11 stages) | |
|---|---|
| Rating | Herbicidal effect: weeding rate (%) based on the non-treated group |
| 0 | 0 |
| 1 | above - 10 |
| 2 | above - 20 |
| 3 | above - 30 |
| 4 | above - 40 |
| 5 | above - 50 |
| 6 | above - 60 |
| 7 | above - 70 |
| 8 | above - 80 |
| 9 | above - 90 |
| 10 | above - 100 (withered) |

TABLE 18

(Prior-germinating soil application test in upland field)

| Compound No. | Amount of active ingredient (g/ha) | Herbicidal effect | | | | | | | | Phytotoxicity | | |
|---|---|---|---|---|---|---|---|---|---|---|---|---|
| | | barnyard grass | giant foxtail | slender Amaranth | velvet-leaf | tall morning-glory | cocklebur | wild mustard | wild sunflower | maize | soybean | cotton |
| 1004b | 100 | 10 | 10 | 10 | 10 | 10 | 10 | 10 | 10 | — | 0 | 0 |
| 1006b | 100 | 10 | 10 | 10 | 10 | 10 | 10 | 10 | 10 | — | 0 | 0 |
| 1010b | 100 | 10 | 10 | 10 | 10 | 10 | 10 | 10 | 10 | — | 0 | 0 |
| 4228b | 100 | 10 | 10 | 10 | 10 | 10 | 10 | 10 | 10 | — | 0 | 0 |
| 4230b | 100 | — | — | 10 | 10 | 10 | 10 | 10 | 10 | 1 | 0 | 0 |
| 2039 | 100 | 10 | 10 | 10 | 10 | 10 | 10 | 10 | 10 | 0 | 0 | 0 |
| 2057b | 100 | 10 | 10 | 10 | 10 | 10 | 10 | 10 | 10 | — | 0 | 0 |
| 7004b | 100 | 10 | 10 | 9 | 10 | 10 | 9 | 10 | 10 | — | 1 | — |
| 2346b | 100 | 10 | 10 | 10 | 10 | 9 | 9 | 10 | — | — | 1 | — |

TEST EXAMPLE 3

Nonselective foliar application test

Plowed field soil was packed into foursided pots (30×30×12 cm), a predetermined amount each of the seeds of the various weeds shown in Table 19 were sown respectively, and the respective plants were grown in a greenhouse up to 1.5 to 3 leaf stage. Wettable powders were prepared according to Preparation example 2 using the compounds of this invention shown in Table 19 respectively. A dilution of each wettable powder with water to which a spreader Surfactant WK (produced by Maruwa Biochemical Co., Ltd.) was added so that the concentraton became 0.25% was evenly applied on the foliages of each plant in the application amount corresponding to 500 1/ha so that the active ingredient amount indicated in Table 19 was given. 21 days after the application, herbicidal effects on the various weeds were evaluated according to the following criterion. The results are shown in Table 19.

TABLE 19

(Nonselective foliar application test)

| Compound No. | amount of active ingredient (g/ha) | barnyard-grass | giant foxtail | slender Amaranth | velvet-leaf | tall morning-glory | cocklebur | wild mustard | wild sunflower | jimsonweed | hairy beggarticks |
|---|---|---|---|---|---|---|---|---|---|---|---|
| 1003b | 50 | 10 | 9 | 10 | 10 | 10 | 10 | 10 | 10 | 10 | 10 |
| 1003b2 | 50 | 10 | 10 | 10 | 10 | 10 | 10 | 10 | 10 | 10 | 10 |
| 1002b | 50 | 10 | 10 | 10 | 10 | 10 | 10 | 10 | 10 | 10 | 10 |
| 1246b | 50 | 10 | 9 | 10 | 10 | 10 | 10 | 10 | 10 | 10 | 10 |
| 1180b | 50 | 10 | 10 | 10 | 10 | 10 | 10 | 10 | 10 | 10 | 10 |

TEST EXAMPLE 4

Nonselective pre-emergence soil application test

Plowed field soil was packed into foursided pots (30×30×12 cm), a predetermined amount each of the seeds of the various weeds shown in Table 20 were sown respectively, and covered with the soil so that the height of the covering soil became 1 cm. Wettable powders were prepared according to Preparation example 2 using the compounds of this invention shown in Table 20. A dilution of each wettable powder was evenly applied on the soil surface in the application amount coresponding to 500 1/ha so that the active ingredient amount indicated in Table 20 was attained. 21 days after the application, hervicidal effects on the various weeds were evaluated according to the criterion in Test example 3. The results are shown in Table 20.

TABLE 20

| Compound No. | amount of active ingredient | barnyard-grass | giant foxtail | slender Amaranth | velvet-leaf | tall morning-glory | cock-lebur | wild mustard | common ragweed | hairy beggarticks |
|---|---|---|---|---|---|---|---|---|---|---|
| | | | | | | (Nonselective prior-germinating soil application test) | | | | |
| 1002b | 100 | 10 | 10 | 10 | 10 | 10 | 10 | 10 | 10 | 10 |
| 4035b | 100 | 10 | 10 | 10 | 10 | 10 | 9 | 10 | 10 | 10 |
| 4048b | 100 | 10 | 10 | 10 | 10 | 10 | 9 | 10 | 10 | 10 |
| 4071b | 100 | 10 | 10 | 10 | 10 | 10 | 9 | 10 | 10 | 10 |
| 4079b | 100 | 10 | 10 | 10 | 10 | 10 | 10 | 10 | 10 | 10 |
| 5156b | 100 | 10 | 10 | 10 | 10 | 10 | 8 | 10 | 10 | 10 |

What is claimed is:

1. Halogen-containing compounds represented by the formula

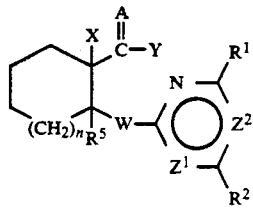

(I')

wherein $Z^1$ is a nitrogen atom and $Z^2$ is group CH,

X represents a fluorine atom,

W represents an oxygen atom, sulfur atom or —OCH$_2$—, n represents an integer of 0, 1, 2 or 3, $R^1$ and $R^2$ each independently represent either a hydrogen atom, halogen atom or mono- or dilower alkylsubstituted amino, or a lower alkyl, lower alkoxy or lower alkylthio each of which may be substituted with a halogen atom, $R^5$ represents a hydrogen atom or lower alkyl group, A represents an oxygen atom, sulfur atom or group =N—B wherein B represents hydroxy, lower alkenyloxy, lower alkynyloxy, benzyloxy or lower alkylcarbonyloxy, or lower alkoxy optionally substituted with hydroxycarbonyl, phenylcarbonyl or lower alkoxycarbonyl, and Y either represents a hydrogen atom, a hydroxy, a mercapto, or a lower alkoxy, lower alkenoxy, lower alkynoxy, lower alkylthio, phenoxy, benzyloxy, phenylthio, benzylthio, lower cycloalkoxy, lower cycloalkenyloxy, pyridylthio, furylmethyloxy, furylthio or thienyloxy each optionally substituted with a halogen atom, hydroxy, lower alkyl, lower alkoxy, leroy alkylthio, lower alkoxycarbonyl, lower alkylcarbonyl, cyano, nitro or azido, or an azido, a trilower alkyl-substituted silyloxy or an imidooxy, or represents a group

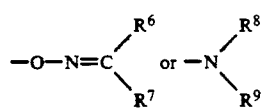

{wherein $R^6$ and $R^7$ each independently represent a hydrogen atom, lower alkyl, lower alkoxy, phenyl or benzyl or $R^6$ and $R^7$ may form together with the carbon atom to which they bind a lower cycloalkane ring, and $R^8$ and $R^9$ each independently represent a hydrogen atom, a hydroxy, a lower alkyl, a lower alkenyl, a lower alkynyl, a lower alkoxy, a lower alkenyloxy, lower alkynyloxy, a lower alkylcarbonyloxy, a cyano, a lower alkylsulfonyl optionally substituted with a halogen atom, a lower alkyl substituted with lower alkoxycarbonyl, a lower alkyl substituted with hydroxycarbonyl, a lower alkoxy substituted with lower alkoxycarbonyl, a lower alkoxy substituted with hydroxycarbonyl, or a phenyl, benzyl, phenyloxy, benzyloxy, and phenylcarbonyloxy, pyridyl,

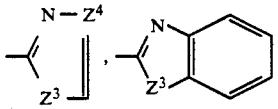

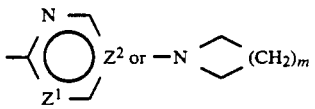

(wherein $Z^3$ represents an oxygen atom, CH or sulfur atom, $Z^4$ represents a nitrogen atom or CH, $Z^1$ and $Z^2$ are as defined above, and m represents an integer of 0 or 1) each optionally substituted with a halogen atom, hydroxy, lower alkyl, lower alkoxy, lower alkyl substituted with halogen atoms, cyano, nitro, amino, mono- or dilower-alkylsubstituted amino or lower alkoxycarbonyl,

(wherein $R^{10}$ and $R^{11}$ each represent a hydrogen atom, a lower alkyl, a lower alkoxycarbonyl, a lower alkyl substituted with lower alkoxycarbonyl, a lower alkyl substituted with hydroxycarbonyl, or a phenyl, benzyl, pyridyl or benzothiazolyl each optionally substituted with a halogen atom, lower alkyl, lower alkyl substituted with a halogen atom, lower alkoxy, cyano, amino or nitro)}, and salts thereof.

2. The compound of claim 1 represented by the following formula (I)

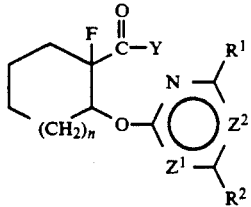
(I')-i wherein
n represents 0, 1, 2 or 3,
R¹ and R² each independently represent either lower alkoxy, lower alkylthio or halogen atom,
Y represents hydroxy, mercapto, lower alkoxy, lower alkenyloxy, lower alkylthio, lower alkynyloxy, a group

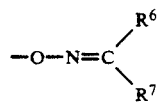

or a group 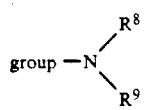

3. The compounds of claim 1 wherein W is an oxygen atom or sulfur atom.

4. The compounds of claim 1 wherein W is an oxygen atom.

5. The compounds of claim 1 wherein R¹ and R² are each independently a halogen atom, lower alkyl or lower alkoxy.

6. The compounds of claim 1 wherein R⁵ is a hydrogen atom.

7. The compounds of claim 1 wherein A is an oxygen atom.

8. The compounds of claim 1 wherein A is a sulfur atom.

9. The compounds of claim 1 wherein Y is hydroxy, mercapto, lower alkoxy, lower alkenyloxy, lower alkynyloxy, lower alkylthio, a group

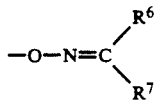

or a group

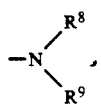

(wherein R⁸ and R⁹ are defined in the formula (I') and either of R⁸ and R⁹ represents a hydrogen atom).

10. The compounds of claim 1 wherein Y is hydroxy, lower alkoxy, lower alkenyloxy, lower alkynyloxy, lower alkylthio, a group

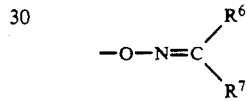

11. A herbicidal composition comprising an effective amount of the compound of formula (I') set forth in claim 1, and agriculturally and horticulturally acceptable diluent(s) or carrier(s).

12. A method for weeding which comprises applying the herbicidal composition of claim 11 to weeds or their growth environment.

* * * * *